US008568737B2

(12) United States Patent
Gardella et al.

(10) Patent No.: US 8,568,737 B2
(45) Date of Patent: Oct. 29, 2013

(54) SCREENING METHODS USING G-PROTEIN COUPLED RECEPTORS AND RELATED COMPOSITIONS

(75) Inventors: Thomas J. Gardella, Needham, MA (US); John T. Potts, Jr., Newton, MA (US); Masaru Shimizu, Shizuoka (JP); Fumihiko Ichikawa, Tokyo (JP); Harald Juppner, Lexington, MA (US); Makoto Okazaki, Shizuoka (JP)

(73) Assignees: The General Hospital Corporation, Boston, MA (US); Chugai Pharmaceutical Co., Ltd., Tokyo (JP)

(*) Notice: Subject to any disclaimer, the term of this patent is extended or adjusted under 35 U.S.C. 154(b) by 192 days.

(21) Appl. No.: 12/671,429

(22) PCT Filed: Aug. 1, 2008

(86) PCT No.: PCT/US2008/009288
§ 371 (c)(1),
(2), (4) Date: Nov. 8, 2010

(87) PCT Pub. No.: WO2009/017809
PCT Pub. Date: Feb. 5, 2009

(65) Prior Publication Data
US 2011/0172153 A1 Jul. 14, 2011

Related U.S. Application Data

(60) Provisional application No. 60/963,867, filed on Aug. 6, 2007, provisional application No. 60/963,082, filed on Aug. 2, 2007, provisional application No. 60/963,117, filed on Aug. 1, 2007.

(51) Int. Cl.
*A61K 38/22* (2006.01)
*C07K 14/575* (2006.01)

(52) U.S. Cl.
USPC ........................................ 424/198.1; 530/399

(58) Field of Classification Search
None
See application file for complete search history.

(56) References Cited

U.S. PATENT DOCUMENTS

| | | |
|---|---|---|
| 4,086,196 A | 4/1978 | Tregear |
| 4,366,241 A | 12/1982 | Tom et al. |
| 4,423,037 A | 12/1983 | Rosenblatt et al. |
| 4,511,502 A | 4/1985 | Builder et al. |
| 4,512,922 A | 4/1985 | Jones et al. |
| 4,518,526 A | 5/1985 | Olson |
| 4,620,948 A | 11/1986 | Builder et al. |
| 4,675,189 A | 6/1987 | Kent et al. |
| 4,698,328 A | 10/1987 | Neer et al. |
| 4,736,866 A | 4/1988 | Leder et al. |
| 4,761,406 A | 8/1988 | Flora et al. |
| 4,771,124 A | 9/1988 | Rosenblatt et al. |
| 4,843,000 A | 6/1989 | Litman et al. |
| 4,849,338 A | 7/1989 | Litman et al. |
| 5,010,010 A | 4/1991 | Gautvik et al. |
| 5,208,041 A | 5/1993 | Sindrey |
| 5,217,896 A | 6/1993 | Kramer et al. |
| 5,227,487 A | 7/1993 | Haugland et al. |
| 5,274,113 A | 12/1993 | Kang et al. |
| 5,326,692 A | 7/1994 | Brinkley et al. |
| 5,350,836 A | 9/1994 | Kopchick et al. |
| 5,382,658 A | 1/1995 | Kronis et al. |
| 5,393,869 A | 2/1995 | Nakagawa et al. |
| 5,405,975 A | 4/1995 | Kuhn et al. |
| 5,433,896 A | 7/1995 | Kang et al. |
| 5,442,045 A | 8/1995 | Haugland et al. |
| 5,451,663 A | 9/1995 | Kang et al. |
| 5,453,517 A | 9/1995 | Kuhn et al. |
| 5,457,034 A | 10/1995 | della Valle et al. |
| 5,459,276 A | 10/1995 | Kuhn et al. |
| 5,462,856 A | 10/1995 | Lerner et al. |
| 5,494,806 A | 2/1996 | Segre et al. |
| 5,496,801 A | 3/1996 | Holthuis et al. |
| 5,501,979 A | 3/1996 | Geller et al. |
| 5,516,864 A | 5/1996 | Kuhn et al. |
| 5,527,772 A | 6/1996 | Holick |
| 5,556,940 A | 9/1996 | Willick et al. |
| 5,573,909 A | 11/1996 | Singer et al. |
| 5,578,461 A | 11/1996 | Sherwin et al. |
| 5,589,452 A | 12/1996 | Krstenansky et al. |
| 5,605,815 A | 2/1997 | Broadus et al. |
| 5,616,560 A | 4/1997 | Geddes et al. |
| 5,648,270 A | 7/1997 | Kuhn et al. |
| 5,656,465 A | 8/1997 | Panicali et al. |
| 5,693,616 A | 12/1997 | Krstenansky et al. |

(Continued)

FOREIGN PATENT DOCUMENTS

| | | |
|---|---|---|
| AU | 668118 | 4/1996 |
| CA | 2126132 | 12/1995 |

(Continued)

OTHER PUBLICATIONS

Abou-Samra et al., "Phorbol 12-Myristate 13-Acetate and Vasopressin Potentiate the Effect of Corticotropin-Releasing Factor on Cyclic Amp Production in Rat Anterior Pituitary Cells. Mechanisms of Action," *J. Biol. Chem.* 262: 1129-1136 (1987).

Abou-Samra et al., "Non-Homologous Sequences of Parathyroid Hormone and the Parathyroid Hormone Related Peptide Bind to a Common Receptor on ROS 17/2.8 Cells," *Endocrinology* 125: 2215-2217 (1989).

Abou-Samra et al., "Cyclic Adenosine 3', 5'-Monophosphate (cAMP)-Dependent and cAMP-Independent Regulation of Parathyroid Hormone Receptors on UMR 106-01 Osteoblastic Osteosarcoma Cells," *Endocrinology* 129: 2547-2554 (1991).

(Continued)

*Primary Examiner* — Ruixiang Li
(74) *Attorney, Agent, or Firm* — Clark & Elbing LLP

(57) ABSTRACT

The present invention provides screening methods for GPCRs based on the discovery that the affinity of a receptor agonist for a GPCR (such as the parathyroid hormone receptor) when not bound to a G-protein is correlated with the length of time over which the agonist is effective, independently of its pharmacokinetic properties. The invention also provides PTH- and PTHrP-derived polypeptides.

9 Claims, 34 Drawing Sheets

(56) References Cited

U.S. PATENT DOCUMENTS

| | | | |
|---|---|---|---|
| 5,695,955 | A | 12/1997 | Krstenansky et al. |
| 5,717,062 | A | 2/1998 | Chorev et al. |
| 5,723,218 | A | 3/1998 | Haugland et al. |
| 5,723,577 | A | 3/1998 | Dong |
| 5,741,486 | A | 4/1998 | Pathak et al. |
| 5,763,416 | A | 6/1998 | Bonadio et al. |
| 5,798,225 | A | 8/1998 | Krstenansky et al. |
| 5,807,823 | A | 9/1998 | Krstenansky et al. |
| 5,814,603 | A | 9/1998 | Oldenburg et al. |
| 5,821,225 | A | 10/1998 | Vickery |
| 5,836,905 | A | 11/1998 | Lemelson et al. |
| 5,840,690 | A | 11/1998 | Holick |
| 5,840,837 | A | 11/1998 | Krstenansky et al. |
| 5,840,853 | A | 11/1998 | Segre et al. |
| 5,854,004 | A | 12/1998 | Czernilofsky et al. |
| 5,871,486 | A | 2/1999 | Huebner et al. |
| 5,874,086 | A | 2/1999 | Krstenansky et al. |
| 5,880,093 | A | 3/1999 | Bagnoli |
| 5,886,148 | A | 3/1999 | Segre et al. |
| 5,917,123 | A | 6/1999 | McTiernan et al. |
| 5,922,927 | A | 7/1999 | Bujard et al. |
| 5,977,070 | A | 11/1999 | Piazza et al. |
| 6,030,790 | A | 2/2000 | Adermann et al. |
| 6,051,686 | A | 4/2000 | Krstenansky et al. |
| 6,066,618 | A | 5/2000 | Holick |
| 6,147,186 | A | 11/2000 | Gardella et al. |
| 6,183,974 | B1 | 2/2001 | Bringhurst et al. |
| 6,362,163 | B1 | 3/2002 | Gardella et al. |
| 6,417,333 | B1 | 7/2002 | Bringhurst et al. |
| 6,495,662 | B1 | 12/2002 | Gardella et al. |
| 6,537,965 | B1 | 3/2003 | Bringhurst et al. |
| 6,541,220 | B1 | 4/2003 | Jüppner et al. |
| 6,756,480 | B2 | 6/2004 | Kostenuik et al. |
| 6,803,213 | B2 | 10/2004 | Bringhurst et al. |
| 7,022,815 | B1 | 4/2006 | Gardella et al. |
| 7,033,773 | B1 | 4/2006 | Bringhurst et al. |
| 7,057,012 | B1 | 6/2006 | Gardella et al. |
| 7,078,487 | B2 | 7/2006 | Jüppner et al. |
| 7,132,260 | B2 | 11/2006 | Segre et al. |
| 7,150,974 | B1 | 12/2006 | Segre et al. |
| 7,153,951 | B2 | 12/2006 | Gardella et al. |
| 7,169,567 | B1 | 1/2007 | Gardella et al. |
| 7,244,834 | B2 | 7/2007 | Gardella et al. |
| 7,253,264 | B1 | 8/2007 | Lauffer et al. |
| 7,371,844 | B2 | 5/2008 | Gardella et al. |
| 7,479,478 | B2 | 1/2009 | Bringhurst et al. |
| 7,521,528 | B2 | 4/2009 | Gardella et al. |
| 7,572,765 | B2 | 8/2009 | Gardella |
| 2002/0110871 | A1 | 8/2002 | Zahradnik et al. |
| 2003/0144209 | A1 | 7/2003 | Bringhurst et al. |
| 2003/0162256 | A1 | 8/2003 | Juppner et al. |
| 2003/0166838 | A1 | 9/2003 | Gardella et al. |
| 2003/0171288 | A1 | 9/2003 | Stewart |
| 2004/0176285 | A1 | 9/2004 | Juppner et al. |
| 2005/0026839 | A1 | 2/2005 | Gardella |
| 2005/0124537 | A1 | 6/2005 | Kostenuik et al. |
| 2005/0203012 | A1 | 9/2005 | Bringhurst et al. |
| 2005/0282749 | A1 | 12/2005 | Henriksen et al. |
| 2006/0078559 | A1 | 4/2006 | Migeotte et al. |
| 2007/0111946 | A1 | 5/2007 | Gardella et al. |
| 2007/0161569 | A1 | 7/2007 | Gardella |
| 2007/0203071 | A1 | 8/2007 | Gardella |

FOREIGN PATENT DOCUMENTS

| | | |
|---|---|---|
| CA | 2126299 | 12/2000 |
| EP | 0 341 962 | 11/1989 |
| EP | 0 464 533 | 1/1992 |
| EP | 0 477 885 | 4/1992 |
| EP | 0 561 412 | 9/1993 |
| EP | 0 748 817 | 12/1996 |
| EP | 0 783 522 | 7/1997 |
| GB | 2 269 176 | 2/1994 |
| JP | 58-96052 | 6/1983 |
| JP | 59-204159 | 11/1984 |
| JP | 5-32696 | 2/1993 |
| JP | 9-157294 | 6/1997 |
| JP | 11-509201 | 8/1999 |
| WO | WO 87/01130 | 2/1987 |
| WO | WO 91/05050 | 4/1991 |
| WO | WO 92/01810 | 2/1992 |
| WO | WO 92/17581 | 10/1992 |
| WO | WO 92/17602 | 10/1992 |
| WO | WO 93/06121 | 4/1993 |
| WO | WO 93/06846 | 4/1993 |
| WO | WO 93/09222 | 5/1993 |
| WO | WO 93/11257 | 6/1993 |
| WO | WO 94/02510 | 2/1994 |
| WO | WO 94/12650 | 6/1994 |
| WO | WO 95/02610 | 1/1995 |
| WO | WO 95/11988 | 5/1995 |
| WO | WO 96/03437 | 2/1996 |
| WO | WO 96/10041 | 4/1996 |
| WO | WO 96/19206 | 6/1996 |
| WO | WO 97/02834 | 1/1997 |
| WO | WO-98/04591 A1 | 2/1998 |
| WO | WO 98/05683 | 2/1998 |
| WO | WO 98/30590 | 7/1998 |
| WO | WO 99/18945 | 4/1999 |
| WO | WO-99/57139 A2 | 11/1999 |
| WO | WO 00/23594 | 4/2000 |
| WO | WO 00/31137 | 6/2000 |
| WO | WO 00/31266 | 6/2000 |
| WO | WO 00/32771 | 6/2000 |
| WO | WO 00/32775 | 6/2000 |
| WO | WO 00/39278 | 7/2000 |
| WO | WO 00/40698 | 7/2000 |
| WO | WO 01/23427 | 4/2001 |
| WO | WO 01/23521 | 4/2001 |
| WO | WO 03/009804 | 2/2003 |
| WO | WO 2004/067021 | 8/2004 |
| WO | WO 2004/093902 | 11/2004 |
| WO | WO 2005/009358 | 2/2005 |
| WO | WO-2006/033912 A2 | 3/2006 |
| WO | WO 2008/019062 | 2/2008 |
| WO | WO 2009/017809 | 2/2009 |

OTHER PUBLICATIONS

Abou-Samra et al., "Expression Cloning of a Common Receptor for Parathyroid Hormone and Parathyroid Hormone-Related Peptide From Rat Osteoblast-Like Cells: A Single Receptor Stimulates Intracellular Accumulation of Both cAMP and Inositol Trisphosphates and Increases Intracellular Free Calcium," *Proc. Natl. Acad. Sci. USA* 89: 2732-2736 (1992).

Abou-Samra et al., "Down-Regulation of Parathyroid (PTH)/PTH-Related Peptide Receptor Immunoreactivity and PTH Binding in Opossum Kidney Cells by PTH and Dexamethasone," *Endocrinology* 135: 2588-2594 (1994).

Adams et al., "Probing the Bimolecular Interactions of Parathyroid Hormone and the Human Parathyroid Hormone/Parathyroid Hormone-Related Protein Receptor. 2. Cloning, Characterization, and Photoaffinity Labeling of the Recombinant Human Receptor," *Biochemistry* 34: 10553-10559 (1995).

Alberts et al., "Chapter 6: Basic Genetic Mechanisms" in: *Molecular Biology of the Cell, 3rd Edition*, pp. 234-237 and the Genetic Code Table (Garland Pub., New York, NY, 1994).

Azarani et al., "Parathyroid Hormone and Parathyroid Hormone-Related Peptide Activate the Na+/H+ Exchanger NHE-1 Isoform in Osteoblastic Cells (UMR-106) via a cAMP-dependent Pathway," *J. Biol. Chem.* 270: 23166-23172 (1995).

Azarani et al., "Structurally Diverse N-terminal Peptides of Parathyroid Hormone (PTH) and PTH-Related Peptide (PTHRP) Inhibit the Na+/H+ Exchanger NHE3 Isoform by Binding to the PTH/PTHRP Receptor Type I and Activating Distinct Signaling Pathways," *J. Biol. Chem.* 271: 14931-14936 (1996).

Barbier et al., "Bioactivities and Secondary Structures of Constrained Analogues of Human Parathyroid Hormone: Cyclic Lactams of the Receptor Binding Region," *J. Med. Chem.* 40: 1373-1380 (1997).

(56) References Cited

OTHER PUBLICATIONS

Barbier et al., "Structural Requirements for Conserved Arginine of Parathyroid Hormone," *Biochemistry* 40: 8955-8961 (2001).
Barbier et al., "Backbone-Methylated Analogues of the Principle Receptor Binding Region of Human Parathyroid Hormone. Evidence for Binding to Both the N-Terminal Extracellular Domain and Extracellular Loop Region," *J. Biol. Chem.* 280: 23771-23777 (2005).
Barden et al., "NMR Study of a 34-Residue N-Terminal Fragment of a Parathyroid Hormon-Related Protein Secreted During Humoral Hypercalcemia of Malignancy," *Eur. J. Biochem.* 184: 379-394 (1989).
Barden et al., "NMR Solution Structure of Human Parathyroid Hormone(1-34)," *Biochemistry* 32: 7126-7132 (1993).
Barden et al., "Stabilized NMR Structure of the Hypercalcemia of Malignancy Peptide PTHrP[Ala-26](1-34)Amide," *Biochim. Biophys. Acta* 1208: 256-262 (1994).
Becker et al., "Procedure Guideline for Thyroid Scintigraphy: 1.0. Society of Nuclear Medicine," *J. Nucl. Med.* 37: 1264-1266 (1996).
Behar et al., "Histidine at Position 5 is the Specificity "Switch" between Two Parathyroid Hormone Receptor Subtypes," *Endocrinology* 137: 4217-4224 (1996).
Behar et al., "Photoaffinity Cross-Linking Identifies Differences in the Interactions of an Agonist and an Antagonist with the Parathyroid Hormone/Parathyroid Hormone-Related Protein Receptor," *J. Biol. Chem.* 275: 9-17 (2000).
Bergwitz et al., "Full Activation of Chimeric Receptors by Hybrids between Parathyroid Hormone and Calcitonin. Evidence for a Common Pattern of Ligand-Receptor Interaction," *J. Biol. Chem.* 271: 26469-26472 (1996).
Bergwitz et al., "Residues in the Membrane-spanning and Extracellular Loop Regions of the Parathyroid Hormone (PTH)-2 Receptor Determine Signaling Selectivity for PTH and PTH-Related Peptide," *J. Biol. Chem.* 272: 28861-28868 (1997).
Bergwitz et al., "Identification, Functional Characterization, and Developmental Expression of Two Nonallelic Parathyroid Hormone (PTH)/PTH-Related Peptide Receptor Isoforms in *Xenopus laevis* (Daudin)," *Endocrinology* 139: 723-732 (1998).
Berlot, "A Highly Effective Dominant Negative Alpha s Construct Containing Mutations that Affect Distinct Functions Inhibits Multiple Gs-Coupled Receptor Signaling Pathways," *J. Biol. Chem.* 277: 21080-21085 (2002).
Berridge et al., "Changes in the Levels of Inositol Phosphates after Agonist-Dependent Hydrolysis of Membrane Phosphoinositides," *Biochem. J.* 212: 473-482 (1983).
Bettoun et al., "Cloning and Characterization of the Promoter Regions of the Human Parathyroid Hormone (PTH)/PTH-Related Peptide Receptor Gene: Analysis of Deoxyribonucleic Acid from Normal Subjects and Patients with Pseudohypoparathyroidism Type 1b," *J. Clin. Endocrinol. Metab.* 82: 1031-1040 (1997).
Bettoun et al., "Developmental Upregulation of Human Parathyroid Hormone (PTH)/PTH-Related Peptide Receptor Gene Expression from Conserved and Human-specific Promoters," *J. Clin. Invest.* 102: 958-967 (1998).
Bisello et al., "Parathyroid Hormone-Receptor Interactions Identified Directly by Photocross-Linking and Molecular Modeling Studies," *J. Biol. Chem.* 273: 22498-22505 (1998).
Bisello et al., "Selective Ligand-Induced Stabilization of Active and Desensitized Parathyroid Hormone Type 1 Receptor Conformations," *J. Biol. Chem.* 277: 38524-38530 (2002).
Bork et al., "Go Hunting in Sequence Databases but Watch Out for the Traps," *Trends Genet.* 12: 425-427 (1996).
Bork, "Powers and Pitfalls in Sequence Analysis: The 70% Hurdle," *Genome Res.* 10: 398-400 (2000).
Born et al., "Inhibition of Parathyroid Hormone Bioactivity by Human Parathyroid Hormone (PTH)-(3-84) and PTH-(8-84) Synthesized in *Escherichia coli*," *Endocrinology* 123:1848-1853 (1988).
Bos et al., "Expression of the Parathyroid Hormone Receptor and Correlation with Other Osteoblastic Parameters in Fetal Rat Osteoblasts," *Calcif. Tisse Int.* 58:95-100 (1996).

Brenner, "Errors in Genome Annotation," *Trends Genet.* 15: 132-133 (1999).
Bringhurst et al., "Cloned, Stably Expressed Parathyroid Hormone (PTH)/PTH-Related Peptide Receptors Activate Multiple Messenger Signals and Biological Responses in LLC-PK1 Kidney Cells," *Endocrinology* 132: 2090-2098 (1993).
Broadus et al., "Parathyroid Hormone-Related Protein: Structure, Processing, and Physiological Actions," in: *The Parathyroids* (eds. J. P. Bilezikan et al.), pp. 259-294 (Raven Press Ltd., New York, NY, 1994).
Bryant et al., "Helix-Inducing α-Aminoisobutyric Acid in Opioid Mimetic Deltorphin C Analogues," *J. Med. Chem.* 40: 2579-2587 (1997).
Bundi et al., "Characterisation of a Local Structure in the Synthetic Parathyroid Hormone Fragment 1-34 by 1H Nuclear-Magnetic-Resonance Techniques," *Eur. J. Biochem.* 91: 201-208 (1978).
Campbell et al., "Totipotency or Multipotentiality of Cultured Cells: Applications and Progress," *Theriogenology* 47: 63-72 (1997).
Carter et al., "Studies of the N-Terminal Region of a Parathyroid Hormone-Related Peptide(1-36) Analog: Receptor Subtype-Selective Agonists, Antagonists, and Photochemical Cross-Linking Agents," *Endocrinology* 140: 4972-4981 (1999).
Carter et al., "Zinc(II)-Mediated Enhancement of the Agonist Activity of Histidine-Substituted Parathyroid Hormone (1-14) Analogues," *Biochem. Biophys. Acta* 1538: 290-304 (2001).
Castro et al., "Dual Regulation of the Parathyroid Hormone (PTH)/PTH-Related Peptide Receptor Signaling by Protein Kinase C and Beta-Arrestins," *Endocrinology* 143: 3854-3865 (2002).
Castro et al., "Turn-On Switch in Parathyroid Hormone Receptor by a Two-Step Parathyroid Hormone Binding Mechanism," *Proc. Natl. Acad. Sci. USA* 102: 16084-16089 (2005).
Catanzariti et al., "A Novel Expression System for Gs-Coupled Receptors," *BioTechniques* 15: 474-479 (1993).
Caulfield et al., "The Bovine Renal Parathyroid Hormone (PTH) Receptor has Equal Affinity for Two Different Amino Acid Sequences: The Receptor Binding Domains of PTH and PTH-related Protein are Located within the 14-34 Region," *Endocrinology* 127: 83-87 (1990).
Caulfield et al., "Parathyroid Hormone-Receptor Interactions," *Trends Endocrinol. Metab.* 1: 164-168 (1990).
Cervini et al., "Human Growth Hormone-Releasing hGHRH(1-29)-NH2: Systematic Structure-Activity Relationship Studies," *J. Med. Chem.* 41: 717-727 (1998).
Chakrabartty, "Large Differences in the Helix Propensities of Alanine and Glycine," *Nature* 351: 586-588 (1991).
Chakravarthy et al., "Parathyroid Hormone Fragment [3-34] Stimulates Protein Kinase C (PKC) Activity in Rat Osteosarcoma and Murine T-lymphoma Cells," *Biochem. Biophys. Res. Commun.* 171: 1105-1110 (1990).
Chauvin et al., "Parathyroid Hormone Receptor Recycling: Role of Receptor Dephosphorylation and Beta-Arrestin," *Mol. Endocrinol.* 16: 2720-2732 (2002).
Chen et al., "Solution Structure of the Osteogenic 1-31 Fragment of Human Parathyroid Hormone," *Biochemistry* 39: 12766-12777 (2000).
Chorev et al., "Modifications of Position 12 in Parathyroid Hormone and Parathyroid Hormone Related Protein: Toward the Design of Highly Potent Antagonists," *Biochemistry* 29: 1580-1586 (1990).
Chorev et al., "Cyclic Parathyroid Hormone Related Protein Antagonists: Lysine 13 to Aspartic Acid 17 [i to (i+4)] Side Chain to Side Chain Lactamization," *Biochemistry* 30: 5968-5974 (1991).
Chu et al., "Porcine Preparathyroid Hormone. Identification, Biosynthesis, and Partial Amino Acid Sequence," *Biochemistry* 14: 3631-3635 (1975).
Civitelli et al., "PTH Elevates Inositol Polyphosphates and Diacylglycerol in a Rat Osteoblast-Like Cell Line," *Am. J. Physiol.* 255: E660-667 (1988).
Civitelli et al., "Parathyroid Hormone-Related Peptide Transiently Increases Cytosolic Calcium in Osteoblast-Like Cells: Comparison with Parathyroid Hormone," *Endocrinology* 125: 1204-1210 (1989).
Cohen et al., "Analogues of Parathyroid Hormone Modified at Positions 3 and 6. Effects on Receptor Binding and Activation of Adenylyl Cyclase in Kidney and Bone," *J. Biol. Chem.* 266: 1997-2004 (1991).

(56) References Cited

OTHER PUBLICATIONS

Cole et al., "Regulation of Sodium-Dependent Phosphate Transport by Parathyroid Hormone in Opossum Kidney Cells: Adenosine 3', 5'-Monophosphate-Dependent and -Independent Mechanisms," *Endocrinology* 122: 2981-2989 (1988).

Colquhoun, "Binding, Gating, Affinity, and Efficacy: The Interpretation of Structure-Activity Relationships for Agonists and of the Effects of Mutating Receptors," *Br. J. Pharmacol.* 125: 924-947 (1998).

Condon et al., "The Bioactive Conformation of Human Parathyroid Hormone. Structural Evidence for the Extended Helix Postulate," *J. Am. Chem. Soc.* 122: 3007-3014 (2000).

Cwirla et al., "Peptide Agonist of the Thrombopoietin Receptor as Potent as the Natural Cytokine," *Science* 276: 1696-1699 (1997).

Dang et al., "Gene Therapy and Translational Cancer Research," *Clin. Cancer Res.* 5: 471-474 (1999).

Dautzenberg et al., "Mapping of the Ligand-Selective Domain of the *Xenopus laevis* Corticotropin-Releasing Factor Receptor 1: Implications for the Ligand-Binding Site," *Proc. Natl. Acad. Sci. USA* 95: 4941-4946 (1998).

DeAlmeida et al., "Identification of Binding Domains of the Growth Hormone-Releasing Hormone Receptor by Analysis of Mutant and Chimeric Receptor Proteins," *Mol. Endocrinol.* 12: 750-765 (1998).

Dean et al., "Mechanisms of Ligand Binding to the Parathyroid Hormone (PTH)/PTH-Related Protein Receptor: Selectivity of a Modified PTH(1-15) Radioligand for GalphaS-Coupled Receptor Conformations," *Mol. Endocrinol.* 20: 931-943 (2006).

Dempster et al., "Anabolic Actions of Parathyroid Hormone on Bone," *Endocrine Rev.* 14: 690-709 (1993).

Dempster et al., "Erratum: Anabolic Actions of Parathyroid Hormone on Bone," *Endocrine Rev.* 15: 261 (1994).

Dempster et al., "On the Mechanism of Cancellous Bone Preservation in Postmenopausal Women with Mild Primary Hyperparathyroidism," *J. Clin. Endocrinol. Metab.* 84: 1562-1566 (1999).

Ding et al., "A Single Amino Acid Determines the Immunostimulatory Activity of Interleukin 10," *J. Exp. Med.* 191: 213-223 (2000).

Doerks et al., "Protein Annotation: Detective Work for Function Prediction," *Trends Genet.* 14: 248-250 (1998).

Dohlman et al., "Model Systems for the Study of Seven-Transmembrane-Segment Receptors," *Annu. Rev. Biochem.* 60: 653-688 (1991).

Donahue et al., "Differential Effects of Parathyroid Hormone and Its Analogues on Cytosolic Calcium Ion and cAMP Levels in Cultured Rat Osteoblast-Like Cells," *J. Biol. Chem.* 263: 13522-13527 (1988).

Dong et al., "Demonstration of a Direct Interaction between Residue 22 in the Carboxyl-Terminal Half of Secretin and the Amino-Terminal Tail of the Secretin Receptor Using Photoaffinity Labeling," *J. Biol. Chem.* 274: 903-909 (1999).

Dunlay et al., "PTH Receptor Coupling to Phospholipase C is an Alternate Pathway of Signal Transduction in Bone and Kidney," *Am. J. Physiol.* 258: F223-F231 (1990).

Ebert et al., "A Moloney MLV-Rat Somatotropin Fusion Gene Produces Biologically Active Somatotropin in a Transgenic Pig," *Mol. Endocrinol.* 2: 277-283 (1988).

Epand, "Relationships Among Several Different Non-Homologous Polypeptide Hormones," *Mol. Cell Biochem.* 57: 41-47 (1983).

Fairwell et al., "Total Solid-Phase Synthesis, Purification, and Characterization of Human Parathyroid Hormone-(1-84)," *Biochemistry* 22: 2691-2697 (1983).

Fischer et al., "Human Parathyroid Hormone. Immunological Characterization of Antibodies Against a Glandular Extract and the Synthetic Amino-Terminal Fragments 1-12 and 1-34 and their Use in the Determination of Immunoreactive Hormone in Human Sera," *J. Clin. Invest.* 54: 1382-1394 (1974).

Freyaldenhoven et al., "Protein Kinase C Differentially Modulates PTH- and PGE2 -Sensitive Adenylate Cyclase in Osteoblast-Like Cells," *Am. J. Physiol.* 262: E87-E95 (1992).

Fujimori et al., "Dissociation of Second Messenger Activation by Parathyroid Hormone Fragments in Osteosarcoma Cells," *Endocrinology* 128: 3032-3039 (1991).

Fujimori et al., "Structure-Function Relationship of Parathyroid Hormone: Activation of Phospholipase-C, Protein Kinase-A and -C in Osteosarcoma Cells," *Endocrinology* 130: 29-36 (1992).

Fukayama et al., "Mechanisms of Desensitization to Parathyroid Hormone in Human Osteoblast-Like SaOS-2 Cells," *Endocrinology* 131: 1757-1769 (1992).

Fukayama et al., "Role of Protein Kinase-A in Homologous Down-Regulation of Parathyroid Hormone (PTH)/PTH-Related Peptide Receptor Messenger Ribonucleic Acid in Human Osteoblast-Like SaOS-2 Cells," *Endocrinology* 134: 1851-1858 (1994).

Gaich et al., "Amino-Terminal Parathyroid Hormone-Related Protein: Specific Binding and Cytosolic Calcium Responses in Rat Insulinoma Cells," *Endocrinology* 132: 1402-1409 (1993).

Gardella et al., "Expression of Human Parathyroid Hormone-(1-84) in *Escherichia coli* as a Factor X-cleavable Fusion Protein," *J. Biol. Chem.* 265: 15854-15859 (1990).

Gardella et al., "Mutational Analysis of the Receptor-Activating Region of Human Parathyroid Hormone," *J. Biol. Chem.* 266: 13141-13146 (1991).

Gardella et al., "Scanning Mutagenesis of the 23-35 Region of Parathyroid Hormone Reveals Important Determinants of Receptor Binding," in: *Calcium Regulating Hormones and Bone Metabolism: Basic and Clinical Aspects* (eds. D.V. Cohn et al.), vol. 11, pp. 218-222 (Excerpta Medica, Amsterdam, 1992).

Gardella et al., "Analysis of Parathyroid Hormone's Principal Receptor-Binding Region by Site-Directed Mutagenesis and Analog Design," *Endocrinology* 132: 2024-2030 (1993).

Gardella et al., "Determinants of [Arg2]PTH-(1-34) Binding and Signaling in the Transmembrane Region of the Parathyroid Hormone Receptor," *Endocrinology* 135: 1186-1194 (1994).

Gardella et al., "Parathyroid Hormone (PTH)-PTH-Related Peptide Hybrid Peptides Reveal Functional Interactions Between the 1-14 and 15-34 Domains of the Ligand," *J. Biol. Chem.* 270: 6584-6588 (1995).

Gardella et al., "Converting Parathyroid Hormone-Related Peptide (PTHrP) into a Potent PTH-2 Receptor Agonist," *J. Biol. Chem.* 271: 19888-19893 (1996).

Gardella et al., "Transmembrane Residues of the Parathyroid Hormone (PTH)/PTH-Related Peptide Receptor that Specifically Affect Binding and Signaling by Agonist Ligands," *J. Biol. Chem.* 271: 12820-12825 (1996).

Gensure et al., "Multiple Sites of Contact between the Carboxyl-Terminal Binding Domain of PTHrP-(1-36) Analogs and the Amino-Terminal Extracellular Domain of the PTH/PTHrP Receptor Identified by Photoaffinity Cross-Linking," *J. Biol. Chem.* 276: 28650-28658 (2001).

Gensure et al., "Identification of a Contact Site for Residue 19 of Parathyroid Hormone (PTH) and PTH-Related Protein Analogs in Transmembrane Domain Two of the Type 1 PTH Receptor," *Mol Endocrinol.* 17: 2647-2658 (2003).

Gensure et al., "Parathyroid Hormone and Parathyroid Hormone-Related Peptide, and their Receptors," *Biochem. Biophys. Res. Commun.* 328: 666-678 (2005).

Goltzman et al., "Influence of Guanyl Nucleotides on Parathyroid Hormone-Stimulated Adenylyl Cyclase Activity in Renal Cortical Membranes," *Endocrinology* 103: 1352-1360 (1978).

Goltzmann et al., "Analysis of the Requirements for Parathyroid Hormone Action in Renal Membranes with the Use of Inhibiting Analogues," *J. Biol. Chem.* 250: 3199-3203 (1975).

Gombert et al., "Alanine and D-Amino Acid Scan of Human Parathyroid Hormone," in: *Peptides: Chemistry, Structure and Biology* (eds. P.T.P. Kaumaya et al.), pp. 661-662 (Mayflower Sci. Ltd., England, 1996).

Goud et al., "Solid-Phase Synthesis and Biologic Activity of Human Parathyroid Hormone (1-84)," *J. Bone Miner. Res.* 6: 781-789 (1991).

Grace et al., "NMR Structure and Peptide Hormone Binding Site of the First Extracellular Domain of a Type B1 G Protein-Coupled Receptor," *Proc. Natl. Acad. Sci. USA* 101: 12836-12841 (2004).

(56) References Cited

OTHER PUBLICATIONS

Greenberg et al., "Mapping the Bimolecular Interface of the Parathyroid Hormone (PTH)-PTH1 Receptor Complex: Spatial Proximity between Lys(27) (of the Hormone Principal Binding Domain) and Leu(261) (of the First Extracellular Loop) of the Human PTH1 Receptor," *Biochemistry* 39: 8142-8152 (2000).
Gronwald et al., "Structure of Recombinant Human Parathyroid Hormone Solution Using Multidimensional NMR Spectroscopy," *Biol. Chem. Hoppe-Seyler* 377: 175-186 (1996).
Guo et al., "Parathyroid Hormone (PTH)/PTH-Related Peptide Receptor Density Modulates Activation of Phospholipase C and Phosphate Transport by PTH in LLC-PK1 Cells," *Endocrinology* 136: 3884-3891 (1995).
Habashita et al., "Synthesis and Biological Activities of hPTH(1-34) Analogues: Modification of the Middle Part and C-terminal Alkylamides," in: *Peptide Science—Present and Future: Proceedings of the 1st International Peptide Symposium* (ed. Y. Shimonishi), pp. 711-713 (Kluwer Acad. Pub., Great Britain, 1997).
Hammer et al., "Genetic Engineering of Mammalian Embryos," *J. Anim. Sci.* 63: 269-278 (1986).
Heinrich et al., "Gene Encoding Parathyroid Hormone. Nucleotide Sequence of the Rat Gene and Deduced Amino Acid Sequence of Rat Preproparathyroid Hormone," *J. Biol. Chem.* 259: 3320-3329 (1984).
Heinrich et al., "Rat Parathyroid Hormone Gene, Exons II and III," Alignment result 8, SEQ ID No. 1, Database: GenEmbl, Accession No. K01268 (Apr. 27, 1993).
Hilliker et al., "Truncation of the Amino Terminus of PTH Alters Its Anabolic Activity on Bone In Vivo," *Bone* 19: 469-477 (1996).
Hjorth et al., "Constitutive Activity of Glucagon Receptor Mutants," *Mol. Endocrinol.* 12: 78-86 (1998).
Hoare et al., "Measurement of Agonist and Antagonist Ligand-Binding Parameters at the Human Parathyroid Hormone Type 1 Receptor: Evaluation of Receptor States and Modulation by Guanine Nucleotide," *J. Pharmacal. Exp. Ther.* 289: 1323-1333 (1999).
Hoare et al., "Evaluating the Signal Transduction Mechanism of the Parathyroid Hormone 1 Receptor," *J. Biol. Chem.* 276: 7741-7753 (2001).
Holtmann et al., "Critical Contributions of Amino-terminal Extracellular Domains in Agonist Binding and Activation of Secretin and Vasoactive Intestinal Polypeptide Receptors. Studies of Chimeric Receptors," *J. Biol. Chem.* 270: 14394-14398 (1995).
Holtmann et al., "Molecular Basis and Species Specificity of High Affinity Binding of Vasoactive Intestinal Polypeptide by the Rat Secretin Receptor. Effect of Receptor-G-Protein Interaction on the Ligand Binding Mechanism and Receptor Conformation," *J. Pharmacol. Exp. Ther.* 279: 555-560 (1996).
Horiuchi et al., "A Parathyroid Hormone Inhibitor In Vivo: Design and Biological Evaluation of a Hormone Analog," *Science* 220: 1053-1055 (1983).
Horiuchi et al., "Evaluation of a Parathyroid Hormone Antagonist in an In Vivo Multiparameter Bioassay," *Am. J. Physiol.* 253: E187-192 (1987).
Hruska et al., "Stimulation of Inositol Trisphosphate and Diacylglycerol Production in Renal Tubular Cells by Parathyroid Hormone," *J. Clin. Invest.* 79: 230-239 (1987).
Iida-Klein et al., "Truncation of the Carboxyl-terminal Region of the Rat Parathyroid Hormone (PTH)/PTH-Related Peptide Receptor Enhances PTH Stimulation of Adenylyl Cyclase but Not Phospholipase C," *J. Biol. Chem.* 270: 8458-8465 (1995).
Iida-Klein et al., "Structural Requirements of Parathyroid Hormone/Parathyroid Hormone-Related Peptide Receptors for Phospholipase C Activation and Regulation of Phosphate Uptake," *Miner. Electrolyte Metab.* 21: 177-179 (1995).
Iida-Klein et al., "Mutations in the Second Cytoplasmic Loop of the Rat Parathyroid Hormone (PTH)/PTH-Related Protein Receptor Result in Selective Loss of PTH-stimulated Phospholipase C Activity," *J. Biol. Chem.* 272: 6882-6889 (1997).
Inomata et al., "Characterization of a Novel Parathyroid Hormone (PTH) Receptor with Specificity for the Carboxyl-Terminal Region of PTH-(1-84)," *Endocrinology* 136: 4732-4740 (1995).

Ishihara et al., "Molecular Cloning and Expression of a cDNA Encoding the Secretin Receptor," *EMBO J.* 10: 1635-1641 (1991).
Iwakura et al., "Effects of the Length of a Glycine Linker Connecting the N-and C-Termini of a Circularly Permuted Dihydrofolate Reductase," *Protein Eng.* 11: 707-713 (1998).
Jans et al., "LLC-PK1 Cell Mutants in cAMP Metabolism Respond Normally to Phorbol Esters," *FEBS Lett.* 205: 127-131 (1986).
Janulis et al., "Structure-Function Requirements of Parathyroid Hormone for Stimulation of 1,25-Dihydroxyvitamin D3 Production by Rat Renal Proximal Tubules," *Endocrinology* 133: 713-719 (1993).
Ji et al., "Human Choriogonadotropin Binds to a Lutropin Receptor with Essentially No N-terminal Extension and Stimulates cAMP Synthesis," J. Biol. Chem. 266: 13076-13079 (1991).
Jin et al., "Crystal Structure of Human Parathyroid Hormone 1-34 at 0.9-A Resolution," *J. Biol. Chem.* 275: 27238-27244 (2000).
Jing et al., "GDNF-Induced Activation of the Ret Protein Tyrosine Kinase Is Mediated by GDNFR-alpha, a Novel Receptor for GDNF," *Cell* 85: 1113-1124 (1996).
Jobert et al., "Parathyroid Hormone-Induced Calcium Release from Intracellular Stores in a Human Kidney Cell Line in the Absence of Stimulation of Cyclic Adenosine 3',5'-Monophosphate Production," Endocrinology 138: 5282-5292 (1997).
Jouishomme et al., "The Protein Kinase-C Activation Domain of the Parathyroid Hormone," *Endocrinology* 130: 53-60 (1992).
Jouishomme et al., "Further Definition of the Protein Kinase C Activation Domain of the Parathyroid Hormone," *J. Bone Miner. Res.* 9: 943-949 (1994).
Joun et al., "Tissue-specific Transcription Start Sites and Alternative Splicing of the Parathyroid Hormone (PTH)/PTH-related Peptide (PTHrP) Receptor Gene: A New PTH/PTHrP Receptor Splice Variant that Lacks the Signal Peptide," *Endocrinology* 138: 1742-1749 (1997).
Jüppner et al., "The Parathyroid Hormone-Like Peptide Associated with Humoral Hypercalcemia of Malignancy and Parathyroid Hormone Bind to the Same Receptor on the Plasma Membrane of ROS 17/2.8 Cells," *J. Biol. Chem.* 263: 8557-8560 (1988).
Jüppner et al., "Properties of Amino-Terminal Parathyroid Hormone-Related Peptides Modified at Positions 11-13," *Peptides* 11: 1139-1142 (1990).
Jüppner et al., "A G Protein-linked Receptor for Parathyroid Hormone and Parathyroid Hormone-Related Peptide," *Science* 254: 1024-1026 (1991).
Jüppner et al., "The Extracellular Amino-Terminal Region of the Parathyroid Hormone (PTH)/PTH-related Peptide Receptor Determines the Binding Affinity for Carboxyl-Terminal Fragments of PTH-(1-34)," *Endocrinology* 134: 879-884 (1994).
Kappel et al., "Regulating Gene Expression in Transgenic Animals," *Curr. Op. Biotechnol.* 3: 548-553 (1992).
Karaplis et al., "Lethal Skeletal Dysplasia From Targeted Disruption of the Parathyroid Hormone-Related Peptide Gene," *Genes Dev.* 8: 277-289 (1994).
Kaufman et al., "Transgenic Analysis of a 100-kb Human Beta-Globin Cluster-Containing DNA Fragment Propagated as a Bacterial Artificial Chromosome," *Blood* 94: 3178-3184 (1999).
Kaufmann et al., "Functional Expression of a Stably Transfected Parathyroid Hormone/Parathyroid Hormone Related Protein Receptor Complementary DNA in CHO cells," *Mol. Cell. Endocrinol.* 104: 21-27 (1994).
Kaul et al., "Stereochemical Control of Peptide Folding," *Bioorg. Med. Chem.* 7: 105-117 (1999).
Kemp et al., "Parathyroid Hormone-Related Protein of Malignancy: Active Synthetic Fragments," *Science* 238: 1568-1570 (1987).
Kimura et al., "Strategy for the Synthesis of Large Peptides: An Application to the Total Synthesis of Human Parathyroid Hormone [hPTH)1-84)]," *Biopolymers* 20: 1823-1832 (1981).
Kimura et al., "Discovery of a Novel Thrombopoietin Mimic Agonist Peptide," *J. Biochem.* 122: 1046-1051 (1997).
Klaus et al., "Investigation of the Solution Structure of the Human Parathyroid Hormone Fragment (1-34) by 1H NMR Spectroscopy, Distance Geometry, and Molecular Dynamics Calculations," *Biochemistry* 30: 6936-6942 (1991).
Kolakowski, "GCRDb: A G-Protein-Coupled Receptor Database," *Receptors and Channels* 2: 1-7 (1994).

(56) References Cited

OTHER PUBLICATIONS

Kong et al., "The Rat, Mouse and Human Genes Encoding the Receptor for Parathyroid Hormone and Parathyroid Hormone-Related Peptide are Highly Homologous," *Biochem. Biophys. Res. Commun.* 200: 1290-1299 (1994).
Kovacs et al., "Parathyroid Hormone-Related Peptide (PTHrP) Regulates Fetal-placental Calcium Transport Through a Receptor Distinct from the PTH/PTHrP Receptor," *Proc. Natl. Acad. Sci. USA* 93: 15233-15238 (1996).
Kronenberg et al., "Parathyroid Hormone: Biosynthesis, Secretion, Chemistry, and Action," in: *Handbook of Experimental Pharmacology* (eds. G.R. Mundy et al.), pp. 507-567 (Springer-Verlag, Heidelberg, Germany, 1993).
Kronenberg et al., "The PTH/PTHrP Receptor: One Receptor for Two Ligands," in: *Molecular Genetics of Endocrine Disorders* (ed. R.V. Thakker), pp. 389-420 (Chapman & Hall, New York, NY, 1997).
Lanske et al., "PTH/PTHrP Receptor in Early Development and Indian Hedgehog-Regulated Bone Growth," *Science* 273: 663-666 (1996).
Lee et al., "Role of the Extracellular Regions of the Parathyroid Hormone (PTH)/PTH-Related Peptide Receptor in Hormone Binding," *Endocrinology* 135: 1488-1495 (1994).
Lee et al., "Homolog-scanning Mutagenesis of the Parathyroid Hormone (PTH) Receptor Reveals PTH-(1-34) Binding Determinants in the Third Extracellular Loop," *Mol. Endocrinol.* 9: 1269-1278 (1995).
Li et al., "Minimization of a Polypeptide Hormone," *Science* 270: 1657-1660 (1995).
Lin et al., "Expression Cloning of an Adenylate Cyclase-Coupled Calcitonin Receptor," *Science* 254: 1022-1024 (1991).
Livnah et al., "Functional Mimicry of a Protein Hormone by a Peptide Agonist: The EPO Receptor Complex at 2.8 A," *Science* 273: 464-471 (1996).
Luck et al., "The (1-14) Fragment of Parathyroid Hormone (PTH) Activates Intact and Amino-terminally Truncated PTH-1 Receptors," *Mol. Endocrinol.* 13: 670-680 (1999).
Majeska et al., "Parathyroid Hormone-Responsive Clonal Cell Lines from Rat Osteosarcoma," *Endocrinology* 107: 1494-1503 (1980).
Mannstadt et al., "Evidence for a Ligand Interaction Site at the Amino-terminus of the Parathyroid Hormone (PTH)/PTH-related Protein Receptor from Cross-Linking and Mutational Studies," *J. Biol. Chem.* 273: 16890-16896 (1998).
Marx et al., "Structure of Human Parathyroid Hormone 1-37 in Solution," *J. Biol. Chem.*, 270: 15194-15202 (1995).
Marx et al., "Structure-Activity Relation of NH2-terminal Human Parathyroid Hormone Fragments," *J. Biol. Chem.* 273: 4308-4316 (1998).
Marx et al., "Solution Structures of Human Parathyroid Hormone Fragments hPTH(1-34) and hPTH (1-3 9) and Bovine Parathyroid Hormone Fragment bPTH(1-37)," *Biochem. Biophys. Res. Commun.* 267: 213-220 (2000).
Matsumoto et al., "Daily Nasal Spray of hPTH(1-34) for 3 Months Increases Bone Mass in Osteoporotic Subjects: A Pilot Study," *Osteoporos. Int.* 17: 1532-1538 (2006).
McCuaig et al., "Molecular Cloning of the Gene Encoding the Mouse Parathyroid Hormone/Parathyroid Hormone-Related Peptide Receptor," *Proc. Natl. Acad. Sci. USA* 91: 5051-5055 (1994).
Menniti et al., "Different Modes of Regulation for Receptors Activating Phospholipase C in the Rat Pancreatoma Cell Line AR4-2J," *Mol. Pharmacol.* 40: 727-733 (1991).
Mickle et al., "Genotype-Phenotype Relationships in Cystic Fibrosis," *Med. Clin. North Am.* 84: 597-607 (2000).
Mikayama et al., "Molecular Cloning and Functional Expression of a cDNA Encoding Glycosylation-Inhibiting Factor," *Proc. Natl. Acad. Sci USA* 90: 10056-10060 (1993).
Mitchell et al., "Mechanisms of Homologous and Heterologous Regulation of Parathyroid Hormone Receptors in the Rat Osteosarcoma Cell Line UMR-106," *Endocrinology* 126: 2650-2660 (1990).
Moretto et al., "(αMe)Nva: Stereoselective Syntheses and Preferred Conformations of Selected Model Peptides," *J. Pept. Res.* 56: 283-297 (2000).
Mullins et al., "Perspective Series: Molecular Medicine in Genetically Engineered Animals," *J. Clin. Invest.* 98: S37-S40 (1996).
Murray et al., "Dexamethasone-Treated ROS 17/2.8 Rat Osteosarcoma Cells are Responsive to Human Carboxylterminal Parathyroid Hormone Peptide hPTH (53-84): Stimulation of Alkaline Phosphatase," *Calcif. Tissue Int.* 49: 120-123 (1991).
Musso et al. "Renal Vasodilatation and Microvessel Adenylate Cyclase Stimulation by Synthetic Parathyroid Hormone-Like Protein Fragments," *Eur. J. Pharmacol.* 174: 139-151 (1989).
Nakamoto et al., "Probing the Bimolecular Interactions of Parathyroid Hormone with the Human Parathyroid Hormone/Parathyroid Hormone-Related Protein Receptor. 1. Design, Synthesis and Characterization of Photoreactive Benzophenone-Containing Analogs of Parathyroid Hormone," *Biochemistry* 34: 10546-10552 (1995).
Nakamura et al., "Action of Fragments of Human Parathyroid Hormone on Blood Pressure in Rats," *Endocrinol. Jpn.* 28: 547-549 (1981).
Neer et al., "Effect of Parathyroid Hormone (1-34) on Fractures and Bone Mineral Density in Postmenopausal Women with Osteoporosis," *N. Engl. J. Med.* 344: 1434-1441 (2001).
Neugebauer et al., "Structural Elements of Human Parathyroid Hormone and their Possible Relation to Biological Activities," *Biochemistry* 31: 2056-2063 (1992).
Neugebauer et al., "Solution Structure and Adenylyl Cyclase Stimulating Activities of C-terminal Truncated Human Parathyroid Hormone Analogues," *Biochemistry* 34: 8835-8842 (1995).
Ngo et al., "Chapter 14: Computational Complexity, Protein Structure Prediction, and the Levinthal Paradox," in: *The Protein Folding Problem and Tertiary Structure Prediction* (eds. K.M. Merz et al.), pp. 492-495 (Birkhäuser Verlag, Boston, MA, 1994).
Nielsen et al., "Identification of Prokaryotic and Eukaryotic Signal Peptides and Prediction of their Cleavage Sites," *Prot. Eng.* 10: 1-6 (1997).
Nissenson et al., "Synthetic Peptides Comprising the Amino-Terminal Sequence of a Parathyroid Hormone-Like Protein from Human Malignancies. Binding to Parathyroid Hormone Receptors and Activation of Adenylate Cyclase in Bone Cells and Kidney," *J. Biol. Chem.* 263: 12866-12871 (1988).
Nussbaum et al., "Parathyroid Hormone • Renal Receptor Interactions. Demonstration of Two Receptor-binding Domains," *J. Biol. Chem.* 255: 10183-10187 (1980).
Nutt et al., "Removal of Partial Agonism from Parathyroid Hormone (PTH)-Related Protein-(7-34)NH2 by Substitution of PTH Amino Acids at Positions 10 and 11," *Endocrinology* 127: 491-493 (1990).
Oldenburg et al., "Conformational Studies on Analogs of Recombinant Parathyroid Hormone and their Interactions with Phospholipids," *J. Biol. Chem.* 271: 17582-17591 (1996).
Orkin et al., "Report and Recommendations of the Panel to Assess the NIH Investment in Research on Gene Therapy," available online at http://www.nih.gov/news/panelrep.html, pp. 1-39 (1995).
Orloff et al., "Analysis of PTHRP Binding and Signal Transduction Mechanisms in Benign and Malignant Squamous Cells," *Am. J. Physiol.* 262: E599-E607 (1992).
Orloff et al., "Further Evidence for a Novel Receptor for Amino-Terminal Parathyroid Hormone-Related Protein on Keratinocytes and Squamous Carcinoma Cell Lines," *Endocrinology* 136: 3016-3023 (1995).
Orloff et al., "A Midregion Parathyroid Hormone-Related Peptide Mobilizes Cytosolic Calcium and Stimulates Formation of Inositol Trisphosphate in a Squamous Carcinoma Cell Line," *Endocrinology* 137: 5376-5385 (1996).
Pang et al., "Purification of Unique alpha Subunits of GTP-Binding Regulatory Proteins (G Proteins) by Affinity Chromatography with Immobilized beta gamma Subunits," *J. Biol. Chem.* 265: 18707-18712 (1990).

(56) References Cited

OTHER PUBLICATIONS

Parsons et al., "Pharmacology of Parathyroid Hormone and Some of its Fragments and Analogues," in: *Calcium-regulating hormones. Proceedings of the Fifth Parathyroid Conference*, Oxford, United Kingdom, Jul. 21-26, 1974 (eds. R.V. Talmage et al.), pp. 33-39 (Am. Elsevier Pub. Co., New York, NY, 1975).
Peggion et al., "Structure-Function Studies of Analogues of Parathyroid Hormone (PTH)-1-34 Containing Beta-Amino Acid Residues in Positions 11-13," *Biochemistry* 41: 8162-8175 (2002).
Pellegrini et al., "Binding Domain of Human Parathyroid Hormone Receptor: From Conformation to Function," *Biochemistry* 37: 12737-12743 (1998).
Pellegrini et al., "Addressing the Tertiary Structure of Human Parathyroid Hormone-(1-34)," *J. Biol. Chem.* 273: 10420-10427 (1998).
Pettit et al., "The Development of Site-Specific Drug-Delivery Systems for Protein and Peptide Biopharmaceuticals," *Trends Biotechnol.* 16: 343-349 (1998).
Phillips, "The Challenge of Gene Therapy and DNA Delivery," *J. Pharm. Pharmacol.* 53: 1169-1174 (2001).
Pines et al., "Generation and Characterization of Human Kidney Cell Lines Stably Expressing Recombinant Human PTH/PTHrP Receptor: Lack of Interaction with a C-Terminal Human PTH Peptide," *Endocrinology* 135: 1713-1716 (1994).
Pines et al., "Inositol 1-,4-,5-Trisphosphate-Dependent Ca2+ Signaling by the Recombinant Human PTH/PTHrP Receptor Stably Expressed in a Human Kidney Cell Line," *Bone* 18: 381-389 (1996).
Plotkin et al., "Dissociation of Bone Formation from Resorption during 2-week Treatment with Human Parathyroid Hormone-Related Peptide-(1-36) in Humans: Potential as an Anabolic Therapy for Osteoporosis," *J. Clin. Endocrinol. Metab.* 83: 2786-2791 (1998).
Potts et al., "Structure Based Design of Parathyroid Hormone Analogs," *J. Endocrinol.* 154 Suppl: S15-S21 (1997).
Potts et al., "Parathyroid Hormone and Parathyroid Hormone-Related Peptide in Calcium Homeostasis, Bone Metabolism, and Bone Development: The Proteins, Their Genes, and Receptors," in: *Metabolic Bone Disease, 3rd Edition* (eds. L.V. Avioli et al.), pp. 51-94 (Acad. Press, San Diego, CA, 1998).
Ray et al., "NMR Solution Structure of the [Ala26]Parathyroid-Hormone-Related Protein(1-34) Expressed in Humoral Hypercalcemia of Malignancy," *Eur. J. Biochem.* 211: 205-211 (1993).
Reid et al., "Parathyroid Hormone Acutely Elevates Intracellular Calcium in Osteoblastlike Cells," *Am. J. Physiol.* 253: E45-E51 (1987).
Reidhaar-Olson et al., "Active Variants of Human Parathyroid Hormone (1-34) with Multiple Amino Acid Substitutions," *Mol. Cell. Endocrinol.* 160: 135-147 (2000).
Rixon et al., "Parathyroid Hormone Fragments May Stimulate Bone Growth in Ovariectomized Rats by Activating Adenylyl Cyclase," *J. Bone Miner. Res.* 9: 1179-1189 (1994).
Roe et al., "Parathyroid Hormone 1-34 (hPTH 1-34) and Estrogen Produce Dramatic Bone Density Increases in Postmenopausal Osteoporosis. Results from a Placebo-Controlled Randomized Trial," *J. Bone Miner. Res.* 14: S137, Abstract No. 1019 (1999).
Rölz et al., "Characterization of the Molecular Motions of Constitutively Active G Protein-Coupled Receptors for Parathyroid Hormone," *Biophys. Chem.* 89: 119-128 (2001).
Romano et al., "Latest Developments in Gene Transfer Technology: Achievements, Perspectives, and Controversies over Therapeutic Applications," *Stem Cells* 18: 19-39 (2000).
Rosenblatt et al., "Design and Synthesis of Parathyroid Hormone Analogues of Enhanced Biological Activity," *Endocr. Res. Commun.* 4: 115-133 (1977).
Rosenblatt et al., "Identification of a Receptor-binding Region in Parathyroid Hormone," *Endocrinology* 107: 545-550 (1980).
Rosenblatt, "Parathyroid Hormone: Chemistry and Structure-Activity Relations," *Pathobiol. Annu.* 11: 53-86 (1981).
Rosol et al., "Sequences of the cDNAs Encoding Canine Parathyroid Hormone-Related Protein and Parathyroid Hormone," *Gene* 160: 241-243 (1995).
Rubin et al., "Molecular Cloning and Expression of Receptors for Parathyroid Hormone (PTH) and PTH-Related (PTHrP) Protein in Zebrafish," *Am. Zoologist* 36: 97A, Abstract No. 373 (1996).
Rubin et al., "Parathyroid Hormone (PTH)/PTH-Related (PTHRP) Receptor Cloning and in Situ Hybridization in the Zebrafish, Danio Rerio," *Am. Zoologist* 37: 181A, Abstract No. 651 (1997).
Rubin et al., "Molecular Cloning of a Zebrafish cDNA Encoding a Novel Parathyroid Hormone (PTH)/PTH-Related Protein (PTHrP) Receptor (PPR)," *Bone* 23: S255, Abstract No. T224 (1998).
Rubin et al., "Zebrafish Express the Common Parathyroid Hormone/Parathyroid Hormone-Related Peptide Receptor (PTH1R) and a Novel Receptor (PTH3R) that is Preferentially Activated by Mammalian and Fugufish Parathyroid Hormone-Related Peptide," *J. Biol. Chem.* 274: 28185-28190 (1999).
Sacchetti et al., "Green Fluorescent Protein Variants Fold Differentially in Prokaryotic and Eukaryotic Cells," *J. Cell. Biochem. Suppl.* 36: 117-128 (2001).
Sargent et al., "Membrane Lipid Phase as Catalyst for Peptide-Receptor Interactions," *Proc. Natl. Acad. Sci. USA* 83: 5774-5778 (1986).
Schipani et al., "Identical Complementary Deoxyribonucleic Acids Encode a Human Renal and Bone Parathyroid Hormone (PTH)/PTH-Related Peptide Receptor," *Endocrinology* 132: 2157-2165 (1993).
Schipani et al., "Pseudohypoparathyroidism Type Ib is not Caused by Mutations in the Coding Exons of the Human Parathyroid Hormone (PTH)/PTH-Related Peptide Receptor Gene," *J. Clin. Endocrinol. Metab.* 80: 1611-1621 (1995).
Schipani et al., "A Constitutively Active Mutant PTH-PTHrP Receptor in Jansen-Type Metaphyseal Chondrodysplasia," *Science* 268: 98-100 (1995).
Schneider et al., "Cloning and Functional Expression of a Human Parathyroid Hormone Receptor," *Eur. J. Pharmacol.* 246: 149-155 (1993).
Schneider et al., "A C-Terminally Truncated Human Parathyroid Hormone Receptor is Functional and Activates Multiple G Proteins," *FEBS Lett.* 351: 281-285 (1994).
Segre et al., "Characterization of Parathyroid Hormone Receptors in Canine Renal Cortical Plasma Membranes Using a Radioiodinated Sulfur-Free Hormone Analogue. Correlation of Binding with Adenylate Cyclase Activity," *J. Biol. Chem.* 254: 6980-6986 (1979).
Segre et al., "Receptors for Secretin, Calcitonin, Parathyroid Hormone (PTH)/PTH-Related Peptide, Vasoactive Intestinal Peptide, Glucagonlike Peptide 1, Growth Hormone-Releasing Hormone, and Glucagon Belong to a Newly Discovered G-protein-Linked Receptor Family," *Trends Endocrinol. Metab.* 4: 309-314 (1993).
Seuwen et al., "Heparin-Insensitive Calcium Release from Intracellular Stores Triggered by the Recombinant Human Parathyroid Hormone Receptor," *Br. J. Pharmacol.* 114: 1613-1620 (1995).
Shen et al., "Effects of Combined and Separate Intermittent Administration of Low-Dose Human Parathyroid Hormone Fragment (1-34) and 17 Beta-Estradiol on Bone Histomorphometry in Ovariectomized Rats with Established Osteopenia," *Calcif. Tissue Int.* 50: 214-220 (1992).
Shigeno et al., "Parathyroid Hormone Receptors are Plasma Membrane Glycoproteins with Asparagine-Linked Oligosaccharides," *J. Biol. Chem.* 263: 3872-3878 (1988).
Shimada et al., "Purification and Characterization of a Receptor for Human Parathyroid Hormone and Parathyroid Hormone-Related Peptide," *J. Biol. Chem.* 277: 31774-31780 (2002).
Shimizu et al., "Type-Substitution Analysis of the Amino-Terminal Fragment of Parathyroid Hormone, PTH(1-14): An Approach toward New Low Molecular Weight PTH Agonists," *J. Bone Miner. Res.* 14: S289, Abstract No. F398 (1999).
Shimizu et al., "Autoactivation of Type-1 Parathyroid Hormone Receptors Containing a Tethered Ligand," *J. Biol. Chem.* 275: 19456-19460 (2000).
Shimizu et al., "Minimization of Parathyroid Hormone. Novel Amino-Terminal Parathyroid Hormone Fragments with Enhanced Potency in Activating the Type-1 Parathyroid Hormone Receptor," *J. Biol. Chem.* 275: 21836-21843 (2000).

(56) References Cited

OTHER PUBLICATIONS

Shimizu et al., "Enhanced Activity in Parathyroid Hormone-(1-14) and -(1-11): Novel Peptides for Probing Ligand-Receptor Interactions," *Endocrinology* 142: 3068-3074 (2001).
Shimizu et al., "Parathyroid Hormone (PTH)-(1-14) and -(1-11) Analogs Conformationally Constrained by α-Aminoisobutyric Acid Mediate Full Agonist Responses via the Juxtamembrane Region of the PTH-1 Receptor," *J. Biol. Chem.* 276: 49003-49012 (2001).
Shimizu et al., "Residue 19 of the Parathyroid Hormone (PTH) Modulates Ligand Interaction with the Juxtamembrane Region of the PTH-1 Receptor," *Biochemistry* 41: 13224-13233 (2002).
Shimizu et al., "Structurally Varied Conformationally Constrained Amino Acids Substitutions at Positions 1 and 3 of PTH(1-14) Preserve or Enhance P1R Binding Affinity and cAMP-signaling Potency," *J. Bone Miner. Res.* 17: S389, Abstract No. SU426 (2002).
Shimizu et al., "Functional Evidence for an Intramolecular Side Chain Interaction between Residues 6 and 10 of Receptor-Bound Parathyroid Hormone Analogues," *Biochemistry* 42: 2282-2290 (2003).
Shimizu et al., "Amino-Terminal Parathyroid Hormone Fragment Analogs Containing α,α-di-alkyl Amino Acids at Positions 1 and 3," *J. Bone Miner. Res.* 19: 2078-2086 (2004).
Shimizu et al., "Novel Parathyroid Hormone (PTH) Antagonists that Bind to the Juxtamembrane Portion of the PTH/PTH-Related Protein Receptor," *J. Biol. Chem.* 280: 1797-1807 (2005).
Shukunami et al., "Chondrogenic Differentiation of Clonal Mouse Embryonic Cell Line ATDC5 In Vitro: Differentiation-dependent Gene Expression of Parathyroid Hormone (PTH)/PTH-related Peptide Receptor," *J. Cell Biol.* 133: 457-468 (1996).
Siegfried et al., "Parathyroid Hormone Stimulates Ecto-5'-Nucleotidase Activity in Renal Epithelial Cells: Role of Protein Kinase-C," *Endocrinology* 136:1267-1275 (1995).
Simon et al., "Diversity of G Proteins in Signal Transduction," *Science* 252: 802-808 (1991).
Skolnick et al., "From Genes to Protein Structure and Function: Novel Applications of Computational Approaches in the Genomic Era," *Trends Biotechnol.* 18: 34-39 (2000).
Slovik et al., "Restoration of Spinal Bone in Osteoporotic Men by Treatment with Human Parathyroid Hormone (1-34) and 1,25-dihydroxyvitamin D," *J. Bone Miner. Res.* 1: 377-381 (1986).
Smith et al., "The Challenges of Genome Sequence Annotation or "The devil is in the details"," *Nat. Biotechnol.* 15: 1222-1223 (1997).
Strathmann et al., "G Protein Diversity: A Distinct Class of alpha Subunits is Present in Vertebrates and Invertebrates," *Proc. Natl. Acad. Sci. USA* 87: 9113-9117 (1990).
Strojek et al., "The Use of Transgenic Animal Techniques for Livestock Improvement," in: *Genetic Engineering: Principles and Methods*, vol. 10 (eds. J.K. Setlow et al.), pp. 221-246 (Plenum Press, New York, NY, 1988).
Stroop et al., "Chimeric Human Calcitonin and Glucagon Receptors Reveal Two Dissociable Calcitonin Interaction Sites," *Biochemistry* 34: 1050-1057 (1995).
Sunyaev et al., "From Analysis of Protein Structrual Alignments Toward a Novel Approach to Align Protein Sequences," *Proteins* 54: 569-582 (2004).
Suva et al., "A Parathyroid Hormone-Related Protein Implicated in Malignant Hypercalcemia: Cloning and Expression," *Science* 237: 893-896 (1987).
Szabo, "In Situ Hybridization," in: *Human Chromosomes: Manual of Basic Techniques* (eds. R.S. Verma et al.), pp. 152-165 (Pergamon Press, New York, NY,1989).
Takasu et al., "The 69-84 Amino Acid Region of the Parathyroid Hormone Molecule is Essential for the Interaction of the Hormone with the Binding Sites with Carboxyl-terminal Specificity," *Endocrinology* 137: 5537-5543 (1996).
Takasu et al., "Human PTH/PTHrP Receptors and Type-2 PTH Receptors Show Discordant Selectivity for Human PTH Analogs with Amino-Terminal Modifications," *Bone* 23:S255, Abstract No. T223 (1998).
Takasu et al., "Phospholipase C Activation via the Human PTH/PTHrP Receptor Requires an Intact Amino-Terminus of Human PTH," *Bone* 23: S447, Abstract No. F148 (1998).
Takasu et al., "Type-1 Parathyroid Hormone (PTH)/PTH-Related Peptide (PTHrP) Receptors Activate Phospholipase C in Response to Carboxyl-truncated Analogs of PTH(1-34)," *Endocrinology* 139: 4293-4299 (1998).
Takasu et al., "Amino Terminal Modifications of Human Parathyroid Hormone (PTH) Selectively Alter Phospholipase C Signaling via the Type 1 PTH Receptor: Implications for Design for Signal-Specific PTH Ligands," *Biochemistry* 38: 13453-13460 (1999).
Takasu et al., "Dual Signaling and Ligand Selectivity of the Human PTH/PTHrP Receptor," *J. Bone Miner. Res.* 14: 11-20 (1999).
Tamura et al., "Parathyroid Hormone 1-34, but not 3-34 or 7-34, Transiently Translocates Protein Kinase C in Cultured Renal (OK) Cells," *Biochem. Biophys. Res. Commun.* 159: 1352-1358 (1989).
Tan et al., "Peptide Agonist Docking in the N-Terminal Ectodomain of a Class II G Protein-Coupled Receptor, the VPAC1 Receptor. Photoaffinity, NMR, and Molecular Modeling," *J. Biol. Chem.* 281: 12792-12798 (2006).
Treanor et al., "Characterization of a Multicomponent Receptor for GDNF," *Nature* 382: 80-83 (1996).
Tregear et al., "Bovine Parathyroid Hormone: Minimum Chain Length of Synthetic Peptide Required for Biological Activity," *Endocrinology* 93: 1349-1353 (1973).
Tregear et al., "Synthetic Analogues of Residues 1-34 of Human Parathyroid Hormone: Influence of Residue No. 1 on Biological Potency in Vitro," *Endocr. Res. Commun.* 2: 561-570 (1975).
Tsomaia et al., "Cooperative Interaction of Arginine-19 and the N-Terminal Signaling Domain in the Affinity and Potency of Parathyroid Hormone," *Biochemistry* 43: 3459-3470 (2004).
Tsomaia et al., "Toward Parathyroid Hormone Minimization: Conformational Studies of Cyclic PTH(1-14) Analogues," *Biochemistry* 43: 690-699 (2004).
Turner et al., "A Putative Selectivity Filter in the G-Protein-Coupled Receptors for Parathyroid Hormone and Secretin," *J. Biol. Chem.* 271: 9205-9208 (1996).
Turner et al., "Single Mutations Allow the PTH2 Receptor to Respond to PTHrP," *J. Bone Miner. Res.* 12: S133, Abstract No. 121 (1997).
Turner et al., "Transmembrane Residues Together with the Amino Terminus Limit the Response of the Parathyroid Hormone (PTH) 2 Receptor to PTH-Related Peptide," *J. Biol. Chem.* 273: 3830-3837 (1998).
Ullrich et al., "Signal Transduction by Receptors with Tyrosine Kinase Activity," *Cell* 61: 203-212 (1990).
Unson et al., "Characterization of Deletion and Truncation Mutants of the Rat Glucagon Receptor. Seven Transmembrane Segments are Necessary for Receptor Transport to the Plasma Membrane and Glucagon Binding," *J. Biol. Chem.* 270: 27720-27727 (1995).
Ureña et al., "Regulation of Parathyroid Hormone (PTH)/PTH-Related Peptide Receptor Messenger Ribonucleic Acid by Glucocorticoids and PTH in ROS 17/2.8 and OK Cells," *Endocrinology* 134: 451-456 (1994).
Usdin et al., "Identification and Functional Expression of a Receptor Selectively Recognizing Parathyroid Hormone, the PTH2 Receptor," *J. Biol. Chem.* 270: 15455-15458 (1995).
Verma et al. "Gene Therapy- Promises, Problems and Prospects," *Nature* 389: 239-242 (1997).
Voet et al., "3. Chemical Evolution," in: *Biochemistry* (eds. D. Voet et al.), pp. 126-128 and 228-234 (Wiley, New York, NY, 1990).
Vogt et al., "An Assessment of Amino Acid Exchange Matrices in Aligning Protein Sequences: The Twilight Zone Revisited," *J. Mol. Biol.* 249: 816-831 (1995).
Wall, "Transgenic Livestock: Progress and Prospects for the Future," *Theriogenology* 45: 57-68 (1996).
Wang et al., "Rapid Analysis of Gene Expression (RAGE) Facilitates Universal Expression Profiling," *Nucleic Acids Res.* 27: 4609-4618 (1999).
Wells, "Additivity of Mutational Effects in Proteins," *Biochemistry* 29: 8509-8517 (1990).
Wells, "Hormone Mimicry," *Science* 273: 449-450 (1996).

(56) References Cited

OTHER PUBLICATIONS

Whitfield et al., "Restoration of Severely Depleted Femoral Trabecular Bone in Ovariectomized Rats by Parathyroid Hormone-(1-34)," *Calcif. Tissue Int.* 56: 227-231 (1995).
Whitfield et al., "Small Bone-Building Fragments of Parathyroid Hormone: New Therapeutic Agents for Osteoporosis," *Trends Pharmacol. Sci.* 16: 382-386 (1995).
Whitfield et al., "Stimulation of the Growth of Femoral Trabecular Bone in Ovariectomized Rats by the Novel Parathyroid Hormone Fragment, hPTH-(1-31)NH2 (Ostabolin)," *Calcif. Tissue Int.* 58: 81-87 (1996).
Whitfield et al., "Comparison of the Ability of Recombinant Human Parathyroid Hormone, rhPTH-(1-84), and hPTH-(1-31)NH2 to Stimulate Femoral Trabecular Bone Growth in Ovariectomized Rats," *Calcif. Tissue Int.* 60: 26-29 (1997).
Wigley et al., "Site-Specific Transgene Insertion: An Approach," *Reprod. Fertil. Dev.* 6: 585-588 (1994).
Wittelsberger et al., "The Mid-Region of Parathyroid Hormone (1-34) Serves as a Functional Docking Domain in Receptor Activation," *Biochemistry* 45: 2027-2034 (2006).
Wrighton et al., "Small Peptides as Potent Mimetics of the Protein Hormone Erythropoietin," *Science* 273: 458-463 (1996).
Wu et al., "Structural and Physiologic Characterization of the Mid-region Secretory Species of Parathyroid Hormone-Related Protein," *J. Biol. Chem.* 271: 24371-24381 (1996).
Yamaguchi et al., "Parathyroid Hormone-Activated Calcium Channels in an Osteoblast-Like Clonal Osteosarcoma Cell Line: cAMP-Dependent and cAMP-Independent Calcium Channels," *J. Biol. Chem.* 262: 7711-7718 (1987).
Yamamoto et al., "Characterization and Agonist-Induced Down-Regulation of Parathyroid Hormone Receptors in Clonal Rat Osteosarcoma Cells," *Endocrinology* 122:1208-1217 (1988).
Yamamoto et al., "Parathyroid Hormone-Related Peptide-(1-34) [PTHrP-(1-34)] Induces Vasopressin Release from the Rat Supraoptic Nucleus In Vitro Through a Novel Receptor Distinct from a Type I or Type II PTH/PTHrP Receptor," *Endocrinology* 138: 2066-2072 (1997).
Yamamoto et al., "Centrally Administered Parathyroid Hormone (PTH)-Related Protein(1-34) but not PTH(1-34) Stimulates Arginine-Vasopressin Secretion and its Messenger Ribonucleic Acid Expression in Supraoptic Nucleus of the Conscious Rats," *Endocrinology* 139: 383-388 (1998). (Printed with erroneous vol. No. 138).
Yan et al., "Two-Amino Acid Molecular Switch in an Epithelial Morphogen that Regulates Binding to Two Distinct Receptors," *Science* 290: 523-527 (2000).

Zhou et al., "Direct Mapping of an Agonist-Binding Domain within the Parathyroid Hormone/Parathyroid Hormone-Related Protein Receptor by Photoaffinity Crosslinking," *Proc. Natl. Acad. Sci. USA* 94: 3644-3649 (1997).
International Preliminary Report on Patentability for PCT/US08/009288 (issued Feb. 2, 2010).
International Search Report for PCT/US08/009288 (mailed Mar. 11, 2009).
Written Opinion for PCT/US08/009288 (mailed Mar. 11, 2009).
Gensure et al., "Identification of Determinants of Inverse Agonism in a Constitutively Active Parathyroid Hormone/Parathyroid Hormone-Related Peptide Receptor by Photoaffinity Cross-Linking and Mutational Analysis," *J. Biol. Chem.* 276:42692-42699 (2001).
Belinsky et al., "Ca(2+) and Extracellular Acidification Rate Responses to Parathyroid Hormone Fragments in Rat ROS 17/2 and Human SaOS-2 Cells," *Biochem. Biophys. Res. Commun.* 266: 448-453 (1999).
Bounoutas et al., "Impact of Impaired Receptor Internalization on Calcium Homeostasis in Knock-in Mice Expressing a Phosphorylation-deficient Parathryoid Hormone (PTH)/PTH-related Peptide Receptor," *Endocrinology* 147: 4674-4679 (2006).
Dean et al., "Altered Selectivity of Parathyroid Hormone (PTH) and PTH-related Protein (PTHrP) for Distinct Conformations of the PTH/PTHrP Receptor," *Mol. Endocrinol.* 22: 156-166 (2008).
Hoare et al., "Conformational States of the Corticotropin Releasing Factor 1 (CRF1) Receptor: Detection, and Pharmacological Evaluation by Peptide Ligands," *Peptides* 24: 1881-1897 (2003).
Hollnagel et al., "Domain-specific Gene Activation by Parathyroid Hormone in Osteoblastic ROS17/2.8 Cells," *J. Biol. Chem.* 271: 21870-21877 (1996).
Rhee et al., "In Vitro & In Vivo Effect of Parathyroid Hormone Analogue (1-14) Containing (alpha)-Amino-iso-butyric Acid Residue (Aib)$^{1,3}$," *Yonsei Med. J.* 47: 214-222 (2006).
Yoshiko et al., "Effects of a Synthetic N-terminal Fragment of Stanniocalcin on the Metabolism of Mammalian Bone In Vitro," *Biochim. Biophys. Acta* 1311: 143-149 (1996).
Supplementary European Search Report for European Application No. 08 794 952.5, dated Sep. 29, 2010 (7 pages).
Horwitz et al., "Short-term, high-dose parathyroid hormone-related protein as a skeletal anabolic agent for the treatment of postmenopausal osteoporosis," J Clin Endocrinol Metab. 88(2):569-75 (2003).
Tashjian and Gagel, "Teriparatide [human PTH(1-34)]: 2.5 years of experience on the use and safety of the drug for the treatment of osteoporosis," J Bone Miner Res. 21(3):354-365 (2006).
European Communication issued for 13001965.6 on Sep. 5, 2013.
Notice of Reasons for Rejection and English translation for 2010-519932 issued on Jul. 8, 2013.

*EC50*
*(nM)*
7.39 hPTH(1-28)NH2
0.37 Ala$^{1,12}$,Aib$^3$,Gln$^{10}$,Har$^{11}$,Trp$^{14}$,Arg$^{19}$-hPTH(1-28)NH$_2$
0.31 hPTH(1-34)NH2
0.21 rPTH(1-34)NH2

Binding to the R0 and RG forms of the rat PTHR *in vitro* : PTHrP(1-36) and I5 substitution.

| MGH# | | Binding IC$_{50}$ nM | | n | selectivity ratio (R0:RG) |
|---|---|---|---|---|---|
| | | Ro | RG | | |
| 1207 | hPTHrP(1-36)OH | 20 ± 3 | 0.44 ± 0.07 | | 46 |
| 1208 | I5-hPTHrP(1-36)OH | 2.3 ± 0.3 | 1.02 ± 0.03 | | 2 |

| Binding to the R0 and RG forms of the rat PTHR in vitro : PTH(1-34) and Mc-PTH(1-14)/PTHrP Hybrid. | | | | |
|---|---|---|---|---|
| | Binding IC$_{50}$ nM | | | selectivity |
| MGH# | Ro | RG | n | ratio (R0:RG) |
| 1202 hPTH(1-34)OH | 93 ± 11 | 0.40 ± 0.03 | | 233 |
| 1161 Mc-PTH(1-14)/PTHrP(15-36)OH | 1.3 ± 0.3 | 0.81 ± 0.15 | 3 | 1.6 |

Mc= (coded amino acids only) A1,3,12,Q10,R11,W14,R19

B

C

PTH(1-34), M-PTH34 analogs : 5nmol/kg, PTHrP : 20nmol/kg, iv, n = 6,
MEAN+/-SE ,P * <0.05 vs vehicle Binding to the R0 and RG forms of the rat PTHR  *in vitro*  : McPTH(1-34) and H5/E19 substitutions.

| MGH# | | Binding IC$_{50}$ nM | | | selectivity |
|------|--|----------------------|--|--|-------------|
| | | Ro | RG | n | ratio (R0:RG) |
| 1205 | Mc-hPTH(1-34)OH | 1.9 ± 0.0 | 0.56 ± 0.06 | | 3 |
| 1206 | H5,Mc-hPTH(1-34)OH | 26 ± 2 | 0.32 ± 0.02 | | 81 |
| 1204 | H5,E19,Mc-hPTH(1-34)OH | 1389 ± 138 | 1.41 ± 0.26 | | 984 |

Mc= (coded amino acids only) A1,3,12,Q10,R11,W14,R19

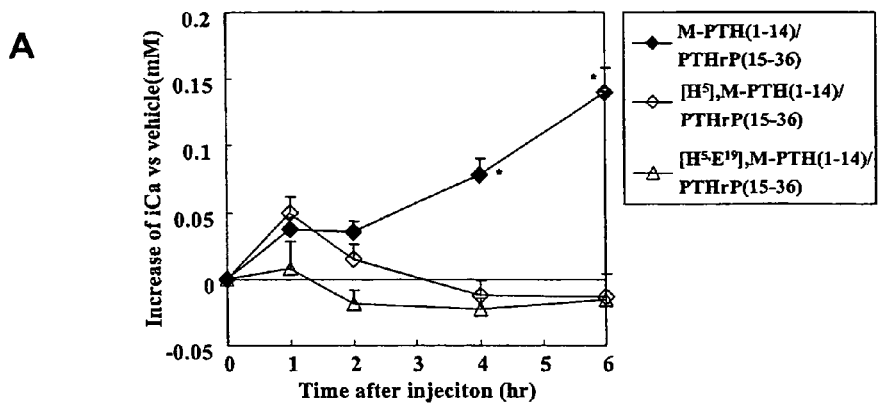
PTH(1-34), M-PTH34 : 5nmol/kg, PTHrP : 20nmol/kg, iv, n = 6,
MEAN+/-SE ,P * <0.05 vs vehicle
Binding to the R0 and RG forms of the rat PTHR  *in vitro* :
Mc-PTH/PTHrP Hybrids and H5/E19 substitutions.
| MGH# | | Binding IC$_{50}$ nM | | n | selectivity |
|---|---|---|---|---|---|
| | | Ro | RG | | ratio (R0:RG) |
| 1161 | Mc-PTH(1-14)/PTHrP(15-36)OH | 1.3 ± 0.3 | 0.81 ± 0.15 | 3 | 1.6 |
| 1212 | H5,Mc-hPTH(1-14)/rP(15-36)OH | 9.0 ± 2.5 | 1.7 ± 0.6 | | 5.3 |
| 1214 | H5,E19,Mc-hPTH(1-14)/rP(15-36)OH | 197 ± 12.2 | 4.8 ± 2.1 | | 41 |
Mc= (coded amino acids only) A1,3,12,Q10,R11,W14,R19
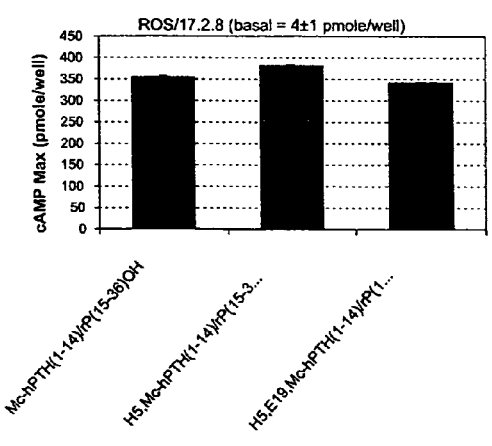
Figures 17A-17C

PTH(1-34), M-PTH34 : 5nmol/kg, PTHrP : 20nmol/kg, iv, n = 6,
MEAN+/-SE ,P * <0.05 vs vehicle Binding to the R0 and RG forms of the rat PTHR *in vitro* :
E19-McPTH(1-34) and Ala23 substitution.

| MGH# | | Binding IC$_{50}$, nM | | selectivity |
|---|---|---|---|---|
| | | R0 | RG | ratio (R0:RG) |
| 1203 | E19,Mc-hPTH(1-34)OH | 2.33 ± 0.19 | 0.57 ± 0.02 | 4.1 |
| 1312 | Ala23,E19-Mc-hPTH(1-34)OH | 20.3 ± 2.5 | 0.49 ± 0.05 | 41 |

Mc= (coded amino acids only) A1,3,12,Q10,R11,W14,R19

A

B

A

B cAMP signaling potency of PTH/PTHrP hybrid analogs on the human PTH receptor in HKRK-B7 cells

| SEQ ID NO: | | cAMP in HRKRK-B7 cells EC50 (nM) |
|---|---|---|
| 5 | hPTH(1-34) | 0.67 |
| 6 | PTHrP(1-36) | 0.55 |
| 134 | PTH(1-14)/PTHrP(15-36) | 1.35 |
| 135 | PTH(1-18)/PTHrP(19-36) | 1.34 |
| 26 | PTH(1-22)/PTHrP(23-36) | 0.89 |
| 136 | PTH(1-26)/PTHrP(27-36) | 1.07 |
| 27 | PTH(1-30)/PTHrP(31-36) | 0.78 |
| 14 | M-PTH(1-11)/PTHrP(12-36) | 0.98 |
| 15 | M-PTH(1-14)/PTHrP(15-36) | 1.25 |
| 139 | M-PTH(1-17)/PTHrP(18-36) | 1.28 |
| 16 | M-PTH(1-18)/PTHrP(19-36) | 0.74 |
| 140 | M-PTH(1-22)/PTHrP(23-36) | 0.66 |
| 141 | M-PTH(1-26)/PTHrP(27-36) | 0.66 |
| 142 | M-PTH(1-30)/PTHrP(31-36) | 0.60 |

Figure 25

Competition analysis of R0 and RG binding of PTH/PTHrP analogs with the human PTH receptor

| MGH # | peptide | SEQ ID NO: | R0 memb: hPTH1R*PTH(1-34)+GTPgS | RG memb: hPTH1R+dnGS*M-PTH(1-15) | R0/RG selectivity | Fold vs hPTH(1-34) | Group |
|---|---|---|---|---|---|---|---|
| 1177 | rPTH(1-34) | 130 | 2.4 ± 0.1 | 0.24 ± 0.00 | 10 | 0.2 | R0 |
| 1202 | hPTH(1-34) | 5 | 8.7 ± 1.2 | 0.13 ± 0.02 | 67 | 1.0 | |
| 1207 | hPTHrP(1-36) | 6 | 37.7 ± 4.7 | 0.14 ± 0.02 | 260 | 3.9 | RG |
| 1208 | I5-hPTHrP(1-36) | 13 | 3.3 ± 0.8 | 0.38 ± 0.04 | 9 | 0.1 | R0 |
| 1203 | E19,Mc-hPTH(1-34) | 21 | 2.5 ± 1.1 | 0.22 ± 0.01 | 11 | 0.2 | R0 |
| 1204 | H5,E19,Mc-hPTH(1-34) | 24 | 67.1 ± 19.5 | 0.34 ± 0.05 | 199 | 3.0 | RG |
| 1205 | Mc-hPTH(1-34) (R19) | 131 | 1.7 ± 0.8 | 0.26 ± 0.03 | 7 | 0.1 | R0 |
| 1206 | H5,M-hPTH(1-34) (R19) | 132 | 3.2 ± 1.4 | 0.09 ± 0.02 | 35 | 0.5 | R0 |
| 1209 | H5-hPTH(1-14)/rP(15-36) | 17 | 5.0 ± 0.6 | 0.75 ± 0.27 | 7 | 0.1 | R0 |
| 1210 | E19-hPTH(1-14)/rP(15-36) | 19 | 7.9 ± 0.4 | 0.98 ± 0.35 | 8 | 0.1 | R0 |
| 1211 | H5,E19-hPTH(1-14)/rP(15-36) | 143 | 12.9 ± 1.3 | 0.57 ± 0.17 | 23 | 0.3 | RG |
| 1212 | H5,Mc-hPTH(1-14)/rP(15-36) | 133 | 20.4 ± 2.7 | 0.53 ± 0.16 | 38 | 0.6 | RG |
| 1213 | E19,Mc-hPTH(1-14)/rP(15-36) | 20 | 11.4 ± 0.6 | 0.84 ± 0.26 | 14 | 0.2 | RG |
| 1214 | H5,E19,Mc-hPTH(1-14)/rP(15-36) | 25 | 321.1 ± 24.0 | 0.65 ± 0.15 | 496 | 7.4 | RG |
| 1155 | PTH(1-11)/PTHrP(12-36) | 137 | 2.8 ± 0.9 | 0.18 ± 0.04 | 16 | 0.2 | R0 |
| 1156 | PTH(1-17)/PTHrP(18-36) | 138 | 4.8 ± 0.8 | 0.23 ± 0.03 | 22 | 0.3 | R0 |
| 1157 | PTH(1-22)/PTHrP(23-36) | 26 | 16.8 ± 2.9 | 0.22 ± 0.12 | 76 | 1.1 | RG |
| 1158 | PTH(1-26)/PTHrP(27-36) | 136 | 7.9 ± 0.8 | 0.31 ± 0.10 | 26 | 0.4 | R0 |
| 1159 | PTH(1-30)/PTHrP(31-36) | 27 | 6.6 ± 1.9 | 0.17 ± 0.04 | 39 | 0.6 | R0 |
| 1160 | Mc-PTH(1-11)/PTHrP(12-36) | 14 | 2.1 ± 0.5 | 0.56 ± 0.09 | 4 | 0.1 | R0 |
| 1161 | Mc-PTH(1-14)/PTHrP(15-36) | 15 | 2.7 ± 1.0 | 0.67 ± 0.05 | 4 | 0.1 | R0 |
| 1162 | Mc-PTH(1-17)/PTHrP(18-36) | 139 | 1.9 ± 0.4 | 0.23 ± 0.02 | 8 | 0.1 | R0 |
| 1163 | Mc-PTH(1-18)/PTHrP(19-36) | 16 | 1.7 ± 0.2 | 0.13 ± 0.02 | 13 | 0.2 | R0 |
| 1164 | E19,Mc-PTH(1-22)/PTHrP(23-36) | 144 | 7.8 ± 2.6 | 0.66 ± 0.02 | 12 | 0.2 | R0 |
| 1165 | E19,Mc-PTH(1-26)/PTHrP(27-36) | 145 | 2.6 ± 0.9 | 0.15 ± 0.04 | 18 | 0.3 | R0 |
| 1166 | E19,Mc-PTH(1-30)/PTHrP(31-36) | 146 | 3.0 ± 0.5 | 0.21 ± 0.03 | 14 | 0.2 | R0 |
| 1311 | A20,E19,Mc-PTH(1-34)OH | 147 | 530.0 ± 81.4 | 0.69 ± 0.15 | 764 | 11.4 | RG |
| 1312 | A23,E19,Mc-PTH(1-34)OH | 28 | 12.5 ± 2.0 | 0.14 ± 0.04 | 87 | 1.3 | RG |
| 1313 | A24,E19,Mc-PTH(1-34)OH | 148 | 64.0 ± 10.4 | 0.23 ± 0.08 | 278 | 4.1 | RG |
| 1314 | A23,M-PTH(1-34)OH | 29 | 4.5 ± 1.4 | 0.21 ± 0.14 | 22 | 0.3 | R0 |
| 1347 | A20-M-PTH(1-34)OH | 149 | 31.9 ± 10.5 | 0.40 ± 0.09 | 80 | 1.2 | RG |
| 1348 | F23-M-PTH(1-34)OH | 150 | 1.2 ± 0.4 | 0.23 ± 0.07 | 5 | 0.1 | R0 |
| 809 | A1,Aib3,M-PTH(1-28)NH2 | 11 | 1.7 ± 0.3 | 0.5 ± 0.07 | 3.4 | 0.1 | R0 |

Mc=A1,3,12,Q10,R11,W14,R19
Cter: OH (free carboxy) unless otherwise noted

Figure 26A

Competition analysis of R0 and RG binding of PTH/PTHrP analogs with the human PTH receptor

| MGH # | peptide | SEQ ID NO: | R0 memb: hPTH1R*PTH(1-34)+GTPgS | RG memb: hPTH1R+dnGS*M-PTH(1-15) | R0/RG selectivity | Fold vs hPTH(1-34) | Group |
|---|---|---|---|---|---|---|---|
| 1348 | F23-M-PTH(1-34)OH | 150 | 1.2 ± 0.4 | 0.23 ± 0.07 | 5 | 0.4 | R0 |
| 1163 | Mc-PTH(1-18)/PTHrP(19-36) | 16 | 1.7 ± 0.2 | 0.13 ± 0.02 | 13 | 1.0 | R0 |
| 809 | A1,Aib3,M-PTH(1-28)NH2 | 11 | 1.7 ± 0.3 | 0.5 ± 0.07 | 3.4 | 0.3 | R0 |
| 1205 | Mc-hPTH(1-34) (R19) | 131 | 1.7 ± 0.8 | 0.26 ± 0.03 | 7 | 0.5 | R0 |
| 1162 | Mc-PTH(1-17)/PTHrP(18-36) | 139 | 1.9 ± 0.4 | 0.23 ± 0.02 | 8 | 0.6 | R0 |
| 1160 | Mc-PTH(1-11)/PTHrP(12-36) | 14 | 2.1 ± 0.5 | 0.56 ± 0.09 | 4 | 0.3 | R0 |
| 1177 | rPTH(1-34) | 130 | 2.4 ± 0.1 | 0.24 ± 0.00 | 10 | 0.8 | R0 |
| 1203 | E19,Mc-hPTH(1-34) | 21 | 2.5 ± 1.1 | 0.22 ± 0.01 | 11 | 0.9 | R0 |
| 1165 | E19,Mc-PTH(1-26)/PTHrP(27-36) | 145 | 2.6 ± 0.9 | 0.15 ± 0.04 | 18 | 1.3 | R0 |
| 1161 | Mc-PTH(1-14)/PTHrP(15-36) | 15 | 2.7 ± 1.0 | 0.67 ± 0.05 | 4 | 0.3 | R0 |
| 1155 | PTH(1-11)/PTHrP(12-36) | 137 | 2.8 ± 0.9 | 0.18 ± 0.04 | 16 | 1.3 | R0 |
| 1166 | E19,Mc-PTH(1-30)/PTHrP(31-36) | 146 | 3.0 ± 0.5 | 0.21 ± 0.03 | 14 | 1.1 | R0 |
| 1206 | H5,M-hPTH(1-34) (R19) | 132 | 3.2 ± 1.4 | 0.09 ± 0.02 | 35 | 2.7 | R0 |
| 1208 | I5-hPTHrP(1-36) | 13 | 3.3 ± 0.8 | 0.38 ± 0.04 | 9 | 0.7 | R0 |
| 1314 | A23,M-PTH(1-34)OH | 29 | 4.5 ± 1.4 | 0.21 ± 0.14 | 22 | 1.7 | R0 |
| 1156 | PTH(1-17)/PTHrP(18-36) | 138 | 4.8 ± 0.8 | 0.23 ± 0.03 | 22 | 1.7 | R0 |
| 1209 | H5-hPTH(1-14)/rP(15-36) | 17 | 5.0 ± 0.6 | 0.75 ± 0.27 | 7 | 0.5 | R0 |
| 1159 | PTH(1-30)/PTHrP(31-36) | 27 | 6.6 ± 1.9 | 0.17 ± 0.04 | 39 | 3.0 | R0 |
| 1164 | E19,Mc-PTH(1-22)/PTHrP(23-36) | 144 | 7.8 ± 2.6 | 0.66 ± 0.02 | 12 | 0.9 | R0 |
| 1210 | E19-hPTH(1-14)/rP(15-36) | 19 | 7.9 ± 0.4 | 0.98 ± 0.35 | 8 | 0.6 | R0 |
| 1158 | PTH(1-26)/PTHrP(27-36) | 136 | 7.9 ± 0.8 | 0.31 ± 0.10 | 26 | 2.0 | R0 |
| 1202 | hPTH(1-34) | 5 | 8.7 ± 1.2 | 0.13 ± 0.02 | 67 | 5.2 | |
| 1213 | E19,Mc-hPTH(1-14)/rP(15-36) | 20 | 11.4 ± 0.6 | 0.84 ± 0.26 | 14 | 1.0 | RG |
| 1312 | A23,E19,Mc-PTH(1-34)OH | 28 | 12.5 ± 2.0 | 0.14 ± 0.04 | 87 | 6.7 | RG |
| 1211 | H5,E19-hPTH(1-14)/rP(15-36) | 143 | 12.9 ± 1.3 | 0.57 ± 0.17 | 23 | 1.7 | RG |
| 1157 | PTH(1-22)/PTHrP(23-36) | 26 | 16.8 ± 2.9 | 0.22 ± 0.12 | 76 | 5.8 | RG |
| 1212 | H5,Mc-hPTH(1-14)/rP(15-36) | 133 | 20.4 ± 2.7 | 0.53 ± 0.16 | 38 | 3.0 | RG |
| 1347 | A20-M-PTH(1-34)OH | 149 | 31.9 ± 10.5 | 0.40 ± 0.09 | 80 | 6.2 | RG |
| 1207 | hPTHrP(1-36) | 6 | 37.7 ± 4.7 | 0.14 ± 0.02 | 260 | 20.1 | RG |
| 1313 | A24,E19,Mc-PTH(1-34)OH | 148 | 64.0 ± 10.4 | 0.23 ± 0.08 | 278 | 21.4 | RG |
| 1204 | H5,E19,Mc-hPTH(1-34) | 24 | 67.1 ± 19.5 | 0.34 ± 0.05 | 199 | 15.3 | RG |
| 1214 | H5,E19,Mc-hPTH(1-14)/rP(15-36) | 25 | 321.1 ± 24.0 | 0.65 ± 0.15 | 496 | 38.2 | RG |
| 1311 | A20,E19,Mc-PTH(1-34)OH | 147 | 530.0 ± 81.4 | 0.69 ± 0.15 | 764 | 58.9 | RG |

Mc=A1,3,12,Q10,R11,W14,R19
Cter: OH (free carboxy) unless otherwise noted

Figure 26B

SCREENING METHODS USING G-PROTEIN COUPLED RECEPTORS AND RELATED COMPOSITIONS

CROSS REFERENCE TO RELATED APPLICATIONS

This application is the national stage of International Application No. PCT/US2008/009288, filed Aug. 1, 2008, which claims the benefit of U.S. Application Nos. 60/963,117, filed Aug. 1, 2007; 60/963,082, filed Aug. 2, 2007; and 60/963,867, filed Aug. 6, 2007, each of which is hereby incorporated by reference.

STATEMENT AS TO FEDERALLY FUNDED RESEARCH

This invention was made with United States Government support under Grant DK 11794 awarded by the National Institute of Health. The Government has certain rights to this invention.

REFERENCE TO A SEQUENCE LISTING

A sequence listing is provided in this patent document as a .txt file entitled "00786.533004 Sequence Listing ST25.txt," created Jun. 21, 2010 (size 91.6 kB). The content of this file is hereby incorporated by reference.

BACKGROUND OF THE INVENTION

In general, the invention relates to a screening method for agonists of G-protein coupled receptors (GPCRs) with prolonged or short-lived activity. More specifically, the invention is related to parathyroid (PTH) hormone or PTH-related protein (PTHrP) ligand analogs that have either more prolonged or shorter-lived activity on the PTH receptor (PTHR) than does PTH(1-34). The invention also relates PTHR ligands identified using the methods of the invention and uses of such ligands in treating disease.

GPCRs are large group of membrane receptors which, in response to activation by an agonist, activate G-proteins which then, in turn, cause activation of at least one signaling cascade, such as the cyclic AMP/protein kinase A cascade. This large groups of receptors is found in organisms ranging from bacteria to man, and are involved in, for example, hormonal, neuronal, and olfactory signal transduction.

The parathyroid hormone receptor (PTHR, SEQ ID NO:1 for human and SEQ ID NO:2 for rat) is the endogenous receptor for both PTH and PTH related protein (PTHrP), yet each ligand has a distinct biological function. PTH regulates calcium and phosphate homeostasis and acts as a gland-secreted endocrine hormone on target cells in bone and kidney. PTH also reduces the reabsorption of inorganic phosphate ($P_i$) largely through its effects on sodium-dependent phosphate transporters ($NaP_i$-IIa and $NaP_i$-IIc) located in renal proximal tubule (PT) cells. PTHrP regulates cell proliferation and differentiation programs in developing tissues, and is secreted and acts in a paracrine fashion within tissue primordia (Kronenberg, H. M. *Ann. N.Y. Acad. Sci.* 1068:1-13 (2006)).

PTH (SEQ ID NO:3) and PTHrP (SEQ ID NO:4) are most homologous in their amino-terminal (residues 1-14) signaling domains (eight amino acid identities), and show moderate homology in their 14-34 binding domains (three identities). It has been generally inferred that the fully active (residues 1-34) portions of PTH and PTHrP interact with the PTHR via largely identical mechanisms (Caulfield et al., *Endocrinology* 127:83-87 (1990); Abou-Samra et al., *Endocrinology* 125:2215-2217 (1989)). This mechanism is thought to consist of two principal components: an interaction between the carboxy-terminal binding domain of the ligand and the amino-terminal extracellular (N) domain of the receptor, and an interaction between the amino-terminal signaling domain of the ligand and the juxtamembrane (J) region of the receptor, which contains the intracellular loops and seven transmembrane helices (Hoare et al., *J. Biol. Chem.* 276:7741-7753 (2001); Castro et al., *Proc. Natl. Acad. Sci. USA* 102:16084-16089 (2005); Witelsberger et al., *Biochemistry* 45:2027-2034 (2006); Shimizu et al., *J. Biol. Chem.* 280:1797-1807 (2005); Gensure et al., *Biochem. Biophys. Res. Commun.* 328:666-678 (2005)). However, the extent, if any, to which the precise mechanisms of binding used by the two ligands differ remains to be determined.

In humans, PTH(1-34) (SEQ ID NO:5) has potent, bone-anabolic effects, and induces marked increases in bone mineral density and bone strength. Indeed, recombinant human PTH(1-34) is now considered to be one of the most effective treatments for osteoporosis (Tashjian and Gagel, *J. Bone Miner. Res* 21:354-365 (2006)). Importantly, hPTH(1-34) must be administered in a pulsatile fashion (e.g., once daily subcutaneous injection) in order for its bone-forming effects to be realized. With more prolonged administrations, as with a sustained infusion pump mechanism, PTH(1-34) exerts a net catabolic effect on bone, due to a greater activation of the bone-resorptive responses mediated by the osteoclasts, relative to the bone-forming responses mediated by the osteoblasts. The duration of exposure of the PTH receptor in bone to a PTH ligand is thus a key determinant of the overall bone-formation response achieved by that ligand, and thus its effectiveness as a treatment for osteoporosis.

Clinical studies have shown that PTHrP(1-36) (SEQ ID NO:6) can also increase bone mineral density in humans, and can do so approximately to the same extent as does PTH(1-34), although higher doses are required (Horwitz et al., *J. Endocrinol. Metab.* 88:569-575 (2003). Importantly, even at such higher doses, PTHrP(1-36) did not stimulate the adverse, bone resorptive and hypercalcemic responses that would be expected for equivalent doses of PTH(1-34) (Horwitz et al., *J. Endocrinol. Metab.* 88:569-575 (2003); Horwitz et al., *J. Bone Miner. Res.* 20:1792-1803 (2005); Horwitz et al., *Osteoporosis Int.* 17:225-230 (2006)). The difference in biological activity of the two peptides is not due merely to a difference in pharamacokinetics. A direct comparison of the two peptides using steady-state infusions methods showed that PTHrP(1-36) is markedly less efficacious than PTH(1-34) for stimulating the renal synthesis of 1,25-$(OH)_2$vitamin D3 (Horwitz et al., *J. Bone. Mineral. Research.* 20:1792-1803 (2005)).

In addition to osteoporosis, hPTH(1-34) (SEQ ID NO:5) has been shown to be effective in treating conditions of PTH deficiency, namely hypoparathyroidism. Thus, PTH(1-34) was shown to be a safe and effective alternative to calcitriol therapy and was able to maintain normal serum calcium levels without hypercalciuria in patients with hypoparathyroidism (Winer et al., *J. Clin. Endocrinol. Metab.* 88:4214-4220 (2003)). The peptide had to be injected at least twice daily, and the authors recognized the need in this disease for a long-acting PTH(1-34) analog (Winer et al., *J. Clin. Endocrinol. Metab.* 88:4214-4220 (2003).

Therefore, there exists a need in the art for PTH or PTHrP analogs that have longer- or shorter-lived actions on the PTH receptor than does PTH(1-34). There also exists a need for assays that allow one to distinguish between PTH peptides that have short-versus long-acting effects.

SUMMARY OF THE INVENTION

According to classical GPCR theory, two forms of a G-protein-coupled receptor can be distinguished: a form (RG) that is bound to a G-protein and a form (R) that is not bound to a G-protein. GPCR signaling requires that the G-protein be directly activated by the receptor, i.e., the RG state must form, and this RG formation can be induced by binding of an agonist ligand. Binding of an agonist ligand induces or stabilizes the RG state, and reciprocally, the RG state stabilizes the high affinity binding of an agonist. Upon binding GTP, or, a non-hydrolyzable GTP analog, such as GTPγS, a receptor-coupled G protein will dissociate from the receptor, causing the receptor to revert to a low affinity state. It is now recognized that some GPCRs, like the PTHR, can form a novel state ($R^0$) that can bind certain agonist ligands with high affinity even in the presence of GTPγS, and hence, even when the receptor is presumably not bound by a G protein. In general, the proportions of a GPCR in a cell that are in the, RG, R, or $R^0$ state may vary, depending on cell type and conditions. For these reasons, prior work on assessing the binding of ligands to a GPCR generally did not clearly distinguish between the RG, R, or $R^0$ states. The present inventors, studying the PTH receptor, an exemplary GPCR, have discovered that ligands which bind with high affinity to the $R^0$ state, in addition to the RG state, have a longer activity half-life than ligands that bind to $R^0$ with lower affinity, and that this prolonged activity does not depend on the bioavailability or the pharmacokinetics of the ligand in vivo. Correspondingly, agonists with a short duration of action have a lower affinity for the $R^0$ form of the receptor. Based on this discovery, the invention provides methods for identification of either long-acting or short-acting GPCR agonists, and peptide agonists identified using the methods of the invention.

In a first aspect, the invention provides a method for determining whether a candidate compound is a long-acting agonist of a G protein coupled receptor (GPCR). The method includes (a) contacting the GPCR with the compound, where the GPCR is in the RG form, (b) measuring the affinity of the compound for the RG form of the GPCR, (c) contacting the GPCR with the compound, where the GPCR is in the $R^0$ form, and (d) measuring the affinity of the compound for the $R^0$ form of the GPCR, where, a compound that (i) has an affinity for the RG form of the GPCR that is at least 1% (e.g., 5, 10, 25, 30, 50, 60, 75, 90, 100, 125, 150, 200, 150, 300, 400, 500, 750, or 1000%) of an endogenous agonist for the GPCR, and (ii) has a greater affinity (e.g., 1, 5, 10, 25, 50, 100, 200, 500, 1000, 2000, 5000, or 10,000% greater) for the $R^0$ form of the GPCR than the endogenous agonist or is identified as a long-acting agonist of the GPCR. The method may further include the steps of (e) administering the candidate compound to an animal, and (f) measuring at least one physiological response of the animal to the compound. The receptor may be a human receptor. The GPCR may be a secretin family receptor (e.g., a PTH/PTHrP receptor such as a human PTH/PTHrP receptor). When the receptor is involved in calcium homeostasis or transport, the measuring step (b) or (f) may be performed by measuring intracellular or blood calcium levels. For any GPCR, the affinity-measuring step (b) or step (d) may be performed using a competition binding assay. The competition binding assay may use a ligand that is specific for the RG form or specific for the $R^0$ form of the GPCR. The measuring step (b) may be performed using a delayed cAMP assay (e.g., as described herein). The $R^0$ form of the GPCR may enriched using a nonhydrolyzable nucleotide analog (e.g., GTPγS). The RG form of the GPCR may be enriched using a dominant-negative G-protein. The receptor may be on a cell or in a membrane. The candidate compound may include a peptide or may be from a chemical library or natural product library.

In another aspect, the invention also features a method for determining whether a candidate compound is a short-acting agonist of a G protein coupled receptor (GPCR). The method includes (a) contacting the GPCR with the compound, where the GPCR is in the RG form, (b) measuring the affinity of the compound for the RG form of the GPCR, (c) contacting the GPCR with the compound, where the GPCR is in the $R^0$ form; and (d) measuring the affinity of the compound for the $R^0$ form of the GPCR, where a compound that (i) has an affinity for the RG form of the GPCR that is at least 1% (e.g., 5, 10, 25, 30, 50, 60, 75, 90, 100, 125, 150, 200, 150, 300, 400, 500, 750, or 1000%) of an endogenous agonist for the GPCR, and (ii) has a lower affinity (e.g., 99, 95, 90, 85, 75, 65, 55, 50, 40, 30, 25, 15, 10, 5, 1, 0.5, 0.1, 0.05, 0.01, 0.005, 0.001, 0.0005, or 0.0001%) for the $R^0$ form of the GPCR than the endogenous agonist is identified as a short-acting agonist of the GPCR. The receptor may be a human receptor. The method may further including the steps of (e) administering the candidate compound to an animal, and (f) measuring at least one physiological response of the animal to the compound. The GPCR may be a secretin family receptor (e.g., a PTH/PTHrP receptor such a human PTH/PTHrP receptor). When the receptor is involved in calcium homeostasis or transport, measuring step (b) may be performed by measuring intracellular calcium levels. For any GPCR, the measuring step (b) or step (d) is performed using a competition binding assay (e.g., using a ligand that is specific for the RG form or specific for the $R^0$ form of the GPCR). The measuring step (b) may be performed using a delayed cAMP assay. In certain embodiments, the $R^0$ form of the GPCR may be enriched using a nonhydrolizable nucleotide analog (e.g., GTPγS). The RG form of the GPCR may be enriched using a dominant-negative G-protein. The receptor may be on a cell or in a membrane. The candidate compound may include a peptide or may be from a chemical library or a natural product library.

In another aspect the invention features a polypeptide having a low affinity for PTH $R^0$ (e.g., and a high affinity for RG). The polypeptide may be a short-acting agonist or may be RG selective. The polypeptide may have an amino acid sequence modified by a substitution, deletion and/or addition of one or more (e.g., 2, 3, 4, 5, 6, 7, 8) amino acids relative to the wild-type PTH or PTHrP sequence. The polypeptide may have a histidine at position 5 or an alanine at position 20, 23, 24, or 28. The polypeptide may be Ala$^{23}$-PTH(1-34) (SEQ ID NO:7), Ala$^{23}$-PTHrP(1-36) (SEQ ID NO:8), His$^5$-PTH(1-34) (SEQ ID NO:9), His$^5$-PTHrP(1-36) (SEQ ID NO:10), or a fragment thereof. The polypeptide may be selected from the group consisting of any of those identified as RG selective in the table of FIG. 26B. The polypeptide may be formulated for pharmaceutical administration (e.g., as described herein) or may be purified.

The invention also features a method for treating osteoporosis in a subject comprising administering the polypeptide of the previous aspect, an RG selective polypeptide (e.g., those described herein), a polypeptide described herein that is a long-acting agonist, or any polypeptide described herein, or a pharmaceutically acceptable form thereof, to the subject in need thereof in an amount sufficient to treat osteoporosis. The invention also features a method for treating fracture repair, osteomalacia, arthritis, thrombocytopenia, hypoparathyroidism or hyperphosphatemia or increasing stem cell mobilization in a subject, comprising administering the polypeptide of the previous aspect or any polypeptide described herein, or a pharmaceutically acceptable form thereof, to the subject in an amount sufficient to treat the disease or condition or to increase stem cell mobilization. The polypeptide or pharmaceutically acceptable form thereof may be administered subcutaneously, intravenously, intranasally, transpulmonarily, transdermally, or orally.

In another aspect, the invention features a polypeptide (PTH analog or PTH derivative) which binds the PTH receptor and has a high affinity for PTH receptor $R^0$ form. The polypeptide may have an amino acid sequence modified by a substitution, deletion and/or addition of one or more amino acids relative to the wild-type PTH or PTHrP sequence. The polypeptide may also have an arginine at position 19 or an isoleucine at position 5. The polypeptide may be $Ala^1,Aib^3$ [M]PTH(1-28) (SEQ ID NO:11), $Ala^1,Aib^3$[M]PTH(1-34) (SEQ ID NO:12), or $Ile^5$-PTHrP(1-36) (SEQ ID NO:13). The polypeptide may be selected from the group consisting of any of the peptides of FIG. 26B having an $IC_{50}$ less than or equal to 2.9 nM or 7.9 nM and $I^5$-hPTHrP(1-36) (SEQ ID NO:13) (#1208), based on the data of FIG. 26B. The polypeptide may be formulated for pharmaceutical administration (e.g., as described herein) or may be purified.

The invention also features a method for treating a disease or condition selected from the group consisting of hypoparathyroidism, hyperphosphatemia, tumoral calcinosis, and osteoporosis in a subject, by administering a polypeptide of the previous aspect, an $R^0$ selective polypeptide described herein, a polypeptide described herein that is a long-acting agonist, or any polypeptide described herein, or a pharmaceutically acceptable form thereof, to a subject in need thereof in an amount sufficient to treat the disease or condition. The invention also features a method for treating a subject needing fracture repair, or having osteomalacia, arthritis, thrombocytopenia, or requiring stem cell mobilization comprising administering the polypeptide of the previous aspect or any polypeptide described herein, or a pharmaceutically acceptable form thereof, to a subject in an amount sufficient to repair the fracture, to treat the disease, or to mobilize stem cells. The polypeptide or pharmaceutical composition thereof may be administered subcutaneously, intravenously, intranasally, transpulmonarily, transdermally, and orally.

The invention also features a PTH or PTHrP polypeptide having an amino acid sequence modified by a substitution, deletion and/or addition of one or more amino acids relative to the wild-type PTH or PTHrP sequence. The polypeptide may have an arginine at position 19 or an isoleucine at position 5. The polypeptide may be selected from the group consisting of AVAEIQLMHQRGKSIQDLRRRFFLH-HHLIAEIHTAEI: M-PTH(1-11)/PTHrP(12-36)OH (SEQ ID NO:14); AVAEIQLMHQRAKWIQDLRRRFFL-HEILIAEIHTAEI: M-PTH(1-14)/PTHrP(15-36)OH (SEQ ID NO:15); AVAEIQLMHQRAKWLNSMRRRFFLHHLI-AEIHTAEI: M-PTH(1-18)/PTHrP(19-36)OH (SEQ ID NO:16); SVSEHQLMHNLGKHIQDLRRRFFLHELI-AEIHTAEL [$H^5$]-hPTH(1-14)/PTHrP(15-36)OH (SEQ ID NO:17); AVAEIQLMHQRAKWLNSMRRVEWL-RKKLQDVHNF: [$R^{19}$],M-hPTH(1-34)OH (SEQ ID NO:18); SVSEIQLMHNLGKHIQDLERRF-FLFIFILIAEIHTAEI: [$E^{19}$]-hPTH(1-14)/PTHrP(15-36)OH (SEQ ID NO:19); AVAEIQLMHQRAKWIQDLERRRFFL-HHLIAEIHTAEI: [$E^{19}$],M-hPTH(1-14)/PTHrP(15-36)OH (SEQ ID NO:20); and AVAEIQLMHQRAKWLNS-MERVEWLRKKLQDVHNF: [$E^{19}$],M-hPTH (1-34)OH (SEQ ID NO:21). The polypeptide may have a histidine at position 5. The polypeptide may be represented by one of the follow formulas $Ala^1,Aib^3$[M]PTH(1-28) (SEQ ID NO:11), $Ala^{23}$PTH (SEQ ID NO:22), and $Ile^5$-PTHrP (SEQ ID NO:23). The polypeptide may be selected from the group consisting of: AVAEHQLMHQRAKWLNSMERVEWL-RKKLQDVHNF: [$H^5,E^{19}$],M-PTH(1-34) (SEQ ID NO:24); AVAEHQLMHQRAKWIQDLERRFFLHHLIAEIHTAEI: [$H^5,E^{19}$],M-hPTH(1-14)/PTHrP(15-36) (SEQ ID NO:25); SVSEIQLMHNLGKHLNSMERVEFLHELIAEIHTAEI: hPTH(1-22)/PTHrP(23-36) (SEQ ID NO:26); SVSEIQLM-HNLGKHLNSMERVEWLRKKLQDIHTAEI: PTH(1-30)/ PTHrP(31-36) (SEQ ID NO:27); AVAEIQLMHQRAK-WLNSMERVEALRKKLQDVIINF: [$A^{23},E^{19}$],M-PTH(1-34) (SEQ ID NO: 28); and AVAEIQLMHQRAKWLNSMRRVEALRKKLQDVHNF [$A^{23}$],M-PTH(1-34) (SEQ ID NO:29). The polypeptide may be used in any treatment methods or any compositions (e.g., pharmaceutical compositions described herein).

In another aspect, the invention features a polypeptide including an amino acid sequence having the formula or including an amino acid sequence substantially identical to an amino acid sequence defined by the formula:

(SEQ ID NO: 30)
X1-Val-X2-Glu-His-Gln-Lys-Met-His-X3-X4-X5-X6-X7, wherein:

X1 is Ser, Ala, Gly, or an α-helix stabilizing residue (e.g., Aib);

X2 is Ser, Ala, or an α-helix stabilizing residue (e.g., Aib);

X3 is Asn, Ala, Glu, Val, Asp, or Gln;

X4 is Val, Ala, Trp, Ile, Met, Lys, Arg, Leu, or Har;

X5 is Gly, His, Arg, Ala, or an α-helix stabilizing residue (e.g., Aib);

X6 is Lys, Gln, Leu, His, Trp, Ala, Arg, or an α-helix stabilizing residue (e.g., Aib); and X7 is Arg, Leu, Phe, Trp, His, or an α-helix stabilizing residue (e.g., Aib);

or a fragment thereof containing amino acids 1-10, 1-11, 1-12, or 1-13, or a pharmaceutically acceptable salt thereof. The α-helix stabilizing residue may be, for example, a non-encoded amino acid such as (2-aminoisobutyric acid), ACPC (1-aminocyclopropylcarboxylic acid), DEG (diethylglycine), or 1-aminocyclopentanecarboxylic acid. In certain embodiments, the amino acid sequence has 1, 2, 3, 4, 5, 6, 7, or 8 substitutions relative to the corresponding wild-type PTH sequence. In certain embodiments, the polypeptide includes an Ala, Gly, or an α-helix stabilizing residue (e.g., Aib) at X1; an Ala or an α-helix stabilizing residue (e.g., Aib) at X2; an Ala, Glu, Val, Asp, or Gln at X3; a Val, Ala, Trp, Ile, Met, Lys, Arg, or Har at X4; a His, Arg, Ala, or an α-helix stabilizing residue (e.g., Aib) at X5; a Gln, Leu, His, Trp, Ala, Arg, or an α-helix stabilizing residue (e.g., Aib) at X6; an Arg, Leu, Phe, Trp, or an α-helix stabilizing residue (e.g., Aib) at X7; or a combination thereof. In any of these embodiments, the polypeptide may have an amino acid sequence fewer than 100, 50, 36, 34, 30, 25, or 20 in length (e.g., 10-14 amino acids). In certain embodiments, the polypeptide is 21, 20, 19, 18, 17, 16, 15, 14, 13, 12, 11, or 10 amino acids in length. The polypeptide may be part of a composition including a pharmaceutically acceptable carrier.

In another aspect, the invention features a polypeptide including an amino acid sequence of the formula, or includes an amino acid sequence substantially identical to an amino acid sequence defined by the formula:

(SEQ ID NO: 31)
X1-Val-X2-Glu-X3-Gln-Leu-Met-His-X4-X5-X6-X7-X8-

Leu-Asn-Ser-Met-Glu-X9-Val-Glu-X10-X11-Arg-Lys-

Lys-X12, wherein:
X1 is Ser, Ala, or an α-helix stabilizing residue (e.g., Aib);
X2 is Ser, Ala, or an α-helix stabilizing residue (e.g., Aib);
X3 is Ile or His;
X4 is Asn, Glu, Val, Asp, or Gln;
X5 is Val, Ala, Trp, Ile, Met, Lys, Arg, Leu, or Har;
X6 is Gly, His, Arg, or Ala;
X7 is Lys, Gln, Leu, His, Trp, Ala or Arg;
X8 is Arg, Leu, Phe, Trp, His, or Ser;
X9 is Arg or Ala;
X10 is Trp, Ala or Phe;
X11 is Leu or Ala; and
X12 is Leu or Ala;
and wherein the amino acid sequence comprises at least one of the amino acids selected from the group consisting of His at position X3, Ala at position X9, Ala at position X10, Ala at position X11, and Ala at position X12, a fragment thereof comprising amino acids 1-24, 1-25, 1-26, or 1-27 of said amino acid sequence, or a pharmaceutically salt thereof. The polypeptide may bind with low affinity to the R⁰ form of a PTH receptor (e.g., bind with high affinity to the RG form of the PTH receptor). The polypeptide may be RG selective or may be a short-acting agonist of the receptor. The polypeptide may include 1, 2, 3, 4, 5, 6, 7, 8, 9, 10, or more substitutions relative to the corresponding wild type sequence. In certain embodiments, the polypeptide includes an Ala or an α-helix stabilizing residue (e.g., Aib) at X1; an Ala or an α-helix stabilizing residue (e.g., Aib) at X2; an His at X3; a Glu, Val, Asp, or Gln at X4; a Val, Ala, Trp, Ile, Met, Lys, Arg, or Har at X5; a His, Arg, or Ala at X6; a Gln, Leu, His, Trp, Ala, or Arg at X7; an Arg, Leu, Phe, Trp, or Ser at X8; an Ala at X9; an Ala or Phe at X10; an Ala at X11; an Ala at X12; or a combination thereof. The polypeptide may be fewer than 100, 75, 60, 50, 40, 36, 34, 33, 32, 31, 30, 29, or 28 amino acids in length. The polypeptide may be 24, 25, 26, 27, 28, 29, 30, 31, 32, 33, 34, 35, 36, 37, 38, 39, or 40 amino acids in length (e.g., 24-28 amino acids in length). In certain embodiments at least one (e.g., 2, 3, or 4) of X9, X10, X11, or X12 is alanine.

In another aspect, the invention features a polypeptide including an amino acid sequence of the formula, or substantially identical to an amino acid sequence defined by the formula:

(SEQ ID NO: 32)
X1-Val-X2-Glu-Ile-Gln-Leu-Met-His-X3-X4-X5-X6-

X7-Leu-Asn-Ser-Met-Arg-Arg-Val-Glu-Trp-Leu-Arg-

Lys-Lys-Leu, wherein
X1 is Ser, Ala, or Aib;
X2 is Ser, Ala, or Aib;
X3 is Asn, Glu, Val, Asp, or Gln;
X4 is Val, Ala, Trp, Ile, Met, Lys, Arg, or Leu;
X5 is Gly, His, Arg, or Ala;
X6 is Lys, Gln, Leu, His, Trp, Ala, or Arg; and
X7 is Arg, Leu, Phe, Trp, His, or Ser, or a fragment thereof containing amino acids 1-24, 1-25, 1-26, or 1-27 of said amino acid sequence, or a pharmaceutically acceptable salt thereof. The polypeptide may be R⁰ selective or may be a long-acting PTH agonist. The amino acid sequence may contain 1, 2, 3, 4, 5, 6, 7, 8, 9, 10, or more substitutions (e.g., at any of the positions described above relative to the wild type PTH sequence). In certain embodiments, the polypeptide includes an Ala or Aib at X1; an Ala or Aib at X2; a Glu, Val, Asp, or Gln at X3; a Val, Ala, Trp, Ile, Met, Lys, or Arg at X4; a His, Arg, or Ala at X5; a Gln, Leu, His, Trp, Ala, or Arg at X6; an Arg, Leu, Phe, Trp, or Ser at X7; or a combination thereof. The polypeptide may be fewer than 100, 75, 60, 50, 40, 36, 34, 33, 32, 31, 30, 29, or 28 amino acids in length. The polypeptide may be 24, 25, 26, 27, 28, 29, 30, 31, 32, 33, 34, 35, 36, 37, 38, 39, or 40 amino acids in length (e.g., 24-28 amino acids in length). The polypeptide may be in a composition with a pharmaceutically acceptable carrier.

In another aspect, the invention features a polypeptide comprising an amino acid sequence having the formula, or an amino acid sequence substantially identical to a polypeptide defined by the formula:

(SEQ ID NO: 33)
Ala-Val-Ser-Glu-His-Glu-Leu-Leu-His-Asp-Lys-Gly-

Lys-Ser-Ile-Gln-Asp-X1-Arg-Arg-Arg-X2-Phe-Leu-

X3-X4-Leu-Ile-X5-X6-X7-X8-X9-X10-Glu-Ile, wherein:
X1 is Leu, Ala, Ser, Met, Phe, or Glu;
X2 is Phe, Ala, Ser, Leu, Asn, Trp, Glu, or Lys;
X3 is His, Leu, Arg, Lys, Trp, Ile, or Phe;
X4 is His, Ala, Ser, Asn, Lys, or Arg;
X5 is Ala, Gly, Ser, Asn, Gln, Trp, Glu, or Lys;
X6 is Glu, Gly, Ser, Leu, Asn, Asp, Lys, or Ala;
X7 is Ile, Leu, Val, Lys, or Ala;
X8 is His or Ala
X9 is Thr, Asn, or Ala; and
X10 is Ala or Phe,
or a fragment thereof containing amino acids 1-24, 1-25, 1-26, 1-27, 1-28, 1-29, 1-30, 1-31, 1-32, 1-33, 1-34, or 1-35 of said amino acid sequence, and wherein said polypeptide comprises at least one amino acid substitution as compared to the corresponding wild type PTHrP sequence or a fragment thereof; or a pharmaceutically acceptable salt thereof. The polypeptide may bind with low affinity to the R⁰ form of a PTH receptor (e.g., bind with high affinity to the RG form of the PTH receptor). The polypeptide may be RG selective or may be a short-acting agonist of the PTH receptor. The polypeptide may include 1, 2, 3, 4, 5, 6, 7, 8, 9, 10, or more substitutions relative to the corresponding wild type PTHrP sequence. In certain embodiments, the polypeptide has an Ala, Ser, Met, Phe, or Glu at X1; an Ala, Ser, Leu, Asn, Trp, Glu, or Lys at X2; a Leu, Arg, Lys, Trp, Ile, or Phe at X3; an Ala, Ser, Asn, Lys, or Arg at X4; Gly, Ser, Asn, Gln, Trp, Glu, or Lys at X5; a Gly, Ser, Leu, Asn, Asp, Lys, or Ala X6; a Leu, Val, Lys, or Ala at X7; an Ala at X8; an Asn or Ala at X9; a Phe at X10; or a combination thereof. In particular embodiments, the polypeptide has an Ala or Glu at X1, an Ala at X2, a Leu at X3, a Lys at X4, or a combination thereof. The polypeptide may be fewer than 100, 75, 60, 50, 40, 36, 34, 33, 32, 31, 30, 29, or 28 amino acids in length. The polypeptide may be 24, 25, 26, 27, 28, 29, 30, 31, 32, 33, 34, 35, 36, 37, 38, 39, or 40 amino acids in length (e.g., 28-36 amino acids in length). The polypeptide may have a free hydroxyl or be amidated at its C-terminus. The polypeptide may include a sequence selected from the amino acid sequences of Table 1, or be substantially identical to such sequences. The polypeptide may be in a composition with a pharmaceutically acceptable carrier.

TABLE 1

(SEQ ID NO: 34-117)

A18-PTHrP(1-28)
S18-PTHrP(1-28)
M18-PTHrP(1-28)
F18-PTHrP(1-28)
E18-PTHrP(1-28)
A22-PTHrP(1-28)
S22-PTHrP(1-28)
L22-PTHrP(1-28)
N22-PTHrP(1-28)
W22-PTHrP(1-28)
E22-PTHrP(1-28)
K22-PTHrP(1-28)
A26-PTHrP(1-28)
S26-PTHrP(1-28)
N26-PTHrP(1-28)
K26-PTHrP(1-28)
R26-PTHrP(1-28)
L25-PTHrP(1-28)
W25-PTHrP(1-28)
K25-PTHrP(1-28)
R25-PTHrP(1-28)
A18,22,26-PTHrP(1-28)
A18,22,K26-PTHrP(1-28)
A18,26,S22-PTHrP(1-28)
A18,S22,K26-PTHrP(1-28)
A18,26,N22-PTHrP(1-28)
A18,N22,K26-PTHrP(1-28)
A18,26,L22-PTHrP(1-28)
A18,L22,K26-PTHrP(1-28)
A18,26,W22-PTHrP(1-28)
A18,W22,K26-PTHrP(1-28)
E18,A22,K26-PTHrP(1-28)
E18,S22,A26-PTHrP(1-28)
E18,N22,A26-PTHrP(1-28)
E18,N22,K26-PTHrP(1-28)

TABLE 1-continued (SEQ ID NO: 34-117)

E18,L22,A26-PTHrP(1-28)
E18,L22,K26-PTHrP(1-28)
E18,W22,A26-PTHrP(1-28)
E18,W22,K26-PTHrP(1-28)
E18,K22,A26-PTHrP(1-28)
E18,K22,26-PTHrP(1-28)
E18,A22,26-PTHrP(1-28)
A18,22,L25,K26-PTHrP(1-28)
A18,22,K25,26-PTHrP(1-28)
A18,22,I25,K26-PTHrP(1-28)
A18,22,W25,K26-PTHrP(1-28)
A18,22,F25,K26-PTHrP(1-28)
A18,S22,L25,K26-PTHrP(1-28)
A18,S22,K25,26-PTHrP(1-28)
E18,A22,L25,K26-PTHrP(1-28)
E18,A22,K25,26-PTHrP(1-28)
E18,S22,L25,K26-PTHrP(1-28)
E18,S22,K25,26-PTHrP(1-28)
A18,22,K26-PTHrP(1-30)
E18,A22,K27-PTHrP(1-30)
A18,22,L25,K26-PTHrP(1-30)
E18,A22,L25,K26-PTHrP(1-30)
A18,22,K26-PTHrP(1-31)
E18,A22,K27-PTHrP(1-31)
A18,22,L25,K26-PTHrP(1-31)
E18,A22,L25,K26-PTHrP(1-31)
E18,A22,L25,K26,G29-PTHrP(1-31)
E18,A22,L25,K26,S29-PTHrP(1-31)
E18,A22,L25,K26,N29-PTHrP(1-31)
E18,A22,L25,K26,Q29-PTHrP(1-31)
E18,A22,L25,K26,W29-PTHrP(1-31)
E18,A22,L25,K26,E29-PTHrP(1-31)
E18,A22,L25,K26,K29-PTHrP(1-31)
E18,A22,L25,K26,G30-PTHrP(1-31)
E18,A22,L25,K26,S30-PTHrP(1-31)
E18,A22,L25,K26,L30-PTHrP(1-31)
E18,A22,L25,K26,N30-PTHrP(1-31)
E18,A22,L25,K26,D30-PTHrP(1-31)
E18,A22,L25,K26,K30-PTHrP(1-31)

TABLE 1-continued (SEQ ID NO: 34-117)

E18,A22,L25,K26,S31-PTHrP(1-31)

E18,A22,L25,K26,L31-PTHrP(1-31)

E18,A22,L25,K26,V31-PTHrP(1-31)

E18,A22,L25,K26,K31-PTHrP(1-31)

E18,A22,L25,K26-PTHrP(1-34)

E18,A22,L25,K26,A30-PTHrP(1-34)

E18,A22,L25,K26,A31-PTHrP(1-34)

E18,A22,L25,K26,A32-PTHrP(1-34)

E18,A22,L25,K26,A33-PTHrP(1-34)

E18,A22,L25,K26,Q29,D30,V31,N33,F34-PTHrP(1-34)

In another aspect, the invention features a PTH or PTHrP polypeptide (e.g., of any of the above aspects or described herein) where the N-terminus is substituted with a bulky residue (e.g., Trp). Such polypeptides include Trp$^1$-PTH(1-34) (SEQ ID NO:118), Trp$^1$-M-PTH(1-34) (SEQ ID NO:119), and TRP$^1$-PTHrP(1-36) (SEQ ID NO:120), or a fragment thereof containing amino acids 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, or 1-35 of said sequence. The polypeptide may have reduced (e.g., by at least 1, 5, 10, 25, 50, 75, 90, 95, 99, 99.5, 99.9, 99.95, or 99.99%) PLC signaling activity at the PTH receptor as compared to the polypeptide lacking the bulky residue substitution. Other bulky residues include Phe, Tyr, and p-benzoylphenylalanine (Bpa). In certain embodiments, the polypeptide includes any one (e.g., 2, 3, 4, 5, 6, or 7) of the mutations set forth in the M or Mc modifications, where M represents [Ala$^{1,12}$,Aib$^3$,Gln$^{10}$,homoarginine$^{11}$, Trp$^{14}$,Arg$^{19}$] and Mc represents Ala$^{1,3,12}$,Gln$^{10}$,Arg$^{11}$,Trp$^{14}$, Arg$^{19}$ PTH sequence, or any combination thereof. Hybrid peptides may further include a substitution at position 5 (e.g., a histidine at position 5). Exemplary polypeptides include Trp$^1$-PTH(1-28) (SEQ ID NO:121) and Trp$^1$-M-PTH(1-28) (SEQ ID NO:122).

In another aspect of the invention, the invention features a polypeptide including a hybrid PTH/PTHrP polypeptide or a polypeptide including an amino acid sequence substantially identical to a hybrid PTH/PTHrP polypeptide. The polypeptide may be represented by the formula PTH(1-X)/PTHrP(Y-36), where X is 8, 9, 10, 11, 12, 13, 14, 15, 16, 17, 18, 19, 20, 21, 22, 23, 24, 25, 26, 27, 28, 29, 30, 31, 32, 33, or 34 and Y=X+1. In certain embodiments, the hybrid polypeptide contains any one (e.g., 2, 3, 4, 5, 6, or 7) of the mutations set forth in the M or Mc modifications, where M represents [Ala$^{1,12}$, Aib$^3$,Gln$^{10}$,homoarginine$^{11}$,Trp$^{14}$,Arg$^{19}$] and Mc represents Ala$^{1,3,12}$,Gln$^{10}$,Arg$^{11}$,Trp$^{14}$, Arg$^{19}$ PTH sequence, or any combination thereof. Hybrid peptides may further include a substitution at position 5 (e.g., a histidine at position 5).

In any of the polypeptides described above, the polypeptide may be biologically active, e.g., have an affinity for the RG form of the GPCR that is at least 1% (e.g., 5, 10, 25, 30, 50, 60, 75, 90, 100, 125, 150, 200, 150, 300, 400, 500, 750, or 1000%) of an endogenous agonist for the GPCR, and have a lower affinity (e.g., 99, 95, 90, 85, 75, 65, 55, 50, 40, 30, 25, 15, 10, 5, 1, 0.5, 0.1, 0.05, 0.01, 0.005, 0.001, 0.0005, or 0.0001%) for the R$^0$ form as compared to a control (e.g., an endogenous ligand for the GPCR). In other embodiments, the polypeptide has an affinity for the RG form of the GPCR that is at least 1% (e.g., 5, 10, 25, 30, 50, 60, 75, 90, 100, 125, 150, 200, 150, 300, 400, 500, 750, or 1000%) of an endogenous agonist for the GPCR, and (ii) has a greater affinity (e.g., 1, 5, 10, 25, 50, 100, 200, 500, 1000, 2000, 5000, or 10,000% greater) for the R$^0$ form of the GPCR than the endogenous agonist or is identified as a long-acting agonist of the GPCR. In the above aspects, the polypeptide may be RG selective, R$^0$ selective, a short-acting agonist, or a long-acting agonist. In certain embodiments, the polypeptide may be modified (e.g., acetylated at the N-terminal, amidated at the C-terminal, or contain any of the modifications described herein).

The invention also features a nucleic acid including a sequence encoding a polypeptide described herein (e.g., those described above). The nucleic acid may be operably linked to promoter and/or part of a vector. The invention also features a cell (e.g., a prokaryotic cell such as bacterial cell or a eukaryotic cell such as yeast or mammalian, for example, human, cell) including the vector.

The invention also features a method of making the polypeptide by growing the cell under conditions which induce expression of said nucleic acid and optionally purifying said polypeptide.

By "GPCR" is meant any polypeptide comprising a G protein coupled receptor or functional fragment thereof. Desirably, a GPCR has at least 70%, 80%, 90%, 95%, 99%, or 100% sequence identity to a naturally occurring GPCR. Exemplary GPCRs are described herein.

By "RG form" of a GPCR is meant the G-protein-bound receptor conformation. The RG form of a GPCR can be induced, for example, by increased G-protein binding of the GPCR. In the assays of the invention, at least 1%, 5%, 10%, 25%, 50%, 75%, 90%, 95%, or 99% of the receptors are in the RG form when affinity for RG form is measured.

By "R$^0$ form" of a GPCR is meant the receptor conformation that occurs when the GPCR is not bound to a G-protein, but is capable of binding at least some ligands of the receptor. The R$^0$ form of a GPCR, relative to RG, can be favored, for example, by preventing or reducing G-protein binding to the GPCR. In the assays of the invention, at least 0.1%, 1%, 5%, 10%, 25%, 50%, 75%, 90%, 95%, or 99% of the receptors may be in the R$^0$ form when affinity for the R$^0$ form is measured.

By "affinity" is meant the ability of a compound to interact with a target receptor. In the assays and polypeptides of the invention, affinity may be measured directly by binding (e.g., competition binding assays or FRET), or indirectly through an activity assay (e.g., cAMP signaling or changes in intracellular calcium). Desirably the compound has an affinity for the receptor of at least 10 mol, 1 mol, 500 nmol, 100 nmol, 50 nmol, 25 nmol, 10 nmol, 5 nmol, 1 nmol, 500 pmol, 200 pmol, 100 pmol, 50 pmol, 25 pmol 10 pmol, or 1 pmol as measured by $EC_{50}$ for the RG form or the R$^0$ form of the GPCR.

By "long-acting agonist" is meant an agonist whose activity (e.g., measured in vivo or in vitro) has a half life that is at least 5%, 10%, 25%, 50%, 75%, 100%, 150%, 200%, 500%, 1000%, or 5000% longer as compared to an endogenous agonist for the same receptor.

By "short-acting agonist" is meant an agonist whose activity (e.g., measured in vivo or in vitro using an assay described herein) has a half life that is less than 95%, 90%, 75%, 60%, 50%, 40%, 30%, 20%, 10%, 5%, or 1% as compared to an endogenous agonist for the same receptor.

By "RG selective agonist" is an agonist that exhibits increased binding to the RG form of a receptor relative to the R$^0$ form of the receptor, as compared to a control agonist (e.g., an endogenous agonist). Receptor selectivity can be expressed as a ratio of binding constants between each receptor form, e.g., $R^O/RG$ ratio, where an increase in this ratio indicates stronger binding to the RG form. As shown in FIGS. 26A and 26B, the $R^O/RG$ ratio of PTH(1-34) (SEQ ID NO:5) is 67 and the relatively more RG selective PTHrP(1-36) (SEQ ID NO:6) is 260 in binding the human PTH receptor expressed on COS-7 cell membranes. An RG selective agonist may have an $R^O/RG$ ratio of at least 100, 150, 200, 250, 300, 400, 500, 1000, 2000, 3000, 5000, 7000, 10,000, 15,000, 20,000, or 50,000 in this system. The $R^O/RG$ ratio may be at least 1.5, 2, 3, 4, 5, 10, 15, 25, 50, 75, or 100-fold that of the control agonist.

By "$R^O$ selective agonist" is an agonist that exhibits decreased binding to the RG form of a receptor relative to the $R^O$ form of the receptor, as compared to a control agonist (e.g., an endogenous agonist). Receptor selectivity can be expressed as a ratio of binding constants between each receptor form, e.g., $R^O/RG$ ratio, where a decrease in this ratio indicates stronger binding to the $R^O$ form. As shown in FIGS. 26A and 26B, the $R^O/RG$ ratio of PTH(1-34) (SEQ ID NO:5) is 67 and the relatively more RG selective PTHrP(1-36) (SEQ ID NO:6) is 260 in binding the human PTH receptor expressed on COS-7 cell membranes. The $R^O$ selective agonist may have an $R^O/RG$ ratio of less than 60, 50, 40, 30, 25, 20, 25, 10, 5, 2, 1, 0 in this system. The $R^O/RG$ ratio thus may be less than 0.9, 0.8, 0.7, 0.6, 0.5, 0.4, 0.3, 0.2, 0.1, 0.08, 0.05, 0.03, 0.01, 0.008, 0.005, 0.003, or 0.001-fold of that the control agonist.

By "endogenous agonist" of a GPCR is meant a compound produced by an organism, or a synthetic phenocopy of that compound, i.e., a compound having the same pharmacological activity as the endogenous agonist. For example, the native PTH peptide (SEQ ID NO:3) is 1-84, and PTHrP (SEQ ID NO:4) is ~1-140 amino acids; phenocopies of these ligands include PTH(1-34) (SEQ ID NO:5) and PTHrP(1-36) (SEQ ID NO:6), respectively. An endogenous agonist is involved in or modulates the normal physiological activation of the GPCR. Some GPCRs have multiple endogenous agonists (e.g., endogenous agonists for the PTHR include PTH and PTHrP); for purposes of the invention, any endogenous agonist may be used to determine whether the candidate compound is short-acting or long-acting.

By "peptide" or "polypeptide" is meant a chain of amino acids of at least 4, 6, 10, 25, 50, 100, 150, 200, 500, or 1000 amino acids.

By "fragment" of a polypeptide is meant a portion of a sequence at least 4, 5, 6, 7, 8, 9, 10, 11, 12, 13, 14, 15, 16, 17, 18, 19, 20, 21, 23, 24, 25, 26, 27, 28, 29, 30, 31, 32, 33, 34, or 35 amino acids in length By "subject" is meant either a human or non-human animal (e.g., a mammal).

By "an amount sufficient to treat" is meant an amount sufficient to reduce, prevent, or eliminate at least one symptom associated with the disease or condition.

By a "purified polypeptide" or "isolated polypeptide" is meant a polypeptide that has been separated from other components. Typically, the polypeptide is substantially pure when it is at least 30%, by weight, free from other components. In certain embodiments, the preparation is at least 50%, 60%, 75%, 85%, 90%, 95%, 96%, 97%, 98%, or 99% by weight, free from other components. A purified polypeptide may be obtained, for example, by extraction from a natural source; by expression of a recombinant polynucleotide encoding such a polypeptide; or by chemically synthesizing the polypeptide. Purity can be measured by any appropriate method, for example, column chromatography, polyacrylamide gel electrophoresis, or by HPLC analysis.

By "biologically active" is meant that the compound or composition (e.g., a polypeptide described herein) has at least one biologically significant effect upon administration to a cell or animal (e.g., a human or non-human mammal). Biological activities of PTH, PTHrP, and analogs thereof (e.g., those described herein) include receptor binding, cAMP or $IP_3$ production, protein kinase A, protein kinase C, phospholipase C, phospholipase D, and phospholipase $A_2$ activation, changes (e.g., increases or decreases) in intracellular, plasma, or urinary calcium or phosphate levels, and changes in bone metabolism or catabolism in vivo or in vitro. A biologically active peptide of the invention (e.g., any peptide described herein), for example, may exhibit increases (e.g., at least 5%, 10%, 25%, 50%, 100%, 500%, 1000%, 10,000%) or decreases (e.g., 95%, 90%, 75%, 50%, 25%, 10%, 5%, 1%, 0.1%, 0.01%, or 0.001%) in any biological activity as compared to an appropriate control (e.g., a wild-type peptide or a phenocopy thereof such as PTH(1-34) (SEQ ID NO:5) or PTHrP(1-36) (SEQ ID NO:6)).

By "substantially identical" is meant a nucleic acid or amino acid sequence that, when optimally aligned, for example, using the methods described below, share at least 60%, 65%, 70%, 75%, 80%, 85%, 90%, 95%, 96%, 97%, 98%, 99% or 100% sequence identity with a second nucleic acid or amino acid sequence, e.g., an PTH or PTHrP sequence or fragment thereof. "Substantial identity" may be used to refer to various types and lengths of sequence, such as full-length sequence, epitopes or immunogenic peptides, functional domains, coding and/or regulatory sequences, exons, introns, promoters, and genomic sequences. Percent identity between two polypeptides or nucleic acid sequences is determined in various ways that are within the skill in the art, for instance, using publicly available computer software such as Smith Waterman Alignment (Smith et al., *J. Mol. Biol.* 147: 195-7 (1981)); "Best Fit" (Smith and Waterman, Advances in Applied Mathematics, 482-489 (1981)) as incorporated into GeneMatcher Plus™, Schwarz and Dayhof (1979) Atlas of Protein Sequence and Structure, Dayhof, M. O., Ed pp 353-358; BLAST program (Basic Local Alignment Search Tool; (Altschul et al., *J. Mol. Biol.* 215: 403-10 (1990)), BLAST-2, BLAST-P, BLAST-N, BLAST-X, WU-BLAST-2, ALIGN, ALIGN-2, CLUSTAL, or Megalign (DNASTAR) software. In addition, those skilled in the art can determine appropriate parameters for measuring alignment, including any algorithms needed to achieve maximal alignment over the length of the sequences being compared. In general, for proteins, the length of comparison sequences will be at least 6 or 8 amino acids, preferably 9, 10, 11, 12, 13, 14, 15, 16, 17, 18, 19, 20, 21, 22, 23, 24, 25, 26, 27, 28, 29, 30, 31, 32, 33, 34, 35, 36, 40, 50, 60, 70, 80, 90, 100, 125, 150, 200, 250, 300, 350, 400, or 500 amino acids or more up to the entire length of the protein. For nucleic acids, the length of comparison sequences will generally be at least 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 125, 150, 200, 250, 300, 350, 400, 450, 500, 550, 600, 650, 700, 800, 900, 1000, 1100, 1200, or at least 1500 nucleotides or more up to the entire length of the nucleic acid molecule. It is understood that for the purposes of determining sequence identity when comparing a DNA sequence to an RNA sequence, a thymine nucleotide is equivalent to a uracil nucleotide. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By "bulky amino acid" is meant any amino acid with a molecular weight greater than 100 Da (e.g., greater than 125, 150, 175, 200, 225, 250, 300, or 400). The molecular weight of each coding amino acid is as follows. Ala: 71.09, Arg: 156.19, Asp: 115.09, Asn: 114.11, Cys: 103.15, Glu: 129.12, Gln: 128.14, Gly: 57.05, His: 137.14, Ile: 113.16, Leu: 113.16, Lys: 128.17, Met: 131.19, Phe: 147.18, Pro: 97.12, Ser: 87.08, Thr: 101.11, Trp: 186.12, Tyr: 163.18, and Val: 99.14.

Other features and advantages of the invention will be apparent from the following Detailed Description, the drawings, and the claims.

BRIEF DESCRIPTION OF THE DRAWINGS

FIG. 13A shows transient calcemic action of PTHrP(1-36) and [I$^5$]-PTHrP(1-36) in normal rats. The His$^5$→Ile substitution in PTHrP(1-36), which increased affinity for R$^0$ by 9-fold (see Table inset) resulted in a more prolonged calcemic effect. FIGS. 13B and 13C show the delayed (60 min; FIG. 13B) and the maximal (FIG. 13C) cAMP response in cells treated with each of these ligands.

FIGS. 14B and 14C show the delayed (60 min; FIG. 14B) and the maximal (FIG. 14C) cAMP response in cells treated with hPTH(1-34) (SEQ ID NO:5) or Mc-hPTH(1-14)/PTHrP(15-36) (SEQ ID NO:15). The Table inset shows binding affinities for the analogs at the R$^0$ and RG receptor conformations, measured in vitro.

FIGS. 17A-17C are graphs showing transient calcemic action of Mc-modified PTH(1-34)/PTHrP(1-36) analogs without the Ile$^5$→His and Arg$^{19}$→Glu substitutions in normal rats and delayed cAMP and maximal response in ROS17/2.8 cells (FIGS. 17B and 17C). The Table inset shows binding affinities for the analogs at the R$^0$ and RG receptor conformations, measured in vitro. The Ile$^5$→His and Arg$^{19}$→Glu substitutions reduce affinity for R$^0$, and reduce duration of cAMP signaling in vitro and the calcemic effect in vivo. The analogs used were Mc-PTH(1-14)/PTHrP(15-36)OH (SEQ ID NO:15), [H$^5$],Mc-hPTH(1-14)/PTHrP(15-36) (SEQ ID NO:133), and [H$^5$,E$^{19}$],Mc-hPTH(1-14)/PTHrP(15-36) (SEQ ID NO:25) (Mc=Ala$^{1,3,12}$,Gln$^{10}$,Arg$^{11}$Trp$^{14}$, Arg$^{19}$).

In FIG. 21A, cells were incubated with peptides in the presence of IBMX for 10 minutes, and cAMP was measured. The EC$_{50}$ values were 0.32, 7.6, and 0.33 nM, respectively. In FIG. 21B, the cells were treated with 10$^{-7}$ M of hPTH(1-34), [A$^1$,Aib$^3$ M]-PTH(1-28), or 10$^{-6}$M of hPTH(1-28) for 10 minutes, washed three times, incubated in buffer alone for the times indicated, treated for a final 5 minutes with IBMX, and then cAMP was measured. The data in FIG. 21B are expressed as a percent of the maximum response observed for each ligand, determined by incubating the cells with ligand in the presence of IBMX for 10 minutes (no ligand wash-out). These values were 67±6; 68±3; and 71±1 pmole/well, respectively. The basal (vehicle) cAMP value was 3.7±0.4 pmole/well.

FIG. 25 is a table showing cAMP signaling potency of PTH/PTHrP hybrid analogs (SEQ ID NOs provided therein) on the human PTH receptor in HKRK-B7 cells.

FIG. 26A is a table showing competition analysis of R$^0$ and RG binding of PTH/PTHrP analogs (SEQ ID NOs provided therein) with the human PTH receptor expressed in COS-7 cell membranes.

FIG. 26B is a table showing the same data as FIG. 26A, sorted by R$^0$ binding values.

FIG. 28B shows in vivo cAMP induction, from C57BL/6 mice (3 month old, male) injected intravenously with either vehicle, PTHrP(1-36) (SEQ ID NO:5), PTHrP(1-28) (SEQ ID NO:151), $A^{18,22},L^{25},K^{26}$ (AALK)-PTHrP(1-28) (SEQ ID NO:76), or $E^{18},A^{22},L^{25},K^{26}$ (EALK)-PTHrP(1-28) SEQ ID NO:83) (n=3). Blood was withdrawn 10 minutes after injection, and the plasma level of cAMP was measured by RIA.

FIGS. 29A and 29B show plasma cAMP concentrations in mice (C57BL/6, males, 3 months) that were administered either vehicle, rPTH(1-34) (SEQ ID NO:130), M-PTH(1-34) (M=$A^1$,Aib$^3$,Q$^{10}$,Har$^{11}$,A$^{12}$,W$^{14}$,R$^{19}$) (SEQ ID NO:12), or $E^{18},A^{22},L^{25},K^{26}$(EALK)-PTHrP(1-30) (SEQ ID NO:90) (5 nmol/kg; n=7 for cAMP, n=4 for calcium) intravenously. FIG. 29B shows ionic calcium levels in mice treated with the same peptides. In the calcium experiment, blood was withdrawn before, and 1, 2, 4 and 6 hours after injection, and ionized calcium was measured using a Ca$^{++}$/pH analyzer.

DETAILED DESCRIPTION

Figure 1A:
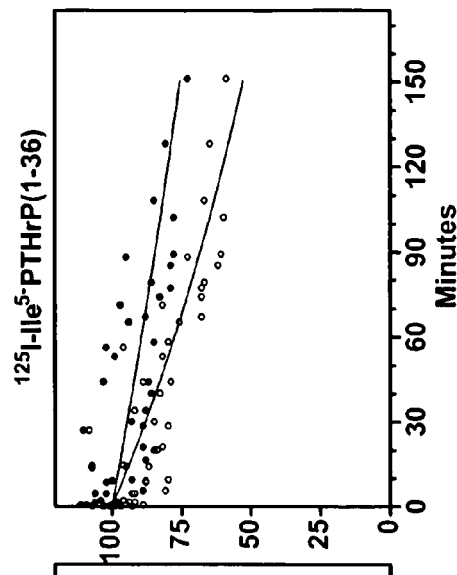
FIGS. 1A-1C are graphs showing dissociation of PTH and PTHrP analogs from the human PTH receptor (PTHR) and the effects of GTPγS. The radioligands $^{125}$I-[Nle$^{8,21}$,Tyr$^{34}$]rPTH(1-34)NH$_2$ (SEQ ID NO:123) (FIG. 1A), $^{125}$I-[Tyr$^{36}$]THrp(1-36)NH$_2$ (SEQ ID NO:124) (FIG. 1B) and $^{125}$I-[Ile$^5$,Tyr$^{36}$]PTHrP(1-36)NH$_2$ (SEQ ID NO:125) (FIG. 1C) were pre-bound to the human PTHR in membranes prepared from HKRK-B7 cells for 90 minutes; then dissociation was initiated (t=0) by the addition of an excess of the unlabeled analog (5×10$^{-7}$ M), added either alone (filled circles) or together with GTPγS (5×10$^{-7}$ M, open circles). At each time point, aliquots were removed from the reaction tubes and immediately subjected to rapid vacuum filtration using a 96-well vacuum filtration plate to separate bound from free radioactivity. Non-specific binding was determined in tubes containing the unlabeled ligand (5×10$^{-7}$M) during both the pre-incubation and dissociation phases. The specifically bound radioactivity (SB) at each time point was then expressed as the percent of the specific binding observed at t=0. Aggregate data from four (FIG. 1A), five (FIG. 1B), or three (FIG. 1C) experiments are shown. Curves were fit to the data using either a two-phase (FIGS. 1A and 1B) or single phase (FIG. 1C) exponential decay equation.

We have discovered a correlation between (i) the ability of a GPCR ligand to bind a GPCR when uncoupled to a G-protein (the $R^0$ state) and (ii) the length of time over which the ligand activates the receptor. In particular, an enhanced ability of a ligand to interact in vitro with the exemplary GPCR, the PTH/PTHrP receptor (PTHR), uncoupled to a G-protein (the $R^0$ form), as compared to PTH or PTHrP, closely correlates its ability to exert more prolonged activity in vivo. The reverse is also true, i.e., that ligands selective for the G-protein coupled forms of GPCR (the RG form) have a shorter duration of activity as compared to the native ligand. This discovery provides the basis for a novel means of determining whether a compound has either long-acting or shorting-acting in vivo activity on a GPCR. On this basis, ligands with therapeutically desirable properties (e.g., long-acting or short-acting ligands) can be identified using the methods described herein. Exemplary ligands with either long-acting or short-acting activity are described herein.

Depending on the disease being treated, long-acting or short-acting therapeutics are desirable. Recent studies using PTHrP(1-36) injected in humans show that bone mineral density increased to about the same extent as with PTH(1-34), the standard therapy for osteoporosis, but without inducing the bone-resorptive responses that would be expected for an equivalent dose of PTH(1-34) (Horwitz et al., *J. Endocrinol. Metab.* 88:569-575 (2003)). Related studies from this group suggest that the differences are not likely based solely on pharmacokinetics, as an acute safety study indicated that PTHrP(1-36) could be administered at doses nearly 20-fold above the usual dose of PTH(1-34) without producing a hypercalcemic effect (Horwitz et al., *Osteoporosis Int.*

17:225-230 (2006)). While both PTHrP(1-36) and PTH(1-34) exhibit similar receptor binding to the RG form of the PTHR, our discovery that PTHrP binds less strongly to the $R^0$ form of the PTHR and correspondingly exhibits less prolonged activity in vivo as compared to PTH can explain the difference. Accordingly, we believe that RG selective ligands of PTHR (i.e., with relatively low $R^0$ affinity) will prove useful for treatment of osteoporosis.

In other situations, a longer acting ligand may be desirable. For example, PTHrP is less effective than PTH(1-34) in stimulating renal production of 1,25,$(OH)_2$vitamin D (Horwitz et al., *J. Bone Mineral. Res.* 20:1792-1803 (2005)), suggesting that PTH(1-34) may be more effecting in treating disease where long-acting PTHR signaling is desired. Such diseases include certain forms of hypoparathyroidism caused by activating mutations in the calcium-sensing receptor. Currently, treating this disease requires twice daily injections of PTH(1-34) (Winer et al., *J. Clin. Endocrinol. Metab.* 88:4214-4220 (2003)). By using the screening methods of the invention, it becomes possible to identify longer acting PTHR ligands, which can prove highly useful in the treatment of such diseases and may allow for less frequent administration of the drug.

PTH(1-34), via its greater capacity to bind stably to $R^0$, may be able to induce a cumulatively greater signaling response in target bone and kidney cells than does PTHrP, and this difference in $R^0$ selectivity then leads to a divergence in biological responses, such as the induction in osteoblasts of factors (RANK Ligand) involved in stimulating osteoclastic bone resorption, and the stimulation in renal proximal tubule cells of 1-α-hydroxylase mRNA synthesis. According to these considerations, a ligand that binds with particularly high selectivity to the RG (versus $R^0$)PTHR conformation might be highly effective in stimulating bone formation responses, and thus useful for treating osteoporosis.

Thus, the two ligands preferentially stabilize distinct receptor conformations. There is now much discussion in the GPCR field regarding the capacity of structurally varied ligands for a given receptor to exhibit altered selectivities for distinct receptor conformations, and thus produce distinct biological effects (Kenakin, T. Sci STKE 342:pe29 (2006)). The results of the kinetic and equilibrium binding assays performed herein suggest that whereas PTH(1-34) and PTHrP(1-36) bind with similar affinities to the G protein-coupled PTHR conformation, RG, PTH(1-34) exhibits a greater capacity to bind to the G protein-uncoupled conformation, $R^0$, defined as a receptor conformation that has the capacity to bind ligand with high affinity in the presence in GTPγS (5,14), than does PTHrP(1-36).

The delayed cAMP assays presented herein demonstrate that altered selectivity for distinct PTHR conformations can lead to altered signaling responses in PTHR-expressing cells. Thus, PTH(1-34) and $Ile^5$-PTHrP(1-36) induced more prolonged, and cumulatively greater, cAMP signaling responses in PTHR-expressing cells. PTH(1-34) and $Ile^5$-PTHrP(1-36), which also have a greater capacity to stabilize $R^0$ than PTHrP (1-36), can induce more prolonged signaling responses due to the eventual coupling of the $LR^0$ complex to a heterotrimeric G protein ($LR^0$-LRG) and activation of the corresponding signaling cascade. Another potential mechanistic consequence of stable $LR^0$ binding is that it may permit multiple (catalytic) rounds of G protein activation, by which an $LR^0$ complex is preserved after successive cycles of G protein coupling, activation and release (Rodbel, M. Adv. Enzyme Regul, 37: 427-435 (1997); Heck and Hofmann, *J. Biol. Chem.* 276:10000-10009 (2001)).

Figures 7A, 7B:
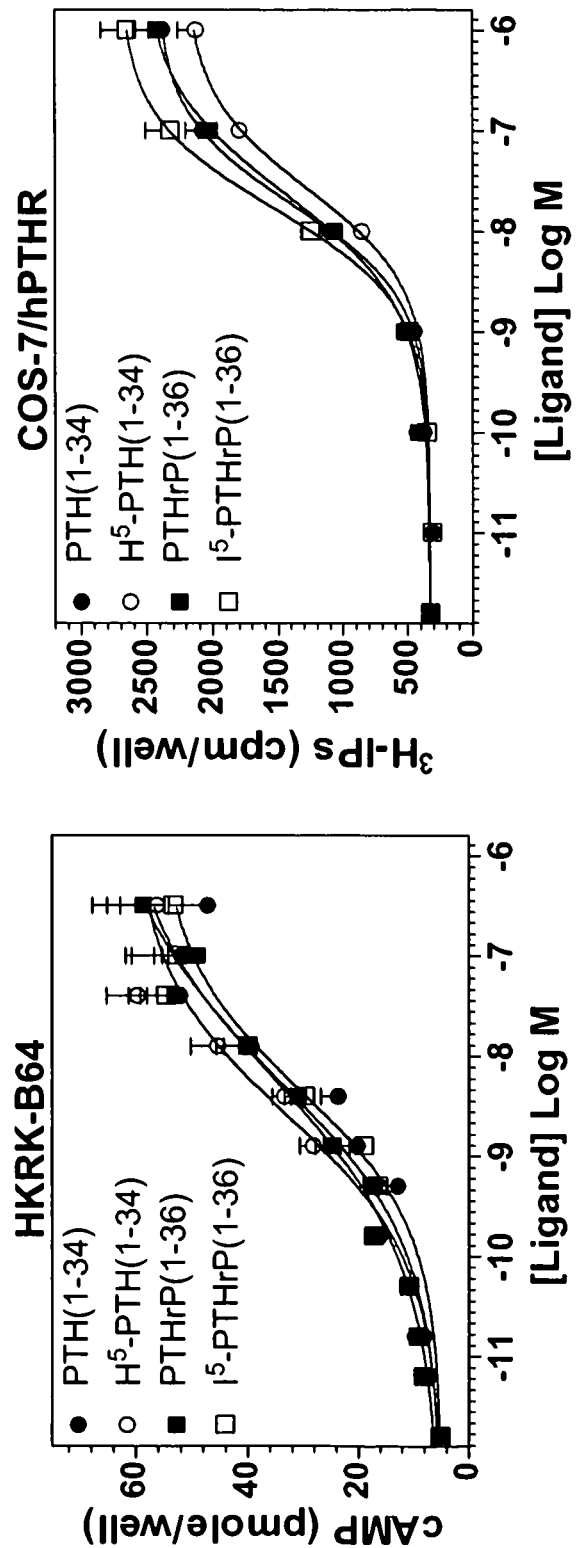
FIGS. 7A and 7B shows a dose-response analysis of analog signaling potency. The capacity of PTH and PTHrP ligands to stimulate cAMP formation was assessed in HKRK-B64 cells (FIG. 7A). Cells were treated for 30 minutes at room temperature with varying concentrations of ligand in the presence of IBMX. The capacity of the ligands to stimulate the production of inositol phosphates (IPs) was assessed in COS-7 cells transiently transfected with the hPTHR (FIG. 7B). Cells were treated for 30 minutes at room temperature with varying concentrations of ligand. The ligands used were [Nle$^{8,21}$, Tyr$^{34}$]rPTH(1-34)NH$_2$ (SEQ ID NO:123); [His$^5$,Nle$^{8,21}$, Tyr$^{34}$]rPTH(1-34)NH$_2$ (SEQ ID NO:127); [Tyr$^{36}$]hPTHrP(1-36)NH$_2$ (SEQ ID NO:124) and [Ile$^5$,Tyr$^{36}$]hPTHrP(1-36) NH$_2$ (SEQ ID NO:125). Data are means (±s.e.m.) of four (FIG. 7A) or five (FIG. 7B) experiments, each performed in duplicate. The EC$_{50}$ and Emax values are reported in Table 6 and were not significantly different between peptides, with the exception of the cAMP EC$_{50}$ values for H$^5$-PTH(1-34) and PTH(1-34) analogs (P=0.02).

Little if any difference in the potencies with which PTH(1-34) and PTHrP(1-36) ligands stimulated cAMP and inositol phosphate responses was detected when the ligands were assessed in conventional dose-response, cAMP and inositol phosphate stimulation assays performed in cells at a single-time-point (FIG. 7). These results are consistent with the view that the two ligands interact with the PTHR via the same, or similar mechanisms. The time-delayed cAMP assays thus identified previously unappreciated differences in the second-messenger signaling properties of the two ligands, evident as differences in the cumulative signal output over time. While the agonist-activated PTHR is known to be subject to desensitization processes involving receptor phosphorylation, beta-arrestin recruitment, and receptor internalization (Biselo, A. et al., (2002); Tawfeek et al., *Mol. Endocrinol.* (2002); Castro et al., *Endocrinology* 143:3854-3865 (2002); Chauvin et al., *Mol. Endocrinol.* 16:2720-2732 (2002)), it is not expected that such a process would operate on receptors in the $R^0$ conformation, as these are, by definition, functionally inactive, at least in terms of G protein coupling. Nevertheless, the possibility that the effects observed in our delayed cAMP assays of FIG. 5 involve, to some extent, differential effects of the ligands on such receptor desensitization mechanisms cannot be excluded.

In general, a stable $LR^0$ binding capacity might facilitate, or augment, the signaling potential of a ligand in target cells that express a low level of the cognate heterotrimeric G protein, relative to the target receptor. It may also facilitate coupling to "secondary" G proteins that presumably have lower affinity for the ligand-receptor complex than does the primary G protein. For the PTHR, this could involve coupling to $G\alpha_{q/11}$, $G\alpha_{i/o}$, or $G\alpha_{12/13}$, each of which has been shown to be activated by the PTHR in response to PTH(1-34). While PTHrP has at least some capacity to bind $R^0$ (FIGS. 3A-3D) and activate delayed cAMP signaling (FIGS. 5A and 5B), the binding is less than that of PTH(1-34). Indeed, some capacity to form a stable $LR^0$ complex may be an intrinsic property of the class B GPCRs, as several of these, including the receptors for calcitonin (Hilton et al., *J. Endocrinol.* 166:213-226 (2002)), corticortropin-releasing hormone (Hoare et al., *Peptides* 24:1881-1897 (2003)) and glucagon (Post et al., *J. Biol. Chem.* 267:25776-25785 (1992)) have been shown to form a stable complex with their cognate peptide ligand in the presence of a non-hydrolyzable guanine nucleotide analog.

The findings described herein may also relate to the mechanisms by which PTH and PTHrP function in normal physiology. PTH, as an endocrine hormone, acts on target cells (in bone and kidney) that are distal from its site of secretion (the parathyroid glands). Concentrations of PTH in the serum, while varying marginally as $Ca^{++}$ levels fluctuate, generally stay within the low picomolar range, well below the affinity with which PTH binds to its receptor. The capacity of PTH to bind stably to the receptor even in the uncoupled, $R^0$ conformation may be an evolutionary adaptation that helps to ensure a response to even minimal increases in the ligand's concentration. By contrast, PTHrP, as a paracrine factor, acts on cells within the same tissue in which it is produced (e.g., the growth-plate chondrocytes of developing long bones). The concentrations of PTHrP in such tissues have not been directly quantified, but they appear to form a gradient across the zones of differentiating cells and high near the sites of production (Chen et al., *J. Bone Miner. Res.* 21:113-123 (2006)). It may be that, as an adaptation for its role in controlling the differentiation events that occur in these cells, PTHrP evolved to bind to the receptor only transiently, so as to induce a relatively short-lived, and more easily timed, signaling response.

G-Protein-Coupled Receptors

The present invention can use any G-protein-coupled receptor. Long-acting and short-lived ligands may be assayed as described herein and useful therapeutic candidates identified. Hundreds of such receptors are known in the art; see, e.g., Fredriksson et al., *Mol. Pharmacol.* 63:1256-1272, 2003, which is hereby incorporated by reference. This reference has characterized the human GPCRs based on sequence homology and function. Human GPCRs can be broken down into five classes: secretin, rhodopsin, glutamate, frizzled/Tas2, and adhesion. Alternatively, receptors may be classified by their ligands, e.g., peptide hormones or small molecules (e.g., biogenic amines). Other classification schemes include the A-F classification, where class A represents receptors related to rhodopsin and the adrenergic receptors, class B, receptors related to the calcitonin and parathyroid hormone receptors, class C, receptors related to the metabotropic receptors, and classes D-F represent receptors found in fungi and archaebacteria.

Using the Fredriksson classification, the secretin receptors have four main subgroups: the CRHRs/CALCRLs, the PTHRs, GLPRs/GCGR/GIPR and the subgroup including secretin and four other receptors. Secretin receptors include the PTHR, as well as the calcitonin receptor (CALCR), the corticotropin-releasing hormone receptors (CRHRs), the glucagon receptor (GCGR), the gastric inhibitory polypeptide receptor (GIPR), the glucagon-like peptide receptors (GLPRs), the growth hormone-releasing hormone receptor (GHRHR), pituitary adenylyl cyclase-activating protein (PACAP), the secretin receptor (SCTR), and vasoactive intestinal peptide receptor (VIPR).

The adhesion receptors feature GPCR-like transmembrane-spanning regions fused together with one or several functional domains with adhesion-like motifs in the N terminus, such as EGF-like repeats, mucin-like regions, and conserved cysteine-rich motifs. Members of this family include the CELSRs (EGF LAG seven-pass G-type receptors), the brain-specific angiogenesis-inhibitory receptors (BAIs), the lectomedin receptors (LECs) and the EGF-like module containing (EMRs). Other receptors include the CD97 antigen receptor (CD97) and EGF-TMVII-latrophilin-related (ETL). These receptors also include HE6 (TMVIILN2) and GPR56 (TMVIIXN1 or TMVIILN4) and a group of recently discovered receptors, related to GPR56 and HE6, named GPR97 and GPR110 to GPR116.

The glutamate receptors consists of eight metabotropic glutamate receptors (GRM), two GABA receptors (e.g., GAB-AbR1, which has two splice variants, a and b, and GAB-AbR2), a single calcium-sensing receptor (CASR), and five receptors believed to be taste receptors (TAS1). Other GPCRs include opioid, muscarinic, dopamine, adrenergic, cAMP, opsins, angiotensin, serotonin, thyrotropin, gonadotropin, substance-K, substance-P and substance-R, and melanocortin, metabotropic glutamate receptors.

The largest group is the rhodopsin receptor family, which includes at least 701 human receptors, 241 of which are non-olfactory. Receptors in this group include various acetylcholine (muscarinic) receptors, adrenergic receptors, dopamine receptors, histamine receptors, serotonin receptors, and octopamine receptors; peptide receptors, e.g., angiotensin, bombesin, bradykinin, endothelin, interleukin-8, chemokine, melanocortin, neuropeptide Y, neurotensin, opioid, somatostatin, tachykinin, thrombin, vasopressin, galanin, proteinase-activated, orexin, and chemokine/chemotatic factor receptors; protein hormone receptors, e.g., FSH, lutropin-choriogonadotropic hormone, and thyrotropin receptors; rhodopsin receptors; olfactory receptors; prostanoid receptors; nucleotide-like receptors, including adenosine and purinoceptors; cannabis receptors; platelet activating factor receptor; gonadotropin-releasing hormone receptor; melatonin receptor, lysosphingolipid and LPA (EDG) receptors, as well as various orphan receptors.

Candidate Compounds

Any type or source of compound may be used in the screening methods of the invention. For example, naturally occurring chemicals (e.g., from a chemical library), peptides, modified peptide hormones, antibodies, nanobodies, chimeric peptides, and fragments of endogenous ligands (e.g., peptide ligands) may all be used in the present invention. Approaches involving random screening, such as natural libraries of compounds, or designed ligands (e.g., ligands based on the PTH sequence) may be used in the screening methods of the invention. In some embodiments, antibodies or nanobodies can be generated against the GPCR or a ligand binding fragment of the GPRC using methods known in the art.

Modified Receptor Agonists

One strategy for identification of new receptor agonists is the modification of existing agonists. Peptide hormones can be modified by point mutations, truncations, insertions, and generation of chimeric peptides. Using the PTH receptor, for example, many modified PTH and PTHrP sequences are known in the art. Peptides can made either recombinantly or synthetically, as is known in the art. See, for example, U.S. Pat. Nos. 7,057,012, 7,022,815, 6,417,333, 6,495,662, hereby incorporated by reference, which describe various PTH sequences, as well as any of those described herein. These sequences can include chimeric peptides. In one particular example, any agonist may be fused to an antibody or antibody fragment (such as an Fc fragment) to generate a candidate therapeutic.

Antibodies and Nanobodies

Antibodies or nanobodies which bind the GPCR can also be used in the methods of the invention and can be raised against the GPCR or a fragment thereof (e.g., a ligand-binding portion of the GPCR) using any method known in the art. In one example, an IgG directed to a GPCR or fragment thereof can be generated in New Zealand white rabbits using a purified protein. The initial immunization protocol consists of an initial intramuscular injection of 10-20 µg purified protein, followed by a boosting immunization 21 days later. Further boosts and/or the addition of adjuvant may be used if no or few antibodies are detected. Antibodies may be quantified by ELISA, analogous to that described (Siber et al., J. Infect. Dis. 152:954-964, 1985; Warren et al., J. Infect. Dis. 163:1256-1266, 1991). IgG may be purified from the rabbit antiserum, for example, by precipitation in 50% ammonium sulfate followed by affinity chromatography on Protein G sepharose 4B (Pharmacia). Monoclonal antibodies to GPCRs can be produced using hybridoma technology. Nanobodies can be generated by immunization of an animal (e.g., a camel or llama) which produce nanobodies, which can then be purified using standard techniques. These antibodies or nanobodies would be screened as described herein for those agonistic molecules that produce long-lived or short-acting effects.

Test Compounds and Extracts

In general, compounds capable of binding a GPCR (e.g., PTHR) are identified from large libraries of both natural product or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and polynucleotide-based compounds. Synthetic compound libraries are commercially available. Alternatively, libraries of natural compounds in the form of bacterial, fungal, plant, and animal extracts are commercially available. In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activity in treating metabolic disorders should be employed whenever possible.

When a crude extract is found to bind the GPCR in its RG state, and either exhibits altered binding (e.g., higher affinity or lower affinity) as compared to the endogenous ligand when the receptor is in its $R^0$ state, further fractionation of the positive lead extract is necessary to isolate chemical constituents responsible for the observed effect. Thus, the goal of the extraction, fractionation, and purification process is the characterization and identification of a chemical entity within the crude extract having activity that may be useful in treating a metabolic disorder (e.g., diabetes and obesity). Methods of fractionation and purification of such heterogenous extracts are known in the art. If desired, compounds shown to be useful agents in the screening methods of the invention are chemically modified according to methods known in the art.

Such test compounds include naturally occurring or synthetic chemical compounds, (including small molecules) as well as amino acid or nucleic acid aptamers. Any of these compounds may include synthetic or modified amino acids or nucleic acids.

Contacting a Receptor with a Candidate Compound

In the screening method of the present invention, a candidate compound is contacted with a GPCR. The receptor may be found on a cell (e.g., in an organism), or a in a membrane preparation. Alternatively, the receptor may be isolated in functional form (Shimada et al., *J. Biol. Chem.* 277:31,774-31780, 2002).

Cells which either naturally express the GPCR of interest (e.g., PTHR) or express the receptor recombinantly can be used in the methods of the invention. Alternatively, or in addition, the cells can be tranfected (e.g., using any method known in the art) to express a recombinant gene encoding the GPCR. Cells expressing a particular GPCR can also be obtained commercially, for example, from Millipore (ChemiScreen™ cell lines).

In other embodiments, the receptor is present in a membrane preparation (e.g., cell free) which contains the GPCR of interest. Such preparations are commercially available; see, e.g., the ChemiSCREEN™ receptor preparations available from Millipore. Membrane preparations can also be produced using methods known in the art (see, e.g., Mills et al., *J. Biol. Chem.* 263:13-16, 1988).

If purified receptor components are utilized, candidate compound are contacted with the receptor or receptor complex in vitro.

Assay Readout—Measuring Ligand Binding or Activity

Any method for analysis of ligand binding or ligand activity may be used in the methods of the invention; the particular readout is not critical. In some embodiments, ligand binding to the GPCR is measured by displacement of a radiolabeled ligand by a non-labeled compound and measuring the radioactivity of the cell or membrane preparation before and after treatment with the non-labeled compound. In general, this approach involves incubating the membranes and radioligand to allow complex formation. Dissociation phase can be initiated by the addition of excess unlabeled compound. Immediately prior to the addition (t=0), and at successive timepoints thereafter, aliquots can be withdrawn and immediately processed by vacuum filtration. Non-specific binding is determined in parallel reaction tubes containing the unlabeled compound in both the pre-incubation and dissociation phases. The specifically bound radioactivity at each time point can be calculated as a percent of the radioactivity specifically bound at t=0. Such dissociation methods are well suited to large scale screening (e.g., libraries of candidate compounds).

As described in Example 1 below, other methods such as FRET can also be used to measure ligand binding to a receptor. In one application, two fluorescent molecules are conjugated to the receptor such that ligand binding results in a conformational change in the receptor that can be detected by a change in FRET signal. FRET allows for real time measurement of ligand binding and is thus useful in the assays of the invention.

Other readouts include measurements of cAMP activity including the delayed cAMP activity assay described herein, which indirectly measures binding of the compound to the RG form of the receptor. Intracellular cAMP levels can be measured using a radioimmuno assay, e.g., as described by Shimizu et al. (*J. Biol. Chem.* 276:49003-49012 (2001)). Briefly, this method includes treatment with a candidate compound, rinsing with 0.5 ml of binding buffer (50 mm Tris-HCl, 100 mM NaCl, 5 mM KCl, 2 mM $CaCl_2$, 5% heat-inactivated horse serum, 0.5% fetal bovine serum, adjusted to pH 7.7 with HCl), and treating with 200 µl of cAMP assay buffer (Dulbecco's modified Eagle's medium containing 2 mM 3-isobutyl-1-methylxanthine, 1 mg/ml bovine serum albumin, 35 mm Hepes-NaOH, pH 7.4) and 100 µl of binding buffer containing varying amounts of the candidate compound (final volume=300 µl). The medium can then be removed after incubation for 30-60 min at room temperature. The cells can then be frozen, lysed with 0.5 ml 50 mM HCl, and refrozen (at −80° C.). The cAMP content of the diluted lysate can be determined by radioimmunoassay. The $EC_{50}$ response values can be calculated using nonlinear regression.

Any suitable physiological change that affects GPCR activity can be used to assess the influence of a test compound on GPCR activity. When the functional consequences are determined using intact cells or animals, a variety of effects such as transmitter release, hormone release, transcriptional changes to both known and uncharacterized genetic markers (e.g., northern blots), changes in cell metabolism such as cell growth or pH changes, and changes in intracellular second messengers such as $Ca^{++}$, $IP_3$, or cAMP, can also be measured.

In one embodiment, the changes in intracellular cAMP can be measured using immunoassays. The method described in Offermanns and Simon, *J. Biol. Chem.* 270:15175-15180 (1995), may be used to determine the level of cAMP. Assay kits for measuring cAMP as described in U.S. Pat. No. 4,115,538, herein incorporated by reference, can also be used. Other assays that may be used include measuring in vivo changes in serum/urinary calcium, phosphate, and markers of bone-turn-over (e.g., deoxypridonoline crosslinks), decreases in serum reciprocal changes in urine.

Measuring $R^0$ or RG Binding

The methods of the present invention involve measurement of binding of a candidate compound to the RG or $R^0$ form of the GPCR (e.g., PTHR). Thus, the readout of the assay can distinguish between the affinity of the compound for each form of the receptor. One possible approach is to use a system or condition where one receptor conformation is favored. $R^0$ can be favored, for example, by forced dissociation of the GPCR from its G-protein, or using a system that lacks G-proteins. One manner in which dissociation of the GPCR from G-proteins can be achieved is by treatment with a compound that prevents binding of the G-protein to its GPCR. Such compounds include nucleotide analogs such non-hydrolyzable nucleotide analogs including GTPγS. GTPγS binds the G-protein, but as it is unable to hydrolyze this compound, the G-protein cannot recycle itself back on the GPCR. Thus, by contacting a cell or cell membrane with GTPγS prior to addition of the candidate compound, it is possible to generate a system in which the $R^0$ state of the GPCRs is highly favored.

To stabilize the RG form of the GPCR, dominant-negative G-proteins can be used. These proteins bind the GPCR in a stable manner, and thus enrich for the RG conformation.

Other approaches to modulate the ratio between $R^0$ and RG include using cells from animals in which expression of one or more G-proteins has been downregulated or eliminated. Genetic knockout technologies are well known in the art and can be used to target specific G-proteins (see, e.g., Dean et al., *Mol. Endocrinol.* 20:931-943 (2006)). In other embodiments, RNAi techniques (e.g., administration of siRNA to a cell) can be used to "knock down" expression of G-proteins, thereby favoring the $R^0$ state of the receptor. Alternatively, it may be possible to favor the RG form by overexpressing the appropriate G protein or G-proteins in a cell.

A second approach for measuring the ability of a compound to bind either the $R^0$ or RG state involves displacement of a ligand known to be selective for a particular state. In the case of the PTH receptor, previous work has shown that $^{125}I$-[$Aib^{1,3}$,M]PTH(1-15) (SEQ ID NO:126) is selective for the RG state. By measuring ligand displacement by a candidate compound of a such ligand, the binding of the compound to that state can be specifically measured, even if the receptor is present in both the RG and the $R^0$ states in the assay.

Compounds identified in the methods of the invention typically bind to the RG form of the receptor with at least 5%, (e.g., at least 10%, 20%, 50%, 100%, 500%, 1000%, 10,000%) of the activity of an endogenous receptor for either long-acting or short-lived agonists. For example, human PTH binds the human PTHR with an EC50 of about 0.13 nmol. Thus desirable compounds typically bind the hPTHR with at least 10% of this affinity, i.e., at least 1.3 nmol EC50.

Ligands Identified Using the Methods of the Invention

Using the screening methods described herein, we have identified a variety of ligands for the exemplary GPCR, the PTH receptor, representing different combinations of either class of peptide (PTH/PTHrP hybrids) chosen on the basis of their relative $R^0$/RG selectivity to be either short-acting ligands or long-acting ligands (FIGS. 26A and 26B). Based on the results of our screening assay, we then tested these peptides for in vitro and in vivo activity to demonstrate proof of concept of the importance of $R^0$/RG selectivity in determining biological activity of the ligand.

The identified peptides represent proof of concept for the PTH receptor and other GPCRs that $R^0$/RG selectivity determines biological action in vivo. These peptides include five different classes. A first class is typified by $Ile^5$-PTHrP, an analog that converts PTHrP to a form with high $R^0$ selectivity and prolonged action. A second class includes hybrid peptides with high $R^0$/RG selectivity composed of MPTH(1-11) combined with PTHrP(12-36) or MPTH(1-14) with PTHrP(15-36). These peptides have very prolonged biological activity in vivo. The third type is [$His^5$,$Arg^{19}$]PTH, which illustrates shorter acting biological activity due to its reduced $R^0$ affinity. A fourth class of compounds is exemplified by $Ala^1$, $Aib^3$-M-PTH(1-28) (SEQ ID NO:11), which has a potent $R^0$-activating activity, as well as striking activity to promote urinary phosphate excretion, a property desirable in the treatment of disorders associated with high phosphate retention. A fifth class is typified by $Ala^{23}$-PTH, which has a much lower $R^0$ affinity and therefore more desirable for the treatment of osteoporosis.

For the PTH receptor ligands, we have identified ligands with variety of $R^0$ and RG binding affinities and various $R^0$/RG selectivities. Exemplary peptides, sorted by $R^0$ affinity are shown in FIG. 26B. The affinity for the $R^0$ form of the receptor may be at least 2000, 1000, 750, 500, 250, 150, 100, 90, 75, 50, 40, 30, 25, 20, 15, 10, 9, 8, 7, 6, 5, 4, 3, 2.5, 2, 1.5, 1, 0.5, 0.2, 0.1, or 0.05 nmol. The affinity for the RG form of the receptor may be at least 100, 50, 25, 20, 15, 10, 9, 8, 7, 6, 5, 4, 3, 2.5, 2, 1.75, 1.5, 0.125, 1, 0.9, 0.8, 0.7, 0.6, 0.5, 0.4, 0.3, 0.25, 0.2, 0.15, 0.1, 0.075, 0.05, 0.025 nmol. The selectivity of $R^0$/RG may be (where a higher values indicates greater RG-selectivity) at least 0.5, 1, 2, 3, 4, 5, 8, 10, 15, 20, 25, 30, 40, 50, 60, 75, 100, 150, 200, 250, 400, 500, 750, 1000, 1250, 1500, 2000, 2500, or 5000. Ligands of the invention may have any of the RG or $R^0$ affinities described herein, or any combination thereof.

RG and $R^0$ Selective Ligands

Using the screening methods described herein, we have developed new RG selective and $R^0$ selective ligands. In one example, we used PTHrP(1-28) (SEQ ID NO:151) as a starting point, as PTHrP binds to the RG receptor conformation with greater selectivity as compared to PTH. Table 2 summarizes the in vitro activities of particular analogs; additional analogs are shown in Table 3. More detailed information regarding these analogs are described below in Example 3. These analogs, A(E)18, A22, (L25), K26-PTHrP(1-28) or (1-30) generally exhibit enhanced potency for cAMP generation, and bind with relatively high selectivity to the RG conformation, as compared to PTHrP(1-36) (Table 2).

TABLE 2

In vitro activities of representative PTHrP analogs

| Analog | SEQ ID NO: | SaOS cAMP EC50 (nM) | MC3T3-E1 cAMP EC50 (nM) | RG binding affinity hPTHR IC50 (nM) | $R^0$ binding affinity hPTHR IC50 (nM) | R0/RG selectivity |
|---|---|---|---|---|---|---|
| PTHrP(1-36) | 6 | 0.190 | 0.322 | 0.33 | 74.8 | 229 |
| PTHrP(1-28) | 151 | 20.3 | 4.09 | 0.66 | 20449 | 31069 |
| A18,22,K26-PTHrP(1-28) | 56 | 0.024 | 0.091 | 0.10 | 1815 | 18079 |
| E18,A22,K26-PTHrP(1-28) | 65 | 0.241 | 0.251 | 0.24 | 9237 | 38327 |
| A18,22,L25,K26-PTHrP(1-28) | 76 | 0.002 | 0.054 | 0.04 | 310 | 6971 |
| E18,A22,L25,K26-PTHrP(1-28) | 83 | 0.010 | 0.083 | 0.10 | 1741 | 18317 |
| A18,22,L25,K26-PTHrP(1-30) | 89 | 0.008 | 0.067 | 0.05 | 144 | 3025 |
| E18,A22,L25,K26-PTHrP(1-30) | 90 | 0.063 | 0.059 | 0.08 | 945 | 11169 |

Additional peptides and binding/activity data for such peptides are shown in Table 3 below.

TABLE 3

Binding/activity of PTHrP analogs

| Sequence (parent shown in bold) | SEQ ID NO: | screen cAMP (% parent)[1] | screen human PIR RG (% parent)[2] | screen human PIR R0 (% parent)[2] | dose-response cAMP in SaOS (EC50, nM) | dose-response cAMP in MC3T3-E1 (EC50, nM) | human PIR RG (IC50 nM) | human PIR R0 (IC50 nM) | rat PIR RG (IC 50 nM) | rat PIR R0 (IC 50 nM) |
|---|---|---|---|---|---|---|---|---|---|---|
| PTHrP(1-28)NH | 151 | | | | | | | | | |
| A18-PTHrP(1-28)NH | 34 | 164 | | | | | | | | |
| S18-PTHrP(1-28)NH | 35 | 121 | | | | | | | | |
| M18-PTHrP(1-28)NH | 36 | 113 | | | | | | | | |
| F18-PTHrP(1-28)NH | 37 | 109 | | | | | | | | |
| E18-PTHrP(1-28)NH | 38 | 140 | | | | | | | | |
| A22-PTHrP(1-28)NH | 39 | 185 | | | | | | | | |
| S22-PTHrP(1-28)NH | 40 | 141 | | | | | | | | |
| L22-PTHrP(1-28)NH | 41 | 142 | | | | | | | | |
| N22-PTHrP(1-28)NH | 42 | 138 | | | | | | | | |
| W22-PTHrP(1-28)NH | 43 | 129 | | | | | | | | |
| E22-PTHrP(1-28)NH | 44 | 121 | | | | | | | | |
| K22-PTHrP(1-28)NH | 45 | 150 | | | | | | | | |
| A26-PTHrP(1-28)NH | 46 | 142 | | | | | | | | |
| S26-PTHrP(1-28)NH | 47 | 107 | | | | | | | | |
| N26-PTHrP(1-28)NH | 48 | 113 | | | | | | | | |
| K26-PTHrP(1-28)NH | 49 | 142 | | | | | | | | |
| R26-PTHrP(1-28)NH | 50 | 143 | | | | | | | | |
| L25-PTHrP(1-28)NH | 51 | 325 | | | | | | | | |

TABLE 3-continued

Binding/activity of PTHrP analogs

| Sequence (parent shown in bold) | SEQ ID NO: | screen cAMP (% parent)[1] | screen human PIR RG (% parent)[2] | screen human PIR R0 (% parent)[2] | dose-response cAMP in SaOS (EC50, nM) | dose-response cAMP in MC3T3-E1 (EC50, nM) | dose-response human PIR RG (IC50 nM) | dose-response human PIR R0 (IC50 nM) | dose-response rat PIR RG (IC50 nM) | dose-response rat PIR R0 (IC50 nM) |
|---|---|---|---|---|---|---|---|---|---|---|
| W25-PTHrP(1-28)NH | 52 | 270 | | | | | | | | |
| K25-PTHrP(1-28)NH | 53 | 163 | | | | | | | | |
| R25-PTHrP(1-28)NH | 54 | 204 | | | | | | | | |
| A18,22,26-PTHrP(1-28)NH | 55 | 343 | 167 | 160 | | | | | | |
| A18,22,K26-PTHrP(1-28)NH | 56 | 405 | 193 | 178 | 0.024 | 0.091 | 0.10 | 1815 | | |
| A18,26,S22-PTHrP(1-28)NH | 57 | 229 | 148 | 133 | | | | | | |
| A18,S22,K26-PTHrP(1-28)NH | 58 | 372 | 175 | 15 | 0.038 | | | | | |
| A18,26,N22-PTHrP(1-28)NH | 59 | 265 | 161 | 136 | | | | | | |
| A18,N22,K26-PTHrP(1-28)NH | 60 | 326 | 172 | 139 | | | | | | |
| A18,26,L22-PTHrP(1-28)NH | 61 | 252 | 163 | 133 | | | | | | |
| A18,L22,K26-PTHrP(1-28)NH | 62 | 350 | 177 | 160 | | | | | | |
| A18,26,W22-PTHrP(1-28)NH | 63 | 188 | 120 | 126 | | | | | | |
| A18,W22,K26-PTHrP(1-28)NH | 64 | 267 | 115 | 136 | | | | | | |
| E18,A22,K26-PTHrP(1-28)NH | 65 | 301 | 145 | 68.8 | 0.241 | 0.251 | 0.24 | 9237 | | |
| E18,S22,A26-PTHrP(1-28)NH | 66 | 119 | 132 | 31.9 | | | | | | |
| E18,N22,A26-PTHrP(1-28)NH | 67 | 171 | 140 | 53.7 | | | | | | |
| E18,N22,K26-PTHrP(1-28)NH | 68 | 236 | 147 | 84.4 | | | | | | |
| E18,L22,A26-PTHrP(1-28)NH | 69 | 139 | 125 | 52.5 | | | | | | |
| E18,L22,K26-PTHrP(1-28)NH | 70 | 264 | 152 | 64.4 | | | | | | |
| E18,W22,A26-PTHrP(1-28)NH | 71 | 75 | 116 | 18.8 | | | | | | |
| E18,W22,K26-PTHrP(1-28)NH | 72 | 165 | 149 | 46.6 | | | | | | |
| E18,K22,A26-PTHrP(1-28)NH | 73 | 315 | 192 | 106.1 | | | | | | |
| E18,K22,26-PTHrP(1-28)NH | 74 | 374 | 208 | 119.8 | | | | | | |
| E18,A22,26-PTHrP(1-28)NH | 75 | 190 | | | | | | | | |
| A18,22,L25,K26-PTHrP(1-28)NH | 76 | 305 | | | 0.002 | 0.054 | 0.04 | 310 | 0.16 | 34.9 |
| A18,22,K25,26-PTHrP(1-28)NH | 77 | 349 | | | 0.012 | | | | | |
| A18,22,I25,K26-PTHrP(1-28)NH | 78 | 342 | | | | | | | | |
| A18,22,W25,K26-PTHrP(1-28)NH | 79 | 329 | | | | | | | | |
| A18,22,F25,K26-PTHrP(1-28)NH | 80 | 337 | | | | | | | | |
| A18,S22,L25,K26-PTHrP(1-28)NH | 81 | 367 | | | 0.009 | | 0.10 | 540 | | |
| A18,S22,K25,26-PTHrP(1-28)NH | 82 | 316 | | | 0.015 | | | | | |
| E18,A22,L25,K26-PTHrP(1-28)NH | 83 | 340 | | | 0.010 | | 0.10 | 1741 | | |
| E18,A22,K25,26-PTHrP(1-28)NH | 84 | 323 | | | 0.054 | | | | | |
| E18,S22,L25,K26-PTHrP(1-28)NH | 85 | 337 | | | 0.055 | | 0.11 | 2056 | | |

TABLE 3-continued

Binding/activity of PTHrP analogs

| Sequence (parent shown in bold) | SEQ ID NO: | screen cAMP (% parent)[1] | screen human PIR RG (% parent)[2] | screen human PIR R0 (% parent)[2] | cAMP in SaOS (EC50, nM) | cAMP in MC3T3-E1 (EC50, nM) | human PIR RG (IC50 nM) | human PIR R0 (IC50 nM) | rat PIR RG (IC 50 nM) | rat PIR R0 (IC 50 nM) |
|---|---|---|---|---|---|---|---|---|---|---|
| E18,S22,K25,26-PTHrP(1-28)NH | 86 | 335 | | | | | | | | |
| PTHrP(1-30)NH | 183 | | | | | | | | | |
| A18,22,K26-PTHrP(1-30)NH | 87 | | | | | 0.058 | | | | |
| E18,A22,K27-PTHrP(1-30)NH | 88 | | | | | 0.082 | | | | |
| A18,22,L25,K26-PTHrP(1-30)NH | 89 | | | | | 0.067 | 0.05 | 144 | 0.13 | 11.1 |
| E18,A22,L25,K26-PTHrP(1-30)NH | 90 | | | | | 0.059 | 0.08 | 945 | 0.21 | 76.3 |
| PTHrP(1-31)NH | 184 | | | | | | | | | |
| A18,22,K26-PTHrP(1-31)NH | 91 | | | | | 0.060 | | | | |
| E18,A22,K27-PTHrP(1-31)NH | 92 | | | | | 0.060 | | | 0.23 | 54.8 |
| A18,22,L25,K26-PTHrP(1-31)NH | 93 | | | | | 0.20 | | | | |
| E18,A22,L25,K26-PTHrP(1-31)NH | 94 | | | | | 0.112 | | | | |
| E18,A22,L25,K26-PTHrP(1-31)OH | 94 | 100 | | | | 0.78 | | | | |
| E18,A22,L25,K26,G29-PTHrP(1-31)OH | 95 | 206 | | | | | | | | |
| E18,A22,L25,K26,S29-PTHrP(1-31)OH | 96 | 209 | | | | 0.41 | | | | |
| E18,A22,L25,K26,N29-PTHrP(1-31)OH | 97 | 210 | | | | | | | | |
| E18,A22,L25,K26,Q29-PTHrP(1-31)OH | 98 | 226 | | | | 0.59 | | | | |
| E18,A22,L25,K26,W29-PTHrP(1-31)OH | 99 | 142 | | | | | | | | |
| E18,A22,L25,K26,E29-PTHrP(1-31)OH | 100 | 100 | | | | | | | | |
| E18,A22,L25,K26,K29-PTHrP(1-31)OH | 101 | 227 | | | | 0.28 | | | | |
| E18,A22,L25,K26,G30-PTHrP(1-31)OH | 102 | 286 | | | | | | | | |
| E18,A22,L25,K26,S30-PTHrP(1-31)OH | 103 | 331 | | | | 0.12 | | | | |
| E18,A22,L25,K26,L30-PTHrP(1-31)OH | 104 | 185 | | | | | | | | |
| E18,A22,L25,K26,N30-PTHrP(1-31)OH | 105 | 189 | | | | | | | | |
| E18,A22,L25,K26,D30-PTHrP(1-31)OH | 106 | 251 | | | | 0.32 | | | | |
| E18,A22,L25,K26,K30-PTHrP(1-31)OH | 107 | 245 | | | | 0.20 | | | | |
| E18,A22,L25,K26,S31-PTHrP(1-31)OH | 108 | 99 | | | | | | | | |
| E18,A22,L25,K26,L31-PTHrP(1-31)OH | 109 | 198 | | | | 0.25 | | | | |
| E18,A22,L25,K26,V31-PTHrP(1-31)OH | 110 | 181 | | | | | | | | |
| E18,A22,L25,K26,K31-PTHrP(1-31)OH | 111 | 134 | | | | | | | | |
| E18,A22,L25,K26-PTHrP(1-34)OH | 112 | 100 | | | | 0.45 | | | | |
| E18,A22,L25,K26,A30-PTHrP(1-34)OH | 113 | 237 | | | | 0.14 | | | | |
| E18,A22,L25,K26,A31-PTHrP(1-34)OH | 114 | 249 | | | | 0.15 | | | | |
| E18,A22,L25,K26,A32-PTHrP(1-34)OH | 115 | 197 | | | | | | | | |
| E18,A22,L25,K26,A33-PTHrP(1-34)OH | 116 | 196 | | | | | | | | |
| E18,A22,L25,K26,Q29,D30,V31 N33,F34-PTHrP(1-34)OH | 117 | 204 | | | | 0.56 | | | | |

We also produced the peptides $A^{20}$,Mc-PTH(1-34)OH (SEQ ID NO:149), $F^{23}$,Mc-PTH(1-34)OH (SEQ ID NO:150), $[A^1,A^3,A^{23},Q^{10},R^{11}]$-PTH(1-34)OH (SEQ ID NO:181), $[A^1,A^3,A^{23}]$-PTH(1-34)OH (SEQ ID NO:182), and $E^{18},A^{22},L^{25},K^{26}$-PTHrP(1-30) (SEQ ID NO:90). $R^0$ and RG binding of these peptides to the human PTH1 receptor is shown in Table 4 below.

TABLE 4

RG and $R^0$ binding of exemplary peptides

| Peptide | SEQ ID NO: | R0 binding IC50 (nM) | RG binding IC50 (nM) | R0/RG ratio |
|---|---|---|---|---|
| hPTH(1-34) | 5 | 8.7 ± 1.2 | 0.13 ± 0.02 | 67 |
| hPTHrP(1-36) | 6 | 37.7 ± 4.7 | 0.14 ± 0.02 | 260 |
| A20,Mc-PTH(1-34)OH | 149 | 31.9 ± 10.5 | 0.40 ± 0.09 | 80 |
| F23,Mc-PTH(1-34)OH | 150 | 1.2 ± 0.4 | 0.23 ± 0.07 | 5 |
| [A1,3,23,Q10,R11]-PTH(1-34)OH | 181 | 197 ± 33 | 0.14 ± 0.00 | 1407 |
| [A1,3,23]-PTH(1-34)OH | 182 | 1845 ± 170 | 0.43 ± 0.09 | 4291 |
| E18,A22,L25,K26-PTHrP(1-30) | 90 | 945.0 ± | 0.08 ± | 11813 |

Mc = A1,3,12,Q10,R11,W14,R19

Polypeptide Modifications

Any of the polypeptides described herein may contain one or more modifications such as N-terminal or C-terminal modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as aiginylation, and ubiquitination. See, for instance, Proteins-Structure and Molecular Properties, 2nd Ed., T. E. Creighton, W. H. Freeman and Company, New York, 1993 and Wold, F., Posttranslational Protein Modifications: Perspectives and Prospects, pgs. 1-12 in Posttranslational Covalent Modification of Proteins, B. C. Johnson, Ed., Academic Press, New York, 1983; Seifter et al, Methods Enzymol 182:626 646 (1990) and Rattan et al, Ann NY Acad Sci 663A& 62 (1992).

Any of the polypeptides of the invention may further include a heterologous sequence (a fusion partner), thus forming a fusion protein. The fusion protein may include a fusion partner such as a purification or detection tag, for example, proteins that may be detected directly or indirectly such as green fluorescent protein, hemagglutinin, or alkaline phosphatase), DNA binding domains (for example, GAL4 or LexA), gene activation domains (for example, GAL4 or VP16), purification tags, or secretion signal peptides (e.g., preprotyrypsin signal sequence). In other embodiments the fusion partner may be a tag, such as c-myc, poly histidine, or FLAG. Each fusion partner may contain one or more domains, e.g., a preprotrypsin signal sequence and FLAG tag. In other cases, the fusion partner is an Fc protein (e.g., mouse Fc or human Fc).

Methods of Treatment of Disease

Any disease associated with PTH dysfunction, or calcium or phosphate imbalances, can be treated with any of the peptides described herein, including those in FIGS. 26A and 26B, those of Table 1, or those identified using the methods of the invention. The peptides may be used to treat osteoporosis, fracture repair, osteomalacia, arthritis, thrombocytopenia, hypoparathyroidism or hyperphosphatemia or may be used to increase stem cell mobilization in a subject. Any mode of administration (e.g., oral, intravenous, intramuscular, ophthalmic, topical, dermal, subcutaneous, and rectal) can be used in the treatment methods of the invention. A physician will determine appropriate dosing for the patient being treated, which will depend in part on the size of the patient, the severity of the disease or condition, and the particular disease or condition being treated.

Formulation of Pharmaceutical Compositions

The administration of any compound described herein (e.g., PTH-derived peptides) or identified using the methods of the invention may be by any suitable means that results in a concentration of the compound that treats the subject disease condition. The compound may be contained in any appropriate amount in any suitable carrier substance, and is generally present in an amount of 1-95% by weight of the total weight of the composition. The composition may be provided in a dosage form that is suitable for the oral, parenteral (e.g., intravenously or intramuscularly), rectal, cutaneous, nasal, vaginal, inhalant, skin (patch), ocular, or intracranial administration route. Thus, the composition may be in the form of, e.g., tablets, ampules, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The pharmaceutical compositions may be formulated according to conventional pharmaceutical practice (see, e.g., Remington: *The Science and Practice of Pharmacy,* 20th edition, 2000, ed. A. R. Gennaro, Lippincott Williams & Wilkins, Philadelphia, and *Encyclopedia of Pharmaceutical Technology*, eds. J. Swarbrick and J. C. Boylan, 1988-1999, Marcel Dekker, New York).

Pharmaceutical compositions may be formulated to release the active compound immediately upon administration or at any predetermined time or time period after administration. The latter types of compositions are generally known as controlled release formulations, which include (i) formulations that create substantially constant concentrations of the agent(s) of the invention within the body over an extended period of time; (ii) formulations that after a predetermined lag time create substantially constant concentrations of the agents of the invention within the body over an extended period of time; (iii) formulations that sustain the agent(s) action during a predetermined time period by maintaining a relatively constant, effective level of the agent(s) in the body with concomitant minimization of undesirable side effects associated with fluctuations in the plasma level of the agent(s) (sawtooth kinetic pattern); (iv) formulations that localize action of agent(s), e.g., spatial placement of a controlled release composition adjacent to or in the diseased tissue or organ; (v) formulations that achieve convenience of dosing, e.g., administering the composition once per week or once every two weeks; and (vi) formulations that target the action of the agent(s) by using carriers or chemical derivatives to deliver the compound to a particular target cell type. Administration of the compound in the form of a controlled release formulation is especially preferred for compounds having a narrow absorption window in the gastro-intestinal tract or a relatively short biological half-life.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the compound is formulated with appropriate excipients into a pharmaceutical composition that, upon administration, releases the compound in a controlled manner. Examples include single or multiple unit tablet or capsule compositions, oil solutions, suspensions, emulsions, microcapsules, molecular complexes, microspheres, nanoparticles, patches, and liposomes.

Parenteral Compositions

The composition containing compounds described herein or identified using the methods of the invention may be administered parenterally by injection, infusion, or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation, or it may be presented as a dry powder to be reconstituted with water or another suitable vehicle before use. Apart from the active agent(s), the composition may include suitable parenterally acceptable carriers and/or excipients. The active agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing agents.

As indicated above, the pharmaceutical compositions according to the invention may be in a form suitable for sterile injection. To prepare such a composition, the suitable active agent(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, dextrose solution, and isotonic sodium chloride solution. The aqueous formulation may also contain one or more preservatives (e.g., methyl, ethyl, or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

The following examples are intended to illustrate rather than limit the invention.

EXAMPLE 1

Identification of Short-Lived and Long-Acting PTH Peptides

Figure 1B:
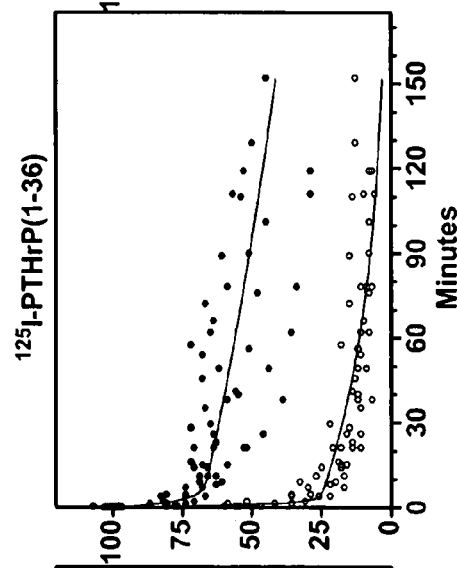
Figure 1C:
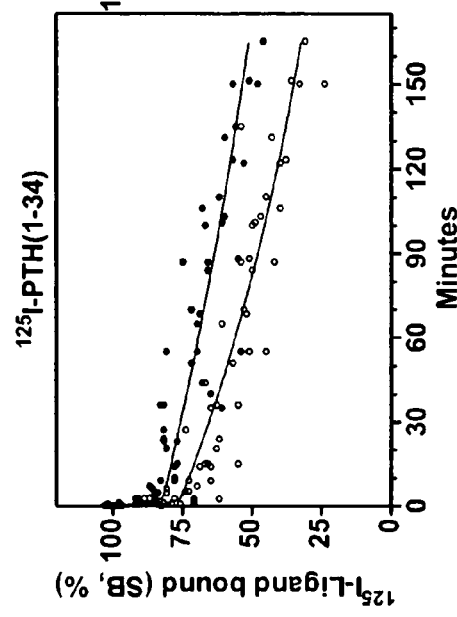

Characterization of ligands using a competitive binding assay. To identify PTHR ligands, kinetic dissociation experiments were first performed to examine the stability of complexes formed between PTH and PTHrP radioligand analogs and the human PTHR expressed in membranes prepared from HKRK-B7 cells. For each radioligand, dissociation was examined in the presence and absence of GTPγS, so as to assess the effects of functionally uncoupling the receptor from heterotrimeric G proteins (FIGS. 1A-1C). For $^{125}$I-PTH (1-34) and $^{125}$I-PTHrP(1-36) (FIGS. 1A and 1B, respectively), the dissociation data, both in the absence and presence of GTPγS (solid and open symbols, respectively), were better fit by a two-phase decay equation than by a single-phase equation. For $^{125}$I-PTH(1-34) and in the absence of GTPγS, 17% of the complexes were unstable and decayed rapidly ($t_{1/2}$<1 min), whereas the remaining 83% were stable and decayed slowly ($t_{1/2}$~4 h). Upon the addition of GTPγS, the rapid, unstable component increased to 21%, such that 77% of the complexes remained stable ($t_{1/2}$~2 h) (FIG. 1A). These findings with $^{125}$I-PTH(1-34) agree closely with previous dissociation studies performed on this radioligand, and highlight the capacity of PTH(1-34) to bind to a high affinity, G protein-uncoupled PTHR conformation)($R^0$ (Shimizu et al., *J. Biol. Chem.* 280:1797-807 (2005); Dean et al., *Mol. Endocrinol.* 20:931-43 (2006)). The complexes formed with $^{125}$I-PTHrP(1-36) and the PTHR were again mostly stable in the absence of GTPγS (68% decayed with a $t_{1/2}$ of ~3 h). By contrast, most of the complexes became unstable upon addition of GTPγS (72% decayed with a $t_{1/2}$ of ~1 minute; FIG. 1B). This rapid dissociation of $^{125}$I-PTHrP(1-36) from the PTHR induced by GTPγS addition mirrors that observed previously for $^{125}$I-[Aib$^{1,3}$,M]PTH(1-15) (Dean et al., *Mol. Endocrinol.* 20:931-43 (2006)); each of these radioligands thus appears to bind predominantly to the PTHR in a G protein-coupled conformation (RG).

The structural differences in PTH(1-34) and PTHrP(1-36) that underlie the functional differences seen for the two ligands in the above dissociation studies then identified. The divergent residues at position 5 in PTH and PTHrP (Ile and His, respectively) have been shown to play important roles in determining the affinity (Shimizu et al., *J. Biol. Chem.* 280: 1797-807 (2005); Gardella et al., *J. Biol. Chem.* 270:6584-6588 (1995)) and subtype selectivity (Gardella et al., *J. Biol. Chem.* 271:19888-19893 (1996); Behar et al., *Endocrinology* 137:4217-4224 (1996)) with which these ligands bind to the receptor. The receptor-dissociation properties of $^{125}$I-Ile$^5$-PTHrP(1-36) were examined, again in the absence and presence of GTPγS. This radioligand dissociated from the receptor slowly, both in the presence and absence of GTPγS, and, in each case, with mono-phasic kinetics ($t_{1/2}$>2 h; FIG. 1C).

Thus, the His⁵Ile substitution markedly enhanced the stability with which PTHrP binds to the PTHR, in the G protein-coupled, and especially in the G protein-uncoupled state.

Figure 2A:
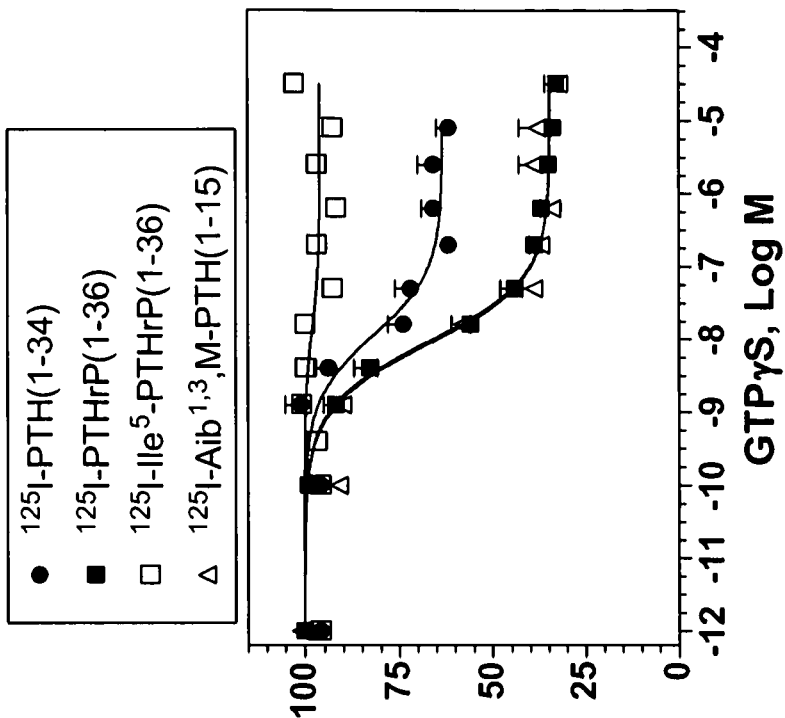
FIGS. 2A and 2B are graphs showing GTPγS sensitivity of PTH and PTHrP analog binding to the human and rat PTHRs. Radioligand analog binding to the PTHR in membranes prepared from HKRK-B7 (FIG. 2A) or ROS17/2.8 cells (FIG. 2B) was assessed under near-equilibrium conditions in the absence or presence of varying concentrations of GTPγS. Data are expressed as a percent of radioactivity specifically bound (SB) in the absence of GTPγS. Data in FIG. 2A are means (±s.e.m.) from three (PTH(1-34)) or five (PTHrP(1-36) analogs) experiments, and those in FIG. 2B are from six experiments, each performed in duplicate. The radioligands studied were $^{125}$I-[Nle$^{8,21}$,Tyr$^{34}$]PTH(1-34)NH$_2$ (SEQ ID NO:123); [Tyr$^{36}$]PTHrP(1-36)NH$_2$ $_{(SEQ\ ID\ NO:}$124); [Ile$^5$,Tyr$^{36}$]PTHrP(1-36)NH$_2$ (SEQ ID NO:125) and [Aib$^{1,3}$,Nle$^8$,Gln$^{10}$,Har$^{11}$,Ala$^{12}$,Trp$^{14}$,Tyr$^{15}$]PTH(1-15)NH$_2$ (SEQ ID NO:126).
Figure 2B:
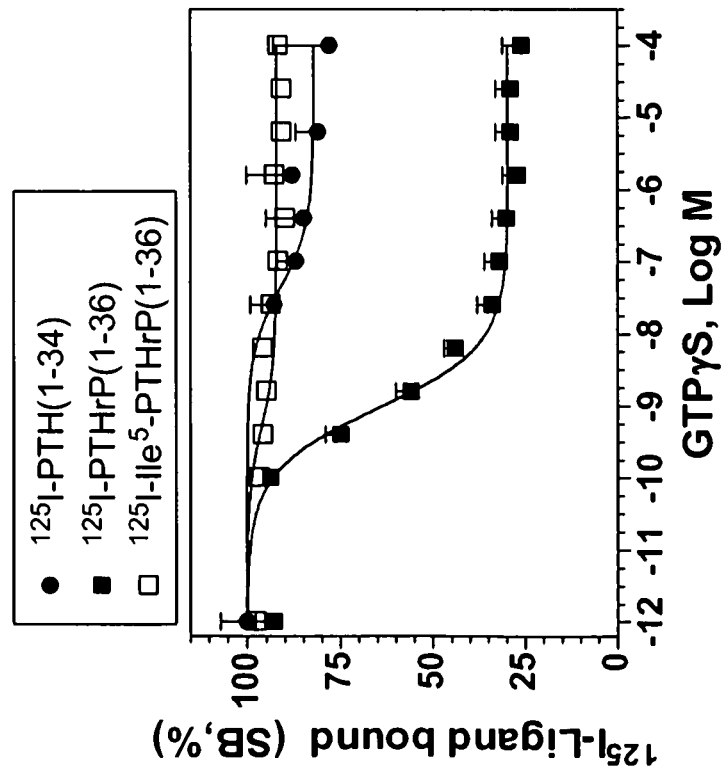

Effects of GTPγS on equilibrium binding. The effects of GTPγS on the binding of these radioligands to the PTHR under approximate-equilibrium conditions was assessed by incubating with cell membranes for 90 minutes in the absence or presence of GTPγS at varying concentrations. The binding of $^{125}$I-PTH(1-34) and $^{125}$I-Ile⁵-PTHrP(1-36) to membranes prepared from HKRK-B7 cells was largely unaffected by GTPγS (<~20% inhibition at 1×10⁻⁴ M GTPγS), whereas the binding of $^{125}$I-PTHrP(1-36) was strongly inhibited by GTPγS (~70% inhibition at 1×10⁻⁷ M GTPγS; IC$_{50}$=1×10⁻⁹ M; FIG. 2A). To assess binding to the rat PTHR, parallel studies were performed using membranes prepared from the rat osteoblastic cell line ROS17/2.8, which endogenously expresses the rat PTHR. As with the human PTHR in HKRK-B7 cell membranes, the binding of $^{125}$I-Ile⁵-PTHrP(1-36) to rat PTHR likewise was largely insensitive to GTPγS (FIG. 2B). The binding of $^{125}$I-PTH(1-34) to the rat PTHR appeared more sensitive to GTPγS than was its binding to the human PTHR (FIG. 2A vs. 2B), although the majority of the binding was resistant to the nucleotide analog. As for the human PTHR, GTPγS strongly inhibited the binding of $^{125}$I-PTHrP(1-36) to the rat PTHR, which was as sensitive to the nucleotide analog as the binding of $^{125}$I-[Aib$^{1,3}$,M]PTH(1-15) (FIG. 2B). Thus, PTH(1-34) and Ile⁵-PTHrP(1-36) bind more strongly to the G protein-uncoupled conformation of the PTHR)(R⁰ than does PTHrP(1-36) or [Aib$^{1,3}$,M]PTH(1-15). By contrast, the later two peptides bind preferentially to the G protein-coupled conformation, RG. Competition methods were then used to analyze the relative affinities with which PTH and PTHrP ligands bind to the RG and R⁰ receptor conformations of the PTHR. To assess binding to RG, $^{125}$I-[Aib$^{1,3}$,M]PTH(1-15) was used as a tracer radioligand, as this peptide binds predominantly to RG. Membranes were prepared from COS-7 cells co-transfected with the hPTHR and a negative-dominant Gα$_s$ subunit (Gα$_s$ND), which enriches for RG, related to R and R⁰, as described previously (Dean et al., *Mol. Endocrinol.* 20:931-943 (2006); Berlot, C. H., *J. Biol. Chem.* 277:21080-21085 (2002); Dean et al., *J. Biol. Chem.* 281:32485-32495 (2006)). To assess binding to R⁰, $^{125}$I-PTH (1-34) was used as a radioligand (binds predominantly to R⁰). Membranes were prepared from COS-7 cells transfected with the hPTHR alone. GTPγS (1×10⁻⁵) was added to the binding reactions so as to functionally uncouple receptor-heterotrimeric G protein complexes, thus enriching for the R⁰ (and R) conformations, relative to RG. The relative apparent affinities obtained for several unlabeled PTH and PTHrP ligand were then compared in these two assays, to assess the selectivity with which each of the ligands bound to the R⁰ vs. RG PTHR conformation.

Figures 3A, 3B, 3C, 3D:
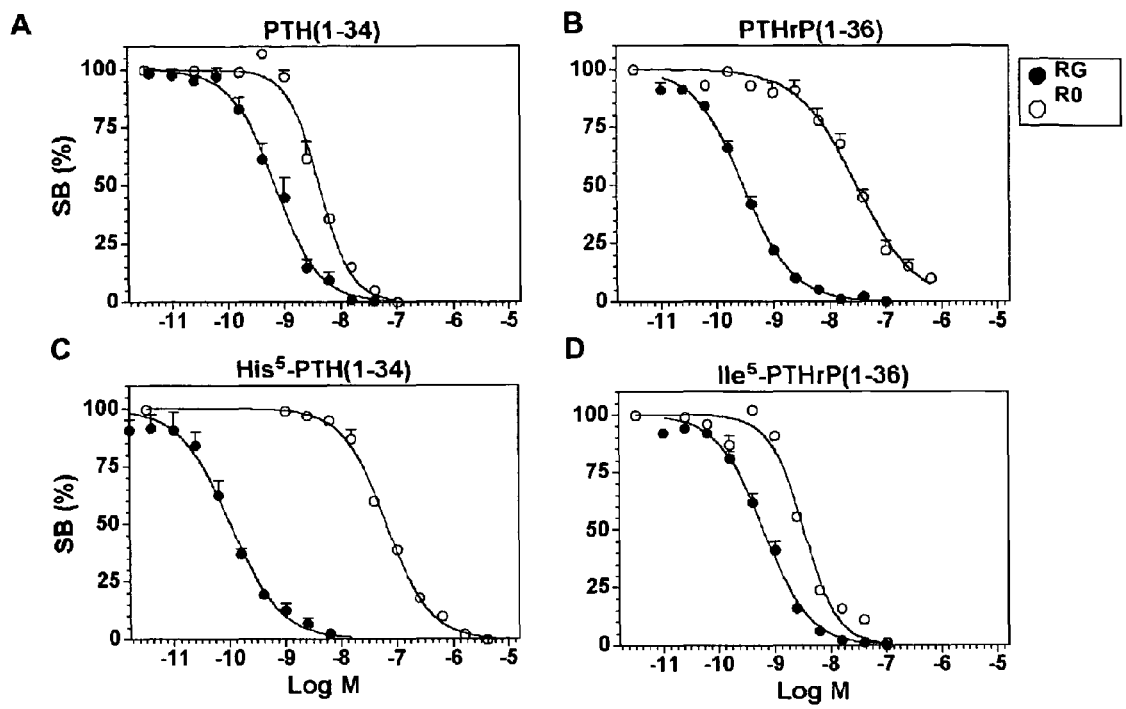
FIGS. 3A-3D are graphs showing binding of PTH and PTHrP analogs to the G protein-coupled and G protein-uncoupled conformations of the hPTHR. The binding of unlabeled PTH and PTHrP analogs to the G protein-coupled PTHR conformation (RG) and G protein-uncoupled PTHR conformation)(R$^0$ was assessed by competition methods using membranes prepared from transiently transfected COS-7 cells. To assess binding to RG, the cells were co-transfected with the hPTHR and a negative-dominant Gαs subunit (Gα$^{ND}$); and $^{125}$I-[Aib$^{1,3}$M]PTH(1-15)NH$_2$ (SEQ ID NO:126) was used as a tracer radioligand. To assess binding to R$^0$, the cells were transfected with the hPTHR alone, $^{125}$I[Nle$^{8,21}$,Tyr$^{34}$]rPTH(1-34)NH$_2$ (SEQ ID NO:123) was used as a tracer radioligand, and the binding reactions were performed in the presence of GTPγS. The unlabeled ligands used were [Nle$^{8,21}$,Tyr$^{36}$]rPTH(1-34)NH$_2$ (SEQ ID NO:123) (FIG. 3A); [Tyr$^{36}$]hPTHrP(1-36)NH$_2$ (SEQ ID NO:124) (FIG. 3B); [His$^5$,Nle$^{8,21}$,Tyr$^{34}$]rPTH(1-34)NH$_2$ (SEQ ID NO:127) (FIG. 3C); and [Ile$^5$,Tyr$^{36}$]hPTHrP(1-36)NH$_2$ (SEQ ID NO:125) (FIG. 3D). Whereas each ligand binds with relatively high affinity to RG, PTHrP(1-36), and His$^5$-PTH(1-34) bind with considerably lower affinity to R$^0$ than do PTH(1-34) and Ile$^5$-PTHrP(1-36), and thus exhibit stronger RG selectivity. Data are means (±s.e.m.) of three to seven experiments, each performed in duplicate (see also Table 5).

PTH(1-34) bound to the R⁰ conformation with a five-fold weaker affinity than it did to the RG conformation (IC$_{50}$=4.2 nM vs. 0.86 nM, P=0.0002; FIG. 3A, Table 5). PTHrP(1-36) exhibited greater selectivity as it bound to R⁰ with a 66-fold weaker affinity than it did to RG (P=0.04; FIG. 3B; Table 5). Thus its selectivity for RG (vs. R⁰) was 13-fold greater than that of PTH(1-34). Reciprocal exchange of residue 5 in the ligands reversed this pattern of conformational selectivity; thus, His⁵-PTH(1-34) bound to R⁰ with a 750-fold weaker affinity than it did to RG, and Ile⁵-PTHrP(1-36) bound to R⁰ with only a three-fold weaker affinity than it did to RG (P<0.002; FIGS. 3C and 3D; Table 5).

TABLE 5

Competition binding to the RG and R⁰ conformations of the human PTH receptor

| | | IC50 (nM) | | | |
|---|---|---|---|---|---|
| | | RG $^{125}$I-PTH(1-15) + | | R⁰ $^{125}$I-PTH(1-34) + | |
| | SEQ ID NO: | G$_s$ND | n | GTPγS | n | R0:RG |
| [Nle$^{8,21}$, Tyr$^{34}$]rPTH(1-34)NH$_2$ | 123 | 0.86 ± 0.24 | 7 | 4.2 ± 0.5 | 7 | 5 |
| [His⁵, Nle$^{8,21}$, Tyr$^{34}$]rPTH(1-34)NH$_2$ | 127 | 0.094 ± 0.019 | 4 | 71 ± 7 | 4 | 753 |
| [Tyr$^{36}$]hPTHrP(1-36)NH$_2$ | 124 | 0.42 ± 0.09 | 3 | 28 ± 6 | 3 | 66 |
| [Ile⁵, Tyr$^{36}$]hPTHrP(1-36)NH$_2$ | 125 | 0.92 ± 0.07 | 3 | 2.9 ± 0.1 | 3 | 3 |
| rPTH(1-34)NH$_2$ | 130 | 0.34 ± 0.16 | 3 | 2.3 ± 0.3 | 3 | 7 |
| [His⁵]rPTH(1-34)NH$_2$ | 185 | 0.19 ± 0.04 | 5 | 26 ± 5 | 5 | 138 |
| hPTH(1-34)NH$_2$ | 5 | 0.39 ± 0.24 | 3 | 6.6 ± 2.4 | 3 | 17 |
| [His⁵]hPTH(1-34)NH$_2$ | 9 | 0.76 ± 0.04 | 5 | 122 ± 35 | 5 | 160 |
| hPTHrP(1-36)NH$_2$ | 6 | 0.59 ± 0.02 | 3 | 24 ± 3 | 3 | 42 |
| [Aib$^{1,3}$,M]rPTH(1-15)NH$_2$ | 126 | 0.74 ± 0.18 | 3 | 1029 ± 148 | 3 | 1,397 |

The Ile⁵→His substitution also strongly reduced affinity for R⁰ without greatly affecting affinity for RG in human-PTH(1-34) and rat-PTH(1-34) peptides that lacked the methionine$^{8,21}$→norleucine and Phe$^{34}$ Tyr$^{34}$ substitutions of our control PTH(1-34) analog (FIGS. 6A, 6B, 6D, and 6E and Table 4). Thus, PTH(1-34) binds with higher affinity to R⁰ than does PTHrP(1-36), whereas both PTH(1-34) and PTHrP (1-36) bind with high affinity to the RG PTHR conformation. Residue 5 in the ligand plays a significant role in modulating the capacity of the ligands to bind to the R⁰ versus RG conformations. In addition, residues carboxy-terminal of position 15 in PTH(1-34) contribute to the capacity of the ligand to bind strongly to R⁰, as shown by [Aib$^{1,3}$,M]PTH(1-15), which binds only weakly to R⁰ but maintains strong affinity for RG (FIG. 6C and Table 4).

Figures 4A, 4B, 4C, 4D:
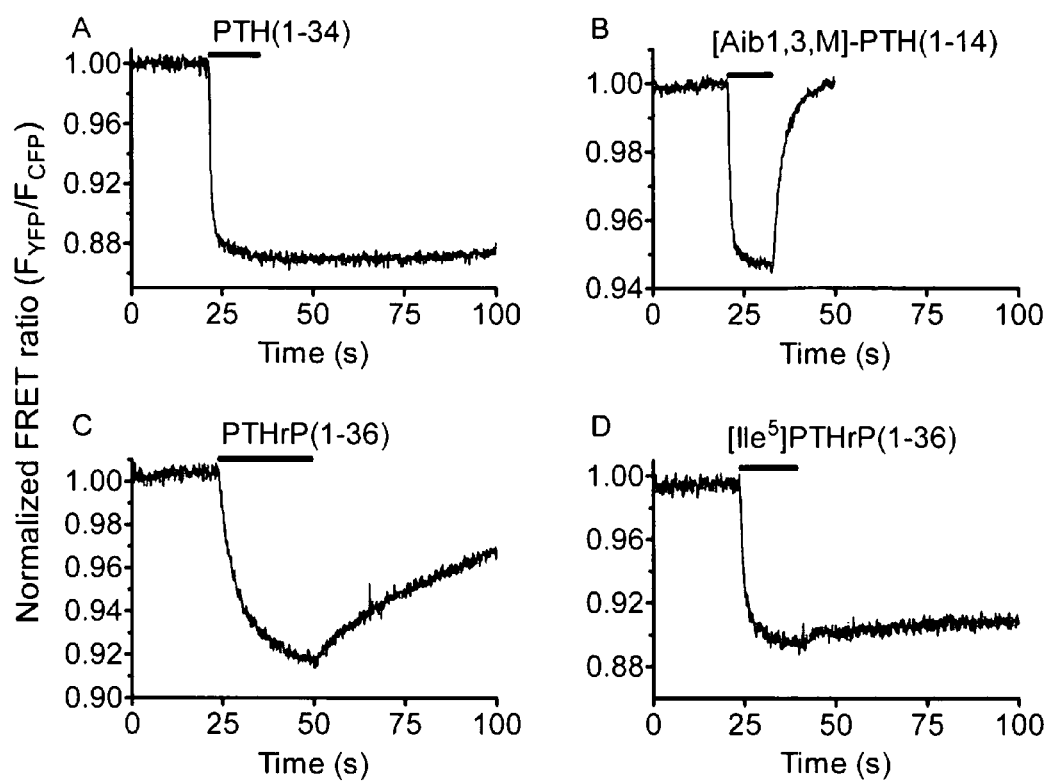
FIGS. 4A-4D are graphs showing fluorescent resonance energy transfer (FRET) analysis of ligand binding to the PTHR in HEK-293 cells. HEK-293 cells stably transfected with a PTHR construct (PTHR-cam) containing cyan fluorescent protein (CFP) in the third intracellular loop and yellow fluorescent protein (YFP) in the carboxy-terminal tail, were used to assess the kinetics of ligand binding to, and dissociation from the PTHR. With PTHR-cam, excitation of the CFP with ultraviolet light ($\lambda_{exc}$=436 nm) produces an intramolecular FRET to the YFP, which is observable as an increase in light emission from YFP ($\lambda_{emm}$=535 nm) and a decrease in light emission from CFP $\lambda_{emm}$=480 nm). This FRET signal occurs in the ground-state receptor and decreases upon agonist binding. In each panel, the trace shows the ratio of the fluorescence signals ($F_{YFP(535)}/F_{CFP(480)}$, normalized for channel spill-over) obtained over time in cells superfused with buffer alone or with buffer containing a PTH peptide ligand (times of peptide addition indicated by the black bars above each trace). The ligands used were hPTH(1-34) (SEQ ID NO:5) (FIG. 4A); [Aib$^{1,3}$,Gln$^{10}$,Har$^{11}$,Ala$^{12}$,Trp$^{14}$]rPTH(1-14)NH$_2$ (SEQ ID NO:128) (FIG. 4B); [Tyr$^{36}$]hPTHrP(1-36)NH$_2$ (SEQ ID NO:124) (FIG. 4C), and [Ile$^5$,Tyr$^{36}$]hPTHrP(1-36)NH$_2$ (SEQ ID NO:125) (FIG. 4D). The onset of the FRET signal induced by PTHrP(1-36) was slower than that induced by the three other analogs. The signals induced by PTH(1-14) and PTHrP(1-36) analogs decayed upon ligand removal, whereas those induced by PTH(1-34) and Ile$^5$-PTHrP(1-36) analogs remained stable. Data are from a single experiment, and identical results were obtained in at least three others.
Figure 5A:
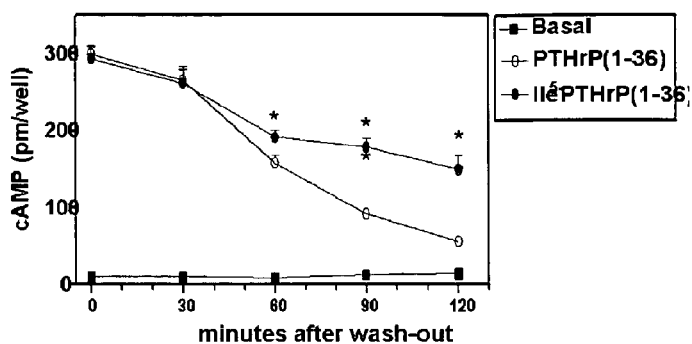
FIGS. 5A and 5B are graphs showing the duration of cAMP-signaling responses induced by PTH and PTHrP analogs in cells stably expressing the human PTHR. The duration of cAMP responses induced by PTHrP(1-36) (SEQ ID NO:6) or Ile$^5$-PTHrP(1-36) (SEQ ID NO:13) in HKRK-B7 cells (950,000 hPTHRs/per cell) was assessed by time course experiments (FIG. 5A). The cells were pre-treated for 10 minutes with either buffer alone (basal) or buffer containing ligand (100 nM); at t=0, the cells were washed, incubated in buffer for the times indicated (wash-out phase), treated with 3-isobutyl-1-methylxanthine (IBMX) for five minutes, and then assessed for intracellular cAMP. The maximum response to each peptide, assessed by incubating cells concomitantly with peptide and IBMX and omitting the wash-out phase, was 185116 and 198118 pmoles/well for PTHrP(1-36) and Ile$^5$-PTHrP(1-36), respectively. The cAMP level in cells treated with IBMX in the absence of ligand was 2.0±0.3 pmole/well. Data are means (±s.e.m.) of three experiments, each performed in duplicate. In these experiments, PTH(1-34) (SEQ ID NO:5) was also analyzed and induced responses at each time point that were not different from those induced by PTHrP(1-36). Analogs were similarly assessed in HKRK-B64 cells (90,000 hPTHRs/cell) at a single time-point, 60 minutes after ligand wash-out (FIG. 5B). For each peptide, the data are expressed as a percentile of the maximum cAMP responses (indicated in side panel) produced in cells treated concomitantly with that ligand and IBMX for 10 minutes and omitting the wash-out phase. The analogs included His$^5$-PTH (1-34) (SEQ ID NO:9) and [Aib$^{1,3}$,M]PTH(1-15) (SEQ ID NO:126) (FIG. 5B). Data are means (±s.e.m) of four experiments, each performed in triplicate. Asterisks indicate statistical analyses of paired responses: PTHrP(1-36) vs. Ile$^5$-PTHrP(1-36) (FIG. 5A), or as indicated by brackets (FIG. 5B): *, P≤0.05; **, P≤0.003.

Direct recording of PTHR activation. The fluorescent resonance energy transfer (FRET) approach has recently been used to assess, in real time and in intact cells, the processes of ligand binding and receptor activation for the PTHR. This approach was therefore used as an independent means to compare the time courses by which PTH and PTHrP ligands interact with the PTHR. The approach used exploits an intramolecular FRET signal that occurs in a human PTHR construct, PTHR-CFP$_{IC3}$/YFP$_{CT}$ (formerly called PTHR-cam). This construct contains cyan-fluorescent protein (CFP) in the third intracellular loop and yellow-fluorescent protein (YFP) in the carboxy-terminal tail. A FRET signal is produced by PTHR-CFP$_{IC3}$/YFP$_{CT}$ in the basal state, and this signal diminishes upon agonist binding, likely due to conformational change that occurs upon activation.

hPTH(1-34) induced a rapid ($t_{1/2}$=0.7 sec) reduction (−13%) in the FRET signal produced by cells expressing PTHR-CFP$_{IC3}$/YFP$_{CT}$ (FIG. 4A). The FRET signal remained suppressed during the 15 seconds of ligand application, as well as for at least 60 seconds after the ligand-containing buffer was exchanged for a ligand-free buffer (ligand application times are marked by the black horizontal line above the graphs in FIGS. 4A-4C). The FRET response profile obtained for hPTH(1-34) replicates the profile observed for this ligand in previous FRET studies (Vilardaga et al., *Nat. Biotechnol.* 21:807-812 (2003)). The amino-terminal peptide, [Aib$^{1,3}$,M] PTH(1-14), induced a FRET response with slightly faster kinetics ($t_{1/2}$=0.5 sec) and with a shallower magnitude (~5%) than that produced by hPTH(1-34) (FIG. 4B). Moreover, the FRET response produced by [Aib$^{1,3}$,M]PTH(1-15) began to decay immediately upon exchange of the buffer to a ligand-free one (FIG. 4B). PTHrP(1-36) induced a relatively slow FRET response ($t_{1/2}$=~2 to 5 seconds), and the signal began to decay immediately upon changing to a ligand-free buffer (FIG. 4C). The Ile$^5$-substituted ligand Ile$^5$-PTHrP(1-36) induced a FRET signal that was remarkably similar to that of PTH(1-34), in that the response was rapid ($t_{1/2}$=0.5-0.7 sec), and stable after ligand removal (FIG. 4D). These kinetic data, derived by a spectroscopic approach, fully agree with those obtained in the above binding radioligand dissociation assays, thus indicating that PTH(1-34) and PTHrP(1-36) bind predominantly to distinct conformations of the PTHR. They also confirm the important role of residue five in the ligands in contributing to this conformational selectivity.

cAMP measurements in HKRK-B7 cells. Given that LR$^0$ complexes can isomerize to LRG complexes, a potential consequence of stable binding of a ligand to R$^0$ is a prolongation of the signaling response induced by that ligand, relative to a ligand that only poorly stabilizes R$^0$. To examine this possibility, the capacity of PTH and PTHrP ligands to produce sustained cAMP responses in PTHR-expressing cells was assessed. Cells were thus treated with a ligand for ten minutes, washed to remove unbound ligand. At various times after washing, IBMX was applied for five minutes, and the resulting intracellular cAMP was measured. Using this approach, only the cAMP produced during the final, five minute IBMX incubation phase is measurable. The experiments of FIG. 5A compare the time courses of the cAMP responses produced by PTHrP(1-36) and Ile$^5$-PTHrP(1-36) in HKRK-B7 cells. Immediately after the wash-out step, cells treated with either ligand produced approximately the same amount of cAMP, which was ~100-fold above the basal cAMP level in untreated cells. Two hours after the wash-out step, the cells treated with Ile$^5$-PTHrP(1-36) maintained a cAMP signaling capacity that was ~50% of the signaling capacity seen immediately after ligand wash-out (FIG. 5A). By contrast, the signaling capacity of cells treated with PTHrP(1-36) at two hours was ~19% of the initial response, and thus ~65% less than the response observed at two hours for Ile$^5$-PTHrP(1-36) (P<0.003). PTH(1-34) produced responses at each time point that were nearly identical to those produced by Ile$^5$-PTHrP(1-36) (P=>0.05, data not shown). Thus, the cAMP signaling responses induced by PTH(1-34) and Ile$^5$-PTHrP(1-36) decayed about twice as slowly as did that of and PTHrP(1-36) ($t_{1/2}$=~2 h vs. ~1 h). These differences in the duration of the cAMP signaling capacity observed for the PTH and PTHrP analogs parallel the differences seen in the rates with which the corresponding radioligands dissociated from the PTHR in the presence of GTPγS (FIGS. 1A-1C).

cAMP measurements in HKRK-B64 cells. The capacity of the ligands to produce sustained (or delayed) cAMP signaling responses was further examined in HKRK-B64 cells, which express the hPTHR at a more physiological level than do HKRK-B7 cells (90,000 per cell vs. 950,000/cell). Time course experiments indicated that differences in the duration of ligand-induced signaling responses were best resolved in these cells 60 minutes after ligand wash-out (data not shown). In these experiments, a maximum response was determined for each peptide by incubating the cells concomitantly with ligand and IBMX for 10 minutes (no wash-out phase); the cAMP responses observed at 60 minutes after ligand washout were then expressed as a percentile of the corresponding maximum response.

Figure 5B:
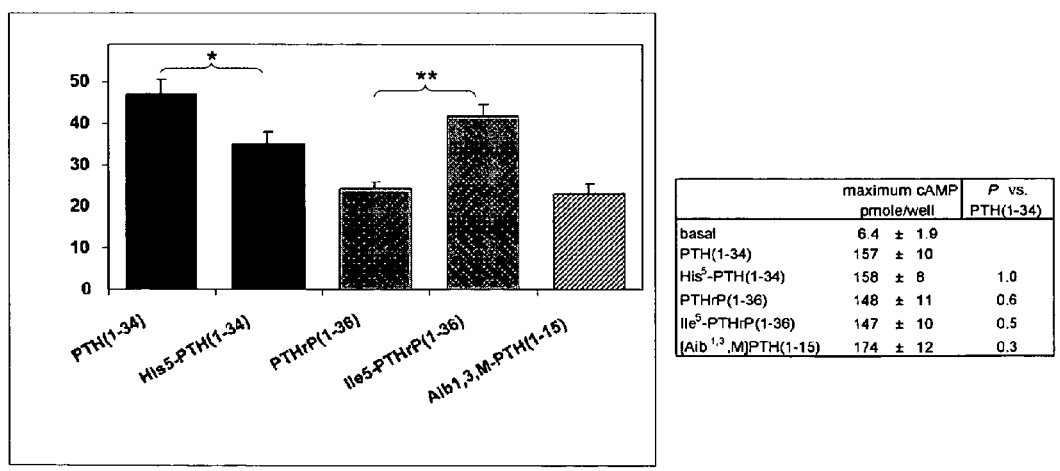
Figures 6A, 6B, 6C, 6D:
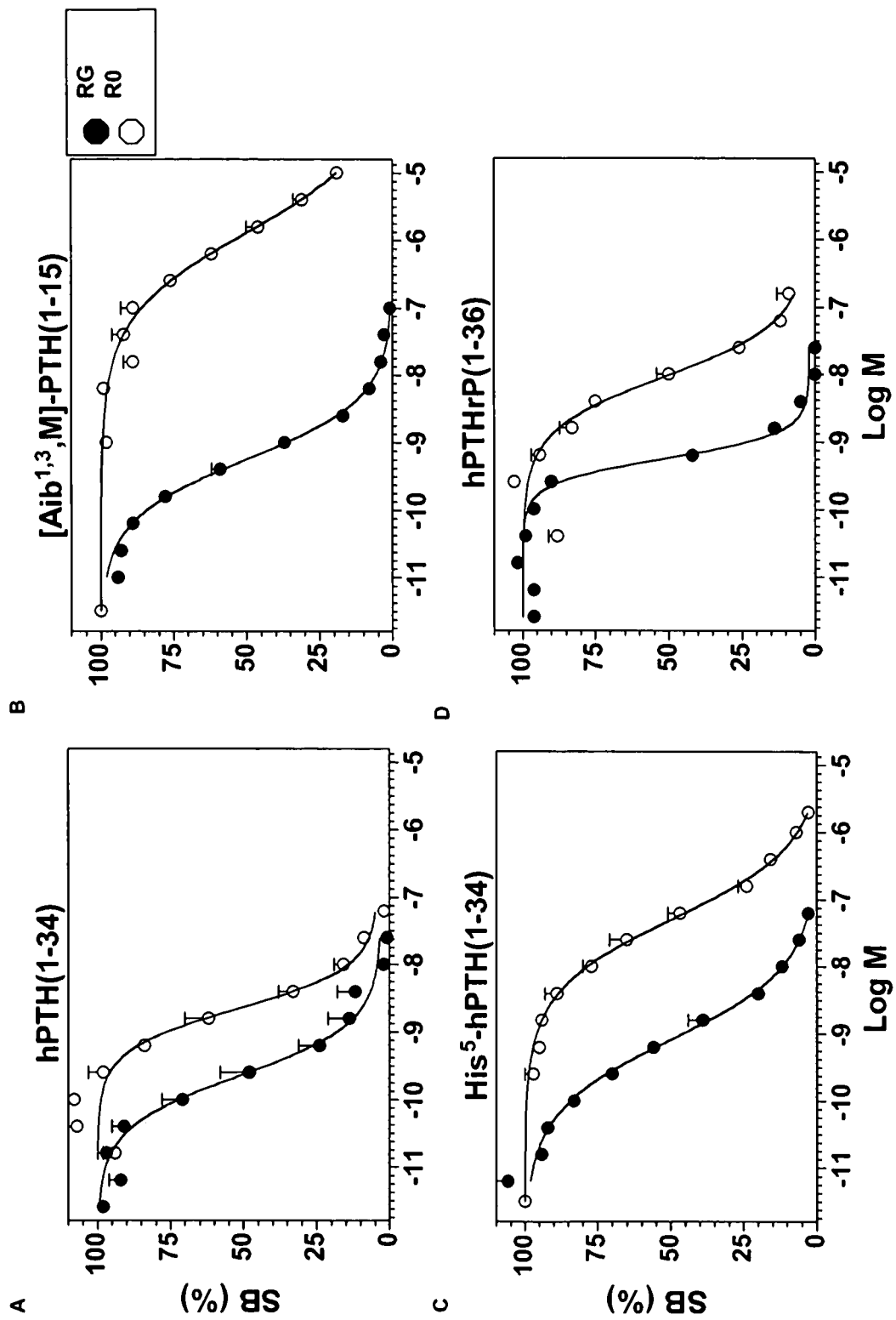
FIGS. 6A-6D are graphs showing binding of PTH and PTHrP analogs to the G protein-coupled and G protein-uncoupled conformations of the hPTHR. Binding reactions were performed as described above for FIGS. 3A-3D. The unlabeled ligands used were hPTH(1-34)NH$_2$ (SEQ ID NO:5) (FIG. 6A); [Aib$^{1,3}$,Nle$^8$,Gln$^{10}$,Har$^{11}$,Ala$^{12}$Trp$^{14}$, Tyr$^{15}$]rPTH(1-15)NH$_2$ (SEQ ID NO:126) (FIG. 6B); [His$^5$] hPTH(1-34)NH$_2$ (SEQ ID NO:9) (FIG. 6C); hPTHrP(1-36) NH$_2$ (SEQ ID NO:6) (FIG. 6D). Data are means (±s.e.m.) of three or five experiments, each performed in duplicate (Table 6).

As in HKRK-B7 cells, PTH(1-34) and Ile$^5$-PTHrP(1-36) produced cAMP responses at 60 minutes after wash-out that were 47% and 40% of their corresponding maximum responses, respectively, in HKRK-B64 cells (FIG. 5B). The analogs His$^5$-PTH(1-34) and PTHrP(1-36) produced responses at 60 minutes that were 34% and 19% of their maximum response. The response induced by [Aib$^{1,3}$,M] PTH(1-15) at two hours was 23% of its maximum response, and thus was comparable to that of PTHrP(1-36) (P=0.7). Different PTH and PTHrP ligand analogs that exhibit the same or comparable activities when assessed in acute dose-response signaling assays (FIG. 7; Table 6), can produce quantitatively different cumulative signaling responses in cells, that are most likely due to the capacity of the ligands to form a stable complex with the receptor.

TABLE 6 cAMP and IP signaling properties of PTH and PTHrP ligands.

| | SEQ ID NO: | cAMP in HKRK-B64 cells [a] | | IP in COS-7/hPTHR cells [c] | |
|---|---|---|---|---|---|
| | | EC$_{50}$ (nM) | E$_{max}$ [b] (picomole/well) | EC$_{50}$ (nM) | E$_{max}$ [d] (cpm/well) |
| [Nle$^{8,21}$,Tyr$^{34}$]rPTH(1-34)NH$_2$ | 123 | 5.1 ± 0.5 | 55 ± 12 | 18 ± 3 | 2,407 ± 138 |
| [His$^5$,Nle$^{8,21}$,Tyr$^{34}$]rPTH(1-34)NH$_2$ | 127 | 2.7 ± 0.6 [e] | 59 ± 12 | 30 ± 12 | 2,231 ± 229 |

TABLE 6-continued cAMP and IP signaling properties of PTH and PTHrP ligands.

| | SEQ ID NO: | cAMP in HKRK-B64 cells [a] | | IP in COS-7/hPTHR cells [c] | |
|---|---|---|---|---|---|
| | | $EC_{50}$ (nM) | $E_{max}$ [b] (picomole/well) | $EC_{50}$ (nM) | $E_{max}$ [d] (cpm/well) |
| [Tyr$^{36}$]hPTHrP(1-36)NH$_2$ | 124 | 5.6 ± 1.3 | 62 ± 15 | 23 ± 8 | 2,514 ± 270 |
| [Ile$^5$,Tyr$^{36}$]hPTHrP(1-36)NH$_2$ | 125 | 5.4 ± 1.9 | 61 ± 14 | 23 ± 7 | 2,793 ± 303 |

Figure 8:
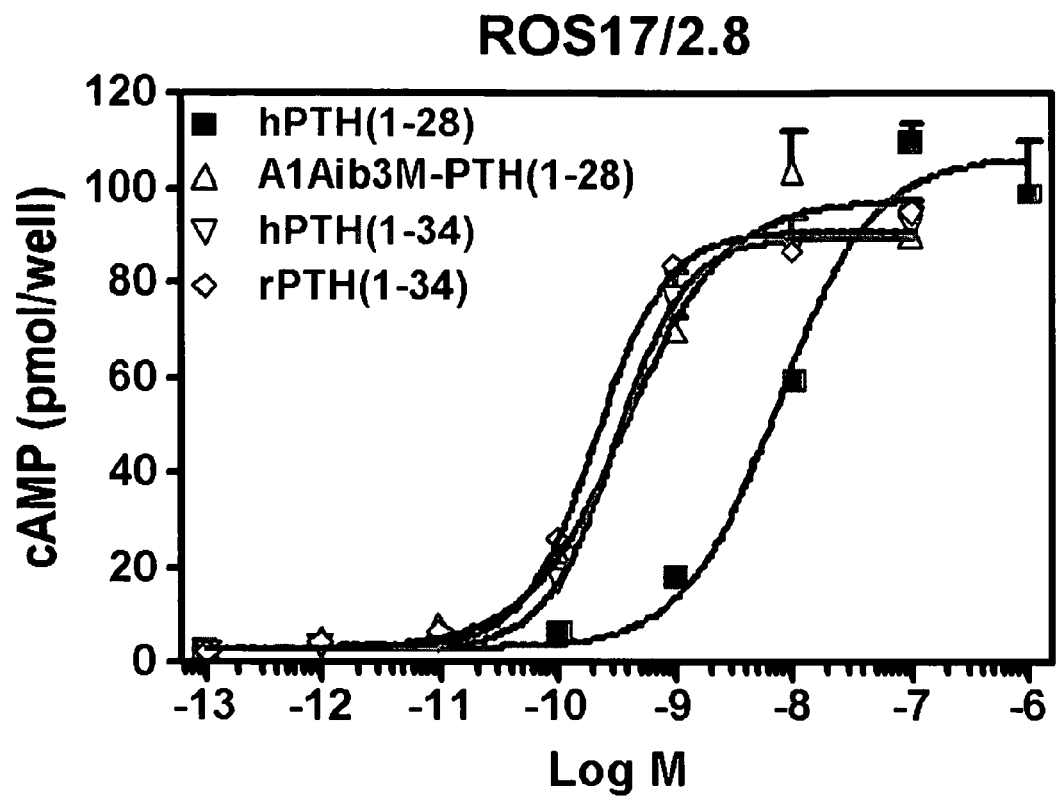
FIG. 8 is a graph showing cAMP dose responses in rat cells. Rat osteoblastic cells treated with hPTH(1-28)NH$_2$ (SEQ ID NO:129); Ala$^{1,12}$,Aib$^3$,Gln$^{10}$,Har$^{11}$,Trp$^{14}$,Arg$^{19}$-hPTH(1-28)NH$_2$ (SEQ ID NO:11); hPTH(1-34)NH$_2$ (SEQ ID NO:5), or r(rat)PTH(1-34)NH$_2$ (SEQ ID NO:130). The resulting intracellular cAMP formed was quantified by radioimmuno assay. EC50 values are listed below the graph. Curve fits were obtained by non-linear regression analysis.
Figures 9A, 9B, 9C, 9D:
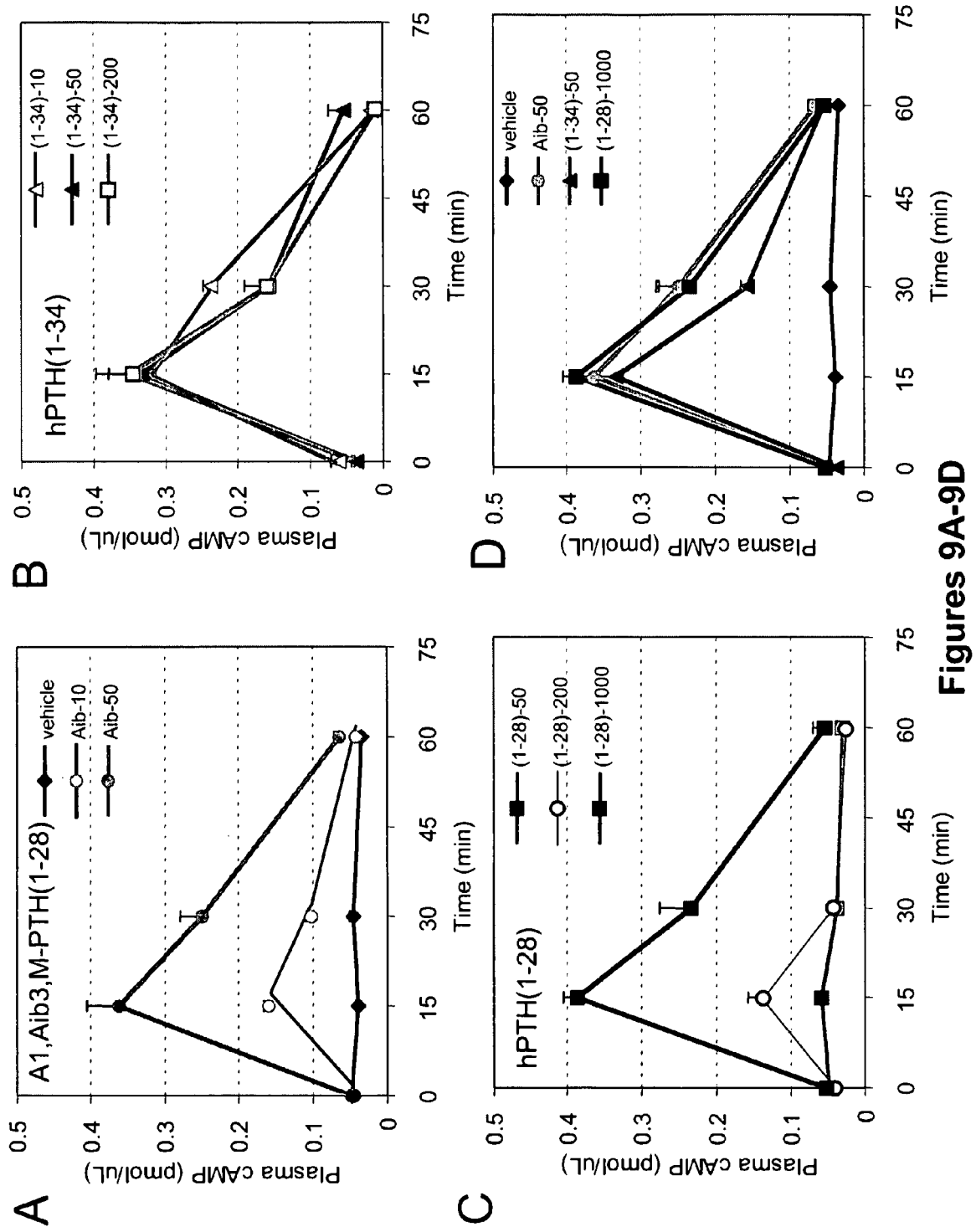
FIGS. 9A-9D are graphs showing in vivo plasma cAMP levels in mice treated with PTH analogs. Wild-type mice were injected subcutaneously with vehicle (0.9% NaCl/0.05% Tween-20), or vehicle containing a PTH peptide at a dose-level of 10 to 1,000 nmol of peptide per kg of body weight, and at indicated times after injection, blood was withdrawn from the tail vein, and the amount of cAMP in the resulting plasma was quantified by radioimmuno assay. Each curve corresponds to a peptide at a defined concentration, as indicated in the graph keys. The plasma cAMP concentrations are plotted as picomole per μl plasma. The data show that at 50 nmol/kg, Ala$^{1,12}$,Aib$^3$,Gln$^{10}$,Har$^{11}$,Trp$^{14}$,Arg$^{19}$-hPTH(1-28) NH$_2$ (SEQ ID NO:11) (Aib-50, FIG. 9A) and hPTH(1-34) NH$_2$ (SEQ ID NO:5) ((1-34)-50, FIG. 9B) produce comparable increases in plasma cAMP concentrations, whereas 1,000 nmol/kg of hPTH(1-28)NH$_2$ (SEQ ID NO:129) is required to achieve the same increase ((1-28)-1000, FIG. 9C, also FIG. 9D).

[a] data are means (±s.e.m.) from four experiments;
[b] basal camp (not subtracted) was 5.2 ± 0.9 pmole/well).
[c] data are means (±s.e.m.) from five experiments;
[d] basal IP value (not subtracted) was 330 ± 8 cpm/well.
[e], P vs. [Nle$^{8,21}$,Tyr$^{34}$]rPTH(1-34)NH$_2$ = 0.02.

cAMP measurements in rat osteoblastic cells. The capacity of certain ligands to produce cAMP signaling responses was further examined in vitro using rat osteoblastic cells (ROS17/2.8 cell line; FIG. 8). ROS17/2.8 cells were treated with hPTH(1-28)NH$_2$; Ala$^{1,12}$,Aib$^3$,Gln$^{10}$,Har$^{11}$, Trp$^{14}$,Arg$^{19}$-hPTH(1-28)NH$_2$; hPTH(1-34)NH$_2$, or r(rat)PTH(1-34)NH$_2$ for 10 minutes at room temperature in the presence of IBMX, and the resulting intracellular cAMP formed was quantified by radioimmuno assay. The $EC_{50}$ values for the various peptides were 7.39 nM for hPTH(1-28)NH$_2$; 0.37 nM for Ala$^{1,12}$, Aib$^3$, Gln$^{10}$,Har$^{11}$,Trp$^{14}$,Arg$^{19}$-hPTH(1-28)NH2; 0.31 nM for hPTH(1-34)NH$_2$; and 0.021 nM for r(rat)PTH(1-34)NH$_2$.

cAMP plasma measurements in mice in vivo. Wild-type mice were injected subcutaneously with vehicle (0.9% NaCl/0.05% Tween-20), or vehicle containing a PTH peptide so as to achieve a concentration ranging from 10 to 1000 nmol/kg of body weight. At the indicated times after injection, blood was withdrawn from the tail vein, and the amount of cAMP in the resulting plasma was quantified by radioimmuno assay (FIGS. 9A-9D).

Figure 10A:
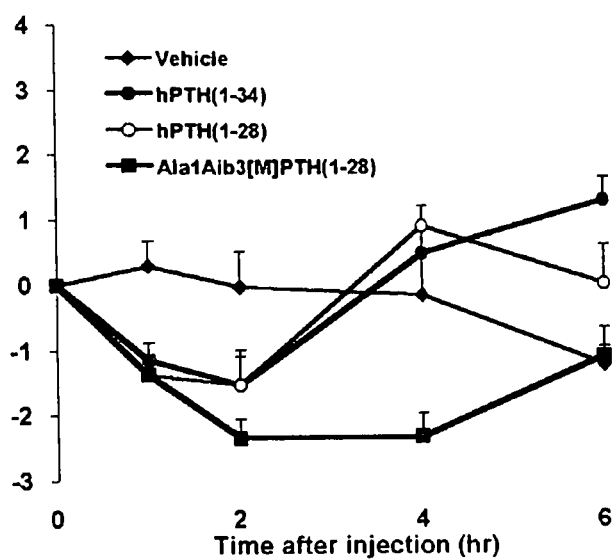
FIGS. 10A and 10B are graphs showing in vivo plasma phosphate and serum ionized calcium levels in mice treated with PTH analogs. Wild-type mice were injected subcutaneously with vehicle (0.9% NaCl/0.05% Tween-20), or vehicle containing Ala$^{1,12}$,Aib$^3$,Gln$^{10}$,Har$^{11}$,Trp$^{14}$,Arg$^{19}$-hPTH(1-28)NH$_2$ (SEQ ID NO:11) or hPTH(1-34)NH$_2$ (SEQ ID NO:5) at a dose level of 50 nanomoles per kg of body weight, or hPTH(1-28)NH$_2$ (SEQ ID NO:129) at a dose level of 1,000 nanomoles per kg of body weight and at the indicated times concentrations of plasma phosphate (FIG. 10A) and serum ionized calcium (FIG. 10B) were determined. Serum ionized calcium concentrations were determined using a Chiron Diagnostics Model 634 Ca$^{++}$/pH analyzer. Data in A are means (±s.e.m.) of one experiment using six mice (n=6) for each injection condition; similar results were obtained in three other experiments. Data in B are means (±s.e.m.) of two experiments, each performed using triplicate mice (n=3) for each injection condition.
Figure 10B:
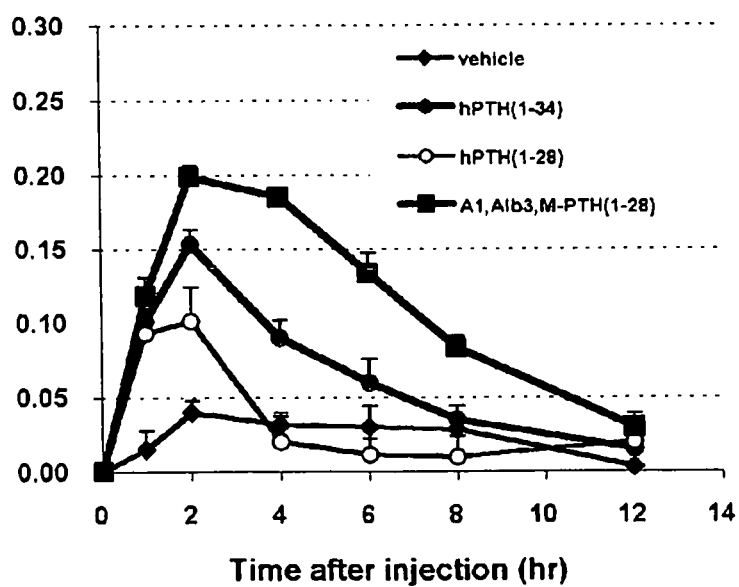

The mice were further analyzed for changes in plasma phosphate and serum ionized calcium concentrations. Wild-type mice were injected subcutaneously with vehicle (0.9% NaCl/0.05% Tween-20), or vehicle containing Ala$^{1,12}$,Aib$^3$, Gln$^{10}$,Har$^{11}$,Trp$^{14}$,Arg$^{19}$-hPTH(1-28)NH$_2$ or hPTH(1-34) NH$_2$ at doses of 50 nmol/kg body weight. At the indicated times after injection, blood was withdrawn from the tail vein and the concentrations of plasma phosphate (FIG. 10A) and serum ionized calcium (FIG. 10B) were determined. Serum ionized calcium concentrations were determined using a Chiron Diagnostics Model 634 Ca$^{++}$/pH analyzer. Plasma phosphate concentrations were measured using a Phosphorous Liqui-UV assay kit (StanBio Laboratory, Boerne, Tex.). Both peptides resulted in similar maximal increases in serum calcium and similar maximal reductions in plasma phosphate, but that the responses to Ala$^{1,12}$,Aib$^3$,Gln$^{10}$,Har$^{11}$,Trp$^{14}$, Arg$^{19}$-hPTH(1-28)NH$_2$ were more prolonged than those to hPTH(1-34)NH$_2$.

Phosphate uptake inhibition in opossum kidney cells. Inhibition of phosphate uptake was assessed using the opossum kidney (OK) cell line, which are derived from the renal proximal tubule. These cells mediate sodium-dependent phosphate transport function which is regulated by PTH receptor ligands. Thus, treating OK cells with PTH(1-34) inhibits their uptake of phosphate from the culture media.

Figure 11:
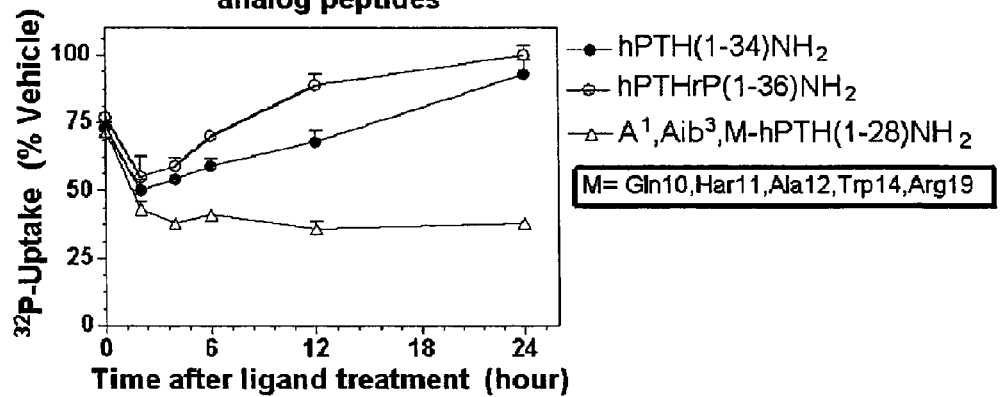
FIG. 11 is a graph showing the time courses of phosphate uptake inhibition in opossum kidney cells for PTH(1-34) (SEQ ID NO:5), PTHrP(1-36) (SEQ ID NO:6), and the long-acting PTH(1-28) analog, Ala$^{1,12}$,Aib$^3$,Gln$^{10}$,Har$^{11}$,Trp$^{14}$, Arg$^{19}$-hPTH(1-28)NH$_2$(SEQ ID NO:11). Data at each time point are plotted as a percentile of the amount of $^{32}$P radioactivity in lysates of cells treated for the same time with vehicle alone; these control levels ranged from 5,864±338 cpm (12 h) to 3,429±224 cpm (0 h). Data are means (±s.e.m.) of two experiments, each performed in duplicate.

Brief (10 minute) exposure of the cells to A$^1$,Aib$^3$,M-PTH (1-28) results in a dramatically prolonged inhibitory effect on phosphate uptake, whereas PTH(1-34) and hPTHrP(1-36) peptides exhibit a much shorter duration of phosphate uptake inhibition (FIG. 11).

Figure 12:
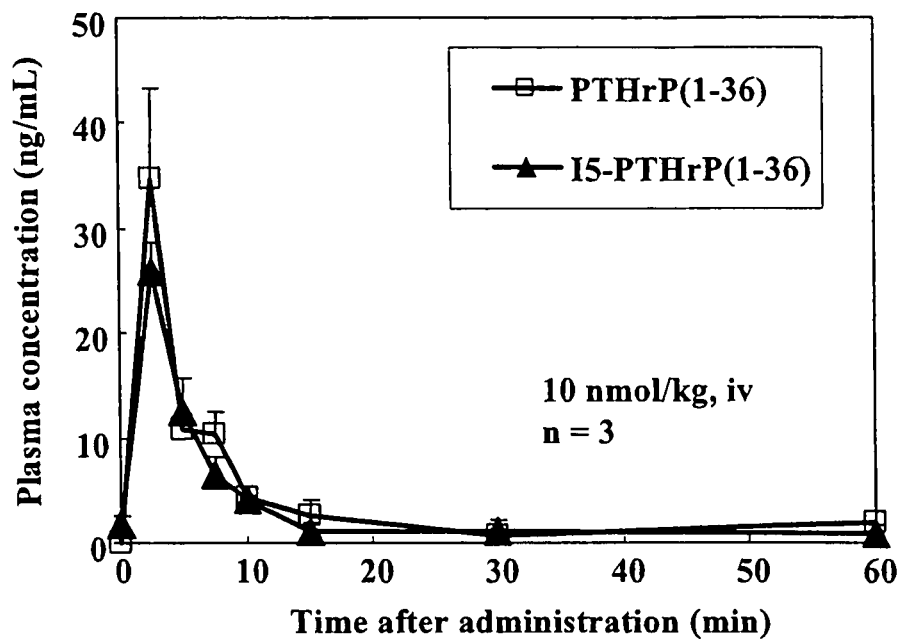
FIG. 12 shows pharmacokinetic profile of PTHrP(1-36) (SEQ ID NO:6) and [I$^5$]-PTHrP(1-36) (SEQ ID NO:13) in normal rats. Plasma concentrations of peptides were measured by radioimmunoassay (RIA). The His$^5$→Ile substitution in PTHrP(1-36) did not significantly change the pharmokinetic profile.

Pharmacokinetics and hypercalcemic action of PTHR ligands in normal rats. Pharmacokinetic profiles of iv injected PTHrP(1-36) and [I$^5$]-PTHrP(1-36) were investigated in normal rats (FIG. 12). Both PTHrP(1-36) and [I$^5$]-PTHrP(1-36) rapidly disappeared from the circulation, and the pharmacokinetic profile of [I$^5$]-PTHrP(1-36) was comparable to that of PTHrP(1-36).

Figure 13A:
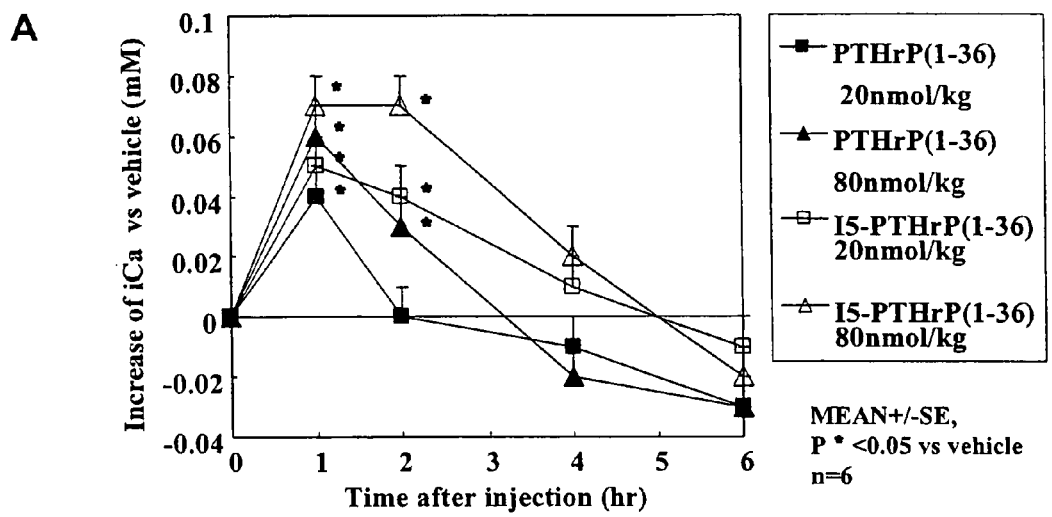
FIGS. 13A-13C are a set of graphs showing the effects of PTHrP(1-36) (SEQ ID NO:6) and [I$^5$]-PTHrP(1-36) (SEQ ID NO:13) in normal rats.
Figure 13B:
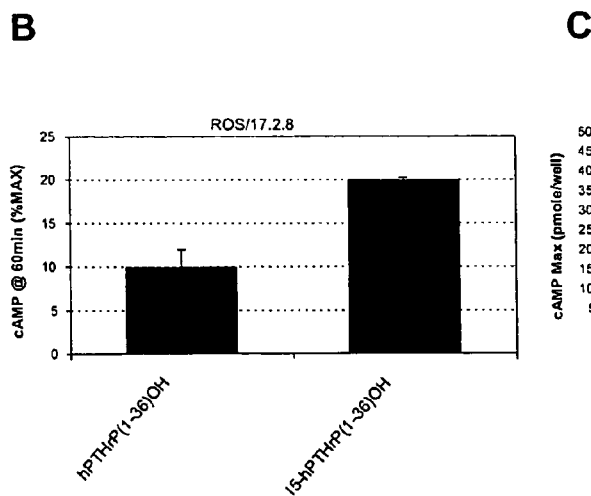
Figure 13C:
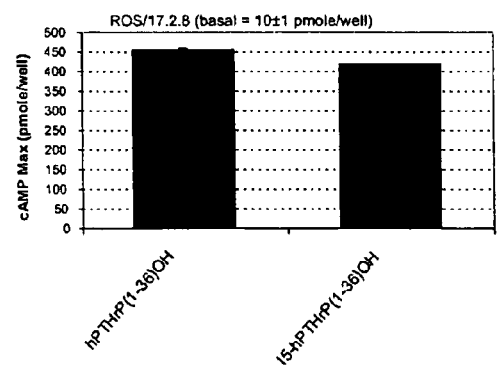
Figure 14A:
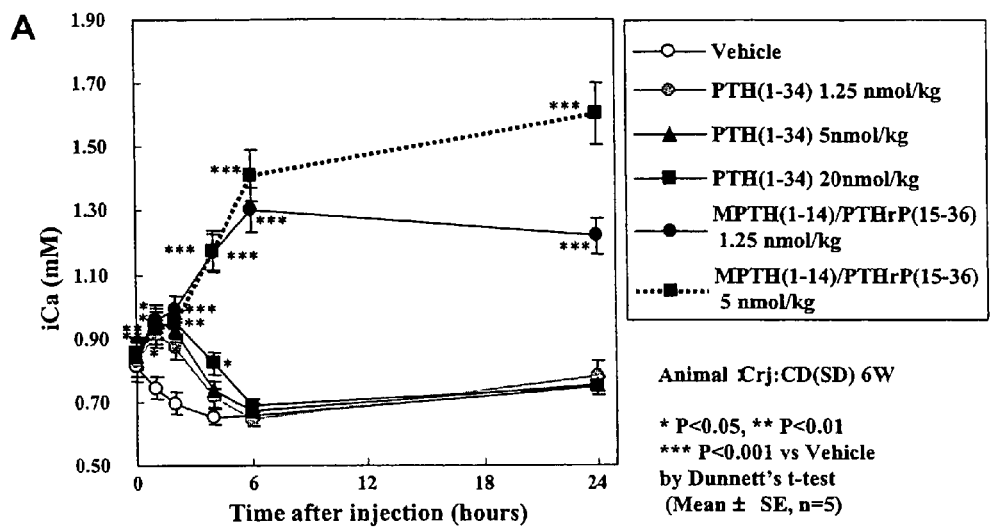
FIGS. 14A-14C are graphs showing prolonged calcemic effects in TPTX rats (FIG. 14A) and prolonged cAMP signaling in ROS17/2.8 cells (FIGS. 14B and 14C) for Mc-PTH (1-14)/PTHrP(15-36) (SEQ ID NO:15) (Mc=Ala$^{1,3,12}$,Gln$^{10}$, Arg$^{11}$,Trp$^{14}$, Arg$^{19}$).
Figure 14B:
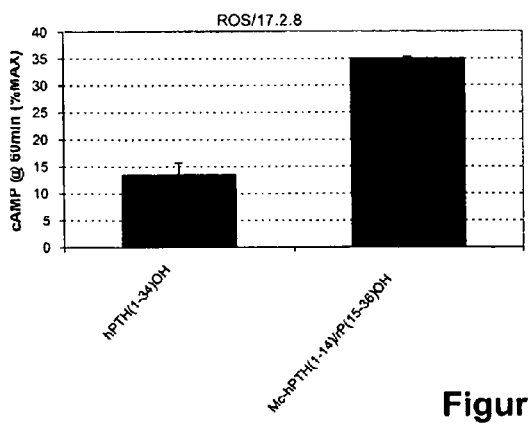
Figure 14C:
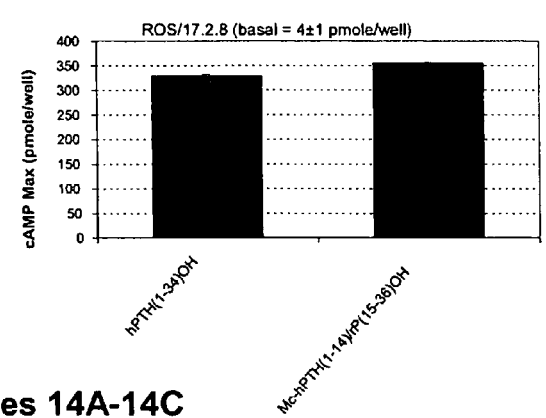
Figures 15A, 15B:
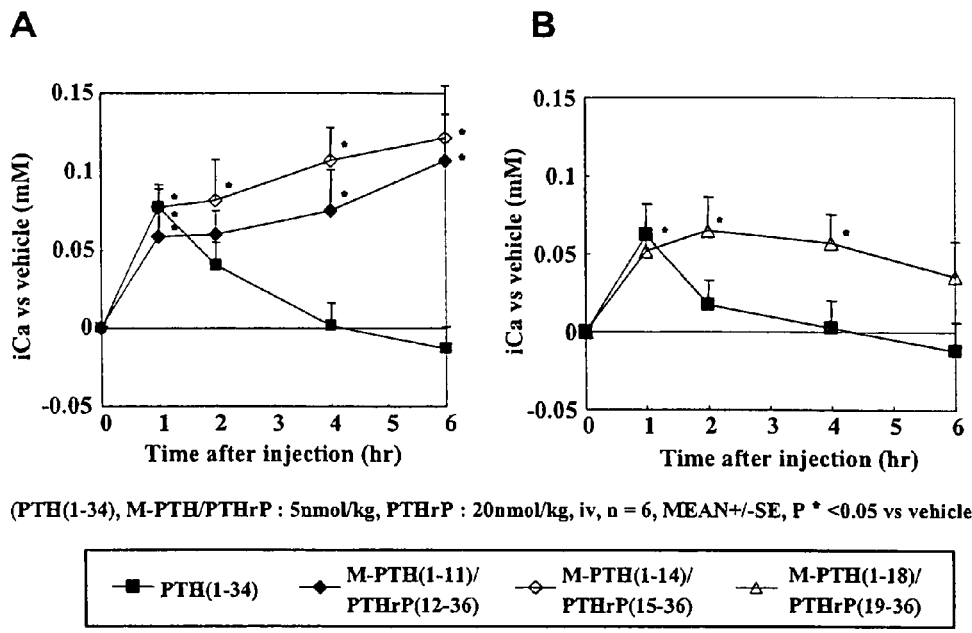
FIGS. 15A and 15B are graphs showing transient calcemic action of modified PTH/PTHrP hybrids in normal rats. Prolonged calcemic effects are observed for Mc-PTH(1-11)/PTHrP(15-36) (SEQ ID NO:14) and Mc-PTH(1-14)/PTHrP (15-36) (SEQ ID NO:15). The Table inset shows binding affinities for the analogs at the R$^0$ and RG receptor conformations, measured in vitro. The analogs used were hPTH(1-34)OH (SEQ ID NO:5), Mc-PTH(1-11)/PTHrP(15-36) (SEQ ID NO:14), Mc-PTH(1-14)/PTHrP(15-36) (SEQ ID NO:15), and Mc-PTH(1-18)/PTHrP(19-36) (SEQ ID NO:16) (Mc=Ala$^{1,3,12}$,Gln$^{10}$,Arg$^{11}$,Trp$^{14}$, Arg$^{19}$).
Figure 16A:
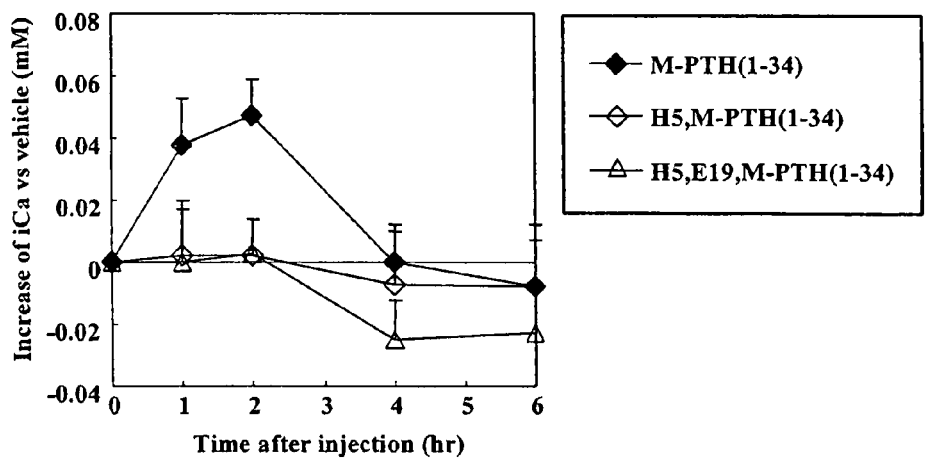
FIGS. 16A-16C are graphs showing calcemic action of Mc-modified PTH(1-34) analogs with or without the Ile$^5$→His and Arg$^{19}$→Glu substitutions, in normal rats (FIG. 16A) and delayed and maximal cAMP responses in ROS 17/2.8 cells (FIGS. 16B and 16C). The Table inset shows binding affinities for the analogs at the R$^0$ and RG receptor conformations, measured in vitro. The Ile$^5$→His and Arg$^{19}$→Glu substitutions reduce affinity for R$^0$, and reduce duration of cAMP signaling in vitro and the calcemic effect in vivo. The analogs used were Mc-hPTH(1-34)OH (SEQ ID NO:131), [H$^5$],Mc-hPTH(1-34)OH (SEQ ID NO:132), and [H$^5$,E$^{19}$],Mc-hPTH(1-34)OH (SEQ ID NO:24)=(Mc=Ala$^{1,3,12}$,Gln$^{10}$,Arg$^{11}$,Trp$^{14}$, Arg$^{19}$).
Figure 16B:
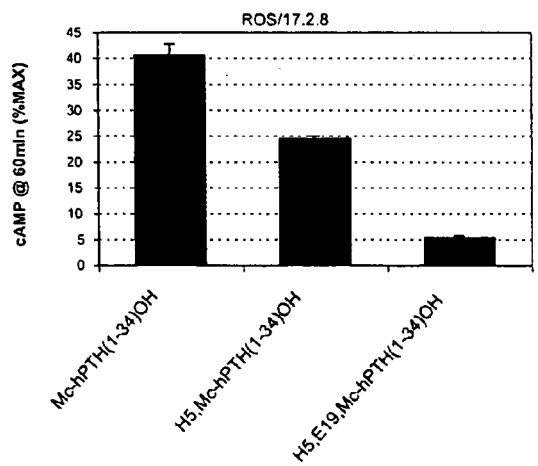
Figure 16C:
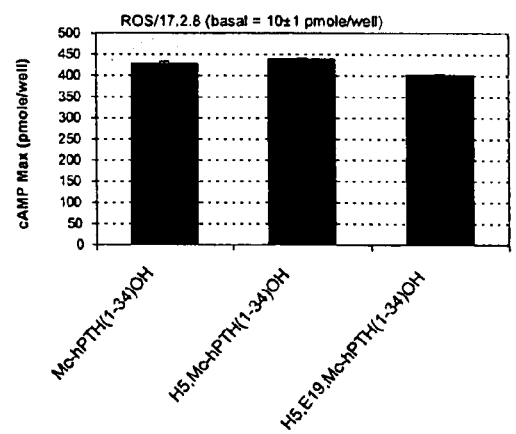
Figure 18A:
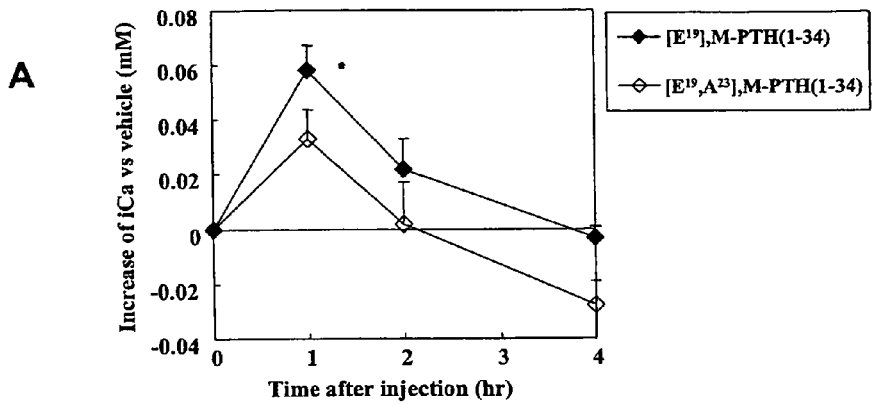
FIGS. 18A and 18B are graphs showing the calcemic and cAMP actions of E$^{19}$,Mc-modified PTH(1-34) analogs, with or without the Trp$^{23}$→Ala substitution in normal rats (FIG. 18A) and in ROS17/2.8 cells (FIG. 18B). The Table inset shows binding affinities for the analogs at the R$^0$ and RG receptor conformations, measured in vitro. The Trp$^{23}$→Ala substitution reduced binding affinity of [E$^{19}$ Mc]PTH(1-34) for R$^0$ by 10-fold, reduced duration of cAMP signaling in cells, and reduced the hypercalcemic effect of this peptide in vivo. The analogs used were [E$^{19}$],Mc-hPTH(1-34)OH (SEQ ID NO:21) and [A$^{23}$,E$^{19}$],Mc-hPTH(1-34)OH (SEQ ID NO:28) (Mc=Ala$^{1,3,12}$,Gln$^{10}$,Arg$^{11}$, Trp$^{14}$, Arg$^{19}$).
Figure 18B:
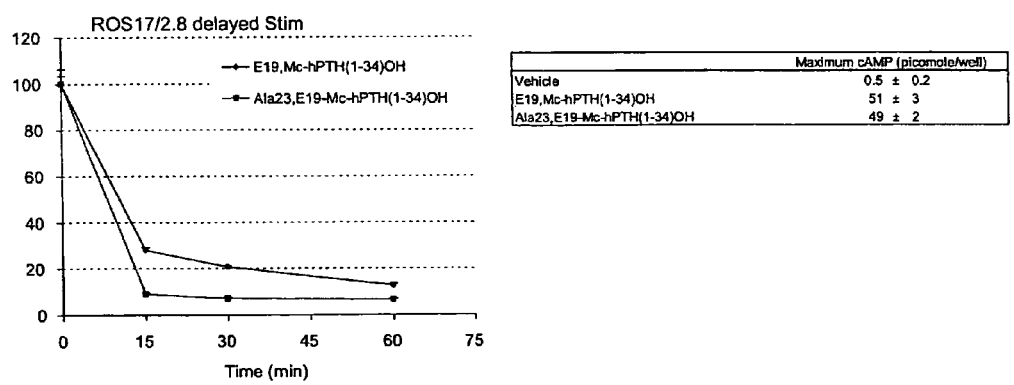
Figure 19A:
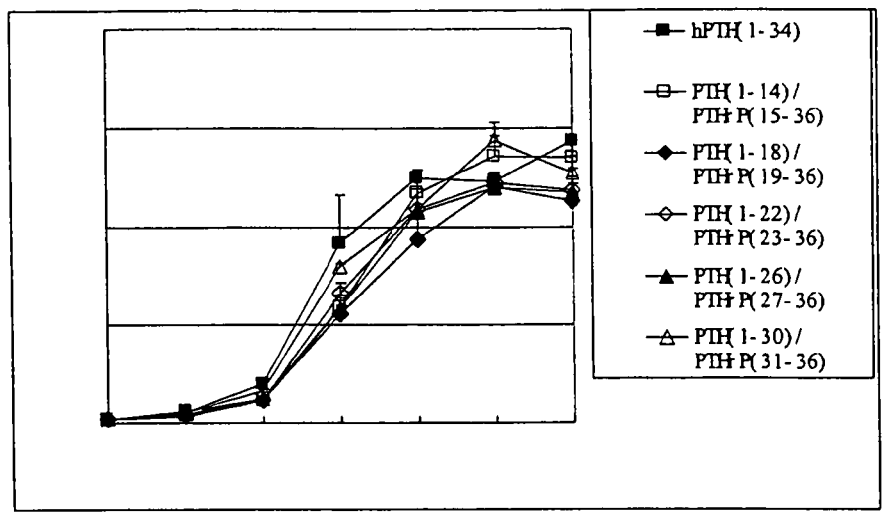
FIGS. 19A and 19B are graphs showing cAMP signaling of native PTH/PTHrP hybrid analogs in cells expressing the human PTH1 receptor. The analogs show similar potencies in acute dose-response assays. The analogs used were hPTH(1-14)/PTHrP(15-36) (SEQ ID NO:134), hPTH(1-18)/PTHrP(19-36) (SEQ ID NO:135), hPTH(1-22)/PTHrP(23-36) (SEQ ID NO:26), hPTH(1-26)/PTHrP(27-36) (SEQ ID NO:136), hPTH(1-30)/PTHrP(31-36) (SEQ ID NO:27), hPTH(1-14)/PTHrP(15-36) (SEQ ID NO:134), hPTH(1-11)/PTHrP(12-36) (SEQ ID NO:137), and hPTH(1-17)/PTHrP(18-36) (SEQ ID NO:138). The controls used were hPTH(1-34) (SEQ ID NO:5) and PTHrP(1-36) (SEQ ID NO:6).
Figure 19B:
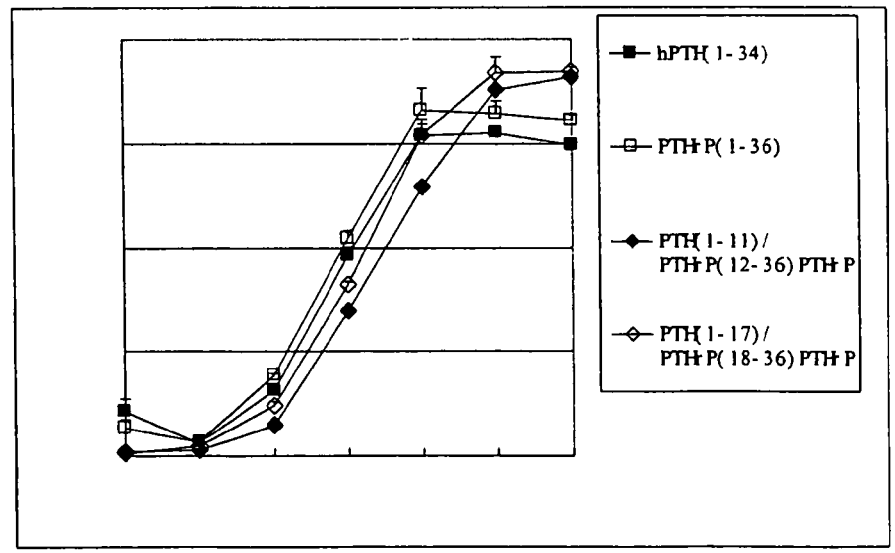
Figure 20A:
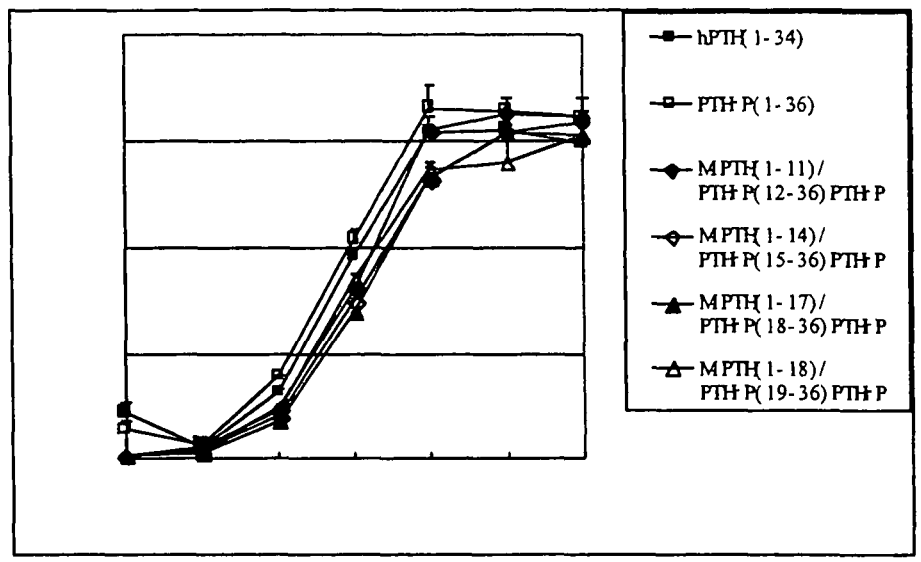
FIGS. 20A and 20B are graphs showing cAMP signaling of Mc-modified PTH/PTHrP hybrid analogs with human PTH1 receptor. The analogs show similar potencies in acute dose-response assays. The analogs used were M-hPTH(1-11)/PTHrP(12-36) (SEQ ID NO:14), M-PTH(1-14)/PTHrP(15-36)OH (SEQ ID NO:15), M-PTH(1-17)/PTHrP(18-36)OH (SEQ ID NO:139), M-PTH(1-18)/PTHrP(19-36)OH (SEQ ID NO:16), M-PTH(1-22)/PTHrP(23-36)OH (SEQ ID NO:140), M-PTH(1-26)/PTHrP(27-36)OH (SEQ ID NO:141), and M-PTH(1-30)/PTHrP(31-36)OH (SEQ ID NO:142). The controls used were hPTH(1-34) (SEQ ID NO:5) and PTHrP(1-36) (SEQ ID NO:6).
Figure 20B:
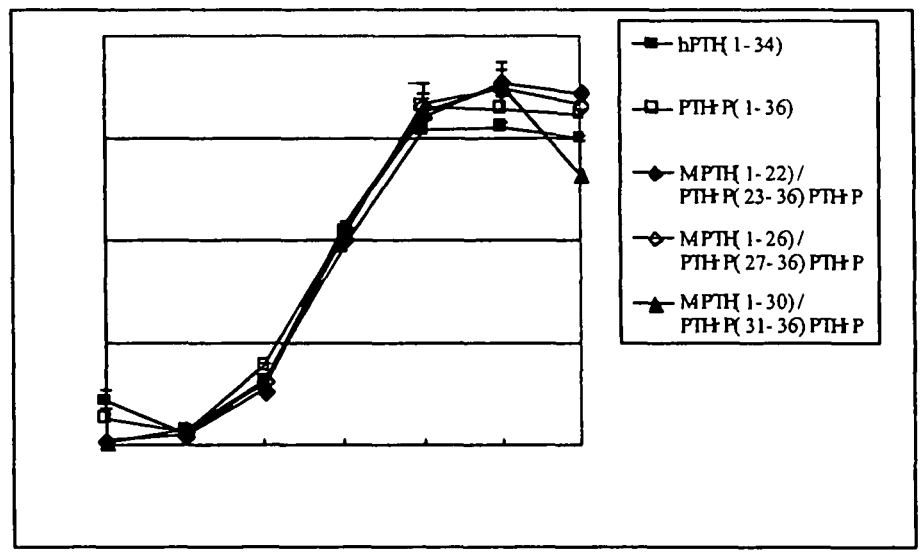
Figures 21A, 21B:
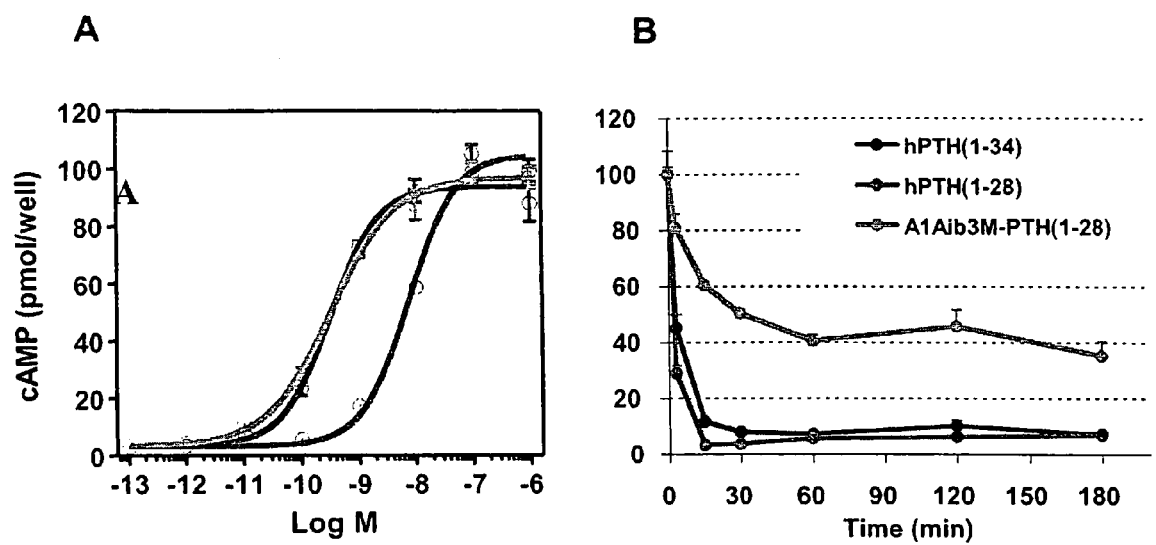
FIGS. 21A and 21B are graphs showing acute (FIG. 21A) and delayed (FIG. 21B) cAMP analyses in ROS17/2.8 cells of hPTH(1-34)NH$_2$ (SEQ ID NO:5), hPTH(1-28)NH$_2$ (SEQ ID NO:129) and [A$^1$,Aib$^3$,M]-PTH(1-28)NH ([A$^{1,12}$,Aib$^3$,Q$^{10}$, homoarginine$^{11}$,W$^{14}$,R$^{19}$]hPTH(1-28)NH$_2$) (SEQ ID NO:11).
Figures 22A, 22B, 22C:
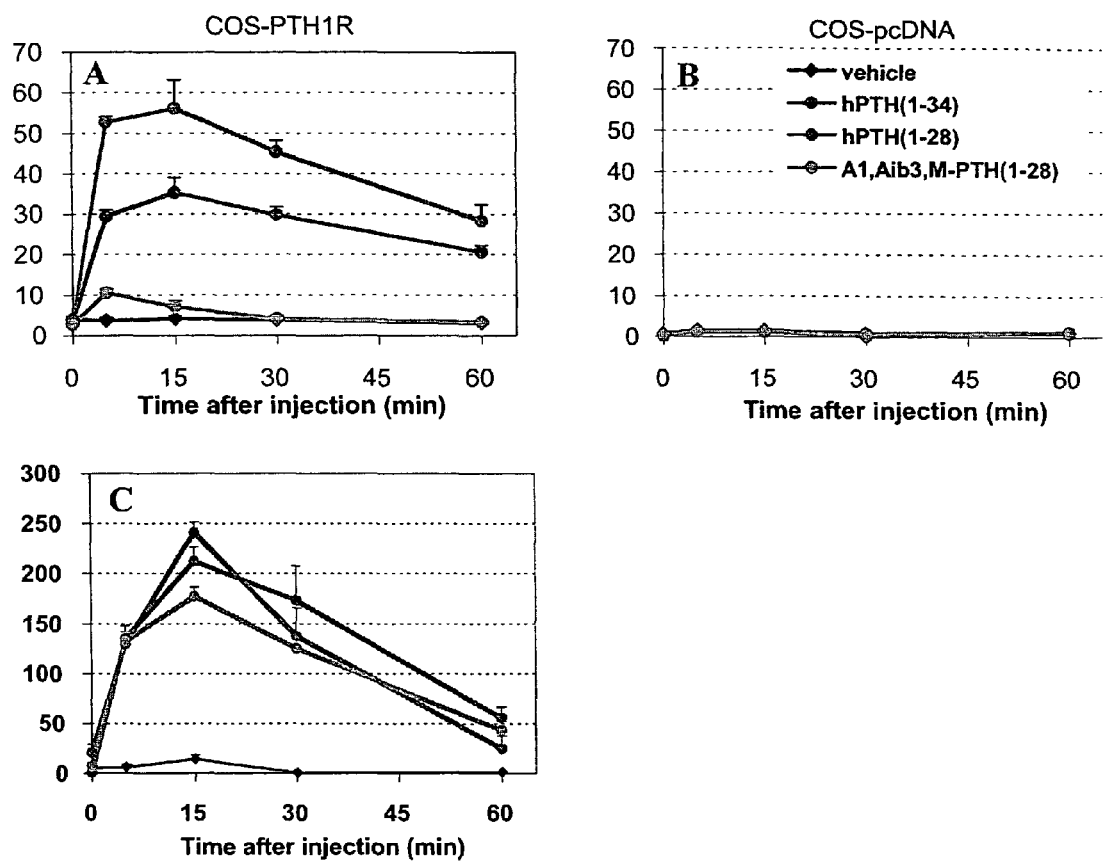
FIGS. 22A-22C are graphs showing pharmacokinetic analysis of PTH ligands injected into mice, assessed by a bioassay procedure using COS-7 cells transfected with the PTHR (FIGS. 22A and 22C) for activity read-out. COS-7 cells transfected with the pcDNA 1 vector were used as controls (FIG. 22B). Mice were injected with vehicle, with hPTH (1-34) (SEQ ID NO:5) (50 nmol/kg), hPTH(1-28) (SEQ ID NO:129) (1,000 nmol/kg), or [A$^1$,Aib$^3$,M]-PTH(1-28) (SEQ ID NO:11) (50 nmol/kg) and at the indicated times after injection, blood was collected from the tail vein, plasma was prepared in the presence of EDTA and proteinase inhibitors, the plasma was diluted 50-fold, and 45 μl of the diluted sample was applied to COS cells in 96-well plates. Then, following a 15 minute incubation, the intracellular cAMP in the COS cells was measured. Each tracing shows data (mean±SE), from six identically treated mice.
Figure 23:
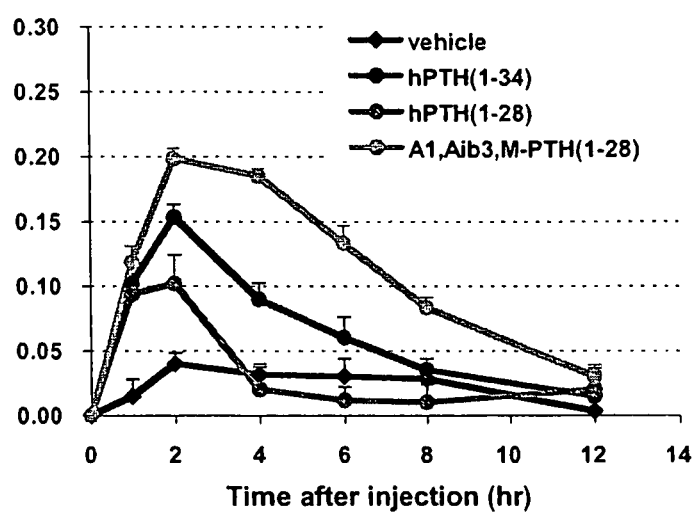
FIG. 23 is a graph showing changes in blood ionized calcium in mice. Shown are the changes in blood ionized calcium (iCa$^{++}$) in mice treated with hPTH(1-34) (SEQ ID NO:5) (50 nmol/kg), hPTH(1-28) (SEQ ID NO:129) (1,000 nmol/kg), or [A$^1$,Aib$^3$,M]-PTH(1-28) (SEQ ID NO:11) (50 mmol/kg), at times after injection (studies performed in conjunction with those of FIGS. 22A-22C). Data are normalized to the iCa$^{++}$ in blood drawn from each mouse prior to injection (pre). Each trace shows data (mean±SE) from six identically treated mice.
Figure 24A:
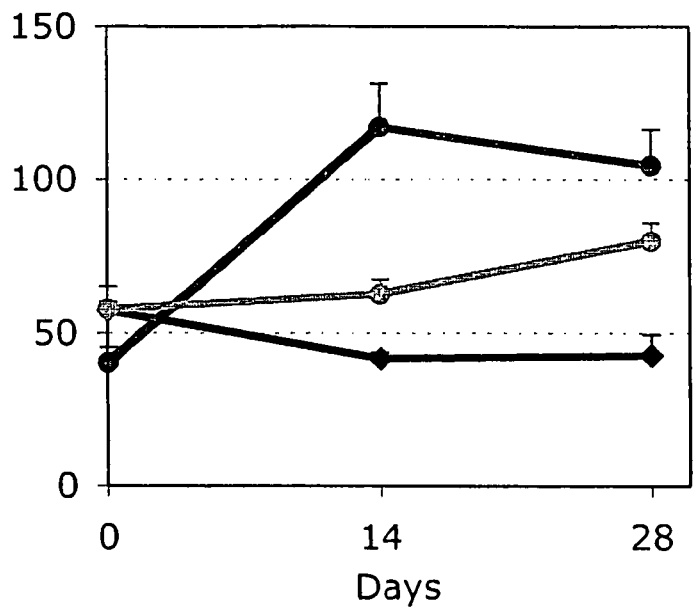
FIGS. 24A and 24B are graphs showing changes in bone-formation and bone-resorption markers in mice after long-term treatment with PTH ligands. Shown are the serum levels of the bone-formation marker osteocalcin (FIG. 24A) and the bone-resorption marker, collagen-type I C-terminal fragment (CTX) (FIG. 24B) in mice treated with hPTH(1-34) (SEQ ID NO:5) (50 nmol/kg), and [A',Aib$^3$],M-PTH(1-28) (SEQ ID NO:11) (50 nmol/kg). Markers were measured using Mouse Osteocalcin EIA kit (Biomedical Technologies) and RatLaps CTX ELISA (Nordic Bioscience) kit. Each trace shows data (mean±SE) from six identically treated mice.
Figure 24B:
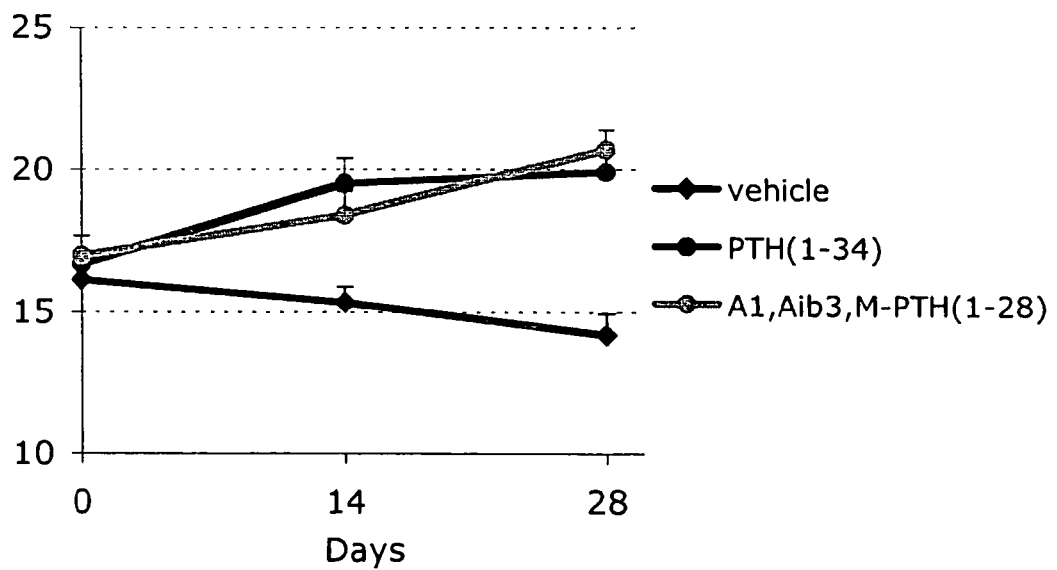

We also measured the calcemic actions of intravenously injected PTHrP(1-36) and [I$^5$]-PTHrP(1-36) in normal rats (FIG. 13). PTHrP(1-36) and [I$^5$]-PTHrP(1-36) at 20 and 80 nmol/kg increased blood ionized calcium levels to the same extent at one hour. Blood ionized calcium levels declined at two hours after injection with PTHrP(1-36), but were sustained at high levels at two hours after injection with [I$^5$]-PTHrP(1-36). Thus, [I$^5$]-PTHrP(1-36) and PTHrP(1-36) exhibited comparable pharmacokinetic profiles (FIG. 12), but [I$^5$]-PTHrP(1-36) exhibited a higher binding affinity for the R$^0$PTHR conformation (FIGS. 3 and 6). Therefore, the prolonged calcemic actions of [I$^5$]-PTHrP(1-36) observed in vivo can best be explained by its high R$^0$ binding affinity.

In vitro and in vivo screening of PTH or PTHrP analogs with human PTH receptor. We designed and synthesized native PTH-PTHrP hybrid analogs, and [A$^{1,3,12}$,Q$^{10}$,R$^{11}$, W$^{14}$] (M-modified) PTH-PTHrP hybrid analogs, and tested their cAMP signaling capacities in HKRK-B7 cells expressing the hPTH receptor. Each of the native, and M-modified PTH/PTHrP hybrid analogs showed cAMP signaling activity comparable to hPTH(1-34) (FIG. 25). We assessed affinity of native or M-modified PTH and PTHrP hybrid analogs for the R$^0$ and RG states of the human PTH receptor (FIGS. 26A and 26B) in COS-7 cell membranes.

Hypercakemic action of PTH and PTHrP analogs in normal and TPTX rats. The transient calcemic actions of the native and M-modified PTH-PTHrP hybrid analogs were evaluated in normal and TPTX rats using PTH(1-34) and PTHrP(1-36) as controls (FIGS. 13A, 14A, 15A, 15B, 16A, 17A, and 18A). I$^5$-PTHrP(1-36), MPTH(1-14)/PTHrP(15-36), PTH(1-14)/PTHrP(15-36), PTH(1-18)/PTHrP(19-36), M-PTH(1-34) showed higher calcemic actions than did PTH (1-34); in contrast, PTH(1-22)/PTHrP(23-36) and PTH(1-26)/PTHrP(27-36) showed weaker calcemic actions than did either PTH(1-34) or PTHrP(1-36) control peptides. Binding to the rat PTHR was also measured in vitro. Length of signaling activity was confirmed using the delayed cAMP assay (FIGS. 13B-13C, 14B-14C, 15B, 16B-16C, 17B-17C, and 18B), which clearly demonstrates a correlation between the R$^0$/RG selectivity from binding data shown in vitro and both the hypercalcemic action in vivo as well as and delayed cAMP response in vitro. The cAMP signaling of all these peptides did not vary substantially (FIGS. 19A, 19B, 20A, and 20B).

Materials and Methods

The following materials and methods were used to perform the above experiments.

Peptides. The peptides used in FIGS. 1-3, and 5-11 were synthesized by the M.G.H. Biopolymer Core facility, as described in Shimizu et al., *J. Biol. Chem.* 276:49003-49012 (2001). These peptides include [Nle$^{8,21}$,Tyr$^{34}$]rat(r)PTH(1-34)NH$_2$ (PTH(1-34) (SEQ ID NO:123); [Aib$^{1,3}$,Nle$^8$,Gln$^{10}$, homoarginine$^{11}$,Ala$^{12}$,Trp$^{14}$,Tyr$^{15}$]rPTH(1-15)NH$_2$ ([Aib$^{1,3}$,M]PTH(1-15), SEQ ID NO:126); [Ala$^{1,12}$,Aib$^3$, Gln$^{10}$,homoarginine$^{11}$,Trp$^{14}$,Arg$^{19}$]human(h)PTH(1-28) NH$_2$ (SEQ ID NO:11) {[Ala$^1$,Aib$^3$,M]PTH(1-28)}; [Tyr$^{36}$] hPTHrP(1-36)NH$_2$ (SEQ ID NO:124) {(PTHrP(1-36)}; [Ile$^5$,Tyr$^{36}$]hPTHrP(1-36)NH$_2$ (SEQ ID NO:125) {Ile$^5$-PTHrP(1-36)}; hPTH(1-34)NH$_2$ (SEQ ID NO:5); [His$^5$] rPTHrP(1-34)NH$_2$ (SEQ ID NO:9); rPTH(1-34)NH$_2$ (SEQ ID NO:130) and [His$^5$]rPTHrP(1-36)NH$_2$ (SEQ ID NO:10). The hPTH(1-34)COOH peptide (free carboxyl) used in FRET analyses (FIG. 4) was purchased from Bachem Calif. (Torrance, Calif.). The rat studies used human PTHrP(1-36) synthesized by American Peptide Company, Inc. (California, USA). Human PTH(1-34) was purchased from Peptide Institute Inc (Osaka, Japan). PTH or PTHrP analogs were synthesized by Sigma Aldrich Japan (Tokyo, Japan). Peptides used in rat studies were dissolved at 1 mM in 10 mM acetic acid, and stocked at −80° C. refrigerator.

The peptides used in FIGS. 12-16 were purchased from either American Peptide Company, Inc., California, USA (hPTHrP(1-36)COOH), Peptide Institute Inc., Osaka, Japan (hPTH(1-34)COOH), or Sigma-Aldrich Japan, Tokyo, Japan (PTH/PTHrP hybrid analogs). All peptides were dissolved in 10 mM acetic acid to a peptide concentration of between 0.1 mM and 4 mM; and stored at −80° C. Peptide purity and quality was verified by analytical high performance liquid chromatography (HPLC), matrix-assisted laser desorption/ ionization (MALDI) mass spectrometry. Radiolabeled peptide variants were prepared by the oxidative chloramine-T procedure using Na$^{125}$I (specific activity: 2,200 Ci/mmol, Perkin Elmer/NEN Life Science Products, Boston, Mass.) and were purified by reversed-phase HPLC.

Cell Culture. Cells were cultured at 37° C. in a humidified atmosphere containing 5% CO$_2$ in Dulbecco's modified Eagle's medium (DMEM), supplemented with 10% fetal bovine serum (HyClone, Logan Utah), 100 units/ml penicillin G, and 100 μg/ml streptomycin sulfate (Invitrogen Corp. Carlsbad, Calif.). The PTHR-expressing cell lines used were HKRK-B7, HKRK-B64, ROS17/2.8, and HEK-PTHR-cam. The HKRK-B7 and HKRK-B64 lines were derived from the porcine kidney cell line, LLC-PK1, via stable transfection with plasmid DNA (pcDNA1 vector, Invitrogen Corp.) encoding the human PTHR, and express the PTHR at approximate surface densities of 950,000 and 90,000 PTH-binding sites per cell, respectively (Takasu et al., *J. Bone Miner. Res.* 14:11-20 (1999)). ROS17/2.8 cells are rat osteosarcoma cells (Majeska et al., *Endocrinology* 107:1494-1503 (1980)) and express the endogenous rat PTHR at an approximate surface density of 70,000 PTH-binding sites per cell (Yamamoto, I. et al., *Endocrinology* 122:1208-1217 (1988)). HEK-PTHR-cam cells were derived from HEK-293 cells by stable DNA transfection and express a human PTHR derivative (PTHR-cam) containing cyan fluorescent protein (CFP) inserted at Gly$^{395}$ in the third intracellular loop and yellow fluorescent protein (YFP) inserted in the carboxy-terminal tail (Vilardaga et al., *Nat. Biotechnol.* 21:807-812 (2003)). Cells were propagated in T75 flasks and divided into 24-well plates for assays with intact cells, six-well plates for membrane preparations, or onto glass cover-slips for FRET studies. COS-7 cells were transiently transfected in six-well plates using Fugene-6 (Roche Diagnostics, Indianapolis Ind.) and CsCl-purified plasmid DNA encoding the PTHR (3 μl Fugene, 1 μg DNA, per well), or co-transfected with plasmids encoding the PTHR and a negative-dominant Gα$_s$ subunit Gα$_s$ND (6 μl Fugene, 1 μg each DNA per well). This Gα$_s$ND subunit binds more effectively, but unproductively, to receptors than does wild-type Gα$_s$ (Berlot, C. H. *J. Biol. Chem.* 277:21080-21085 (2002)), and has been found to enhance the binding of $^{125}$I-[Aib$^{1,3}$,M]PTH(1-15)NH$_2$ radioligand to the PTHR in cell membranes (see below) (Dean, T. et al., J. Biol. Chem. (2006)).

Binding Studies. Binding studies were performed using cell membranes as described (Dean et al., *Mol Endocrinol* 20(4):931-43 (2006)). Briefly, reactions were incubated at room temperature in membrane assay buffer (20 mM HEPES, pH 7.4, 0.1 M NaCl, 3 mM MgSO$_4$, 20% glycerol, 3 mg/ml bovine serum albumin, protease inhibitor cocktail—final concentrations: 1 mM AEBSF, 0.8 μM Aprotonin, 20 μM leupeptin, 40 μM Bestatin, 15 μM Pepstatin A, 14 μM E-64-Sigma-Aldrich Inc., St. Louis, Mo.). Reactions contained a total membrane protein concentration of 20 to 100 μg/mL, and a total radioactivity concentration of approximately 150, 000 cpm/ml. Unlabeled peptide ligands and/or GTPγS (Sigma-Aldrich Inc. St. Louis, Mo.) were added to the reactions as indicated. At the end of the reaction, bound and free radioligand were separated by vacuum filtration using a 96-well vacuum filter plate and vacuum filter apparatus (Multi-Screen system with Durapore HV, 0.65 μM filters; Millipore Corp., Milford, Mass.); the air-dried filters were then detached from the plate and counted for gamma radio-activity using a gamma counter.

Radioligand dissociation. These studies were performed as bulk reactions in 15 mL round-bottom polystyrene snap-cap tubes (Falcon) (total reaction volume=5.0 ml). Membranes and radioligand were pre-incubated for 90 minutes to allow complex formation; the dissociation phase was then initiated by the addition of an excess of the unlabeled analog of the radioligand (5×10$^{-7}$ M final concentration), with or without GTPγS (5×10$^{-5}$ M). Immediately prior to this addition (t=0), and at successive time-points thereafter, 0.2 ml aliquots (~30, 000 cpm) were withdrawn and immediately processed by vacuum filtration, as described above. Non-specific binding was determined in parallel reaction tubes containing the unlabeled analog of the radioligand (5×10$^{-7}$ M) in both the pre-incubation and dissociation phases. The specifically bound radioactivity at each time point was calculated as a percent of the radioactivity specifically bound at t=0. Equilibrium competition binding and GTPγS inhibition. Binding reactions performed with $^{125}$I-Aib$^{1,3}$,MPTH(1-15) radioligand were assembled and incubated in the wells of the 96-well, Multi-Screen vacuum filtration plates. Membranes, tracer radioligand, and various concentrations of unlabeled ligands and/or GTPγS were incubated in the wells for 90 minutes, following which, the reaction plates were processed by rapid vacuum filtration to separate bound from free radioligand, as described above. Binding reactions performed with $^{125}$I-PTH (1-34) radioligand were assembled and incubated in 96-well polystyrene micro-titer plates (Falcon, total reaction volume=230 μl), and at the end of the incubation were transferred to wells of a 96-well, Multi-Screen vacuum filtration plate and processed, as described above. This transfer maneuver was performed for the $^{125}$I-PTH(1-34)-containing reactions to minimize non-specific binding of the radioligand to the Multi-screen filter membranes. For both radioligands, the non-specific binding was determined in reactions containing a saturating concentration of the unlabeled analog of the radioligand. The specifically bound radioactivity was calculated as a percent of the radioactivity specifically bound in the absence of a competing ligand or GTPγS.

To assess the capacities of various unlabeled peptide ligands to bind to the G protein-uncoupled and G protein-coupled PTHR conformations ($R^0$ and RG, respectively), membranes were prepared from transiently transfected COS-7 cells and the following assay conditions. To assess binding to $R^0$, membranes were prepared from cells transfected with the PTHR, $^{125}$I-PTH(1-34) as a tracer radioligand, and GTPγS ($1 \times 10^{-5}$ M) was added to the binding reactions. This binding format is based on the premise that $^{125}$I-PTH(1-34) binds predominantly to the $R^0$ conformation of the PTHR, and that this conformation is enriched in the membranes, relative to RG, by the presence of GTPγS (Hoare et al., *J. Biol. Chem.* 276:7741-53 (2001); Dean et al., *Mol Endocrinol* (2006)). To assess binding to RG, membranes prepared from cells co-transfected with the PTHR and a negative dominant Gα$_s$ subunit (Gα$_s$ND) were used, and $^{125}$I-[Aib$^{1,3}$,M]PTH(1-15) was used as a tracer radioligand. This binding format is based on the premise that $^{125}$I-[Aib$^{1,3}$,M]PTH(1-15) binds predominantly to the RG conformation of the PTHR, and that this conformation is enriched in the membranes, relative to R or $R^0$, by the presence of Gα$_s^{ND}$ (Hoare, S. *J. Biol. Chem.* (2001); Berlot, C. H. *J. Biol. Chem.* (2002); Dean, T. et al., *J. Biol. Chem.* (2006)). Analysis of binding to any low affinity PTHR conformation (R) present in the membrane preparations is precluded by the low concentrations (~25 µM) of tracer radioligands in the reactions.

Fluorescent Resonance Energy Transfer (FRET). HEK-293 cells stably expressing HEK-PTHR-CFP$_{IC3}$/YFP$_{CT}$ (previously called HEK-PTHR-Cam cells (Vilardaga et al., *Nat. Biotechnol.* 21:807-812 (2003)) were grown on glass coverslips and processed for FRET analysis as described. With these cells, excitation of the CFP (donor) in PTHR-CFP$_{IC3}$/YFP$_{CT}$ with ultraviolet light ($\lambda_{max.ex.}$=436 nm; $\lambda_{max.em.}$=480 nm) produces an intramolecular FRET to the YFP (acceptor), resulting in emission from that YFP ($\lambda_{max.ex.}$=480 nm, $\lambda_{max.em.}$=535 nm). This FRET response is observable as a decrease in intensity of CFP light emission at 480 nm, and an increase in intensity of YFP light emission at 535 nm. The FRET signal is produced by PTHR-CFP$_{IC3}$/YFP$_{CT}$ in the ground-state receptor and decreases upon binding of an agonist. PTH ligands were added to the cells, and washed from the cells using a computer-assisted, solenoid valve-controlled, rapid superfusion device (ALA Scientific Instruments, Westbury, N.Y.); solution-exchange times were 5 ms to 10 ms. Fluorescence was monitored using a Zeiss inverted microscope equipped with a 100× objective and a dual emission photometric system (Til Photonics), coupled to an avalanche photodiode detection system and an analog-digital converter (Axon Instruments). The FRET signal detected upon excitation at 436 nm was calculated as the normalized FRET ratio: $F_{YFP(535\,nm)}/F_{CFP(480\,nm)}$ where $F_{YFP(535\,nm)}$ is the emission at 535 nm, corrected for spillover of the CFP signal into the YFP channel, and $F_{CFP(480nm)}$ is the emission at 480 nm, corrected for spillover (minimal) of the YFP emission into the CFP channel. Changes in fluorescence emissions due to photo-bleaching were subtracted.

Stimulation of Intracellular cAMP. Following treatment of cells with a ligand, the intracellular cAMP levels were measured by radioimmuno assay, as described (Shimizu et al., *J. Biol. Chem.* 276:49003-49012 (2001)). The capacities of ligands to produce a delayed cAMP response in cells after a brief exposure to the ligand was assessed as follows. The cells in 24-well plates were rinsed in binding buffer (50 mM Tris-HCl, pH 7.7, 100 mM NaCl, 5 mM KCl, 2 mM CaCl$_2$, 5% heat-inactivated horse serum, 0.5% heat-inactivated fetal bovine serum) and then incubated in binding buffer with or without a peptide ligand ($1 \times 10^{-7}$ or $3 \times 10$ M) for 10 minutes at room temperature; the buffer was then removed, the cells were washed three times with binding buffer, incubated further in binding buffer for varying times (1 to 120 minutes); the buffer was then replaced by binding buffer containing IBMX (2 mM), and after an additional five minute incubation, the intracellular cAMP was quantified. By this approach, which has been used previously for the PTH receptor (Tawfeek, H., and Abou-Samra, A., *J. Bone Miner. Res.* 14:SU444 (1999); Biselo et al., *J. Biol. Chem.* 277:38524-38530 (2002)), only the cAMP produced during the final IBMX-containing stage of the incubation is measurable, because cAMP produced prior to IBMX addition is degraded by cellular phosphodiesterases.

In the cAMP experiments of FIG. 14, HKRK-B7 were seeded in 96 well plates at $1 \times 10^5$ cells/well and incubated overnight. On the following day, the cells were washed once with 200 µl of binding buffer (50 mM Tris-HCl, pH 7.7, 100 mM NaCl, 5 mM KCl, 2 mM CaCl$_2$, 5% heat-inactivated horse serum, 0.5% heat-inactivated fetal bovine serum), followed by addition of 100 µl cAMP assay buffer (DMEM, 2 mM IBMX, 1 mg/ml bovine serum albumin, 35 mM Hepes-NaOH, pH 7.4) on ice. Then, 50 µl of binding buffer containing varying amounts of human PTH(1-34), human PTHrP(1-36), or PTH analogs (final volume=150 µl), were added to each well, and placed in a water bath at 37° C., and incubated for 15 minutes. After removing the medium, the plates were placed on powdered dry ice to freeze the cells and then removed from dry ice. The cells were thawed with 50 µl of 50 mM HCl and frozen again on dry ice. The level of intracellular cAMP was measured with a commercially available cAMP EIA kit (Biotrack cAMP EIA system, GE Healthcare).

Stimulation of inositol phosphate. The stimulation of intracellular inositol phosphates (IPs) was measured in transiently transfected COS-7 cells that were pre-labeled (16 hours) with $^3$H-myo-D-inositol (2 µCi/ml). Cells were treated with ligand in DMEM containing fetal bovine serum (10%) and LiCl (30 mM) for 30 minutes; cells were lysed with ice cold trichloro acetic acid (5%) and IPs were extracted from the acid-lysates by ion-exchange filtration, as described (Shimizu et al., *J. Biol. Chem.* 276:49003-49012 (2001)).

OK cell methods. Cells were treated for 10 minutes at 37° C. with media (vehicle) or media containing a peptide ligand ($1 \times 10^{-7}$ M); then (t=0), the cells were then rinsed three times with media and incubated in alone at 37° C. for varying times. At each time point, $^{32}$PO$_4$ was then added to the media, and after five minutes of incubation, the cells were washed, lysed, and the lysate was counted for $^{32}$P beta radioactivity by liquid scintillation counting. The results of these experiments are shown in FIG. 11, plotted as a percentile of the amount of $^{32}$P radioactivity in lysates of cells treated for the same time with vehicle alone.

Data calculations for in vitro binding and signaling assays. Data were processed for curve fitting and parameter determination using Microsoft Excel and GraphPad Prism 4.0 software packages. Dissociation time course data were analyzed using a bi-exponential decay equation, except when an F test analysis indicated a mono-exponential equation provided a better fit (Palpha>0.02). Data from equilibrium binding, cAMP and IP dose-response assays were analyzed using a sigmoidal dose-response equation with variable slope. This analysis yielded curves for the data and values of EC$_{50}$, IC$_{50}$ (the concentration of a ligand that produces half of the maximal effect) and $E_{max}$ (the maximum response obtained by a ligand). Paired data sets were statistically compared using the Student's t-test (two-tailed) assuming unequal variances for the two sets.

Pharmacokinetic analysis of PTHrP(1-36) and 15-PTHrP (1-36) in normal rats. Concentration of human PTHrP(1-36) and [$I^5$]-PTHrP(1-36) in stock solution were adjusted by dilution with 25 mmol/L phosphate-citrate buffer/100 mmol/L NaCl/0.05% Tween 80 (pH.5.0) (PC-buffer). Both peptides were allowed to stand on ice immediately before administration.

Female SD-IGS rats at 8 weeks of age (Charles River Japan, Inc.) were measured for their body weight. Rats received intravenous administration of Human PTHrP(1-36) and [$I^5$]-PTHrP(1-36) at a dose of 10 nmol/1 ml/kg. Peptides were administered to groups of 3 rats for each peptide-dose and/or time point. At 2.5, 5, 7.5, 10, 15, 30, 60, 120 min after administration, blood was collected by tail vein in tubes with EDTA (final 0.2%) and aprotinin (final 0.6 TIU/ml) to monitor the time course of concentration of human PTHrP(1-36) and [$I^5$]-PTHrP(1-36) in rat plasma. Samples were centrifuged to collect plasma and stored at $-80°$ C., until assayed for human PTHrP(1-36) and [$I^5$]-PTHrP(1-36) levels.

The level of human PTHrP(1-36) and [$I^5$]-PTHrP(1-36) were determined by EIA analysis using PTH-RP 1-34 (Human, Rat) Enzyme Immunoassay kit (Peninsula Laboratories Inc.) [$I^5$]-PTHrP(1-36) cross-reacted with PTHrP EIA kit, and [$I^5$]-PTHrP(1-36) was used as a standard for measurement of the level of [$I^5$]-PTHrP(1-36) in plasma.

Hypercalcemic action of human PTH(1-34), PTHrP(1-36) and PTH or PTHrP analogs in normal rats. Human PTH(1-34), PTHrP(1-36), and PTH or PTHrP analogs were studied for hypercalcemic effects in normal rat as follows. Concentration of peptides in stock solution were adjusted by dilution with 25 mmol/L phosphate-citrate buffer/100 mmol/L NaCl/0.05% Tween 80 (pH.5.0) (PC-buffer). All peptides were allowed to stand on ice immediately before administration.

Female SD-IGS rat at 8 weeks of age (Charles River Japan, Inc.) were measured for their body weight. Blood was collected by tail vein into heparinized capillary tubes and measured for baseline levels of blood ionized calcium and pH using $Ca^{++}$/pH analyzer (Model 634/Bayer Medical Ltd.) to give the corrected level of ionized calcium at pH 7.4 for each sample. Rats received intravenous administration of each peptides at a dose of 1 ml/kg. Peptides were administered to groups of 6 rats each respectively. At 1, 2, 4, or 6 hours after administration, blood was collected by tail vein to monitor the time course of corrected blood ionized calcium levels. The time course of changes in corrected ionized calcium levels, compared to vehicle, and are expressed as means+/−standard error.

Statistical Analysis. Statistical analysis was carried out by analysis of variance (ANOVA), using SAS software. The significance of differences was determined using Student's t-test or Dunnett's multiple test. P<0.05 was considered a statistically significant.

Calcemic action of [$A^{1,3,12}, Q^{10}, R^{11}, W^{14}$]-hPTH(1-14)/PTHrP(15-36)(MPTH14) in thyroparathyroidectomy rats. Five-week-old male Crl:CD(SD) rats were obtained from Charles River Laboratories Japan, Inc. (Kanagawa, Japan) and acclimated for 1 week under standard laboratory conditions at 20-26° C. and 35-75% humidity. The rats received free access to tap water and standard rodent chow (CE-2) containing 1.1% calcium, 1.0% phosphate and 250 IU/100 g of vitamin $D_3$ (Clea Japan, Inc., Shizuoka, Japan).

Thyroparathyroidectomy (TPTX) was performed on six-week-old rats. TPTX rats were selected for use based on serum ionized calcium (iCa) levels (<1.0 mM) in samples taken from tail vein bleeding at 24 hours or 72 hours after the operation using the electrode method. The TPTX rats were divided into six groups of five animals based on iCa levels at 48 hours after the operation. TPTX-vehicle group intravenously received the vehicle alone (10 mM acetic acid solution) at a dose of 1 ml/kg body weight administered to the tail vein. Human parathyroid hormone (1-34) (hPTH(1-34)) and M-PTH(1-14)/rP(15-36) (MPTH14) were intravenously injected into the TPTX rats at doses of 1.25, 5, 20 nmol/kg (3 groups) and 1.25, 5 nmol/kg (2 groups), respectively.

Blood was obtained from the tail vein for detecting iCa at 1, 2, 4, 6, and 24 hours after each injection. Ionized calcium levels were determined by the electrode method using an autoanalyzer (M-634, Chiba Corning Diagnostics Co. Ltd., Tokyo, Japan).

Mouse studies. Wild-type mice were injected subcutaneously with vehicle (0.9% NaCl/0.05% Tween-20), or vehicle containing a PTH peptide at a dose level of 10 to 1000 nmol/kg of body weight. At indicated times after injection, blood was withdrawn from the tail vein, and the amount of cAMP in the resulting plasma was quantified by radioimmuno assay. Ionized calcium in serum was measured as above and phosphate was measured by a U.V. spectroscopic kit assay.

Statistical analysis for animal studies. Data are represented as the mean±standard error (SE). Statistical significance was determined using SAS (Ver.5.00.010720, SAS Institute Japan, Tokyo, Japan). A p value of <0.05 was considered statistically significant. *P<0.05, P<0.01, *P<0.001 versus TPTX-vehicle level by Dunnett's multiple comparison test.

EXAMPLE 2

Characterization of Alanine Substitutions in PTH and PTHrP

As shown above, PTH(1-34) has a greater capacity to bind to the $R^0$ receptor conformation than does PTHrP(1-36), which favors the RG conformation. To explore the molecular basis for this differential binding and conformational selectivity, we compared the effects of substitutions in the N-terminal and C-terminal regions of PTH and PTHrP peptides on the interaction of the ligands with the PTHR. Unlike in PTH (1-14), where alanine substitutions at positions 1, 3, 10, 11, 12 and 14 increased cAMP activity, each alanine substitution in PTHrP(1-14) abolished activity in cells expressing PTHR. Thus, the (1-14) regions of PTH and PTHrP interact with the juxtamembrane (J) region of the PTHR differently. Both PTHrP(1-14) and PTHrP(1-36) were much less potent for cAMP activity in cells expressing a PTHR lacking the extracellular N-terminal (N) domain (deiNT), as compared to their respective PTH(1-14) and PTH(1-34) counterparts. PTHrP(1-36) activity therefore depends more heavily on interactions between the C-terminal ligand region and the PTHR N domain than does PTH (1-34) activity. We therefore studied the C-terminal region of the PTHrP sequence, as described in Example 3.

EXAMPLE 3

C-Terminal Substitutions in PTH(1-28) and PTHrP(1-28)

Figures 27A, 27B, 27C, 27D:
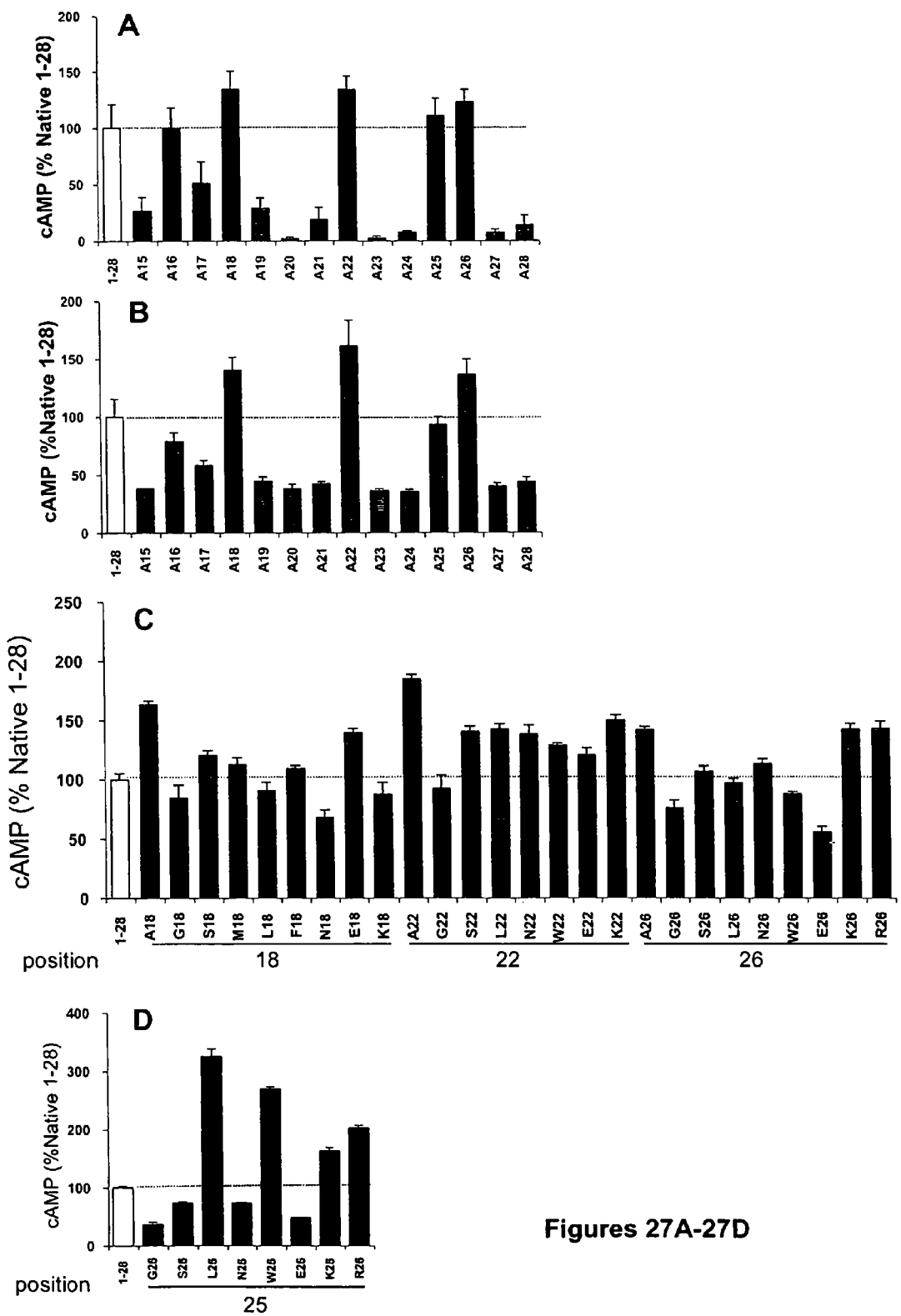
FIGS. 27A-27D are graphs showing alanine-scan and type-substitution of PTHrP(1-28) (SEQ ID NO:151). The effects of alanine substitutions in the 15-28 region of PTHrP(1-28) on cAMP activity was examined in renal tubule LLCPK1-B64 (FIG. 27A) and ROS17/2.8 (FIG. 27B) cells. Alanine substitution at position 18, 22, 25 and 26 increased activity in at least one cell type. These positions were further substituted to various types of amino acids, and cAMP activity was analyzed in LLCPK1-B64 cells (FIG. 27C) or SaOS-2 cells (FIG. 27D). Cells were treated with analogs at 3×10$^{-9}$M in the presence of IBMX for 30 minutes at room temperature. Responses for each analog were normalized to the response for the parent (native) PTHrP(1-28) peptide. Alanine substitutions were $A^{15}$ to $A^{17}$ (SEQ ID NO:152-154), $A^{18}$ (SEQ ID NO:34), $A^{19}$ to $A^{21}$ (SEQ ID NO:155-157), $A^{22}$ (SEQ ID NO:39), $A^{23}$ to $A^{25}$ (SEQ ID NO:158-160), $A^{26}$ (SEQ ID NO:46), and $A^{27}$ to $A^{28}$ (SEQ ID NO:161-162). Substitutions at position 18 were $A^{18}$ (SEQ ID NO: 34), $G^{18}$ (SEQ ID NO:163), $S^{18}$ (SEQ ID NO:35), $M^{18}$ (SEQ ID NO:36), $L^{18}$ (SEQ ID NO:164), $F^{18}$ (SEQ ID NO:37), $N^{18}$ (SEQ ID NO:165), $E^{18}$ (SEQ ID NO:38), and $K^{18}$ (SEQ ID NO:166). Substitutions at position 22 were $A^{22}$ (SEQ ID NO:39), (SEQ ID NO:167), and $S^{22}$ to $K^{22}$ (SEQ ID NO:40-45). Substitutions at position 26 were $A^{26}$ (SEQ ID NO:46), $G^{26}$ (SEQ ID NO:168), (SEQ ID NO:47), $L^{26}$ (SEQ ID NO:169), $N^{26}$ (SEQ ID NO:48), $K^{26}$ to $E^{26}$ (SEQ ID NO:170-171), and $K^{26}$ to $R^{26}$ (SEQ ID NO:49-50). Substitutions at position 25 were $G^{25}$ to $S^{25}$ (SEQ ID NO:172-173), $L^{25}$ (SEQ ID NO:51), $N^{25}$ (SEQ ID NO:174), $W^{25}$ (SEQ ID NO:52), $E^{25}$ (SEQ ID NO:175), and $K^{25}$ to $R^{25}$ (SEQ ID NO:53-54).

Using alanine-scan and type-substitution strategies, we were able to generate peptides with much greater selectivity for RG receptor conformation than the native PTHrP(1-28) sequence. We focused our studies on the C-terminal region of the PTHrP sequence, and thus performed an alanine-scan of the 15-28 region of PTH(1-28) (data not shown) and PTHrP (1-28). Ala-scan analysis of the C-terminal regions of PTH (1-28) and PTHrP(1-28) revealed for each peptide strong reductions in activity at positions $Arg^{20}$, $Trp/Phe^{23}$, $Leu^{24}$, and $Leu/Ile^{28}$, known in PTH to form the core N domain-binding motif Enhancements in activity were found at several, but different positions in each scaffold: $Leu^{18}$, $Phe^{22}$, and $His^{26}$ in PTHrP(1-28) and $Asn^{16}$, $Glu^{19}$, and $Ala^{22}$ in PTH(1-28). The alanine substitutions at positions 16, 19, and 22 in PTH increased binding to delNT (PTH receptor missing the N-terminal ligand binding domain), whereas those at positions 18, 22, 26 in PTHrP decreased binding to delNT. The enhancing effects of the Ala substitutions at positions 16, 19, and 22 of PTH are thus mediated via the PTHR J domain, whereas, those at positions 18, 22, 26 of PTHrP require the PTHR N domain. Further type substitution analysis of positions 16, 19, 22, as well as 25 (neutral to Ala substitution) in PTHrP(1-28) resulted in the analog [$Ala^{18,22}$,$Leu^{25}$,$Lys^{26}$]-PTHrP(1-28), which exhibits a cAMP potency and RG binding affinity that is greater than that of PTH(1-34) and among the highest observed of any PTH or PTHrP peptide. This scan revealed that alanine substitutions at positions 18, 22, 25, and 26 each enhance cAMP activity in human and rat PTHR-expressing cells (FIGS. 27A and 27B). Following the alanine scan, these positions were further substituted individually with various amino acids; of which some were found to increase cAMP activity (FIGS. 27C and 27D). We then combined these mutations in various combinations, thus obtaining a number of PTHrP analogs with markedly enhanced activity, as described herein.

EXAMPLE 4

Characterization of Exemplary Substituted PTHrP(1-28) Peptides

Figures 28A, 28B:
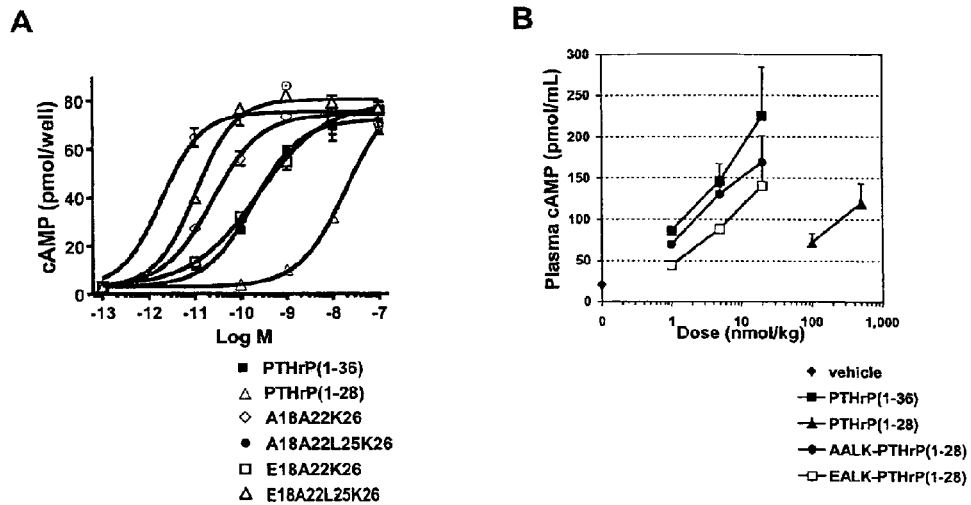
FIGS. 28A and 28B are graphs showing cAMP activity in vitro (FIG. 28A) and in vivo (FIG. 28B) by peptides having substitutions in the PTHrP(1-28) scaffold. Dose response curves of cAMP activity of representative modified PTHrP (1-28) analogs in SaOS cells are shown in (FIG. 28A), where analogs used were $A^{18,22},K^{26}$ (SEQ ID NO:56), $A^{18,22},L^{25}$, $K^{26}$ (SEQ ID NO:76), $E^{18},A^{22},K^{26}$ (SEQ ID NO:65), or $E^{18}$, $A^{22},L^{25},K^{26}$ (SEQ ID NO:83).

Dose-response curves for cAMP production in SaOS cells using PTHrP(1-36), PTHrP(1-28), $A^{18,22}$,$K^{26}$-PTHrP(1-28), $A^{18,22}$,$L^{25}$,$K^{26}$ PTHrP(1-28), $E^{18}$,$A^{22}$,$L^{22}$,$L^{26}$-PTHrP(1-28), or $E^{18}$,$A^{22}$,$L^{25}$,$K^{26}$ (EALK)-PTHrP(1-28) were generated (FIG. 28A). Marked enhancements of cAMP-inducing activity were found for $A(E)^{18,22}$,$L^{25}$,$K^{26}$-PTHrP(1-28) (AALK or EALK), as compared to parental PTHrP(1-28).

These enhancing effects were confirmed in vivo studies (FIG. 28B) by injecting C57BL/6 mice (3-month-old, male) intravenously with either vehicle, PTHrP(1-36), PTHrP(1-28), AALK-PTHrP(1-28), or EALK-PTHrP(1-28) (n=3). Blood was withdrawn 10 minutes after injection and plasma level of cAMP was measured by RIA. Marked enhancements were also observed in the mouse assay for the AALK-PTHrP (1-28) and EALK-PTHrP(1-28) as compared to wt PTHrP(1-28). The greater apparent potency of PTHrP(1-36) peptide in these assays may reflect slower clearance of the longer-length peptide from the blood.

EXAMPLE 5

Characterization of the RG Selective Peptide EALK-PTHrP(1-30)

We also characterized the effects of the EALK-PTHrP(1-30) peptide on cAMP production. Three month old male C57BL/6 mice were intravenously injected with either vehicle, rPTH(1-34), M-PTH(1-34) (M=$A^1$,$Aib^3$,$Q^{10}$,$Har^{11}$, $A^{12}$,$W^{14}$,$R^{19}$,) or $E^{18}$,$A^{22}$,$L^{25}$,$K^{26}$(EALK)-PTHrP(1-30) (5 nmol/kg). In the cAMP experiment (FIG. 29A), blood was withdrawn 10 minutes after injection and plasma level of cAMP was measured by RIA. In the calcium experiment (FIG. 29B), blood was withdrawn prior to injection and 1, 2, 4, and 6 hours after injection. Ionized calcium was measured using a $Ca^{++}$/pH analyzer. The ligands induced approximately the same level of plasma cAMP, but the $R^0$ selective ligand, M-PTH(1-34) induced an ionized calcium response markedly more robust and more sustained than that of PTH (1-34). By contrast, the RG-selective ligand, EALK-PTHrP (1-30) induced an ionized calcium response that was, similar, if not lower, than that of PTH(1-34).

Figures 30A, 30B, 30C, 30D, 30E, 30F:
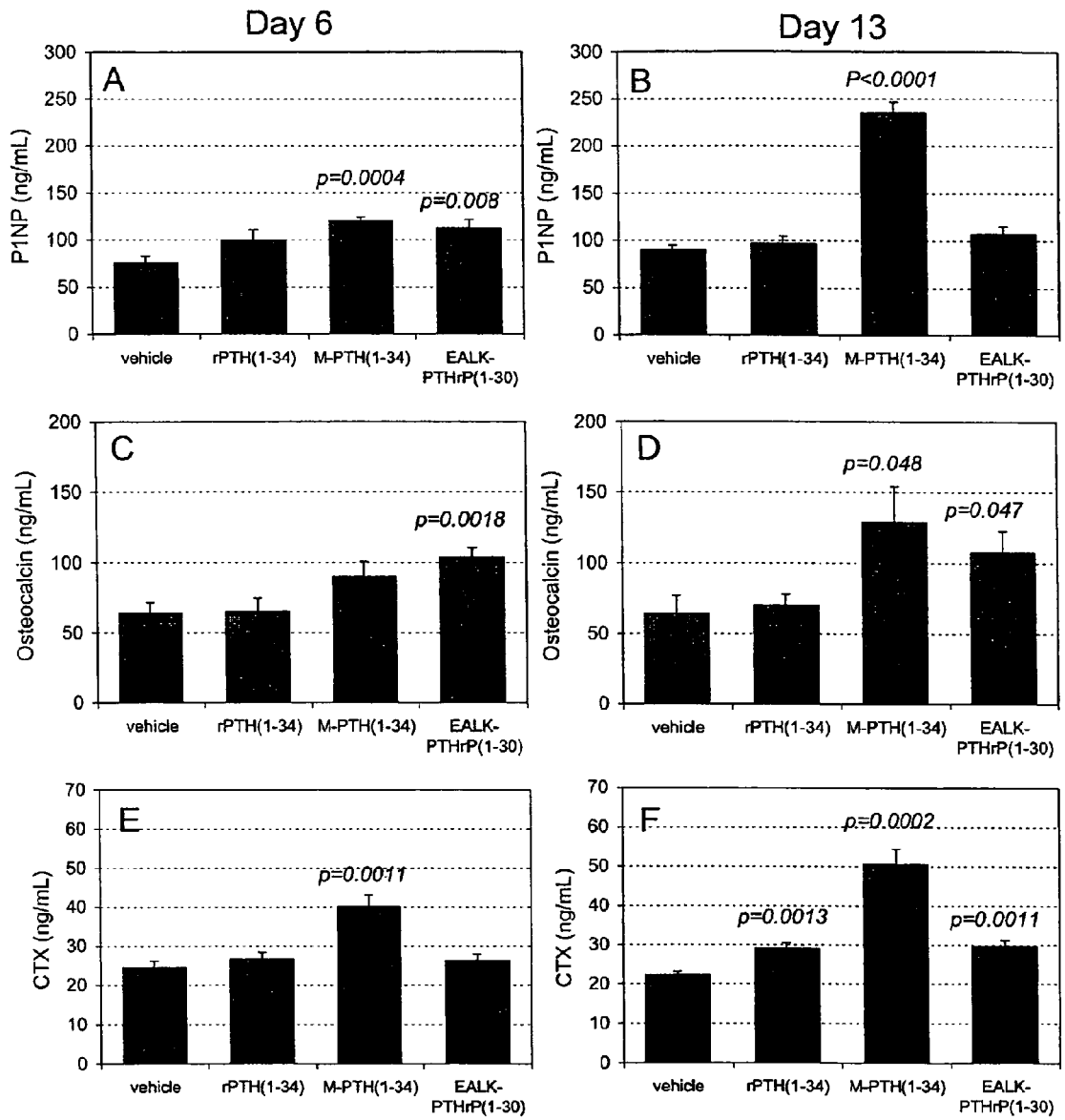
FIGS. 30A-30F are graphs showing the effects of PTH analogs on plasma bone markers in mice. Mice (C57BL/6, males, 3 months) were intravenously injected daily with either vehicle, rPTH(1-34) (SEQ ID NO:130), M-PTH(1-34) (SEQ ID NO:12), or (EALK)-PTHrP(1-30) (SEQ ID NO:90) (5 nmol/kg; n=7 group) for 14 days. Markers of bone turnover (PINP, CTX and osteocalcin) were assessed by ELISA in blood at day 6 (FIGS. 30A, 30C, and 30E, respectively) and 13 (FIGS. 30B, 30D, and 30F, respectively).

A second set of experiments was performed in which mice received 5 nmol/kg intravenous daily treatment with rPTH(1-34), M-PTH(1-34), or EALK-PTHrP(1-30) for 14 days. Blood samples were taken at days 6 and 13, and markers of bone turnover (PINP, osteocalcin and CTX) were assessed by ELISA. The $R^0$ selective ligand, M-PTH(1-34) strongly induced increases in markers of both bone formation (PINP, FIGS. 30A and 30B; osteocalcin, FIG. 30D) and bone resorption (CTX, FIGS. 30E and 30F), as early as day 6. By contrast, the RG-selective ligand, EALK-PTHrP(1-30) increased bone formation markers, with relatively smaller effects on the resorption marker, as evident on day 6 (FIGS. 30A, 30C, and 30E). Under the dose and time conditions analyzed, PTH(1-34) had only minor effects on bone markers.

Figures 29A, 29B:
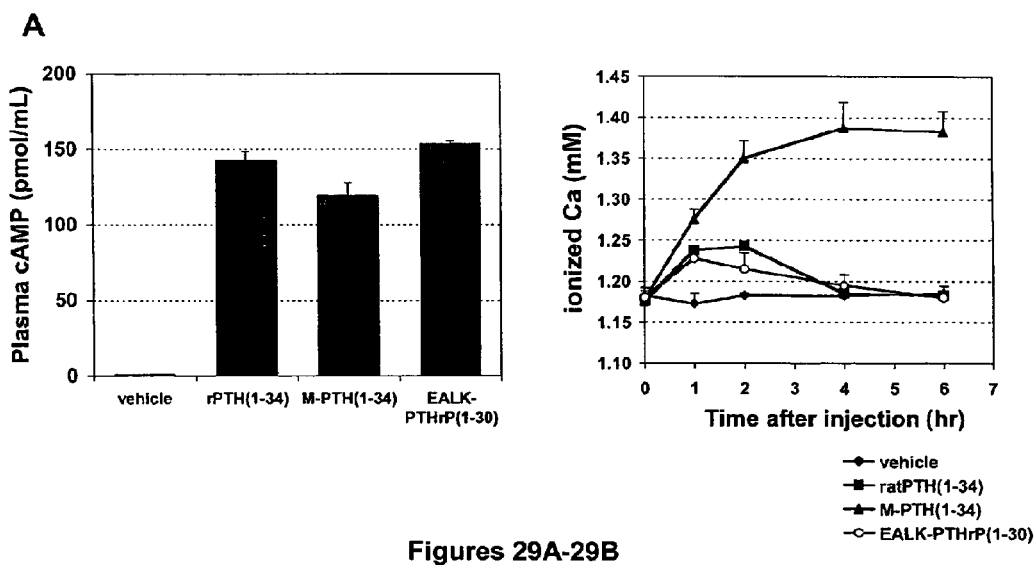
FIGS. 29A and 29B are graphs showing the effect of $R^0$ and RG selective PTH analogs on plasma cAMP and calcium in mice.
Figure 31:
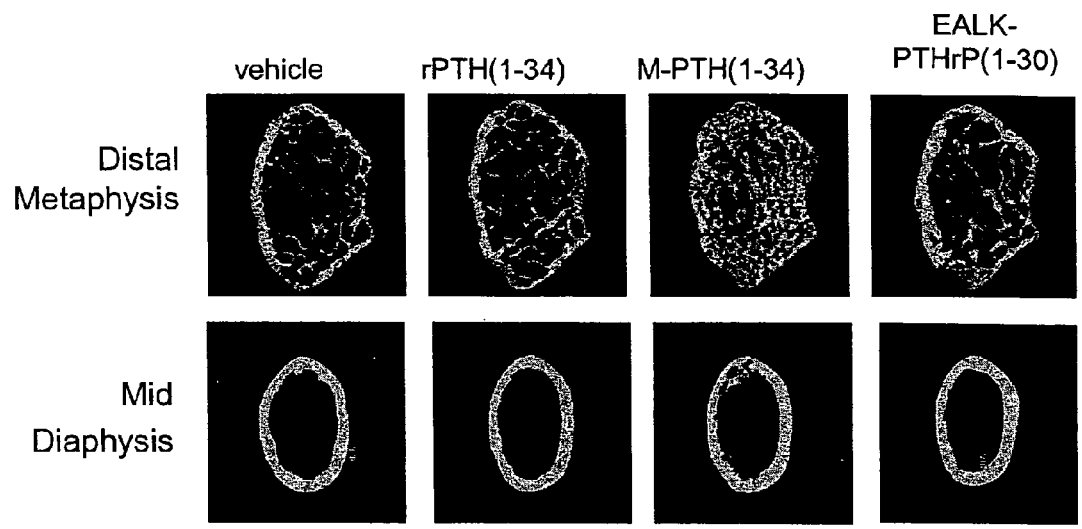
FIG. 31 is a set of images showing the effects of two-week daily treatment of $R^0$ and RG ligands on trabecular and cortical bone structure in mice. Mice (C57BL/6, males, 3 months) were treated (i.v.) with either vehicle, rPTH(1-34) (SEQ ID NO:130), M-PTH(1-34) (SEQ ID NO:12), or $E^{18}$, $A^{22},L^{25},K^{26}$ (EALK)PTHrP(1-30) (SEQ ID NO:90) (5 nmol/ kg; n=7 group), daily for 14 days, and femurs were analyzed by μCT.

Consistent with the effects on bone markers, M-PTH(1-34) robustly increased trabecular bone, but also detectably diminished cortical bone (FIG. 31), consistent with its severe hypercalcemic actions (FIG. 29B). By contrast, EALK-PTHrP(1-30) increased cortical bone thickness with significance in the distal femur (FIG. 30 and Table xx), without inducing severe hypercalcemia. These findings demonstrate that the modified ligands with different $R^0$/RG selectivities have differential effects on bone metabolism. The findings also show that RG selective analogs, such as EALK-PTHrP(1-30), preferentially stimulate bone formation over bone resorption, and have beneficial effects on cortical bones with minimum effects on blood calcium levels. M-PTH(1-34) greatly increases the trabecular bone at the distal femur metaphysis, but induced cortical bone resorption at the mid-femur diaphysis, as indicated by erosion of endosteal surface.

Table 7 shows quantitation of bone structural parameters following two weeks of daily treatment of the above peptides. As described above, mice were treated intravenously) with either vehicle, rPTH(1-34), M-PTH(1-34), or EALK-PTHrP (1-30) daily for 14 days. All analogs significantly increased bone mineral density at both femur and lumbar spine. Cortical wall thickness was significantly lower in both distal and mid femur region for M-PTH(1-34). In contrast, EALK-PTHrP (1-30) increased cortical bone thickness with significance in the distal femur.

TABLE 7

Bone structural parameters after two-week daily treatment in mice

|  | vehicle | PTH(1-34) (SEQ ID NO: 130) | P vs. veh | M-PTH(1-34) (SEQ ID NO: 12) | P vs. veh | EALK-PTHrP (1-30) (SEQ ID NO: 90) | P vs. veh |
|---|---|---|---|---|---|---|---|
| Piximus[a] | | | | | | | |
| Total Femur BMD (g/cm$^2$) | 0.0599 ± 0.0002 | 0.0615 ± 0.0003 | 0.003 | 0.664 ± 0.0003 | <0.0001 | 0.620 ± 0.0003 | 0.0004 |
| Lumbar Spine BMD (g/cm$^2$) | 0.0455 ± 0.0001 | 0.0464 ± 0.0002 | 0.001 | 0.0524 ± 0.0002 | <0.0001 | 0.0464 ± 0.0002 | 0.001 |
| microCT[b] distal femur | | | | | | | |
| TrabecularBV/TV (%) | 17.6 ± 0.8 | 17.4 ± 1.2 | 0.883 | 35.0 ± 3.0 | 0.001 | 16.5 ± 1.3 | 0.506 |
| Tb.N (1/mm) | 4.37 ± 0.08 | 4.02 ± 0.14 | 0.055 | 5.22 ± 0.34 | 0.047 | 4.13 ± 0.16 | 0.201 |
| Tb.Th (μm) | 55.4 ± 1.7 | 57.5 ± 1.4 | 0.361 | 71.5 ± 1.8 | <0.0001 | 57.8 ± 2.1 | 0.393 |
| TbSp (μm) | 224 ± 5 | 246 ± 10 | 0.076 | 208 ± 17 | 0.398 | 238 ± 10 | 0.235 |
| Conn-Dens. (1/mm$^3$) | 132 ± 4 | 116 ± 8 | 0.091 | 263 ± 25 | 0.002 | 117 ± 9 | 0.132 |
| Cort Th. (μm) | 213 ± 7 | 229 ± 11 | 0.229 | 166 ± 6 | 0.0003 | 238 ± 9 | 0.048 |
| mid femur | | | | | | | |
| TA (mm$^2$) | 2.05 ± 0.07 | 2.17 ± 0.05 | 0.197 | 2.10 ± 0.06 | 0.630 | 2.03 ± 0.06 | 0.840 |
| BA (mm$^2$) | 0.813 ± 0.019 | 0.839 ± 0.032 | 0.503 | 0.837 ± 0.022 | 0.423 | 0.821 ± 0.027 | 0.825 |
| MA (mm$^2$) | 1.24 ± 0.05 | 1.33 ± 0.02 | 0.177 | 1.26 ± 0.04 | 0.792 | 1.21 ± 0.03 | 0.702 |
| BA/TA (%) | 39.7 ± 0.9 | 38.7 ± 0.7 | 0.380 | 40.0 ± 0.8 | 0.837 | 40.3 ± 0.6 | 0.614 |
| Cort Th. (μm) | 172 ± 4 | 172 ± 5 | 0.965 | 151 ± 3 | 0.003 | 176 ± 4 | 0.558 |

EXAMPLE 6

Optimization of EALK-PTHrP Peptides

Figures 32A, 32B:
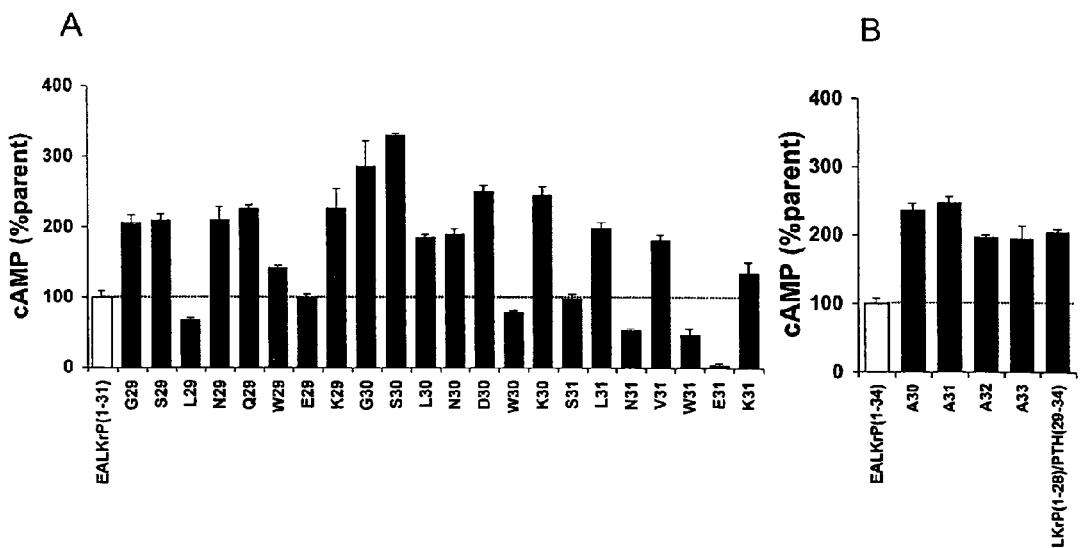
FIGS. 32A and 32B are graphs showing the effects of amino acid substitutions in the 29-31 region of EALK-PTHrP (1-31) (SEQ ID NO:94) (FIG. 32A) and the 29-33 region of EALK-PTHrP(1-34) (SEQ ID NO:112) (FIG. 32B) on induction of cAMP activity in MC3T3-E1 cells. Substitutions at position 29 for EALK-PTHrP(1-31) were $G^{29}$ to $S^{29}$ (SEQ ID NO:95-96), $L^{29}$ (SEQ ID NO:176), and $N^{29}$ to $K^{29}$ (SEQ ID NO:97-101). Substitutions at position 30 for EALK-PTHrP (1-31) were $G^{30}$ to $D^{30}$ (SEQ ID NO:102-106), $W^{30}$ (SEQ ID NO:177), and $K^{30}$ (SEQ ID NO:107). Substitutions at position 31 for EALK-PTHrP(1-31) were $S^{31}$ to $L^{31}$ (SEQ ID NO:108-109), $N^{31}$ (SEQ ID NO:178), $V^{31}$ (SEQ ID NO:110), $W^{31}$ to $E^{31}$ (SEQ ID NO:179-180), and $K^{31}$ (SEQ ID NO:111). Substitutions for EALK-PTHrP(1-34) $A^{30}$ to $A^{33}$ (SEQ ID NO:113-116) and EALK-PTHrP(1-28)/PTH(29-34) (SEQ ID NO:117).

To optimize the activity of the EALK-PTHrP peptides, we generated EALK-PTHrP(1-30) and PTHrP(1-34) variants with substitutions in the 29-33 region. In the 1-30 scaffold, Gly, Ser, Leu, Asn, Gln, Trp, Glu, and Lys were substituted at position 29; Gly, Ser, Leu, Asn, Asp, Trp, and Lys were substituted at position 30; and Ser, Leu, Asn, Val, Trp, Glu, and Lys were substituted at position 31. In EALK-PTHrP(1-34), the 30-33 region was substituted with alanine, or the C-terminal six amino acids were replaced by the corresponding region of PTH(1-34). A predicted advantage of these longer-length peptides, relative to the PTHrP(1-30) scaffold, is that they will have longer a longer half-life in circulation due to slower clearance. The C-terminal substitutions were thus designed to provide the added chain length, but to avoid increasing $R^0$ binding affinity, which occurs when the native PTHrP(29-34) region (SEQ ID NO:186) is installed. These peptides were tested for cAMP activity in MC3T3-E1 cells. As shown in FIGS. 32A and 32B, several of these peptides exhibited greater activity than the unsubstituted C-terminal sequence.

EXAMPLE 7

Characterization of Trp$^1$-M-PTH in Renal Phosphate Transport

To help elucidate further the signaling mechanisms by which PTH ligands regulate renal phosphate transport, we developed a derivative of M-PTH(1-28) that is defective for PLC/PKC signaling, yet retains potent cAMP/PKA signaling activity. Such a peptide allows for study of the relative roles of the PKA and PKC signaling pathways in modulating the function and surface expression of the Pi transporters NaPi-IIa and NaPi-IIc in proximal tubule (PT) cells. The analog M-PTH(1-28) (M=Ala$^1$,Aib$^3$,Gln$^{10}$,Har$^{11}$,Ala$^{12}$,Trp$^{14}$, Arg$^{19}$), a potent agonist for cAMP and IP$_3$ signaling pathways, induces, when injected into mice, prolonged hypophosphatemic and hypercalcemic effects. The analog also induced prolonged reductions in NaPi-IIa immunoreactivity at the brush border membrane and cytoplasmic compartments of renal PT cells of injected mice.

To impair PLC signaling, we replaced alanine at position 1 of M-PTH(1-28) with tryptophan, in accordance with findings of Bisello and colleagues (J Biol Chem 277:38524-30, 2002) showing that such bulky substitutions at this position selectively impair PLC signaling. In HEK-293 cells transiently transfected with the rat PTHR, Trp$^1$-M-PTH(1-28) was about as potent as M-PTH(1-28) for stimulating cAMP formation, but at least 100-fold less potent than the parent peptide for stimulating IP$_3$ formation. Trp$^1$-M-PTH(1-28) retained the capacity to produce a prolonged cAMP response in MC3T3-E1 cells after ligand wash-out, as seen with MPTH (1-28). When injected into mice (20 nmol/kg) Trp$^1$-M-PTH (1-28), like M-PTH(1-28), induced prolonged suppression of plasma phosphate levels, as compared to effects of PTH(1-34): maximal suppression at 2 h for each analog; recovery to vehicle control levels at 4 h for PTH(1-34), and at 6 h for M-PTH(1-28) and Trp$^1$-M-PTH(1-28). Apical and cytoplasmic NaPi-IIa staining in renal PT cells was reduced in mice treated with each peptide at 2 h, but where staining returned to vehicle control levels at 6 h with PTH(1-34), it remained reduced for at least six hours in mice treated with M-PTH(1-28) or Trp$^1$-M-PTH(1-28). Immunostaining of NaPi-IIc in renal PT cells was reduced in mice treated with M-PTH(1-28) over the interval 4 to 6 h, but was unchanged in mice treated with Trp$^1$-M-PTH(1-28) or PTH(1-34). M-PTH(1-28) inhibited $^{32}$P uptake in early passage LLC-PK1 cells (NHERF-1/ezrin positive) virally transduced to express NaPi-IIc transporter and the rat PTHR (Mahon, Am J Physiol Renal Physiol. 294:F667-75 (2008)), but Trp$^1$-M-PTH(1-28) failed to inhibit this activity. The findings suggest that PTHR-mediated regulation of renal Pi transport involves, as one component, the cAMP/PKA-dependent control of NaPi-IIa down regulation, and, as another, perhaps slower and minor component, the PLC-dependent control of NaPi-IIc down regulation.

EXAMPLE 8

Figure 33:
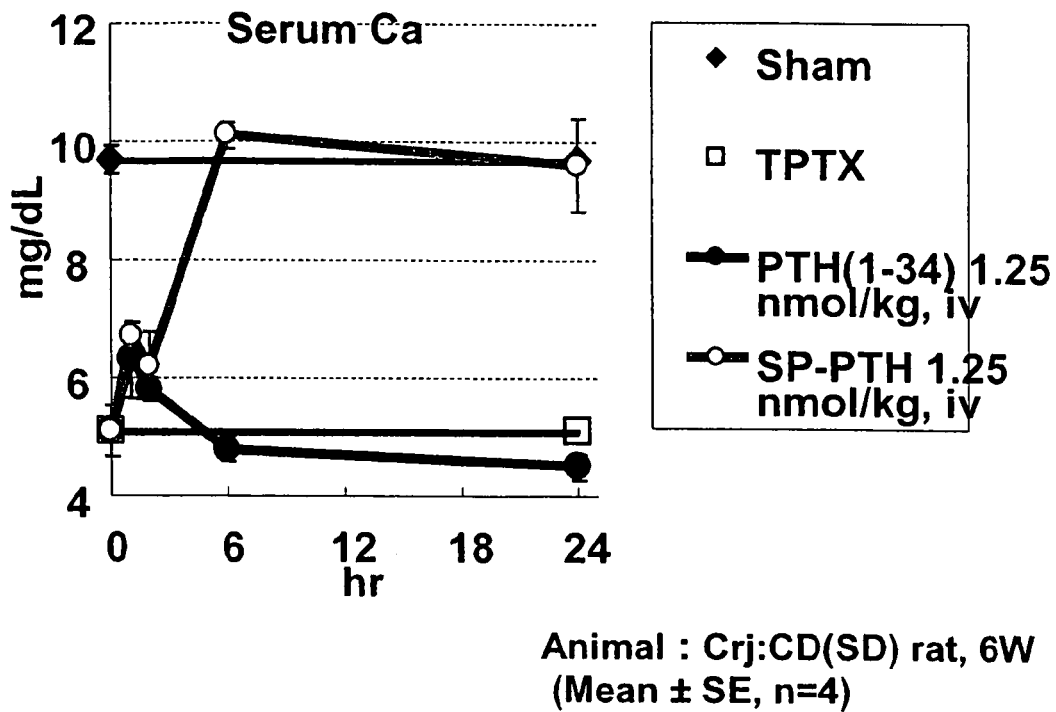
FIG. 33 is a graph showing calcemic action of PTH(1-34) (SEQ ID NO:5) and M-PTH(1-14)/PTHrP(15-36) (SEQ ID NO:15) (SP-PTH) in TPTX rats from time zero to 24 hours.
Figure 34:
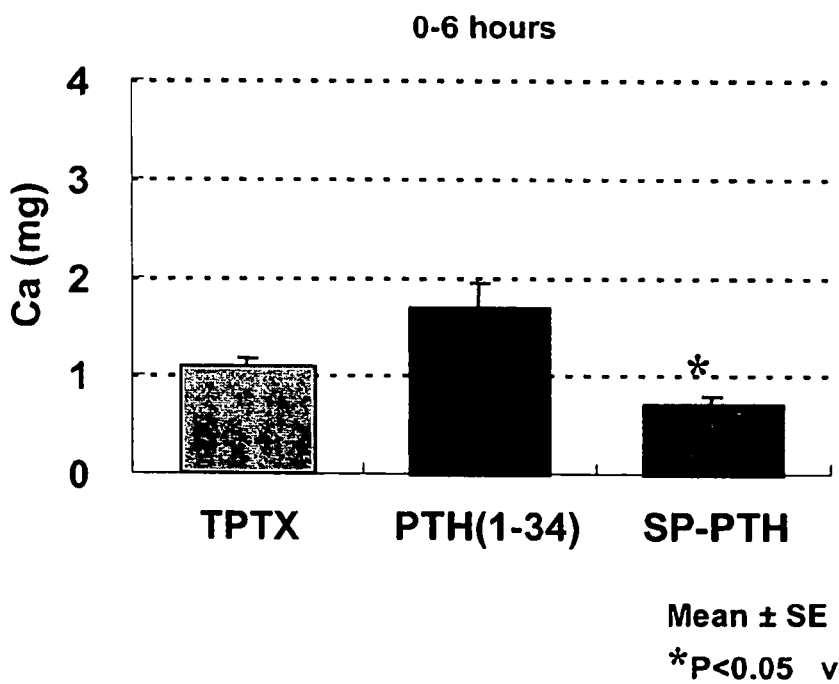
FIG. 34 is a graph showing urinary calcium at 0-6 hours following a single injection of SP-PTH (SEQ ID NO:15) or PTH(1-34) (SEQ ID NO:5) in TPTX rats.
Figure 35:
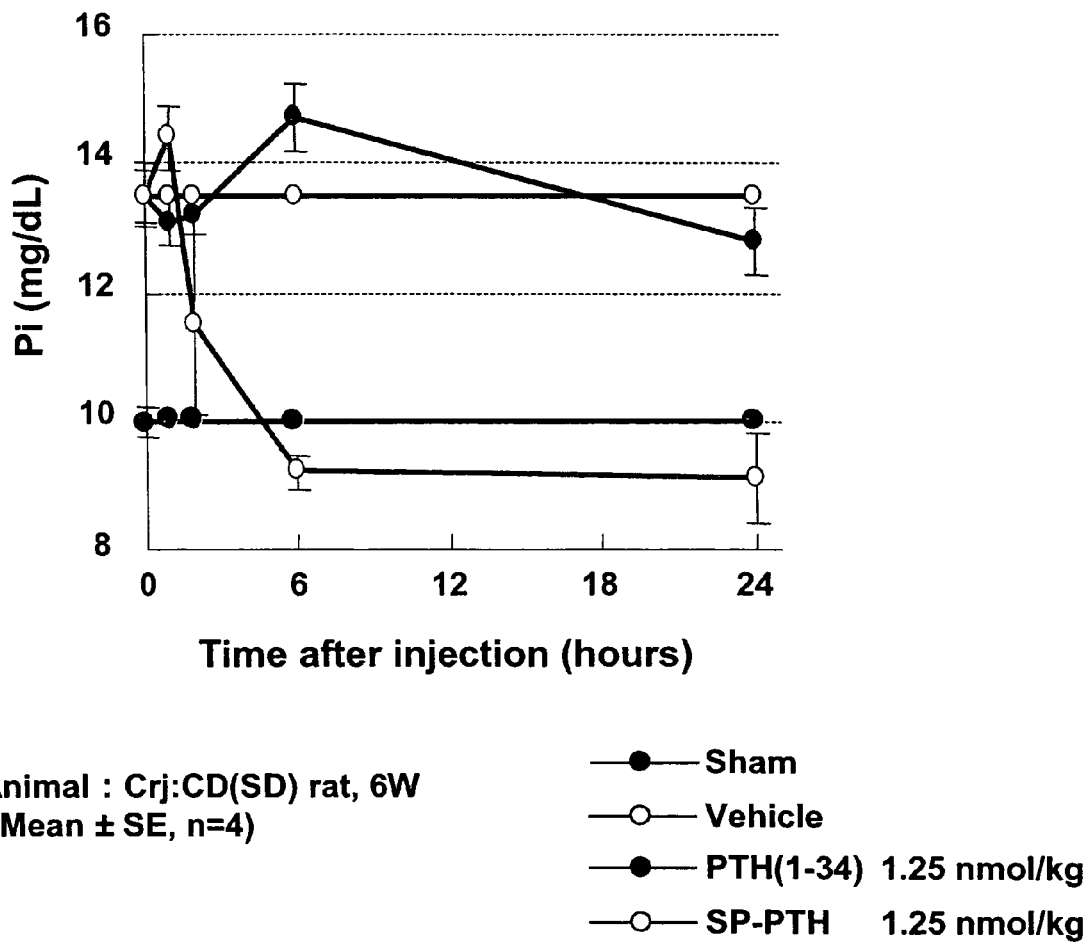
FIG. 35 is graph showing hypophosphatemic action of PTH(1-34) (SEQ ID NO:5) and SP-PTH (SEQ ID NO:15) in TPTX rats.
Figure 36:
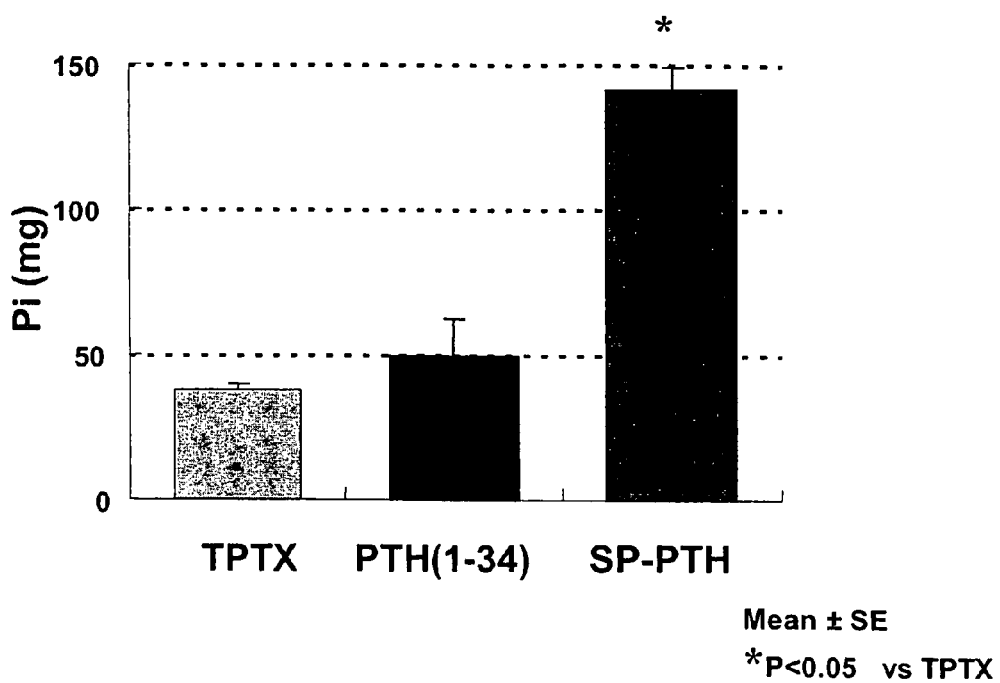
FIG. 36 is a graph showing urinary phosphorus at 0-6 hours after a single injection of SP-PTH (SEQ ID NO:15) or PTH (1-34) (SEQ ID NO:5) in TPTX rats.

Characterization of M-PTH(1-14)/PTHrP(15-36) on Serum and Urinary Calcium and Phosphate in TPTX Rats We also studied the effects of the M-PTH(1-14)/PTHrP (15-36) hybrid peptide (SP-PTH) on serum and urinary calcium and phosphate. A single intravenous injection into thyroparathyroidectomized (TPTX) rats, PTH(1-34) at 1.25 nmol/kg, transiently increased serum calcium(sCa) and decreased serum phosphorus (sPi) levels at 1 hr, but not to the normal range, as levels returned to pre-injection conditions by 6 hrs (FIGS. 33 and 35, respectively). PTH(1-34) did not change urinary calcium (FIG. 34) or urinary phosphate levels (FIG. 36) over 0-6 hours. By contrast, administration of SP-PTH at 1.25 nmol/kg, increased sCa and decreased sPi to normal levels within 6 hrs, and these levels were maintained for 24 hrs. SP-PTH decreased urinary calcium and increased urinary phosphate level at 0-6 hours. These results indicate that SP-PTH can normalize hypocalcemia in TPTX rats without causing hypercalciuria, thus suggesting that this peptide can be used to treat hypoparathyroidism with decreased risk of renal complications.

EXAMPLE 9 cAMP Stimulation Using PTH or PTHrP Analogs

Figure 37:
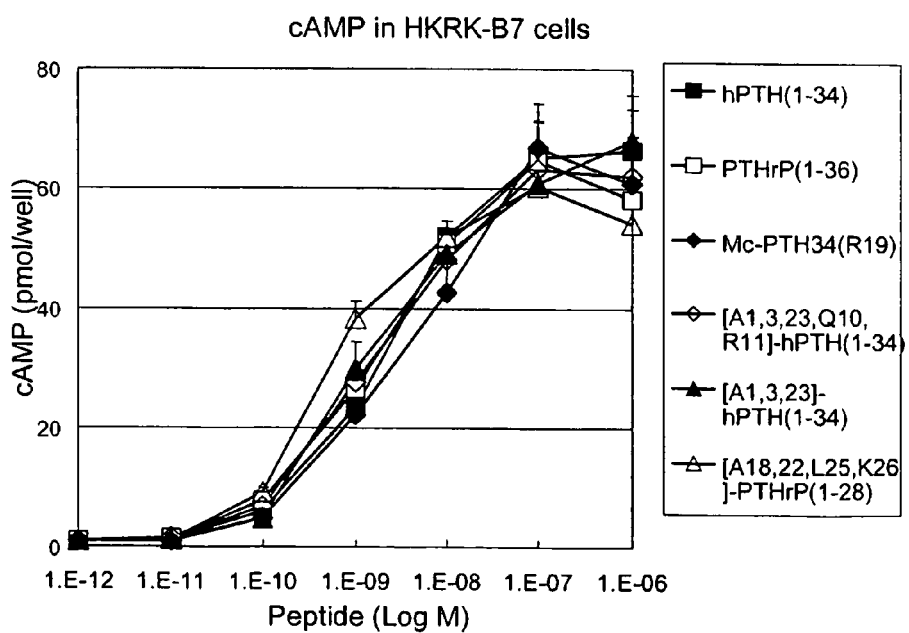
FIG. 37 is a graph showing a dose-response analysis of cAMP signaling potency for Mc-PTH(1-34) (SEQ ID NO:131), [$A^{1,3},A^{23},Q^{10},R^{11}$]-hPTH(1-34) (SEQ ID NO:181), [$A^{1,3},A^{23}$]-hPTH(1-34) (SEQ ID NO:182), and [$A^{18},A^{22},L^{25},K^{26}$]-PTHrP(1-28) (SEQ ID NO:76). For comparison, hPTH(1-34) (SEQ ID NO:5) and PTHrP(1-36) (SEQ ID NO:6) are also shown. The capacity of these peptides to stimulate cAMP formation was assessed on the human PTH1 receptor in HKRK-B7 cells. These PTH analogs show comparable cAMP signaling to hPTH(1-34).

HKRK-B, which are LLC-PK1 cells over-expressing human PTH1 receptor at levels of $9.5 \times 10^5$ per cell were used in the cAMP signaling assay. The cells were cultured at 37° C. in a humidified atmosphere containing 5% $CO_2$ in Dulbecco's modified Eagle's medium (DMEM), supplemented with 10% fetal bovine serum (Hyclone), 100 units/ml penicillin G, and 100 μg/ml streptomycin sulfate (Invitrogen Corp). Human PTHrP(1-36) was synthesized by American Peptide Company, Inc. (California, USA), Human PTH(1-34) (SEQ ID NO:5) was purchased from Peptide Institute Inc. (Osaka, Japan), and the PTH or PTHrP analogs (Mc-PTH(1-34) (SEQ ID NO:131), $[A^1,A^3,A^{23},Q^{10},R^{11}]$-hPTH(1-34) (SEQ ID NO:181), $[A^1,A^3,A^{23}]$-hPTH(1-34) (SEQ ID NO:182), and $[A^{18},A^{22},L^{25},K^{26}]$ PTHrP(1-28) (SEQ ID NO:76)) were synthesized by Sigma Aldrich Japan (Tokyo, Japan). All peptides were dissolved at 1 mM in 10 mM acetic acid, and stored at −80° C. The cAMP stimulation assay was performed as described above for HKRK-B7 cells. PTH(1-34) and PTHrP (1-36) were used as controls. Cells were treated for 15 minutes at 37° C. with varying concentrations of ligands in the presence of IBMX. The $EC_{50}$ and Emax values are reported in Table 8. All M-modified PTH analogs with C-terminal modification show comparable cAMP signaling to hPTH(1-34) (FIG. 37).

TABLE 8

| | cAMP in HKRK-B7 cells | | |
|---|---|---|---|
| | SEQ ID NO: | EC50 (nM) | Max (pm/well) |
| hPTH(1-34) | 5 | 2.26 | 67.2 |
| PTHrP(1-36) | 6 | 1.47 | 61.9 |
| Mc-PTH34(R19) | 131 | 3.25 | 65.5 |

TABLE 8-continued

| | cAMP in HKRK-B7 cells | | |
|---|---|---|---|
| | SEQ ID NO: | EC50 (nM) | Max (pm/well) |
| [A1,3,23,Q10,R11]-hPTH(1-34) | 181 | 1.76 | 63.8 |
| [A1,3,23]-hPTH(1-34) | 182 | 1.93 | 66.6 |
| [A 18,22,L25,K26]-PTHrP(1-28) | 76 | 0.52 | 56.4 |

EXAMPLE 10

Use of Short-Acting PTH Peptides for Treatment of Osteoporosis

Short-acting peptides, such as those described above, are administered to a patient having osteoporosis. Generally, in the case of the therapy of osteoporosis by intermittent i.v./i.m. or subcutaneous injection, the dosage given is in the range of 100 to 1200 units (mg)/day.

The exact doses and regimen for administration of these compounds and compositions will necessarily be dependent upon the needs of the individual subject being treated, the type of treatment, the degree of affliction or need and, of course, the judgment of the medical practitioner. In general, parenteral administration requires lower dosage than other methods of administration which are more dependent upon absorption.

EXAMPLE 11

Use of Long-Acting PTH Peptides for Treatment of PTH Deficiency

Long-acting peptides, such as those described above, are administered to a patient having a disease linked to PTH deficiency. Examples of these diseases include hyperphosphatemia associated with tumoral calcinosis, early stage chronic kidney disease and hypoparathyroidism. The daily dosage of peptide to be administered depends upon the indication. Generally, in the case of daily i.v./i.m. or subcutaneous injection preferably at 300-2400 units (μg)/day.

The exact doses and regimen for administration of these compounds and compositions will necessarily be dependent upon the needs of the individual subject being treated, the type of treatment, the degree of affliction or need and, of course, the judgment of the medical practitioner. In general, parenteral administration requires lower dosage than other methods of administration, which are more dependent upon absorption.

OTHER EMBODIMENTS

All patents, patent applications, and publications mentioned in this specification are herein incorporated by reference to the same extent as if each independent patent, patent application, or publication was specifically and individually indicated to be incorporated by reference. U.S. Provisional Application Nos. 60/963,117, 60/963,082, and 60/963,867, filed Aug. 1, 2007, Aug. 2, 2007, and Aug. 6, 2007, respectively, are hereby incorporated by reference.

What is claimed is:

1. A polypeptide of the formula PTH(1-X)/PTHrP(Y-36), or a pharmaceutically acceptable salt thereof, wherein X is an integer between 11 and 18 and Y is X+1, wherein said PTH (1-X) represents the amino acids 1 to X of the human PTH sequence (SEQ ID NO:5) and said PTHrP(Y-36) represents amino acids Y to 36 of the human PTHrP sequence (SEQ ID NO:6), wherein said polypeptide has a high affinity for the R° form of the PTH receptor, and wherein one or more of the following mutations are present in said polypeptide: Ala at position 1; Ala or Aib at position 3; Gln at position 10; Arg or homoarginine at position 11; Ala at position 12; and Trp at position 14.

2. The polypeptide of claim 1, wherein said polypeptide has Ala at positions 1 and 12; Ala or Aib at position 3; Gln at position 10; Arg or homoarginine at position 11; Trp at position 14; and Arg at position 19.

3. The polypeptide of claim 2, wherein said polypeptide has Ala at positions 1, 3 and 12; Gln at position 10; Arg at positions 11 and 19; and Trp at position 14.

4. The polypeptide of claim 1, wherein said polypeptide is Mc-PTH(1-18)/PTHrP(19-36) (SEQ ID NO:16).

5. The polypeptide of claim 1, wherein said polypeptide is Mc-PTH(1-14)/PTHrP(15-36) (SEQ ID NO:15).

6. The polypeptide of claim 1, wherein said polypeptide is Mc-PTH(1-17)/PTHrP(18-36) (SEQ ID NO:139).

7. The polypeptide of claim 1, wherein said polypeptide is Mc-PTH(1-11)/PTHrP(12-36) (SEQ ID NO:14).

8. The polypeptide of claim 1, wherein said polypeptide has a hydroxyl group or is amidated at its C-terminus.

9. A pharmaceutical composition comprising the polypeptide of claim 1 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 8,568,737 B2 | Page 1 of 1 |
| APPLICATION NO. | : 12/671429 | |
| DATED | : October 29, 2013 | |
| INVENTOR(S) | : Gardella et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 441 days.

Signed and Sealed this
Tenth Day of March, 2015

Michelle K. Lee
*Deputy Director of the United States Patent and Trademark Office*

SEQUENCE LISTING

<160> NUMBER OF SEQ ID NOS: 186

<210> SEQ ID NO 1
<211> LENGTH: 593
<212> TYPE: PRT
<213> ORGANISM: Homo sapiens

<400> SEQUENCE: 1

Met Gly Thr Ala Arg Ile Ala Pro Gly Leu Ala Leu Leu Leu Cys Cys
1               5                   10                  15

Pro Val Leu Ser Ser Ala Tyr Ala Leu Val Asp Ala Asp Asp Val Met
            20                  25                  30

Thr Lys Glu Glu Gln Ile Phe Leu Leu His Arg Ala Gln Ala Gln Cys
        35                  40                  45

Glu Lys Arg Leu Lys Glu Val Leu Gln Arg Pro Ala Ser Ile Met Glu
    50                  55                  60

Ser Asp Lys Gly Trp Thr Ser Ala Ser Thr Ser Gly Lys Pro Arg Lys
65                  70                  75                  80

Asp Lys Ala Ser Gly Lys Leu Tyr Pro Glu Ser Glu Glu Asp Lys Glu
                85                  90                  95

Ala Pro Thr Gly Ser Arg Tyr Arg Gly Arg Pro Cys Leu Pro Glu Trp
            100                 105                 110

Asp His Ile Leu Cys Trp Pro Leu Gly Ala Pro Gly Glu Val Val Ala
        115                 120                 125

Val Pro Cys Pro Asp Tyr Ile Tyr Asp Phe Asn His Lys Gly His Ala
    130                 135                 140

Tyr Arg Arg Cys Asp Arg Asn Gly Ser Trp Glu Leu Val Pro Gly His
145                 150                 155                 160

Asn Arg Thr Trp Ala Asn Tyr Ser Glu Cys Val Lys Phe Leu Thr Asn
                165                 170                 175

Glu Thr Arg Glu Arg Glu Val Phe Asp Arg Leu Gly Met Ile Tyr Thr
            180                 185                 190

Val Gly Tyr Ser Val Ser Leu Ala Ser Leu Thr Val Ala Val Leu Ile
        195                 200                 205

Leu Ala Tyr Phe Arg Arg Leu His Cys Thr Arg Asn Tyr Ile His Met
    210                 215                 220

His Leu Phe Leu Ser Phe Met Leu Arg Ala Val Ser Ile Phe Val Lys
225                 230                 235                 240

Asp Ala Val Leu Tyr Ser Gly Ala Thr Leu Asp Glu Ala Glu Arg Leu
                245                 250                 255

Thr Glu Glu Glu Leu Arg Ala Ile Ala Gln Ala Pro Pro Pro Pro Ala
            260                 265                 270

Thr Ala Ala Ala Gly Tyr Ala Gly Cys Arg Val Ala Val Thr Phe Phe
        275                 280                 285

Leu Tyr Phe Leu Ala Thr Asn Tyr Tyr Trp Ile Leu Val Glu Gly Leu
    290                 295                 300

Tyr Leu His Ser Leu Ile Phe Met Ala Phe Phe Ser Glu Lys Lys Tyr
305                 310                 315                 320

Leu Trp Gly Phe Thr Val Phe Gly Trp Gly Leu Pro Ala Val Phe Val
                325                 330                 335

Ala Val Trp Val Ser Val Arg Ala Thr Leu Ala Asn Thr Gly Cys Trp
            340                 345                 350

Asp Leu Ser Ser Gly Asn Lys Lys Trp Ile Ile Gln Val Pro Ile Leu
        355                 360                 365

Ala Ser Ile Val Leu Asn Phe Ile Leu Phe Ile Asn Ile Val Arg Val
    370                 375                 380

Leu Ala Thr Lys Leu Arg Glu Thr Asn Ala Gly Arg Cys Asp Thr Arg
385                 390                 395                 400

Gln Gln Tyr Arg Lys Leu Leu Lys Ser Thr Leu Val Leu Met Pro Leu
                405                 410                 415

Phe Gly Val His Tyr Ile Val Phe Met Ala Thr Pro Tyr Thr Glu Val
            420                 425                 430

Ser Gly Thr Leu Trp Gln Val Gln Met His Tyr Glu Met Leu Phe Asn
        435                 440                 445

Ser Phe Gln Gly Phe Phe Val Ala Ile Ile Tyr Cys Phe Cys Asn Gly
    450                 455                 460

Glu Val Gln Ala Glu Ile Lys Lys Ser Trp Ser Arg Trp Thr Leu Ala
465                 470                 475                 480

Leu Asp Phe Lys Arg Lys Ala Arg Ser Gly Ser Ser Ser Tyr Ser Tyr
                485                 490                 495

Gly Pro Met Val Ser His Thr Ser Val Thr Asn Val Gly Pro Arg Val
            500                 505                 510

Gly Leu Gly Leu Pro Leu Ser Pro Arg Leu Leu Pro Thr Ala Thr Thr
        515                 520                 525

Asn Gly His Pro Gln Leu Pro Gly His Ala Lys Pro Gly Thr Pro Ala
    530                 535                 540

Leu Glu Thr Leu Glu Thr Thr Pro Pro Ala Met Ala Ala Pro Lys Asp
545                 550                 555                 560

Asp Gly Phe Leu Asn Gly Ser Cys Ser Gly Leu Asp Glu Glu Ala Ser
                565                 570                 575

Gly Pro Glu Arg Pro Pro Ala Leu Leu Gln Glu Glu Trp Glu Thr Val
            580                 585                 590

Met

<210> SEQ ID NO 2
<211> LENGTH: 591
<212> TYPE: PRT
<213> ORGANISM: Rattus norvegicus

<400> SEQUENCE: 2

Met Gly Ala Ala Arg Ile Ala Pro Ser Leu Ala Leu Leu Leu Cys Cys
1               5                   10                  15

Pro Val Leu Ser Ser Ala Tyr Ala Leu Val Asp Ala Asp Asp Val Phe
                20                  25                  30

Thr Lys Glu Glu Gln Ile Phe Leu Leu His Arg Ala Gln Ala Gln Cys
            35                  40                  45

Asp Lys Leu Leu Lys Glu Val Leu His Thr Ala Ala Asn Ile Met Glu
    50                  55                  60

Ser Asp Lys Gly Trp Thr Pro Ala Ser Thr Ser Gly Lys Pro Arg Lys
65                  70                  75                  80

Glu Lys Ala Ser Gly Lys Phe Tyr Pro Glu Ser Lys Glu Asn Lys Asp
                85                  90                  95

Val Pro Thr Gly Ser Arg Arg Arg Gly Arg Pro Cys Leu Pro Glu Trp
            100                 105                 110

Asp Asn Ile Val Cys Trp Pro Leu Gly Ala Pro Gly Glu Val Val Ala
    115                 120                 125

Val Pro Cys Pro Asp Tyr Ile Tyr Asp Phe Asn His Lys Gly His Ala
    130                 135                 140

```
Tyr Arg Arg Cys Asp Arg Asn Gly Ser Trp Glu Val Val Pro Gly His
145                 150                 155                 160

Asn Arg Thr Trp Ala Asn Tyr Ser Glu Cys Leu Lys Phe Met Thr Asn
                165                 170                 175

Glu Thr Arg Glu Arg Glu Val Phe Asp Arg Leu Gly Met Ile Tyr Thr
            180                 185                 190

Val Gly Tyr Ser Met Ser Leu Ala Ser Leu Thr Val Ala Val Leu Ile
        195                 200                 205

Leu Ala Tyr Phe Arg Arg Leu His Cys Thr Arg Asn Tyr Ile His Met
210                 215                 220

His Met Phe Leu Ser Phe Met Leu Arg Ala Ala Ser Ile Phe Val Lys
225                 230                 235                 240

Asp Ala Val Leu Tyr Ser Gly Phe Thr Leu Asp Glu Ala Glu Arg Leu
                245                 250                 255

Thr Glu Glu Glu Leu His Ile Ile Ala Gln Val Pro Pro Pro Pro Ala
            260                 265                 270

Ala Ala Ala Val Gly Tyr Ala Gly Cys Arg Val Ala Val Thr Phe Phe
        275                 280                 285

Leu Tyr Phe Leu Ala Thr Asn Tyr Tyr Trp Ile Leu Val Glu Gly Leu
290                 295                 300

Tyr Leu His Ser Leu Ile Phe Met Ala Phe Phe Ser Glu Lys Lys Tyr
305                 310                 315                 320

Leu Trp Gly Phe Thr Ile Phe Gly Trp Gly Leu Pro Ala Val Phe Val
                325                 330                 335

Ala Val Trp Val Gly Val Arg Ala Thr Leu Ala Asn Thr Gly Cys Trp
            340                 345                 350

Asp Leu Ser Ser Gly His Lys Lys Trp Ile Ile Gln Val Pro Ile Leu
        355                 360                 365

Ala Ser Val Val Leu Asn Phe Ile Leu Phe Ile Asn Ile Ile Arg Val
370                 375                 380

Leu Ala Thr Lys Leu Arg Glu Thr Asn Ala Gly Arg Cys Asp Thr Arg
385                 390                 395                 400

Gln Gln Tyr Arg Lys Leu Leu Arg Ser Thr Leu Val Leu Val Pro Leu
                405                 410                 415

Phe Gly Val His Tyr Thr Val Phe Met Ala Leu Pro Tyr Thr Glu Val
            420                 425                 430

Ser Gly Thr Leu Trp Gln Ile Gln Met His Tyr Glu Met Leu Phe Asn
        435                 440                 445

Ser Phe Gln Gly Phe Phe Val Ala Ile Ile Tyr Cys Phe Cys Asn Gly
450                 455                 460

Glu Val Gln Ala Glu Ile Arg Lys Ser Trp Ser Arg Trp Thr Leu Ala
465                 470                 475                 480

Leu Asp Phe Lys Arg Lys Ala Arg Ser Gly Ser Ser Ser Tyr Ser Tyr
                485                 490                 495

Gly Pro Met Val Ser His Thr Ser Val Thr Asn Val Gly Pro Arg Ala
            500                 505                 510

Gly Leu Ser Leu Pro Leu Ser Pro Arg Leu Pro Pro Ala Thr Thr Asn
        515                 520                 525

Gly His Ser Gln Leu Pro Gly His Ala Lys Pro Gly Ala Pro Ala Thr
530                 535                 540

Glu Thr Glu Thr Leu Pro Val Thr Met Ala Val Pro Lys Asp Asp Gly
545                 550                 555                 560

Phe Leu Asn Gly Ser Cys Ser Gly Leu Asp Glu Glu Ala Ser Gly Ser
                565                 570                 575
```

```
Ala Arg Pro Pro Leu Leu Gln Glu Glu Trp Glu Thr Val Met
        580                 585                 590

<210> SEQ ID NO 3
<211> LENGTH: 115
<212> TYPE: PRT
<213> ORGANISM: Homo sapiens
<220> FEATURE:
<221> NAME/KEY: mat_peptide
<222> LOCATION: (32)..(115)
<223> OTHER INFORMATION: The native peptide is 1-84, which is shown by
      residues 32 to 115 in this sequence.

<400> SEQUENCE: 3

Met Ile Pro Ala Lys Asp Met Ala Lys Val Met Ile Val Met Leu Ala
    -30                 -25                 -20

Ile Cys Phe Leu Thr Lys Ser Asp Gly Lys Ser Val Lys Lys Arg Ser
-15                 -10                  -5                  -1   1

Val Ser Glu Ile Gln Leu Met His Asn Leu Gly Lys His Leu Asn Ser
                 5                  10                  15

Met Glu Arg Val Glu Trp Leu Arg Lys Lys Leu Gln Asp Val His Asn
            20                  25                  30

Phe Val Ala Leu Gly Ala Pro Leu Ala Pro Arg Asp Ala Gly Ser Gln
        35                  40                  45

Arg Pro Arg Lys Lys Glu Asp Asn Val Leu Val Glu Ser His Glu Lys
50                  55                  60                  65

Ser Leu Gly Glu Ala Asp Lys Ala Asp Val Asn Val Leu Thr Lys Ala
                70                  75                  80

Lys Ser Gln

<210> SEQ ID NO 4
<211> LENGTH: 177
<212> TYPE: PRT
<213> ORGANISM: Homo sapiens
<220> FEATURE:
<221> NAME/KEY: mat_peptide
<222> LOCATION: (37)..(177)
<223> OTHER INFORMATION: The native peptide is ~1-140, which is
      approximately shown by residues 37 to 177 in this sequence.

<400> SEQUENCE: 4

Met Gln Arg Arg Leu Val Gln Gln Trp Ser Val Ala Val Phe Leu Leu
    -35                 -30                 -25

Ser Tyr Ala Val Pro Ser Cys Gly Arg Ser Val Glu Gly Leu Ser Arg
-20                 -15                 -10                  -5

Arg Leu Lys Arg Ala Val Ser Glu His Gln Leu Leu His Asp Lys Gly
                -1   1                   5                  10

Lys Ser Ile Gln Asp Leu Arg Arg Arg Phe Phe Leu His His Leu Ile
        15                  20                  25

Ala Glu Ile His Thr Ala Glu Ile Arg Ala Thr Ser Glu Val Ser Pro
        30                  35                  40

Asn Ser Lys Pro Ser Pro Asn Thr Lys Asn His Pro Val Arg Phe Gly
45                  50                  55                  60

Ser Asp Asp Glu Gly Arg Tyr Leu Thr Gln Glu Thr Asn Lys Val Glu
                65                  70                  75

Thr Tyr Lys Glu Gln Pro Leu Lys Thr Pro Gly Lys Lys Lys Lys Gly
        80                  85                  90

Lys Pro Gly Lys Arg Lys Glu Gln Glu Lys Lys Arg Arg Thr Arg
        95                  100                 105
```

```
Ser Ala Trp Leu Asp Ser Gly Val Thr Gly Ser Gly Leu Glu Gly Asp
        110                 115                 120

His Leu Ser Asp Thr Ser Thr Thr Ser Leu Glu Leu Asp Ser Arg Arg
125                 130                 135                 140

His

<210> SEQ ID NO 5
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 6
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala Glu Ile
        35

<210> SEQ ID NO 7
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Val Ser Glu Ile Gln Leu Met His Asn Leu Gly Lys His Leu Asn
1               5                   10                  15

Ser Met Glu Arg Val Glu Ala Leu Arg Lys Lys Leu Gln Asp Val His
            20                  25                  30

Asn Phe

<210> SEQ ID NO 8
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Val Ser Glu His Gln Leu Leu His Asp Lys Gly Lys Ser Ile Gln
1               5                   10                  15
```

```
Asp Leu Arg Arg Arg Phe Ala Leu His His Leu Ile Ala Glu Ile His
            20                  25                  30

Thr Ala Glu Ile
        35

<210> SEQ ID NO 9
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Val Ser Glu His Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 10
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala Glu Ile
        35

<210> SEQ ID NO 11
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (11)..(11)
<223> OTHER INFORMATION: Har

<400> SEQUENCE: 11

Ala Val Xaa Glu Ile Gln Leu Met His Gln Xaa Ala Lys Trp Leu Asn
1               5                   10                  15

Ser Met Arg Arg Val Glu Trp Leu Arg Lys Lys Leu
            20                  25

<210> SEQ ID NO 12
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (3)..(3)
<223> OTHER INFORMATION: Aib
<220> FEATURE:
<221> NAME/KEY: MOD_RES
<222> LOCATION: (11)..(11)
<223> OTHER INFORMATION: Har

<400> SEQUENCE: 12

Ala Val Xaa Glu Ile Gln Leu Met His Gln Xaa Ala Lys Trp Leu Asn
1               5                   10                  15

Ser Met Arg Arg Val Glu Trp Leu Arg Lys Lys Leu Gln Asp Val His
            20                  25                  30

Asn Phe

<210> SEQ ID NO 13
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Val Ser Glu Ile Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala Glu Ile
        35

<210> SEQ ID NO 14
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Val Ala Glu Ile Gln Leu Met His Gln Arg Gly Lys Ser Ile Gln
1               5                   10                  15

Asp Leu Arg Arg Arg Phe Phe Leu His His Leu Ile Ala Glu Ile His
            20                  25                  30

Thr Ala Glu Ile
        35

<210> SEQ ID NO 15
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Val Ala Glu Ile Gln Leu Met His Gln Arg Ala Lys Trp Ile Gln
1               5                   10                  15

Asp Leu Arg Arg Arg Phe Phe Leu His His Leu Ile Ala Glu Ile His
            20                  25                  30

Thr Ala Glu Ile
        35

<210> SEQ ID NO 16
<211> LENGTH: 36
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Val Ala Glu Ile Gln Leu Met His Gln Arg Ala Lys Trp Leu Asn
1               5                   10                  15

Ser Met Arg Arg Arg Phe Phe Leu His His Leu Ile Ala Glu Ile His
            20                  25                  30

Thr Ala Glu Ile
            35

<210> SEQ ID NO 17
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Val Ser Glu His Gln Leu Met His Asn Leu Gly Lys His Ile Gln
1               5                   10                  15

Asp Leu Arg Arg Arg Phe Phe Leu His His Leu Ile Ala Glu Ile His
            20                  25                  30

Thr Ala Glu Ile
            35

<210> SEQ ID NO 18
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Val Ala Glu Ile Gln Leu Met His Gln Arg Ala Lys Trp Leu Asn
1               5                   10                  15

Ser Met Arg Arg Val Glu Trp Leu Arg Lys Lys Leu Gln Asp Val His
            20                  25                  30

Asn Phe

<210> SEQ ID NO 19
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Val Ser Glu Ile Gln Leu Met His Asn Leu Gly Lys His Ile Gln
1               5                   10                  15

Asp Leu Glu Arg Arg Phe Phe Leu His His Leu Ile Ala Glu Ile His
            20                  25                  30

Thr Ala Glu Ile
            35

<210> SEQ ID NO 20
<211> LENGTH: 36
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 20

Ala Val Ala Glu Ile Gln Leu Met His Gln Arg Ala Lys Trp Ile Gln
1               5                   10                  15

Asp Leu Glu Arg Arg Phe Phe Leu His His Leu Ile Ala Glu Ile His
            20                  25                  30

Thr Ala Glu Ile
        35

<210> SEQ ID NO 21
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Val Ala Glu Ile Gln Leu Met His Gln Arg Ala Lys Trp Leu Asn
1               5                   10                  15

Ser Met Glu Arg Val Glu Trp Leu Arg Lys Lys Leu Gln Asp Val His
            20                  25                  30

Asn Phe

<210> SEQ ID NO 22
<211> LENGTH: 84
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Val Ser Glu Ile Gln Leu Met His Asn Leu Gly Lys His Leu Asn
1               5                   10                  15

Ser Met Glu Arg Val Glu Ala Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 23
<211> LENGTH: 141
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Val Ser Glu Ile Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30
```

```
Thr Ala Glu Ile Arg Ala Thr Ser Glu Val Ser Pro Asn Ser Lys Pro
        35                  40                  45

Ser Pro Asn Thr Lys Asn His Pro Val Arg Phe Gly Ser Asp Asp Glu
 50                  55                  60

Gly Arg Tyr Leu Thr Gln Glu Thr Asn Lys Val Glu Thr Tyr Lys Glu
 65                  70                  75                  80

Gln Pro Leu Lys Thr Pro Gly Lys Lys Lys Gly Lys Pro Gly Lys
                85                  90                  95

Arg Lys Glu Gln Glu Lys Lys Arg Arg Thr Arg Ser Ala Trp Leu
                100                 105                 110

Asp Ser Gly Val Thr Gly Ser Gly Leu Glu Gly Asp His Leu Ser Asp
            115                 120                 125

Thr Ser Thr Thr Ser Leu Glu Leu Asp Ser Arg Arg His
            130                 135                 140

<210> SEQ ID NO 24
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Val Ala Glu His Gln Leu Met His Gln Arg Ala Lys Trp Leu Asn
 1               5                  10                  15

Ser Met Glu Arg Val Glu Trp Leu Arg Lys Lys Leu Gln Asp Val His
                20                  25                  30

Asn Phe

<210> SEQ ID NO 25
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Val Ala Glu His Gln Leu Met His Gln Arg Ala Lys Trp Ile Gln
 1               5                  10                  15

Asp Leu Glu Arg Arg Phe Phe Leu His His Leu Ile Ala Glu Ile His
                20                  25                  30

Thr Ala Glu Ile
        35

<210> SEQ ID NO 26
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Val Ser Glu Ile Gln Leu Met His Asn Leu Gly Lys His Leu Asn
 1               5                  10                  15

Ser Met Glu Arg Val Glu Phe Leu His His Leu Ile Ala Glu Ile His
                20                  25                  30

Thr Ala Glu Ile
        35
```

```
<210> SEQ ID NO 27
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Ile His
            20                  25                  30

Thr Ala Glu Ile
        35

<210> SEQ ID NO 28
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Val Ala Glu Ile Gln Leu Met His Gln Arg Ala Lys Trp Leu Asn
1               5                   10                  15

Ser Met Glu Arg Val Glu Ala Leu Arg Lys Lys Leu Gln Asp Val His
            20                  25                  30

Asn Phe

<210> SEQ ID NO 29
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Val Ala Glu Ile Gln Leu Met His Gln Arg Ala Lys Trp Leu Asn
1               5                   10                  15

Ser Met Arg Arg Val Glu Ala Leu Arg Lys Lys Leu Gln Asp Val His
            20                  25                  30

Asn Phe

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser, Ala, Gly or Aib
<220> FEATURE:
<221> NAME/KEY: MOD_RES
<222> LOCATION: (3)..(3)
<223> OTHER INFORMATION: Ser, Ala or Aib
<220> FEATURE:
<221> NAME/KEY: MOD_RES
<222> LOCATION: (10)..(10)
<223> OTHER INFORMATION: Ala, Asn, Glu, Val, Asp or Gln
<220> FEATURE:
<221> NAME/KEY: MOD_RES
```

```
<222> LOCATION: (11)..(11)
<223> OTHER INFORMATION: Leu, Val, Ala, Trp, Ile, Met, Lys, Arg or Har
<220> FEATURE:
<221> NAME/KEY: MOD_RES
<222> LOCATION: (12)..(12)
<223> OTHER INFORMATION: Gly, His, Arg, Ala or Aib
<220> FEATURE:
<221> NAME/KEY: MOD_RES
<222> LOCATION: (13)..(13)
<223> OTHER INFORMATION: Lys, Gln, Leu, His, Trp, Ala, Arg or Aib
<220> FEATURE:
<221> NAME/KEY: MOD_RES
<222> LOCATION: (14)..(14)
<223> OTHER INFORMATION: His, Arg, Leu, Phe, Trp or Aib
<220> FEATURE:
<221> NAME/KEY: MOD_RES
<222> LOCATION: (14)..(14)
<223> OTHER INFORMATION: His, Arg, Leu, Phe, Trp or Aib

<400> SEQUENCE: 30

Xaa Val Xaa Glu His Gln Lys Met His Xaa Xaa Xaa Xaa Xaa
1               5                   10

<210> SEQ ID NO 31
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser, Ala or Aib
<220> FEATURE:
<221> NAME/KEY: MOD_RES
<222> LOCATION: (3)..(3)
<223> OTHER INFORMATION: Ser, Ala or Aib
<220> FEATURE:
<221> NAME/KEY: MOD_RES
<222> LOCATION: (5)..(5)
<223> OTHER INFORMATION: Ile or His
<220> FEATURE:
<221> NAME/KEY: MOD_RES
<222> LOCATION: (10)..(10)
<223> OTHER INFORMATION: Asn, Glu, Val, Asp or Gln
<220> FEATURE:
<221> NAME/KEY: MOD_RES
<222> LOCATION: (11)..(11)
<223> OTHER INFORMATION: Leu, Val, Ala, Trp, Ile, Met, Lys, Arg or Har
<220> FEATURE:
<221> NAME/KEY: MOD_RES
<222> LOCATION: (12)..(12)
<223> OTHER INFORMATION: Gly, His, Arg or Ala
<220> FEATURE:
<221> NAME/KEY: MOD_RES
<222> LOCATION: (13)..(13)
<223> OTHER INFORMATION: Lys, Gln, Leu, His, Trp, Ala or Arg
<220> FEATURE:
<221> NAME/KEY: MOD_RES
<222> LOCATION: (14)..(14)
<223> OTHER INFORMATION: His, Arg, Leu, Phe, Trp or Ser
<220> FEATURE:
<221> NAME/KEY: MOD_RES
<222> LOCATION: (20)..(20)
<223> OTHER INFORMATION: Arg or Ala
<220> FEATURE:
<221> NAME/KEY: MOD_RES
<222> LOCATION: (23)..(23)
<223> OTHER INFORMATION: Trp, Phe or Ala
<220> FEATURE:
<221> NAME/KEY: MOD_RES
<222> LOCATION: (24)..(24)
<223> OTHER INFORMATION: Leu or Ala
<220> FEATURE:
<221> NAME/KEY: MOD_RES
<222> LOCATION: (28)..(28)
<223> OTHER INFORMATION: Leu or Ala
```

<400> SEQUENCE: 31

Xaa Val Xaa Glu Xaa Gln Leu Met His Xaa Xaa Xaa Xaa Xaa Leu Asn
1               5                   10                  15

Ser Met Glu Xaa Val Glu Xaa Xaa Arg Lys Lys Xaa
            20                  25

<210> SEQ ID NO 32
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser, Ala or Aib
<220> FEATURE:
<221> NAME/KEY: MOD_RES
<222> LOCATION: (3)..(3)
<223> OTHER INFORMATION: Ser, Ala or Aib
<220> FEATURE:
<221> NAME/KEY: MOD_RES
<222> LOCATION: (10)..(10)
<223> OTHER INFORMATION: Asn, Glu, Val, Asp or Gln
<220> FEATURE:
<221> NAME/KEY: MOD_RES
<222> LOCATION: (11)..(11)
<223> OTHER INFORMATION: Leu, Val, Ala, Trp, Ile, Met, Lys or Arg
<220> FEATURE:
<221> NAME/KEY: MOD_RES
<222> LOCATION: (12)..(12)
<223> OTHER INFORMATION: Gly, His, Arg or Ala
<220> FEATURE:
<221> NAME/KEY: MOD_RES
<222> LOCATION: (13)..(13)
<223> OTHER INFORMATION: Lys, Gln, Leu, His, Trp, Ala or Arg
<220> FEATURE:
<221> NAME/KEY: MOD_RES
<222> LOCATION: (14)..(14)
<223> OTHER INFORMATION: His, Arg, Leu, Phe, Trp or Ser

<400> SEQUENCE: 32

Xaa Val Xaa Glu Ile Gln Leu Met His Xaa Xaa Xaa Xaa Xaa Leu Asn
1               5                   10                  15

Ser Met Arg Arg Val Glu Trp Leu Arg Lys Lys Leu
            20                  25

<210> SEQ ID NO 33
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Leu, Ala, Ser, Met, Phe or Glu
<220> FEATURE:
<221> NAME/KEY: MOD_RES
<222> LOCATION: (22)..(22)
<223> OTHER INFORMATION: Phe, Ala, Ser, Leu, Asn, Trp, Glu or Lys
<220> FEATURE:
<221> NAME/KEY: MOD_RES
<222> LOCATION: (25)..(25)
<223> OTHER INFORMATION: His, Leu, Arg, Lys, Trp, Ile or Phe
<220> FEATURE:
<221> NAME/KEY: MOD_RES
<222> LOCATION: (26)..(26)
<223> OTHER INFORMATION: His, Ala, Ser, Asn, Lys or Arg
<220> FEATURE:
<221> NAME/KEY: MOD_RES

```
<222> LOCATION: (29)..(29)
<223> OTHER INFORMATION: Ala, Gly, Ser, Asn, Gln, Trp, Glu or Lys
<220> FEATURE:
<221> NAME/KEY: MOD_RES
<222> LOCATION: (30)..(30)
<223> OTHER INFORMATION: Glu, Gly, Ser, Leu, Asn, Asp, Lys or Ala
<220> FEATURE:
<221> NAME/KEY: MOD_RES
<222> LOCATION: (31)..(31)
<223> OTHER INFORMATION: Ile, Leu, Val, Lys or Ala
<220> FEATURE:
<221> NAME/KEY: MOD_RES
<222> LOCATION: (32)..(32)
<223> OTHER INFORMATION: His or Ala
<220> FEATURE:
<221> NAME/KEY: MOD_RES
<222> LOCATION: (33)..(33)
<223> OTHER INFORMATION: Thr, Asn or Ala
<220> FEATURE:
<221> NAME/KEY: MOD_RES
<222> LOCATION: (34)..(34)
<223> OTHER INFORMATION: Ala or Phe

<400> SEQUENCE: 33

Ala Val Ser Glu His Glu Leu Leu His Asp Lys Gly Lys Ser Ile Gln
1               5                   10                  15

Asp Xaa Arg Arg Arg Xaa Phe Leu Xaa Xaa Leu Ile Xaa Xaa Xaa Xaa
            20                  25                  30

Xaa Xaa Glu Ile
        35

<210> SEQ ID NO 34
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Val Ser Glu His Gln Leu Leu His Asp Lys Gly Lys Ser Ile Gln
1               5                   10                  15

Asp Ala Arg Arg Arg Phe Phe Leu His His Leu Ile
            20                  25

<210> SEQ ID NO 35
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Val Ser Glu His Gln Leu Leu His Asp Lys Gly Lys Ser Ile Gln
1               5                   10                  15

Asp Ser Arg Arg Arg Phe Phe Leu His His Leu Ile
            20                  25

<210> SEQ ID NO 36
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ala Val Ser Glu His Gln Leu Leu His Asp Lys Gly Lys Ser Ile Gln
```

```
                1               5                  10                  15
Asp Met Arg Arg Arg Phe Phe Leu His His Leu Ile
             20                  25

<210> SEQ ID NO 37
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ala Val Ser Glu His Gln Leu Leu His Asp Lys Gly Lys Ser Ile Gln
1               5                  10                  15

Asp Phe Arg Arg Arg Phe Phe Leu His His Leu Ile
             20                  25

<210> SEQ ID NO 38
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ala Val Ser Glu His Gln Leu Leu His Asp Lys Gly Lys Ser Ile Gln
1               5                  10                  15

Asp Glu Arg Arg Arg Phe Phe Leu His His Leu Ile
             20                  25

<210> SEQ ID NO 39
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Val Ser Glu His Gln Leu Leu His Asp Lys Gly Lys Ser Ile Gln
1               5                  10                  15

Asp Leu Arg Arg Arg Ala Phe Leu His His Leu Ile
             20                  25

<210> SEQ ID NO 40
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Val Ser Glu His Gln Leu Leu His Asp Lys Gly Lys Ser Ile Gln
1               5                  10                  15

Asp Leu Arg Arg Arg Ser Phe Leu His His Leu Ile
20                  25

<210> SEQ ID NO 41
<211> LENGTH: 28
<212> TYPE: PRT
<213> ORGANISM: Artificial Sequence
<220> FEATURE:
<223> OTHER INFORMATION: Description of Artificial Sequence: Synthetic
```

-continued

```
     peptide

<400> SEQUENCE: 41

Ala Val Ser Glu His Gln Leu Leu His Asp Lys Gly Lys Ser Ile Gln
1               5                  10                  15

Asp Leu Arg Arg Arg Leu Phe Leu His His Leu Ile
            20                  25

<210> SEQ ID NO 42
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Val Ser Glu His Gln Leu Leu His Asp Lys Gly Lys Ser Ile Gln
1               5                  10                  15

Asp Leu Arg Arg Arg Asn Phe Leu His His Leu Ile
            20                  25

<210> SEQ ID NO 43
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ala Val Ser Glu His Gln Leu Leu His Asp Lys Gly Lys Ser Ile Gln
1               5                  10                  15

Asp Leu Arg Arg Arg Trp Phe Leu His His Leu Ile
            20                  25

<210> SEQ ID NO 44
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ala Val Ser Glu His Gln Leu Leu His Asp Lys Gly Lys Ser Ile Gln
1               5                  10                  15

Asp Leu Arg Arg Arg Glu Phe Leu His His Leu Ile
            20                  25

<210> SEQ ID NO 45
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Val Ser Glu His Gln Leu Leu His Asp Lys Gly Lys Ser Ile Gln
1               5                  10                  15

Asp Leu Arg Arg Arg Lys Phe Leu His His Leu Ile
            20                  25

<210> SEQ ID NO 46
```

```
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Val Ser Glu His Gln Leu Leu His Asp Lys Gly Lys Ser Ile Gln
1               5                   10                  15

Asp Leu Arg Arg Arg Phe Phe Leu His Ala Leu Ile
            20                  25

<210> SEQ ID NO 47
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Val Ser Glu His Gln Leu Leu His Asp Lys Gly Lys Ser Ile Gln
1               5                   10                  15

Asp Leu Arg Arg Arg Phe Phe Leu His Ser Leu Ile
            20                  25

<210> SEQ ID NO 48
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ala Val Ser Glu His Gln Leu Leu His Asp Lys Gly Lys Ser Ile Gln
1               5                   10                  15

Asp Leu Arg Arg Arg Phe Phe Leu His Asn Leu Ile
            20                  25

<210> SEQ ID NO 49
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Val Ser Glu His Gln Leu Leu His Asp Lys Gly Lys Ser Ile Gln
1               5                   10                  15

Asp Leu Arg Arg Arg Phe Phe Leu His Lys Leu Ile
            20                  25

<210> SEQ ID NO 50
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ala Val Ser Glu His Gln Leu Leu His Asp Lys Gly Lys Ser Ile Gln
1               5                   10                  15
```

Asp Leu Arg Arg Arg Phe Phe Leu His Arg Leu Ile
            20                  25

<210> SEQ ID NO 51
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ala Val Ser Glu His Gln Leu Leu His Asp Lys Gly Lys Ser Ile Gln
1               5                   10                  15

Asp Leu Arg Arg Arg Phe Phe Leu Leu His Leu Ile
            20                  25

<210> SEQ ID NO 52
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ala Val Ser Glu His Gln Leu Leu His Asp Lys Gly Lys Ser Ile Gln
1               5                   10                  15

Asp Leu Arg Arg Arg Phe Phe Leu Trp His Leu Ile
            20                  25

<210> SEQ ID NO 53
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Val Ser Glu His Gln Leu Leu His Asp Lys Gly Lys Ser Ile Gln
1               5                   10                  15

Asp Leu Arg Arg Arg Phe Phe Leu Lys His Leu Ile
            20                  25

<210> SEQ ID NO 54
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ala Val Ser Glu His Gln Leu Leu His Asp Lys Gly Lys Ser Ile Gln
1               5                   10                  15

Asp Leu Arg Arg Arg Phe Phe Leu Arg His Leu Ile
            20                  25

<210> SEQ ID NO 55
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Val Ser Glu His Gln Leu Leu His Asp Lys Gly Lys Ser Ile Gln
1               5                   10                  15

Asp Ala Arg Arg Arg Ala Phe Leu His Ala Leu Ile
            20                  25

<210> SEQ ID NO 56
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ala Val Ser Glu His Gln Leu Leu His Asp Lys Gly Lys Ser Ile Gln
1               5                   10                  15

Asp Ala Arg Arg Arg Ala Phe Leu His Lys Leu Ile
            20                  25

<210> SEQ ID NO 57
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ala Val Ser Glu His Gln Leu Leu His Asp Lys Gly Lys Ser Ile Gln
1               5                   10                  15

Asp Ala Arg Arg Arg Ser Phe Leu His Ala Leu Ile
            20                  25

<210> SEQ ID NO 58
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ala Val Ser Glu His Gln Leu Leu His Asp Lys Gly Lys Ser Ile Gln
1               5                   10                  15

Asp Ala Arg Arg Arg Ser Phe Leu His Lys Leu Ile
            20                  25

<210> SEQ ID NO 59
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ala Val Ser Glu His Gln Leu Leu His Asp Lys Gly Lys Ser Ile Gln
1               5                   10                  15

Asp Ala Arg Arg Arg Asn Phe Leu His Ala Leu Ile
            20                  25

<210> SEQ ID NO 60
<211> LENGTH: 28
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 60

Ala Val Ser Glu His Gln Leu Leu His Asp Lys Gly Lys Ser Ile Gln
1               5                   10                  15

Asp Ala Arg Arg Arg Asn Phe Leu His Lys Leu Ile
            20                  25

<210> SEQ ID NO 61
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ala Val Ser Glu His Gln Leu Leu His Asp Lys Gly Lys Ser Ile Gln
1               5                   10                  15

Asp Ala Arg Arg Arg Leu Phe Leu His Ala Leu Ile
            20                  25

<210> SEQ ID NO 62
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ala Val Ser Glu His Gln Leu Leu His Asp Lys Gly Lys Ser Ile Gln
1               5                   10                  15

Asp Ala Arg Arg Arg Leu Phe Leu His Lys Leu Ile
            20                  25

<210> SEQ ID NO 63
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ala Val Ser Glu His Gln Leu Leu His Asp Lys Gly Lys Ser Ile Gln
1               5                   10                  15

Asp Ala Arg Arg Arg Trp Phe Leu His Ala Leu Ile
            20                  25

<210> SEQ ID NO 64
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ala Val Ser Glu His Gln Leu Leu His Asp Lys Gly Lys Ser Ile Gln
1               5                   10                  15

Asp Ala Arg Arg Arg Trp Phe Leu His Lys Leu Ile
            20                  25
```

<210> SEQ ID NO 65
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Val Ser Glu His Gln Leu Leu His Asp Lys Gly Lys Ser Ile Gln
1               5                   10                  15

Asp Glu Arg Arg Arg Ala Phe Leu His Lys Leu Ile
            20                  25

<210> SEQ ID NO 66
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ala Val Ser Glu His Gln Leu Leu His Asp Lys Gly Lys Ser Ile Gln
1               5                   10                  15

Asp Glu Arg Arg Arg Ser Phe Leu His Ala Leu Ile
            20                  25

<210> SEQ ID NO 67
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ala Val Ser Glu His Gln Leu Leu His Asp Lys Gly Lys Ser Ile Gln
1               5                   10                  15

Asp Glu Arg Arg Arg Asn Phe Leu His Ala Leu Ile
            20                  25

<210> SEQ ID NO 68
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ala Val Ser Glu His Gln Leu Leu His Asp Lys Gly Lys Ser Ile Gln
1               5                   10                  15

Asp Glu Arg Arg Arg Asn Phe Leu His Lys Leu Ile
            20                  25

<210> SEQ ID NO 69
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

```
Ala Val Ser Glu His Gln Leu Leu His Asp Lys Gly Lys Ser Ile Gln
1               5                   10                  15

Asp Glu Arg Arg Arg Leu Phe Leu His Ala Leu Ile
            20                  25
```

<210> SEQ ID NO 70
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

```
Ala Val Ser Glu His Gln Leu Leu His Asp Lys Gly Lys Ser Ile Gln
1               5                   10                  15

Asp Glu Arg Arg Arg Leu Phe Leu His Lys Leu Ile
            20                  25
```

<210> SEQ ID NO 71
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

```
Ala Val Ser Glu His Gln Leu Leu His Asp Lys Gly Lys Ser Ile Gln
1               5                   10                  15

Asp Glu Arg Arg Arg Trp Phe Leu His Ala Leu Ile
            20                  25
```

<210> SEQ ID NO 72
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

```
Ala Val Ser Glu His Gln Leu Leu His Asp Lys Gly Lys Ser Ile Gln
1               5                   10                  15

Asp Glu Arg Arg Arg Trp Phe Leu His Lys Leu Ile
            20                  25
```

<210> SEQ ID NO 73
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

```
Ala Val Ser Glu His Gln Leu Leu His Asp Lys Gly Lys Ser Ile Gln
1               5                   10                  15

Asp Glu Arg Arg Arg Lys Phe Leu His Ala Leu Ile
            20                  25
```

<210> SEQ ID NO 74
<211> LENGTH: 28
<212> TYPE: PRT
<213> ORGANISM: Artificial Sequence
<220> FEATURE:

-continued

```
<223> OTHER INFORMATION: Description of Artificial Sequence: Synthetic
      peptide

<400> SEQUENCE: 74

Ala Val Ser Glu His Gln Leu Leu His Asp Lys Gly Lys Ser Ile Gln
1               5                   10                  15

Asp Glu Arg Arg Arg Lys Phe Leu His Lys Leu Ile
            20                  25

<210> SEQ ID NO 75
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ala Val Ser Glu His Gln Leu Leu His Asp Lys Gly Lys Ser Ile Gln
1               5                   10                  15

Asp Glu Arg Arg Arg Ala Phe Leu His Ala Leu Ile
            20                  25

<210> SEQ ID NO 76
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ala Val Ser Glu His Gln Leu Leu His Asp Lys Gly Lys Ser Ile Gln
1               5                   10                  15

Asp Ala Arg Arg Arg Ala Phe Leu Leu Lys Leu Ile
            20                  25

<210> SEQ ID NO 77
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ala Val Ser Glu His Gln Leu Leu His Asp Lys Gly Lys Ser Ile Gln
1               5                   10                  15

Asp Ala Arg Arg Arg Ala Phe Leu Lys Lys Leu Ile
            20                  25

<210> SEQ ID NO 78
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ala Val Ser Glu His Gln Leu Leu His Asp Lys Gly Lys Ser Ile Gln
1               5                   10                  15

Asp Ala Arg Arg Arg Ala Phe Leu Ile Lys Leu Ile
            20                  25
```

```
<210> SEQ ID NO 79
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ala Val Ser Glu His Gln Leu Leu His Asp Lys Gly Lys Ser Ile Gln
1               5                   10                  15

Asp Ala Arg Arg Arg Ala Phe Leu Trp Lys Leu Ile
            20                  25

<210> SEQ ID NO 80
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ala Val Ser Glu His Gln Leu Leu His Asp Lys Gly Lys Ser Ile Gln
1               5                   10                  15

Asp Ala Arg Arg Arg Ala Phe Leu Phe Lys Leu Ile
            20                  25

<210> SEQ ID NO 81
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ala Val Ser Glu His Gln Leu Leu His Asp Lys Gly Lys Ser Ile Gln
1               5                   10                  15

Asp Ala Arg Arg Arg Ser Phe Leu Leu Lys Leu Ile
            20                  25

<210> SEQ ID NO 82
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ala Val Ser Glu His Gln Leu Leu His Asp Lys Gly Lys Ser Ile Gln
1               5                   10                  15

Asp Ala Arg Arg Arg Ser Phe Leu Lys Lys Leu Ile
            20                  25

<210> SEQ ID NO 83
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ala Val Ser Glu His Gln Leu Leu His Asp Lys Gly Lys Ser Ile Gln
1               5                   10                  15
```

```
Asp Glu Arg Arg Arg Ala Phe Leu Leu Lys Leu Ile
            20                  25

<210> SEQ ID NO 84
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ala Val Ser Glu His Gln Leu Leu His Asp Lys Gly Lys Ser Ile Gln
1               5                   10                  15

Asp Glu Arg Arg Arg Ala Phe Leu Lys Lys Leu Ile
            20                  25

<210> SEQ ID NO 85
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ala Val Ser Glu His Gln Leu Leu His Asp Lys Gly Lys Ser Ile Gln
1               5                   10                  15

Asp Glu Arg Arg Arg Ser Phe Leu Leu Lys Leu Ile
            20                  25

<210> SEQ ID NO 86
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ala Val Ser Glu His Gln Leu Leu His Asp Lys Gly Lys Ser Ile Gln
1               5                   10                  15

Asp Glu Arg Arg Arg Ser Phe Leu Lys Lys Leu Ile
            20                  25

<210> SEQ ID NO 87
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ala Val Ser Glu His Gln Leu Leu His Asp Lys Gly Lys Ser Ile Gln
1               5                   10                  15

Asp Ala Arg Arg Arg Ala Phe Leu His Lys Leu Ile Ala Glu
            20                  25                  30

<210> SEQ ID NO 88
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 88

Ala Val Ser Glu His Gln Leu Leu His Asp Lys Gly Lys Ser Ile Gln
1               5                   10                  15

Asp Glu Arg Arg Arg Ala Phe Leu His His Lys Ile Ala Glu
            20                  25                  30

<210> SEQ ID NO 89
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ala Val Ser Glu His Gln Leu Leu His Asp Lys Gly Lys Ser Ile Gln
1               5                   10                  15

Asp Ala Arg Arg Arg Ala Phe Leu Leu Lys Leu Ile Ala Glu
            20                  25                  30

<210> SEQ ID NO 90
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ala Val Ser Glu His Gln Leu Leu His Asp Lys Gly Lys Ser Ile Gln
1               5                   10                  15

Asp Glu Arg Arg Arg Ala Phe Leu Leu Lys Leu Ile Ala Glu
            20                  25                  30

<210> SEQ ID NO 91
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Val Ser Glu His Gln Leu Leu His Asp Lys Gly Lys Ser Ile Gln
1               5                   10                  15

Asp Ala Arg Arg Arg Ala Phe Leu His Lys Leu Ile Ala Glu Ile
            20                  25                  30

<210> SEQ ID NO 92
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ala Val Ser Glu His Gln Leu Leu His Asp Lys Gly Lys Ser Ile Gln
1               5                   10                  15

Asp Glu Arg Arg Arg Ala Phe Leu His His Lys Ile Ala Glu Ile
            20                  25                  30

<210> SEQ ID NO 93
<211> LENGTH: 31
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ala Val Ser Glu His Gln Leu Leu His Asp Lys Gly Lys Ser Ile Gln
1               5                   10                  15

Asp Ala Arg Arg Arg Ala Phe Leu Leu Lys Leu Ile Ala Glu Ile
            20                  25                  30

<210> SEQ ID NO 94
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ala Val Ser Glu His Gln Leu Leu His Asp Lys Gly Lys Ser Ile Gln
1               5                   10                  15

Asp Glu Arg Arg Arg Ala Phe Leu Leu Lys Leu Ile Ala Glu Ile
            20                  25                  30

<210> SEQ ID NO 95
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ala Val Ser Glu His Gln Leu Leu His Asp Lys Gly Lys Ser Ile Gln
1               5                   10                  15

Asp Glu Arg Arg Arg Ala Phe Leu Leu Lys Leu Ile Gly Glu Ile
            20                  25                  30

<210> SEQ ID NO 96
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ala Val Ser Glu His Gln Leu Leu His Asp Lys Gly Lys Ser Ile Gln
1               5                   10                  15

Asp Glu Arg Arg Arg Ala Phe Leu Leu Lys Leu Ile Ser Glu Ile
            20                  25                  30

<210> SEQ ID NO 97
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ala Val Ser Glu His Gln Leu Leu His Asp Lys Gly Lys Ser Ile Gln
1               5                   10                  15

Asp Glu Arg Arg Arg Ala Phe Leu Leu Lys Leu Ile Asn Glu Ile
```

<210> SEQ ID NO 98
<211> LENGTH: 31
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 98

Ala Val Ser Glu His Gln Leu Leu His Asp Lys Gly Lys Ser Ile Gln
1               5                   10                  15

Asp Glu Arg Arg Arg Ala Phe Leu Leu Lys Leu Ile Gln Glu Ile
            20                  25                  30

<210> SEQ ID NO 99
<211> LENGTH: 31
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 99

Ala Val Ser Glu His Gln Leu Leu His Asp Lys Gly Lys Ser Ile Gln
1               5                   10                  15

Asp Glu Arg Arg Arg Ala Phe Leu Leu Lys Leu Ile Trp Glu Ile
            20                  25                  30

<210> SEQ ID NO 100
<211> LENGTH: 31
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 100

Ala Val Ser Glu His Gln Leu Leu His Asp Lys Gly Lys Ser Ile Gln
1               5                   10                  15

Asp Glu Arg Arg Arg Ala Phe Leu Leu Lys Leu Ile Glu Glu Ile
            20                  25                  30

<210> SEQ ID NO 101
<211> LENGTH: 31
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 101

Ala Val Ser Glu His Gln Leu Leu His Asp Lys Gly Lys Ser Ile Gln
1               5                   10                  15

Asp Glu Arg Arg Arg Ala Phe Leu Leu Lys Leu Ile Lys Glu Ile
            20                  25                  30

<210> SEQ ID NO 102
<211> LENGTH: 31
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 102

```
Ala Val Ser Glu His Gln Leu Leu His Asp Lys Gly Lys Ser Ile Gln
1               5                   10                  15

Asp Glu Arg Arg Arg Ala Phe Leu Leu Lys Leu Ile Ala Gly Ile
            20                  25                  30

<210> SEQ ID NO 103
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ala Val Ser Glu His Gln Leu Leu His Asp Lys Gly Lys Ser Ile Gln
1               5                   10                  15

Asp Glu Arg Arg Arg Ala Phe Leu Leu Lys Leu Ile Ala Ser Ile
            20                  25                  30

<210> SEQ ID NO 104
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ala Val Ser Glu His Gln Leu Leu His Asp Lys Gly Lys Ser Ile Gln
1               5                   10                  15

Asp Glu Arg Arg Arg Ala Phe Leu Leu Lys Leu Ile Ala Leu Ile
            20                  25                  30

<210> SEQ ID NO 105
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ala Val Ser Glu His Gln Leu Leu His Asp Lys Gly Lys Ser Ile Gln
1               5                   10                  15

Asp Glu Arg Arg Arg Ala Phe Leu Leu Lys Leu Ile Ala Asn Ile
            20                  25                  30

<210> SEQ ID NO 106
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ala Val Ser Glu His Gln Leu Leu His Asp Lys Gly Lys Ser Ile Gln
1               5                   10                  15

Asp Glu Arg Arg Arg Ala Phe Leu Leu Lys Leu Ile Ala Asp Ile
            20                  25                  30

<210> SEQ ID NO 107
<211> LENGTH: 31
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 107

Ala Val Ser Glu His Gln Leu Leu His Asp Lys Gly Lys Ser Ile Gln
1               5                   10                  15

Asp Glu Arg Arg Arg Ala Phe Leu Leu Lys Leu Ile Ala Lys Ile
            20                  25                  30

<210> SEQ ID NO 108
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ala Val Ser Glu His Gln Leu Leu His Asp Lys Gly Lys Ser Ile Gln
1               5                   10                  15

Asp Glu Arg Arg Arg Ala Phe Leu Leu Lys Leu Ile Ala Glu Ser
            20                  25                  30

<210> SEQ ID NO 109
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ala Val Ser Glu His Gln Leu Leu His Asp Lys Gly Lys Ser Ile Gln
1               5                   10                  15

Asp Glu Arg Arg Arg Ala Phe Leu Leu Lys Leu Ile Ala Glu Leu
            20                  25                  30

<210> SEQ ID NO 110
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ala Val Ser Glu His Gln Leu Leu His Asp Lys Gly Lys Ser Ile Gln
1               5                   10                  15

Asp Glu Arg Arg Arg Ala Phe Leu Leu Lys Leu Ile Ala Glu Val
            20                  25                  30

<210> SEQ ID NO 111
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Ala Val Ser Glu His Gln Leu Leu His Asp Lys Gly Lys Ser Ile Gln
1               5                   10                  15

Asp Glu Arg Arg Arg Ala Phe Leu Leu Lys Leu Ile Ala Glu Lys
            20                  25                  30
```

```
<210> SEQ ID NO 112
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Ala Val Ser Glu His Gln Leu Leu His Asp Lys Gly Lys Ser Ile Gln
1               5                   10                  15

Asp Glu Arg Arg Arg Ala Phe Leu Leu Lys Leu Ile Ala Glu Ile His
            20                  25                  30

Thr Ala

<210> SEQ ID NO 113
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ala Val Ser Glu His Gln Leu Leu His Asp Lys Gly Lys Ser Ile Gln
1               5                   10                  15

Asp Glu Arg Arg Arg Ala Phe Leu Leu Lys Leu Ile Ala Ala Ile His
            20                  25                  30

Thr Ala

<210> SEQ ID NO 114
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ala Val Ser Glu His Gln Leu Leu His Asp Lys Gly Lys Ser Ile Gln
1               5                   10                  15

Asp Glu Arg Arg Arg Ala Phe Leu Leu Lys Leu Ile Ala Glu Ala His
            20                  25                  30

Thr Ala

<210> SEQ ID NO 115
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ala Val Ser Glu His Gln Leu Leu His Asp Lys Gly Lys Ser Ile Gln
1               5                   10                  15

Asp Glu Arg Arg Arg Ala Phe Leu Leu Lys Leu Ile Ala Glu Ile Ala
            20                  25                  30

Thr Ala

<210> SEQ ID NO 116
<211> LENGTH: 34
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 116

Ala Val Ser Glu His Gln Leu Leu His Asp Lys Gly Lys Ser Ile Gln
1               5                   10                  15

Asp Glu Arg Arg Arg Ala Phe Leu Leu Lys Leu Ile Ala Glu Ile His
            20                  25                  30

Ala Ala

<210> SEQ ID NO 117
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Ala Val Ser Glu His Gln Leu Leu His Asp Lys Gly Lys Ser Ile Gln
1               5                   10                  15

Asp Glu Arg Arg Arg Ala Phe Leu Leu Lys Leu Ile Gln Asp Val His
            20                  25                  30

Asn Phe

<210> SEQ ID NO 118
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Trp Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 119
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (11)..(11)
<223> OTHER INFORMATION: Har

<400> SEQUENCE: 119

Trp Val Xaa Glu Ile Gln Leu Met His Gln Xaa Ala Lys Trp Leu Asn
1               5                   10                  15

Ser Met Arg Arg Val Glu Trp Leu Arg Lys Lys Leu Gln Asp Val His
            20                  25                  30

Asn Phe
```

```
<210> SEQ ID NO 120
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Trp Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala Glu Ile
35

<210> SEQ ID NO 121
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Trp Val Ser Glu Ile Gln Leu Met His Asn Leu Gly Lys His Leu Asn
1               5                   10                  15

Ser Met Glu Arg Val Glu Trp Leu Arg Lys Lys Leu
            20                  25

<210> SEQ ID NO 122
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (11)..(11)
<223> OTHER INFORMATION: Har

<400> SEQUENCE: 122

Trp Val Xaa Glu Ile Gln Leu Met His Gln Xaa Ala Lys Trp Leu Asn
1               5                   10                  15

Ser Met Arg Arg Val Glu Trp Leu Arg Lys Lys Leu
            20                  25

<210> SEQ ID NO 123
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (21)..(21)
<223> OTHER INFORMATION: Nle

<400> SEQUENCE: 123
```

Ala Val Ser Glu Ile Gln Leu Xaa His Asn Leu Gly Lys His Leu Ala
1               5                   10                  15

Ser Val Glu Arg Xaa Gln Trp Leu Arg Lys Lys Leu Gln Asp Val His
                20                  25                  30

Asn Tyr

<210> SEQ ID NO 124
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
                20                  25                  30

Thr Ala Glu Tyr
        35

<210> SEQ ID NO 125
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ala Val Ser Glu Ile Gln Leu Leu His Asp Lys Gly Lys Ser Ile Gln
1               5                   10                  15

Asp Leu Arg Arg Arg Phe Phe Leu His His Leu Ile Ala Glu Ile His
                20                  25                  30

Thr Ala Glu Tyr
        35

<210> SEQ ID NO 126
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aib
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (11)..(11)
<223> OTHER INFORMATION: Har

<400> SEQUENCE: 126

Xaa Val Xaa Glu Ile Gln Leu Xaa His Gln Xaa Ala Lys Trp Tyr
1               5                   10                  15

```
<210> SEQ ID NO 127
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (21)..(21)
<223> OTHER INFORMATION: Nle

<400> SEQUENCE: 127

Ala Val Ser Glu His Gln Leu Xaa His Asn Leu Gly Lys His Leu Ala
1               5                   10                  15

Ser Val Glu Arg Xaa Gln Trp Leu Arg Lys Lys Leu Gln Asp Val His
            20                  25                  30

Asn Tyr

<210> SEQ ID NO 128
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aib
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (11)..(11)
<223> OTHER INFORMATION: Har

<400> SEQUENCE: 128

Xaa Val Xaa Glu Ile Gln Leu Met His Gln Xaa Ala Lys Trp
1               5                   10

<210> SEQ ID NO 129
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ser Val Ser Glu Ile Gln Leu Met His Asn Leu Gly Lys His Leu Asn
1               5                   10                  15

Ser Met Glu Arg Val Glu Trp Leu Arg Lys Lys Leu
            20                  25

<210> SEQ ID NO 130
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130
```

```
Ala Val Ser Glu Ile Gln Leu Met His Asn Leu Gly Lys His Leu Ala
1               5                   10                  15

Ser Val Glu Arg Met Gln Trp Leu Arg Lys Lys Leu Gln Asp Val His
            20                  25                  30

Asn Phe

<210> SEQ ID NO 131
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ala Val Ala Glu Ile Gln Leu Met His Gln Arg Ala Lys Trp Leu Asn
1               5                   10                  15

Ser Met Arg Arg Val Glu Trp Leu Arg Lys Lys Leu Gln Asp Val His
            20                  25                  30

Asn Phe

<210> SEQ ID NO 132
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ala Val Ala Glu His Gln Leu Met His Gln Arg Ala Lys Trp Leu Asn
1               5                   10                  15

Ser Met Arg Arg Val Glu Trp Leu Arg Lys Lys Leu Gln Asp Val His
            20                  25                  30

Asn Phe

<210> SEQ ID NO 133
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ala Val Ala Glu His Gln Leu Met His Gln Arg Ala Lys Trp Ile Gln
1               5                   10                  15

Asp Leu Arg Arg Arg Phe Phe Leu His His Leu Ile Ala Glu Ile His
            20                  25                  30

Thr Ala Glu Ile
        35

<210> SEQ ID NO 134
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ser Val Ser Glu Ile Gln Leu Met His Asn Leu Gly Lys His Ile Gln
1               5                   10                  15
```

Asp Leu Arg Arg Arg Phe Phe Leu His His Leu Ile Ala Glu Ile His
            20                  25                  30

Thr Ala Glu Ile
        35

<210> SEQ ID NO 135
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ser Val Ser Glu Ile Gln Leu Met His Asn Leu Gly Lys His Leu Asn
1               5                   10                  15

Ser Met Arg Arg Arg Phe Phe Leu His His Leu Ile Ala Glu Ile His
            20                  25                  30

Thr Ala Glu Ile
        35

<210> SEQ ID NO 136
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Ser Val Ser Glu Ile Gln Leu Met His Asn Leu Gly Lys His Leu Asn
1               5                   10                  15

Ser Met Glu Arg Val Glu Trp Leu Arg Lys Leu Ile Ala Glu Ile His
            20                  25                  30

Thr Ala Glu Ile
        35

<210> SEQ ID NO 137
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ser Val Ser Glu Ile Gln Leu Met His Asn Leu Gly Lys Ser Ile Gln
1               5                   10                  15

Asp Leu Arg Arg Arg Phe Phe Leu His His Leu Ile Ala Glu Ile His
            20                  25                  30

Thr Ala Glu Ile
        35

<210> SEQ ID NO 138
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ser Val Ser Glu Ile Gln Leu Met His Asn Leu Gly Lys His Leu Asn
1               5                   10                  15

```
Ser Leu Arg Arg Arg Phe Phe Leu His His Leu Ile Ala Glu Ile His
            20                  25                  30

Thr Ala Glu Ile
        35

<210> SEQ ID NO 139
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Ala Val Ala Glu Ile Gln Leu Met His Gln Arg Ala Lys Trp Leu Asn
1               5                   10                  15

Ser Leu Arg Arg Arg Phe Phe Leu His His Leu Ile Ala Glu Ile His
            20                  25                  30

Thr Ala Glu Ile
        35

<210> SEQ ID NO 140
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ala Val Ala Glu Ile Gln Leu Met His Gln Arg Ala Lys Trp Leu Asn
1               5                   10                  15

Ser Met Arg Arg Val Glu Phe Leu His His Leu Ile Ala Glu Ile His
            20                  25                  30

Thr Ala Glu Ile
        35

<210> SEQ ID NO 141
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Ala Val Ala Glu Ile Gln Leu Met His Gln Arg Ala Lys Trp Leu Asn
1               5                   10                  15

Ser Met Arg Arg Val Glu Trp Leu Arg Lys Leu Ile Ala Glu Ile His
            20                  25                  30

Thr Ala Glu Ile
        35

<210> SEQ ID NO 142
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Ala Val Ala Glu Ile Gln Leu Met His Gln Arg Ala Lys Trp Leu Asn
1               5                   10                  15
```

```
Ser Met Arg Arg Val Glu Trp Leu Arg Lys Lys Leu Gln Asp Ile His
            20                  25                  30

Thr Ala Glu Ile
        35

<210> SEQ ID NO 143
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ser Val Ser Glu His Gln Leu Met His Asn Leu Gly Lys His Ile Gln
1               5                   10                  15

Asp Leu Glu Arg Arg Phe Phe Leu His His Leu Ile Ala Glu Ile His
            20                  25                  30

Thr Ala Glu Ile
        35

<210> SEQ ID NO 144
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ala Val Ala Glu Ile Gln Leu Met His Gln Arg Ala Lys Trp Leu Asn
1               5                   10                  15

Ser Met Glu Arg Val Glu Phe Leu His His Leu Ile Ala Glu Ile His
            20                  25                  30

Thr Ala Glu Ile
        35

<210> SEQ ID NO 145
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ala Val Ala Glu Ile Gln Leu Met His Gln Arg Ala Lys Trp Leu Asn
1               5                   10                  15

Ser Met Glu Arg Val Glu Trp Leu Arg Lys Leu Ile Ala Glu Ile His
            20                  25                  30

Thr Ala Glu Ile
        35

<210> SEQ ID NO 146
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ala Val Ala Glu Ile Gln Leu Met His Gln Arg Ala Lys Trp Leu Asn
1               5                   10                  15
```

-continued

Ser Met Glu Arg Val Glu Trp Leu Arg Lys Lys Leu Gln Asp Ile His
            20                  25                  30

Thr Ala Glu Ile
        35

<210> SEQ ID NO 147
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Ala Val Ala Glu Ile Gln Leu Met His Gln Arg Ala Lys Trp Leu Asn
1               5                   10                  15

Ser Met Glu Ala Val Glu Trp Leu Arg Lys Lys Leu Gln Asp Val His
            20                  25                  30

Asn Phe

<210> SEQ ID NO 148
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ala Val Ala Glu Ile Gln Leu Met His Gln Arg Ala Lys Trp Leu Asn
1               5                   10                  15

Ser Met Glu Arg Val Glu Trp Ala Arg Lys Lys Leu Gln Asp Val His
            20                  25                  30

Asn Phe

<210> SEQ ID NO 149
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ala Val Ala Glu Ile Gln Leu Met His Gln Arg Ala Lys Trp Leu Asn
1               5                   10                  15

Ser Met Arg Ala Val Glu Trp Leu Arg Lys Lys Leu Gln Asp Val His
            20                  25                  30

Asn Phe

<210> SEQ ID NO 150
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ala Val Ala Glu Ile Gln Leu Met His Gln Arg Ala Lys Trp Leu Asn
1               5                   10                  15

Ser Met Arg Arg Val Glu Phe Leu Arg Lys Lys Leu Gln Asp Val His
            20                  25                  30

Asn Phe

```
<210> SEQ ID NO 151
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ala Val Ser Glu His Gln Leu Leu His Asp Lys Gly Lys Ser Ile Gln
1               5                   10                  15

Asp Leu Arg Arg Arg Phe Phe Leu His His Leu Ile
            20                  25

<210> SEQ ID NO 152
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Ala Val Ser Glu His Gln Leu Leu His Asp Lys Gly Lys Ser Ala Gln
1               5                   10                  15

Asp Leu Arg Arg Arg Phe Phe Leu His His Leu Ile
            20                  25

<210> SEQ ID NO 153
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ala Val Ser Glu His Gln Leu Leu His Asp Lys Gly Lys Ser Ile Ala
1               5                   10                  15

Asp Leu Arg Arg Arg Phe Phe Leu His His Leu Ile
            20                  25

<210> SEQ ID NO 154
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ala Val Ser Glu His Gln Leu Leu His Asp Lys Gly Lys Ser Ile Gln
1               5                   10                  15

Ala Leu Arg Arg Arg Phe Phe Leu His His Leu Ile
            20                  25

<210> SEQ ID NO 155
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155
```

```
Ala Val Ser Glu His Gln Leu Leu His Asp Lys Gly Lys Ser Ile Gln
1               5                   10                  15

Asp Leu Ala Arg Arg Phe Phe Leu His His Leu Ile
            20                  25

<210> SEQ ID NO 156
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ala Val Ser Glu His Gln Leu Leu His Asp Lys Gly Lys Ser Ile Gln
1               5                   10                  15

Asp Leu Arg Ala Arg Phe Phe Leu His His Leu Ile
            20                  25

<210> SEQ ID NO 157
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Ala Val Ser Glu His Gln Leu Leu His Asp Lys Gly Lys Ser Ile Gln
1               5                   10                  15

Asp Leu Arg Arg Ala Phe Phe Leu His His Leu Ile
            20                  25

<210> SEQ ID NO 158
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ala Val Ser Glu His Gln Leu Leu His Asp Lys Gly Lys Ser Ile Gln
1               5                   10                  15

Asp Leu Arg Arg Arg Phe Ala Leu His His Leu Ile
            20                  25

<210> SEQ ID NO 159
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Ala Val Ser Glu His Gln Leu Leu His Asp Lys Gly Lys Ser Ile Gln
1               5                   10                  15

Asp Leu Arg Arg Arg Phe Phe Ala His His Leu Ile
            20                  25

<210> SEQ ID NO 160
<211> LENGTH: 28
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 160

Ala Val Ser Glu His Gln Leu Leu His Asp Lys Gly Lys Ser Ile Gln
1               5                   10                  15

Asp Leu Arg Arg Arg Phe Phe Leu Ala His Leu Ile
            20                  25

<210> SEQ ID NO 161
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Ala Val Ser Glu His Gln Leu Leu His Asp Lys Gly Lys Ser Ile Gln
1               5                   10                  15

Asp Leu Arg Arg Arg Phe Phe Leu His His Ala Ile
            20                  25

<210> SEQ ID NO 162
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Ala Val Ser Glu His Gln Leu Leu His Asp Lys Gly Lys Ser Ile Gln
1               5                   10                  15

Asp Leu Arg Arg Arg Phe Phe Leu His His Leu Ala
            20                  25

<210> SEQ ID NO 163
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ala Val Ser Glu His Gln Leu Leu His Asp Lys Gly Lys Ser Ile Gln
1               5                   10                  15

Asp Gly Arg Arg Arg Phe Phe Leu His His Leu Ile
            20                  25

<210> SEQ ID NO 164
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ala Val Ser Glu His Gln Leu Leu His Asp Lys Gly Lys Ser Ile Gln
1               5                   10                  15

Asp Leu Arg Arg Arg Phe Phe Leu His His Leu Ile
            20                  25
```

```
<210> SEQ ID NO 165
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Ala Val Ser Glu His Gln Leu Leu His Asp Lys Gly Lys Ser Ile Gln
1               5                   10                  15

Asp Asn Arg Arg Arg Phe Phe Leu His His Leu Ile
            20                  25

<210> SEQ ID NO 166
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ala Val Ser Glu His Gln Leu Leu His Asp Lys Gly Lys Ser Ile Gln
1               5                   10                  15

Asp Lys Arg Arg Arg Phe Phe Leu His His Leu Ile
            20                  25

<210> SEQ ID NO 167
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Ala Val Ser Glu His Gln Leu Leu His Asp Lys Gly Lys Ser Ile Gln
1               5                   10                  15

Asp Leu Arg Arg Arg Gly Phe Leu His His Leu Ile
            20                  25

<210> SEQ ID NO 168
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Ala Val Ser Glu His Gln Leu Leu His Asp Lys Gly Lys Ser Ile Gln
1               5                   10                  15

Asp Leu Arg Arg Arg Phe Phe Leu His Gly Leu Ile
            20                  25

<210> SEQ ID NO 169
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Ala Val Ser Glu His Gln Leu Leu His Asp Lys Gly Lys Ser Ile Gln
```

```
1               5                  10                  15
Asp Leu Arg Arg Arg Phe Phe Leu His Leu Leu Ile
            20                  25

<210> SEQ ID NO 170
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Ala Val Ser Glu His Gln Leu Leu His Asp Lys Gly Lys Ser Ile Gln
1               5                  10                  15

Asp Leu Arg Arg Arg Phe Phe Leu His Trp Leu Ile
            20                  25

<210> SEQ ID NO 171
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Ala Val Ser Glu His Gln Leu Leu His Asp Lys Gly Lys Ser Ile Gln
1               5                  10                  15

Asp Leu Arg Arg Arg Phe Phe Leu His Glu Leu Ile
            20                  25

<210> SEQ ID NO 172
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ala Val Ser Glu His Gln Leu Leu His Asp Lys Gly Lys Ser Ile Gln
1               5                  10                  15

Asp Leu Arg Arg Arg Phe Phe Leu Gly His Leu Ile
            20                  25

<210> SEQ ID NO 173
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ala Val Ser Glu His Gln Leu Leu His Asp Lys Gly Lys Ser Ile Gln
1               5                  10                  15

Asp Leu Arg Arg Arg Phe Phe Leu Ser His Leu Ile
            20                  25

<210> SEQ ID NO 174
<211> LENGTH: 28
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 174

Ala Val Ser Glu His Gln Leu Leu His Asp Lys Gly Lys Ser Ile Gln
1               5                   10                  15

Asp Leu Arg Arg Arg Phe Phe Leu Asn His Leu Ile
            20                  25

<210> SEQ ID NO 175
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ala Val Ser Glu His Gln Leu Leu His Asp Lys Gly Lys Ser Ile Gln
1               5                   10                  15

Asp Leu Arg Arg Arg Phe Phe Leu Glu His Leu Ile
            20                  25

<210> SEQ ID NO 176
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Ala Val Ser Glu His Gln Leu Leu His Asp Lys Gly Lys Ser Ile Gln
1               5                   10                  15

Asp Glu Arg Arg Arg Ala Phe Leu Leu Lys Leu Ile Leu Glu Ile
            20                  25                  30

<210> SEQ ID NO 177
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Ala Val Ser Glu His Gln Leu Leu His Asp Lys Gly Lys Ser Ile Gln
1               5                   10                  15

Asp Glu Arg Arg Arg Ala Phe Leu Leu Lys Leu Ile Ala Trp Ile
            20                  25                  30

<210> SEQ ID NO 178
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ala Val Ser Glu His Gln Leu Leu His Asp Lys Gly Lys Ser Ile Gln
1               5                   10                  15

Asp Glu Arg Arg Arg Ala Phe Leu Leu Lys Leu Ile Ala Glu Asn
            20                  25                  30

<210> SEQ ID NO 179

```
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ala Val Ser Glu His Gln Leu Leu His Asp Lys Gly Lys Ser Ile Gln
1               5                   10                  15

Asp Glu Arg Arg Arg Ala Phe Leu Leu Lys Leu Ile Ala Glu Trp
            20                  25                  30

<210> SEQ ID NO 180
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Ala Val Ser Glu His Gln Leu Leu His Asp Lys Gly Lys Ser Ile Gln
1               5                   10                  15

Asp Glu Arg Arg Arg Ala Phe Leu Leu Lys Leu Ile Ala Glu Glu
            20                  25                  30

<210> SEQ ID NO 181
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ala Val Ala Glu Ile Gln Leu Met His Gln Arg Gly Lys His Leu Asn
1               5                   10                  15

Ser Met Glu Arg Val Glu Ala Leu Arg Lys Lys Leu Gln Asp Val His
            20                  25                  30

Asn Phe

<210> SEQ ID NO 182
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Ala Val Ala Glu Ile Gln Leu Met His Asn Leu Gly Lys His Leu Asn
1               5                   10                  15

Ser Met Glu Arg Val Glu Ala Leu Arg Lys Lys Leu Gln Asp Val His
            20                  25                  30

Asn Phe

<210> SEQ ID NO 183
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183
```

```
Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu
            20                  25                  30

<210> SEQ ID NO 184
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile
            20                  25                  30

<210> SEQ ID NO 185
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Ala Val Ser Glu His Gln Leu Met His Asn Leu Gly Lys His Leu Ala
1               5                   10                  15

Ser Val Glu Arg Met Gln Trp Leu Arg Lys Lys Leu Gln Asp Val His
            20                  25                  30

Asn Phe

<210> SEQ ID NO 186
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ala Glu Ile His Thr Ala
1               5
```